US012731664B2

(12) United States Patent
Harnach

(10) Patent No.: US 12,731,664 B2
(45) Date of Patent: Sep. 8, 2026

(54) SYSTEM AND METHOD FOR IMPLEMENTING HEALTH CARE COST SAVINGS

(71) Applicant: Care Coordination Systems, LLC, Akron, OH (US)

(72) Inventor: Bob Harnach, Akron, OH (US)

(73) Assignee: Care Coordination Systems, LLC, Akron, OH (US)

( * ) Notice: Subject to any disclaimer, the term of this patent is extended or adjusted under 35 U.S.C. 154(b) by 0 days.

(21) Appl. No.: 19/187,464

(22) Filed: Apr. 23, 2025

(65) Prior Publication Data

US 2025/0266138 A1 Aug. 21, 2025

Related U.S. Application Data

(63) Continuation-in-part of application No. 18/400,093, filed on Dec. 29, 2023, now Pat. No. 12,592,299, which is a continuation-in-part of application No. 17/805,452, filed on Jun. 4, 2022, now abandoned, which is a continuation of application No. 16/514,626, filed on Jul. 17, 2019, now Pat. No. 11,393,563.

(60) Provisional application No. 62/819,947, filed on Mar. 18, 2019.

(51) Int. Cl.

| | |
|---|---|
| ***G16H 10/60*** | (2018.01) |
| ***G16H 40/20*** | (2018.01) |
| ***G16H 40/67*** | (2018.01) |
| ***H03F 1/02*** | (2006.01) |
| ***H03F 3/24*** | (2006.01) |
| ***H04B 1/40*** | (2015.01) |
| ***H04W 52/02*** | (2009.01) |

(52) U.S. Cl.

CPC ............ *G16H 10/60* (2018.01); *G16H 40/20* (2018.01); *G16H 40/67* (2018.01); *H03F 1/02* (2013.01); *H03F 3/24* (2013.01); *H04B 1/40* (2013.01); *H04W 52/029* (2013.01)

(58) Field of Classification Search

CPC .............................. G16H 20/00; G16H 40/20
See application file for complete search history.

(56) References Cited

U.S. PATENT DOCUMENTS

| | | | | |
|---|---|---|---|---|
| 7,945,458 | B1 * | 5/2011 | Jackson | G06Q 10/10 705/2 |
| 2024/0296963 | A1 * | 9/2024 | Vinti | G06Q 50/22 |

* cited by examiner

*Primary Examiner* — Joseph D Burgess
(74) *Attorney, Agent, or Firm* — Daniel A. Thomson; Emerson Thomson Bennett®, LLC

(57) ABSTRACT

A system and method for creating efficient and cost saving care plans for clients through the use of artificial intelligence and passing those savings on to care providers and health-care services and programs to further increase efficiency and greater profitability while significantly reducing overall Medicare and Medicaid expenses to governments.

20 Claims, 77 Drawing Sheets

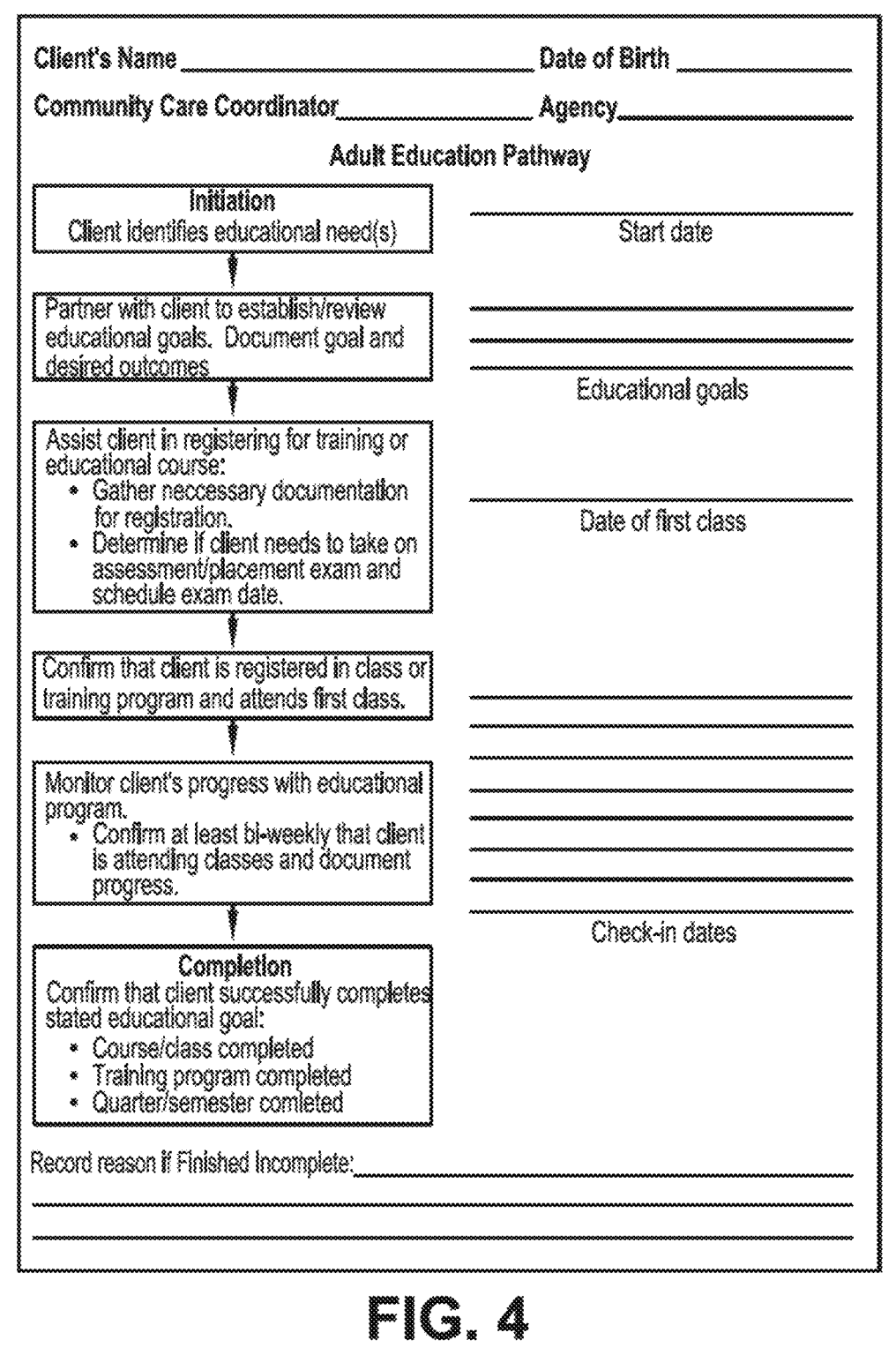

Client's Name ______________ Date of Birth ______________

Community Care Coordinator ______________ Agency ______________

Adult Education Pathway

Initiation
Client identifies educational need(s)

______________ Start date

↓

Partner with client to establish/review educational goals. Document goal and desired outcomes ______________ Educational goals

↓

Assist client in registering for training or educational course:
- Gather neccessary documentation for registration.
- Determine if client needs to take on assessment/placement exam and schedule exam date.

______________ Date of first class

↓

Confirm that client is registered in class or training program and attends first class.

↓

Monitor client's progress with educational program.
- Confirm at least bi-weekly that client is attending classes and document progress.

______________ Check-in dates

↓

Completion
Confirm that client successfully completes stated educational goal:
- Course/class completed
- Training program completed
- Quarter/semester comleted Record reason if Finished Incomplete: ______________

FIG. 4

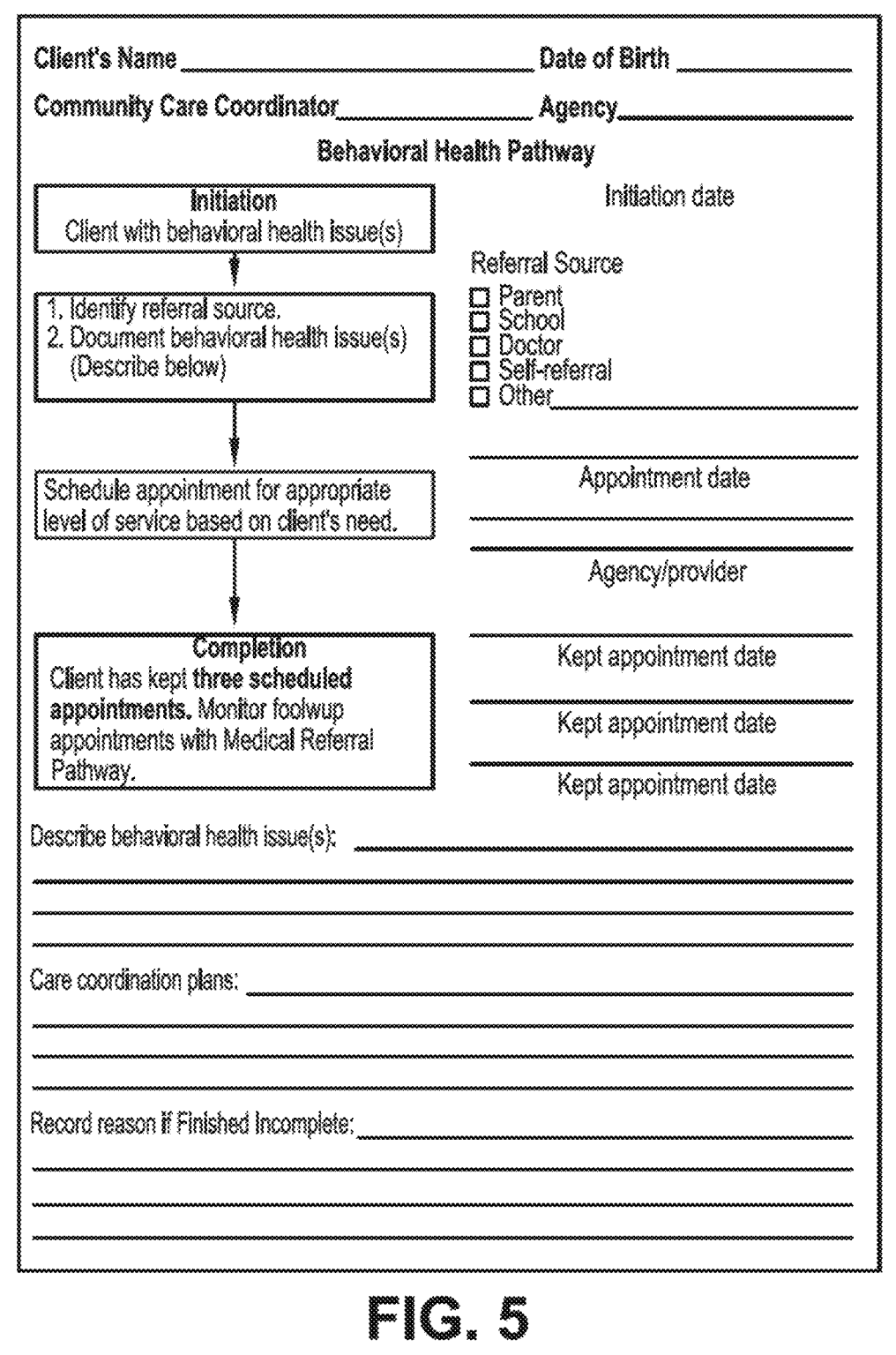

Client's Name ____________ Date of Birth ____________

Community Care Coordinator ____________ Agency ____________

Behavioral Health Pathway

Initiation
Client with behavioral health issue(s)

↓

1. Identify referral source.
2. Document behavioral health issue(s) (Describe below)

↓

Schedule appointment for appropriate level of service based on client's need.

↓

Completion
Client has kept three scheduled appointments. Monitor foolwup appointments with Medical Referral Pathway.

Initiation date

Referral Source
- ☐ Parent
- ☐ School
- ☐ Doctor
- ☐ Self-referral
- ☐ Other ____________

____________
Appointment date
____________

____________
Agency/provider

____________
Kept appointment date
____________
Kept appointment date
____________
Kept appointment date Describe behavioral health issue(s): ____________

Care coordination plans: ____________

Record reason if Finished Incomplete: ____________

FIG. 5

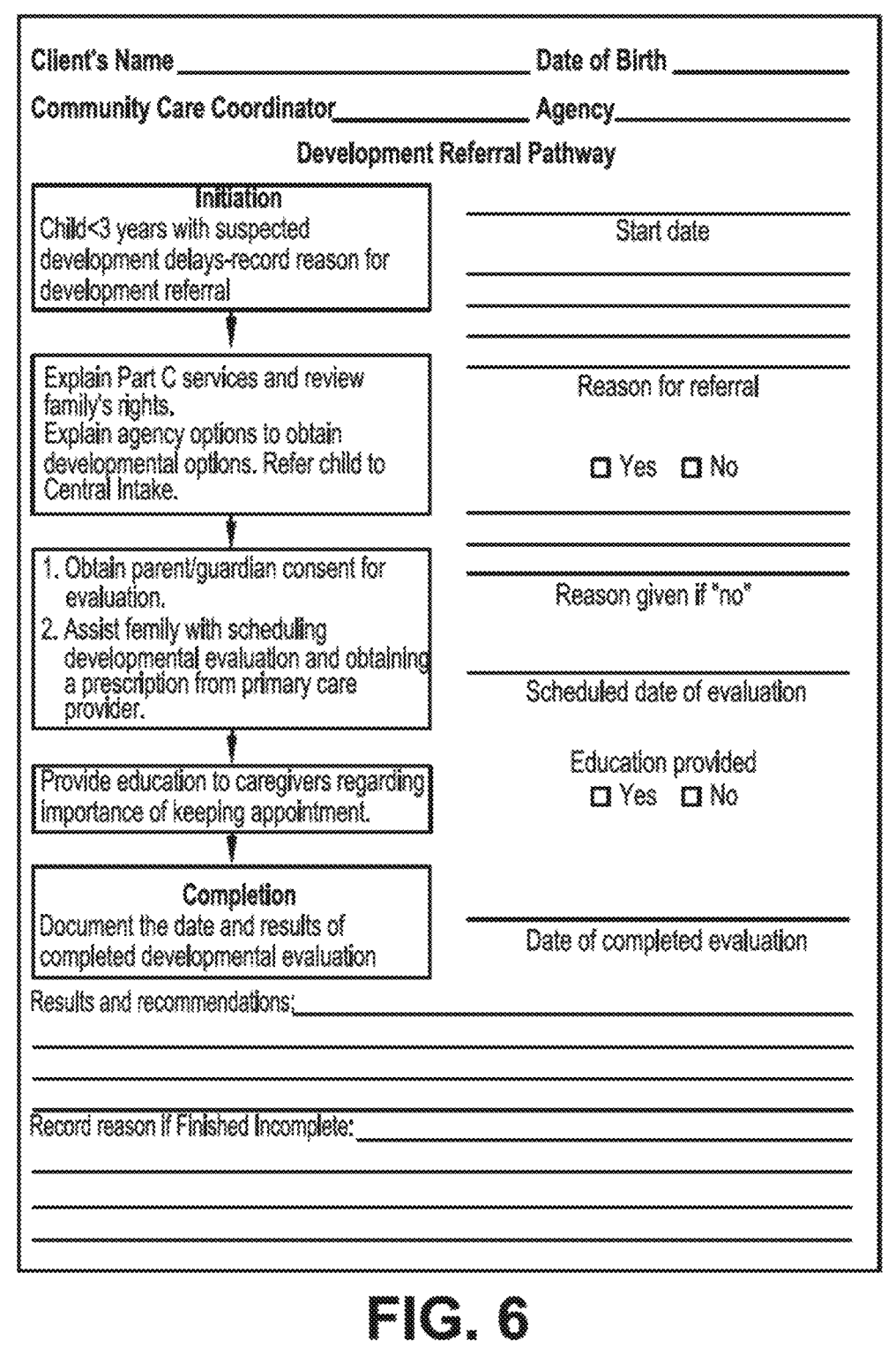

Client's Name ____________ Date of Birth ____________

Community Care Coordinator ____________ Agency ____________

Development Referral Pathway

Initiation
Child<3 years with suspected development delays-record reason for development referral ____________
Start date
____________
____________
____________
____________
Reason for referral

↓

Explain Part C services and review family's rights.
Explain agency options to obtain developmental options. Refer child to Central Intake.

☐ Yes ☐ No
____________
____________
____________
Reason given if "no"

↓

1. Obtain parent/guardian consent for evaluation.
2. Assist family with scheduling developmental evaluation and obtaining a prescription from primary care provider.

____________
Scheduled date of evaluation

↓

Provide education to caregivers regarding importance of keeping appointment.

Education provided
☐ Yes ☐ No

↓

Completion
Document the date and results of completed developmental evaluation ____________
Date of completed evaluation Results and recommendations: ____________

Record reason if Finished Incomplete: ____________

FIG. 6

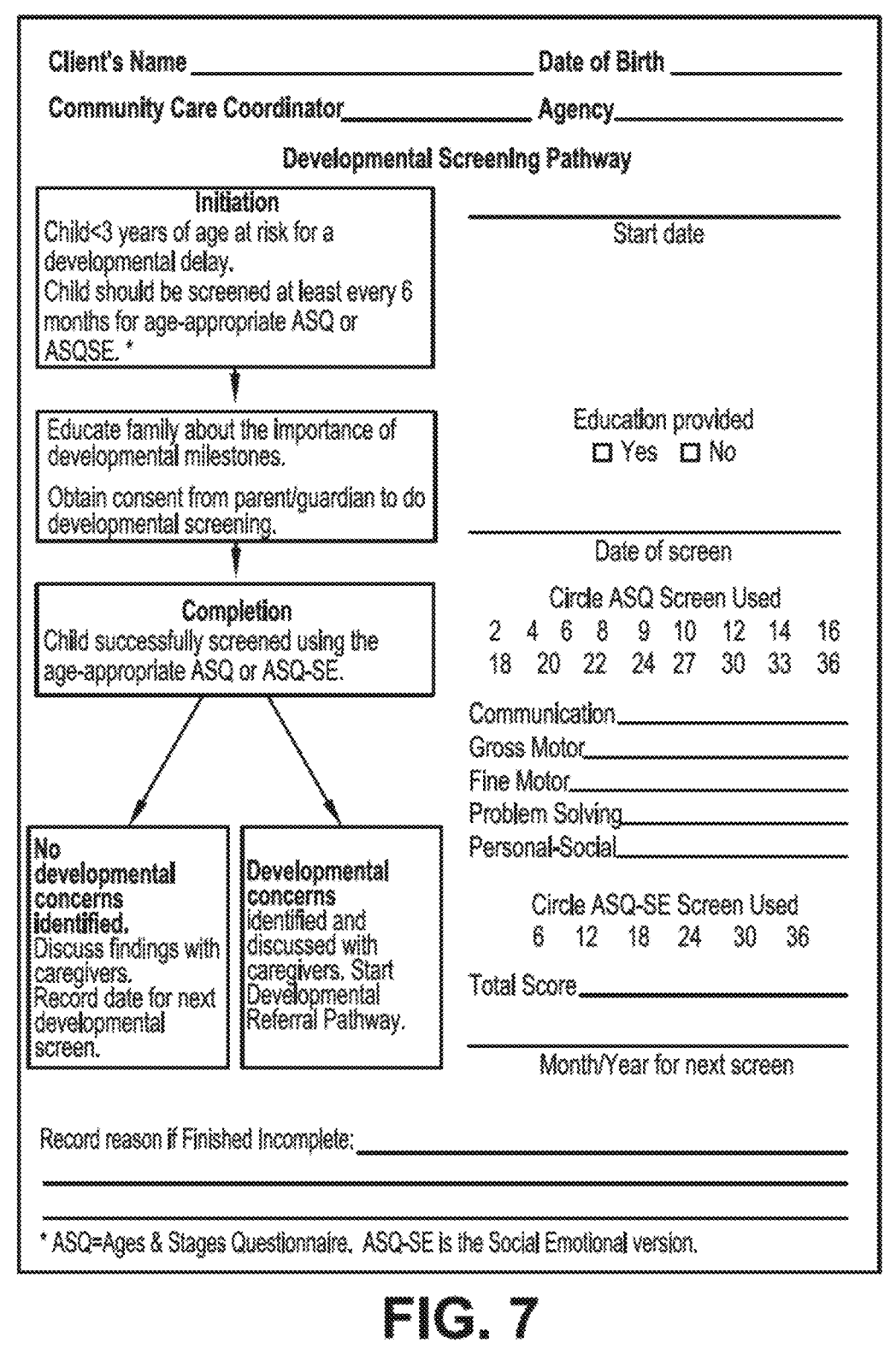

Client's Name ____________ Date of Birth ____________

Community Care Coordinator____________ Agency____________

Developmental Screening Pathway

Initiation
Child<3 years of age at risk for a developmental delay.
Child should be screened at least every 6 months for age-appropriate ASQ or ASQSE. *

____________
Start date

Educate family about the importance of developmental milestones.

Obtain consent from parent/guardian to do developmental screening.

Education provided
☐ Yes ☐ No

____________
Date of screen

Completion
Child successfully screened using the age-appropriate ASQ or ASQ-SE.

Circle ASQ Screen Used
2 4 6 8 9 10 12 14 16
18 20 22 24 27 30 33 36

Communication____________
Gross Motor____________
Fine Motor____________
Problem Solving____________
Personal-Social____________

No developmental concerns identified.
Discuss findings with caregivers.
Record date for next developmental screen.

Developmental concerns identified and discussed with caregivers. Start Developmental Referral Pathway.

Circle ASQ-SE Screen Used
6 12 18 24 30 36

Total Score____________

____________
Month/Year for next screen

Record reason if Finished Incomplete:____________

* ASQ=Ages & Stages Questionnaire. ASQ-SE is the Social Emotional version.

FIG. 7

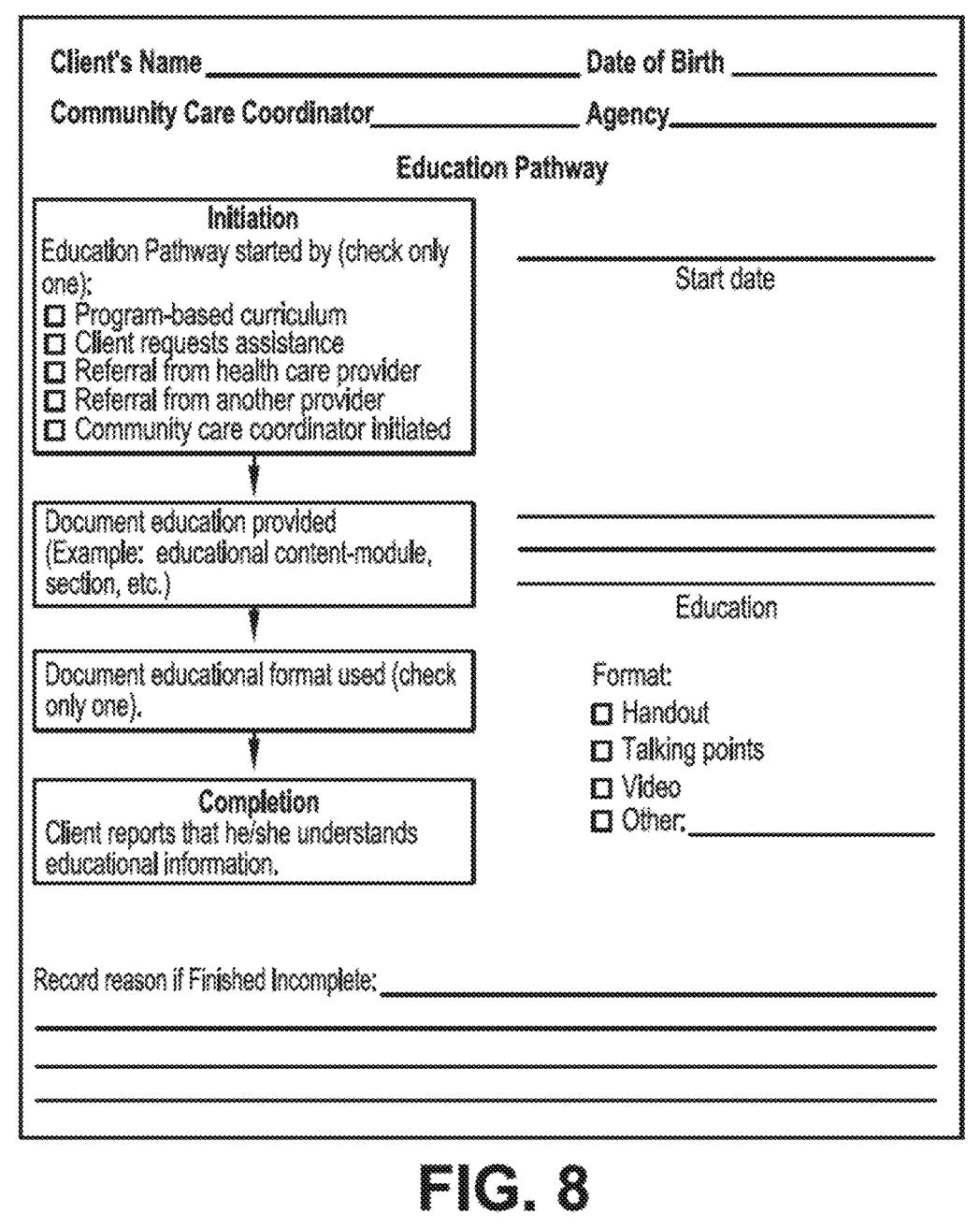

Client's Name ____ Date of Birth ____

Community Care Coordinator ____ Agency ____

Education Pathway

Initiation
Education Pathway started by (check only one):
- ☐ Program-based curriculum
- ☐ Client requests assistance
- ☐ Referral from health care provider
- ☐ Referral from another provider
- ☐ Community care coordinator initiated ____
Start date Document education provided (Example: educational content-module, section, etc.)

____
____
____
Education

Document educational format used (check only one).

Format:
- ☐ Handout
- ☐ Talking points
- ☐ Video
- ☐ Other: ____

Completion
Client reports that he/she understands educational information.

Record reason if Finished Incomplete: ____

FIG. 8

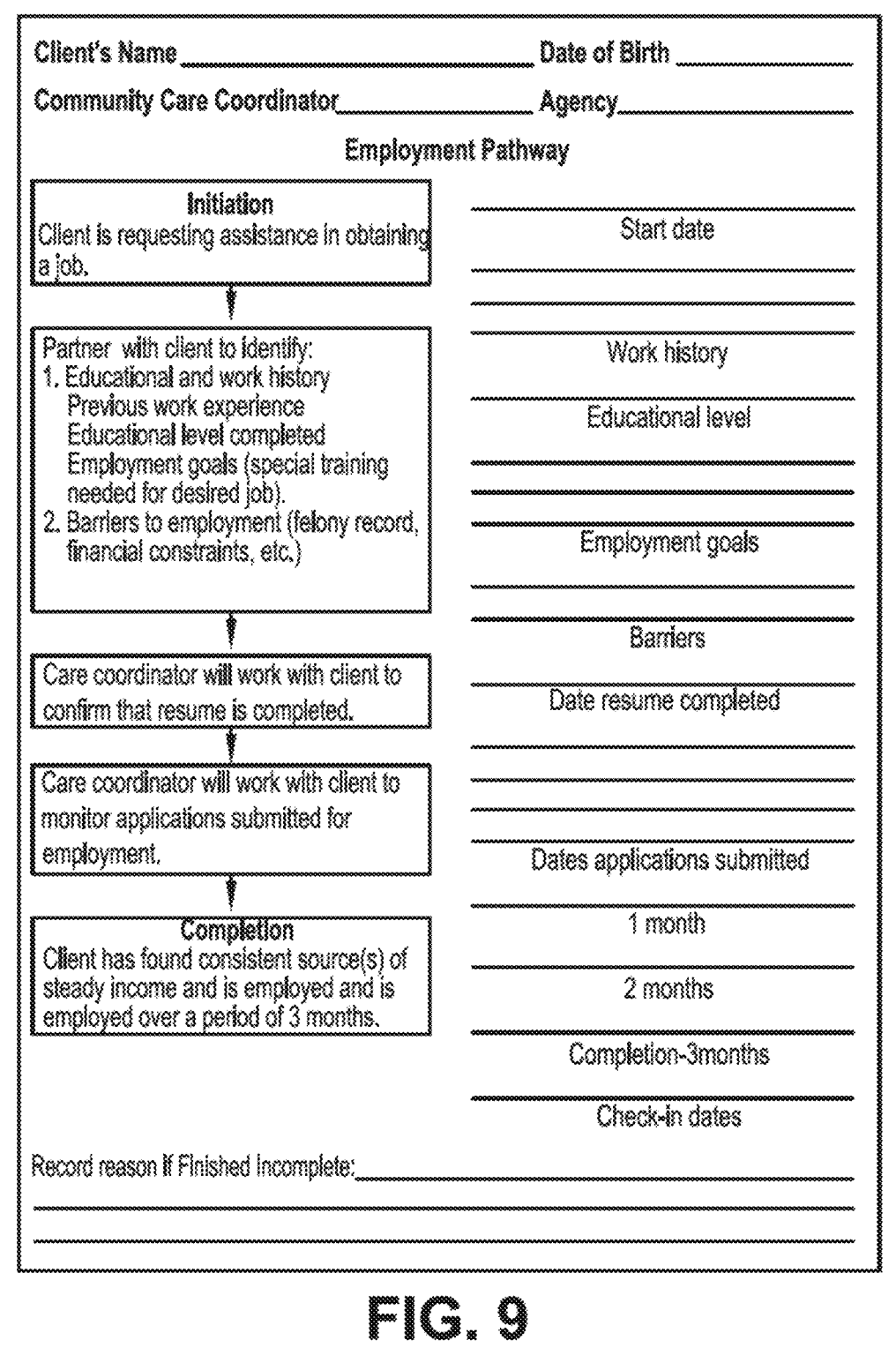

Client's Name ____________ Date of Birth ____________

Community Care Coordinator ____________ Agency ____________

Employment Pathway

Initiation
Client is requesting assistance in obtaining a job.

↓

Partner with client to identify:
1. Educational and work history
   Previous work experience
   Educational level completed
   Employment goals (special training needed for desired job).
2. Barriers to employment (felony record, financial constraints, etc.)

↓

Care coordinator will work with client to confirm that resume is completed.

↓

Care coordinator will work with client to monitor applications submitted for employment.

↓

Completion
Client has found consistent source(s) of steady income and is employed and is employed over a period of 3 months.

____________
Start date

____________
____________
Work history
____________
Educational level
____________
____________
____________
Employment goals
____________
____________
Barriers
____________
Date resume completed
____________
____________
____________
____________
Dates applications submitted
____________
1 month
____________
2 months
____________
Completion-3months
____________
Check-in dates Record reason If Finished Incomplete: ____________

FIG. 9

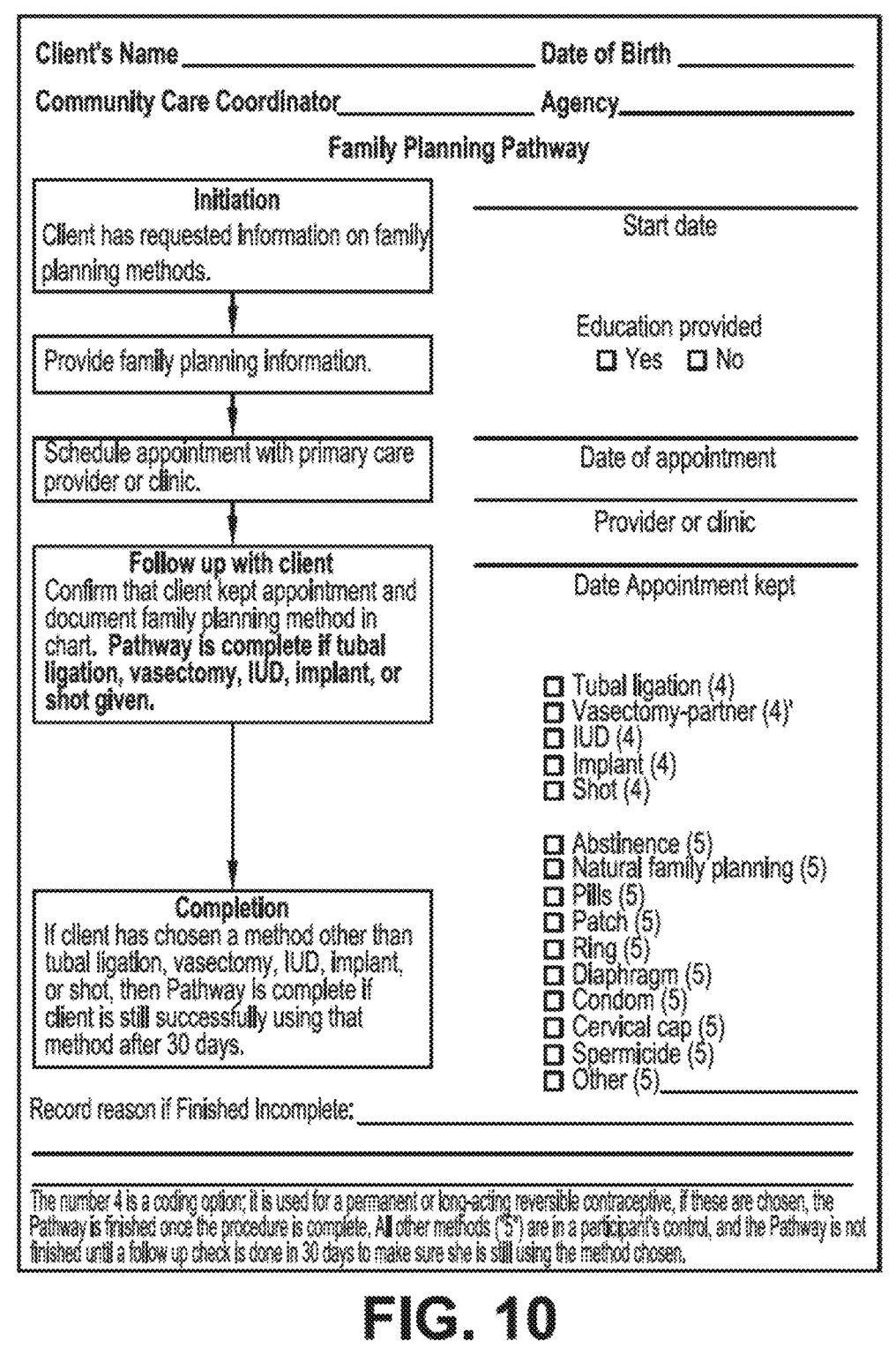

Client's Name ____________ Date of Birth ____________

Community Care Coordinator ____________ Agency ____________

Family Planning Pathway

Initiation
Client has requested information on family planning methods.

Start date ____________

Provide family planning information.

Education provided
☐ Yes ☐ No

Schedule appointment with primary care provider or clinic.

Date of appointment ____________

Provider or clinic ____________

Follow up with client
Confirm that client kept appointment and document family planning method in chart. Pathway is complete if tubal ligation, vasectomy, IUD, implant, or shot given.

Date Appointment kept ____________

- ☐ Tubal ligation (4)
- ☐ Vasectomy-partner (4)'
- ☐ IUD (4)
- ☐ Implant (4)
- ☐ Shot (4)

- ☐ Abstinence (5)
- ☐ Natural family planning (5)
- ☐ Pills (5)
- ☐ Patch (5)
- ☐ Ring (5)
- ☐ Diaphragm (5)
- ☐ Condom (5)
- ☐ Cervical cap (5)
- ☐ Spermicide (5)
- ☐ Other (5) ____________

Completion
If client has chosen a method other than tubal ligation, vasectomy, IUD, implant, or shot, then Pathway is complete if client is still successfully using that method after 30 days.

Record reason if Finished Incomplete: ____________

The number 4 is a coding option; it is used for a permanent or long-acting reversible contraceptive, if these are chosen, the Pathway is finished once the procedure is complete. All other methods ("5") are in a participant's control, and the Pathway is not finished until a follow up check is done in 30 days to make sure she is still using the method chosen.

FIG. 10

Figure 11:
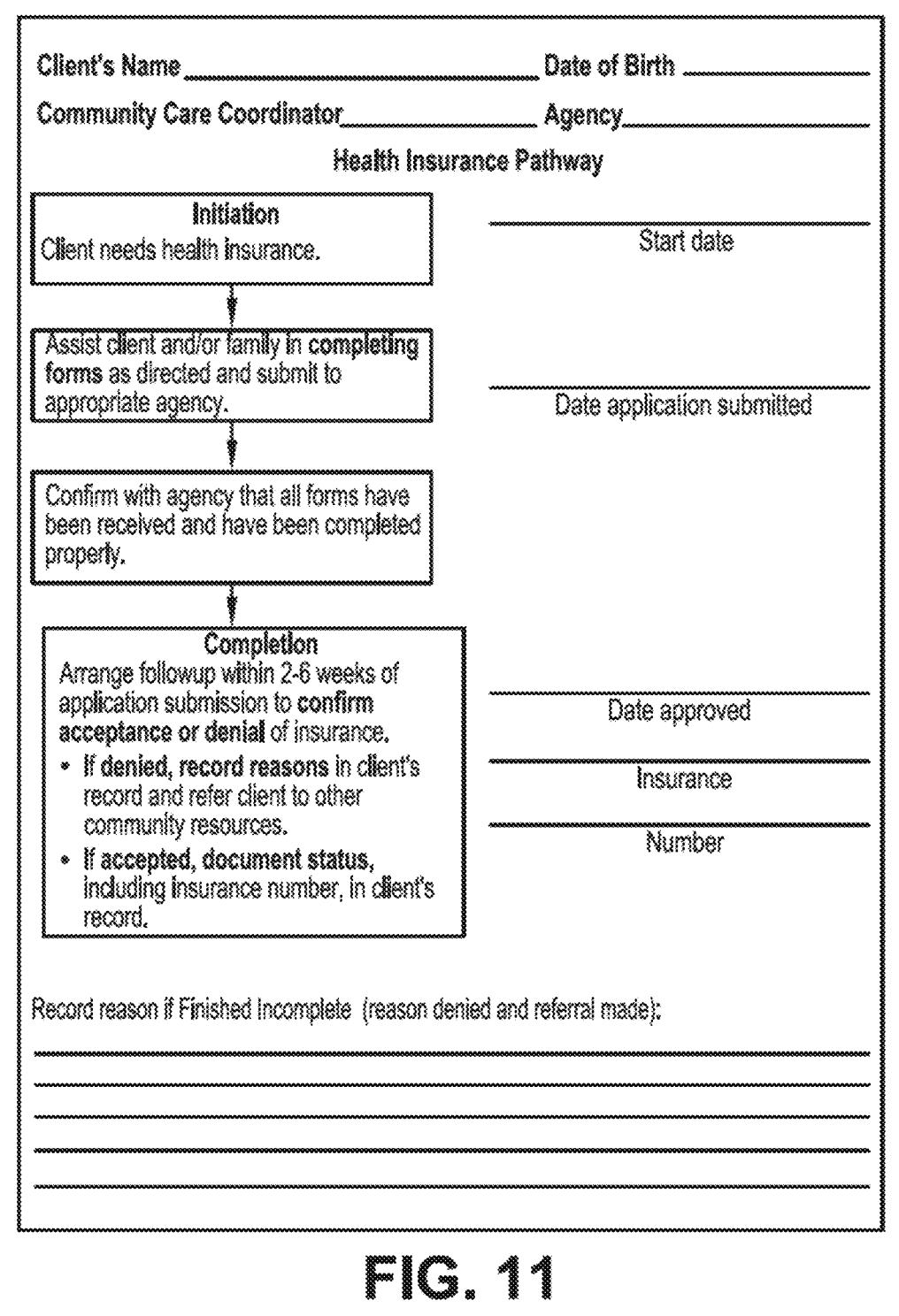

Client's Name ______________ Date of Birth ______________

Community Care Coordinator ______________ Agency ______________

Health Insurance Pathway

Initiation
Client needs health insurance.

______________ Start date

Assist client and/or family in completing forms as directed and submit to appropriate agency.

______________ Date application submitted

Confirm with agency that all forms have been received and have been completed properly.

Completion
Arrange followup within 2-6 weeks of application submission to confirm acceptance or denial of insurance.

- If denied, record reasons in client's record and refer client to other community resources.
- If accepted, document status, including insurance number, in client's record.

______________ Date approved

______________ Insurance

______________ Number

Record reason if Finished Incomplete (reason denied and referral made):

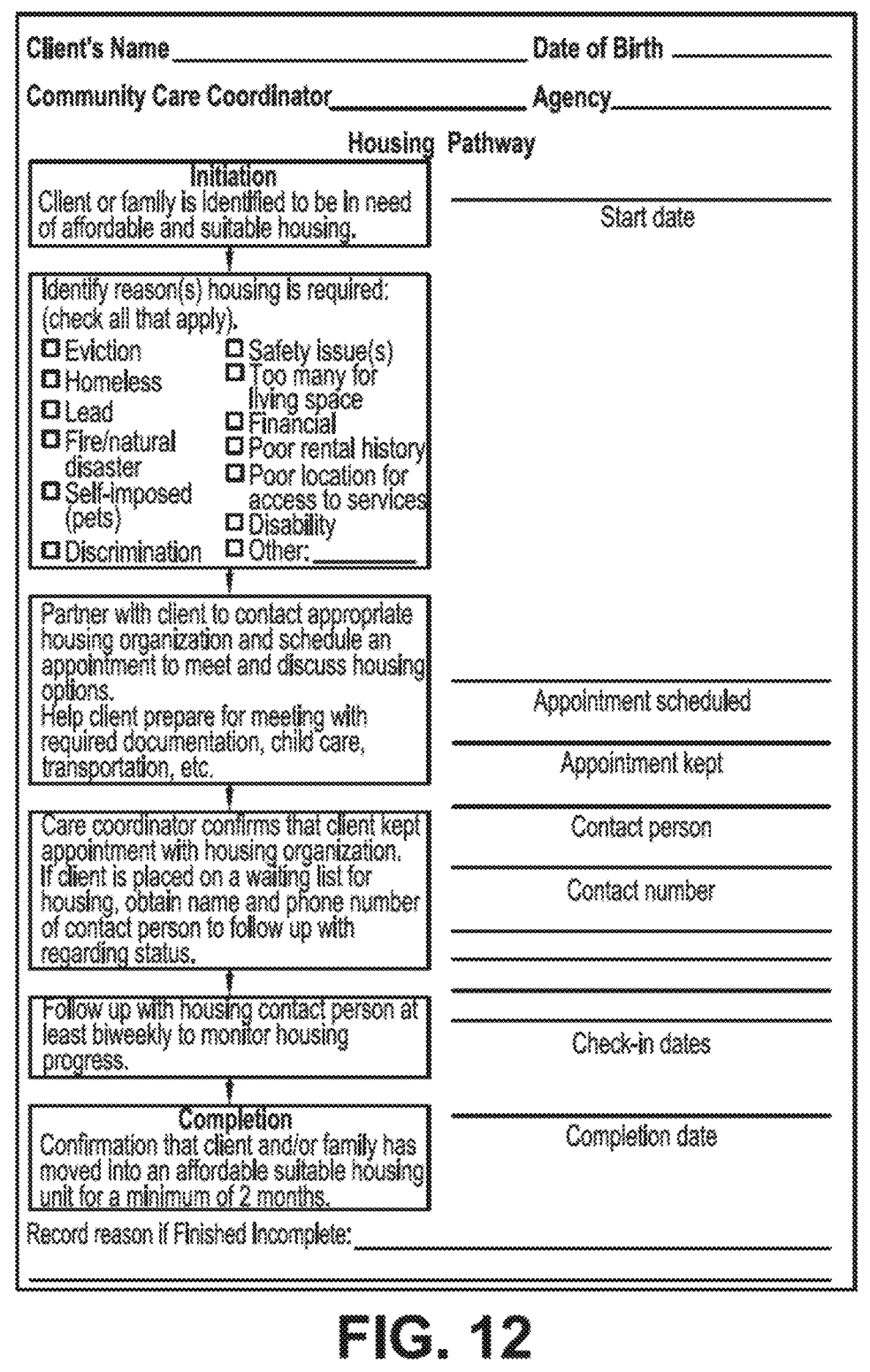

Client's Name ______ Date of Birth ______

Community Care Coordinator ______ Agency ______

Housing Pathway

Initiation
Client or family is identified to be in need of affordable and suitable housing.

______ Start date

Identify reason(s) housing is required: (check all that apply).

- ☐ Eviction
- ☐ Homeless
- ☐ Lead
- ☐ Fire/natural disaster
- ☐ Self-imposed (pets)
- ☐ Discrimination
- ☐ Safety issue(s)
- ☐ Too many for living space
- ☐ Financial
- ☐ Poor rental history
- ☐ Poor location for access to services
- ☐ Disability
- ☐ Other: ______

Partner with client to contact appropriate housing organization and schedule an appointment to meet and discuss housing options.
Help client prepare for meeting with required documentation, child care, transportation, etc.

______ Appointment scheduled

______ Appointment kept

Care coordinator confirms that client kept appointment with housing organization.
If client is placed on a waiting list for housing, obtain name and phone number of contact person to follow up with regarding status.

______ Contact person

______ Contact number

Follow up with housing contact person at least biweekly to monitor housing progress.

______
______
______
______ Check-in dates

Completion
Confirmation that client and/or family has moved into an affordable suitable housing unit for a minimum of 2 months.

______ Completion date

Record reason if Finished Incomplete: ______

FIG. 12

Figure 13:
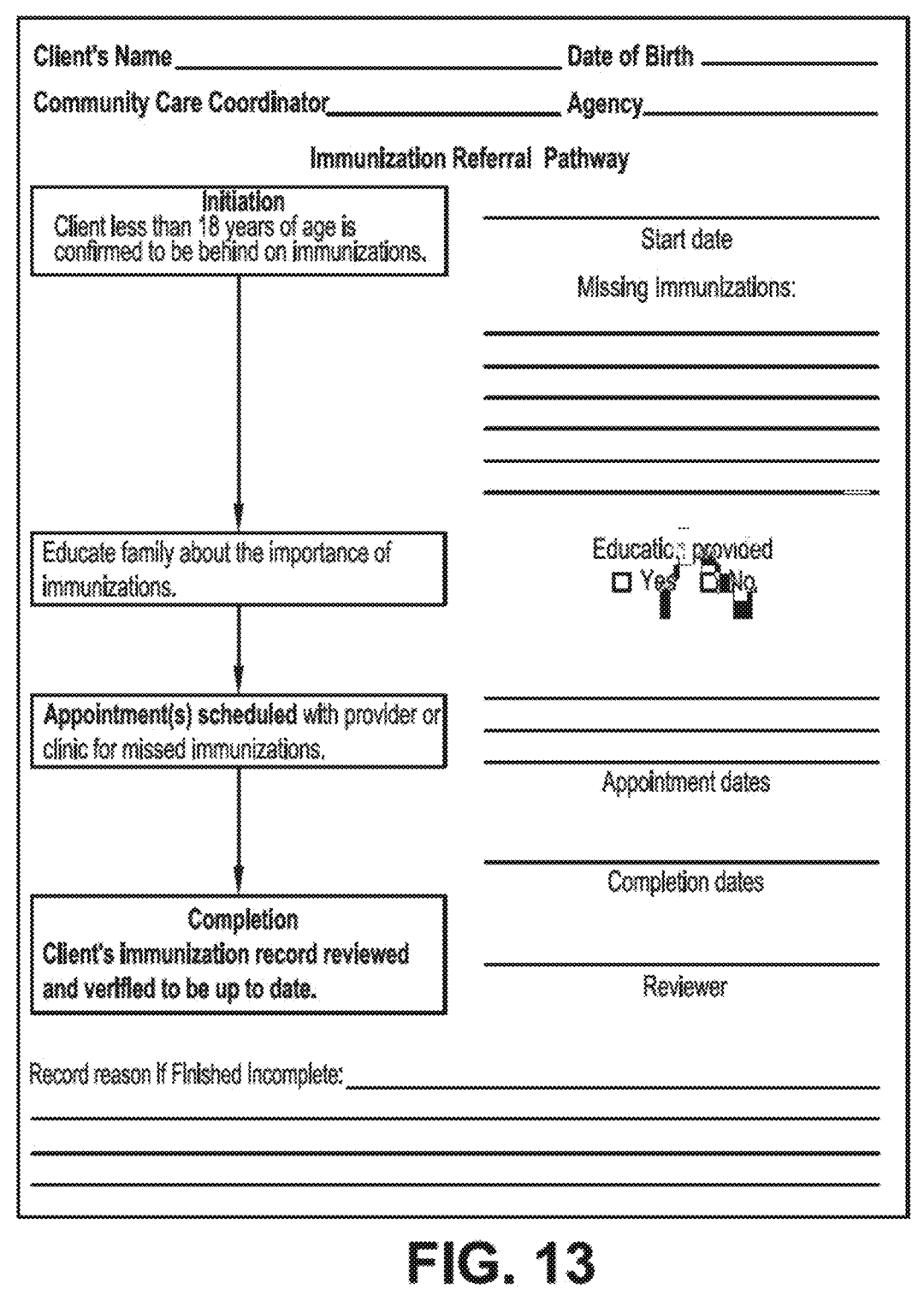

Client's Name ____________________ Date of Birth ____________

Community Care Coordinator ____________ Agency ____________

Immunization Referral Pathway

| | |
|---|---|
| **Initiation** Client less than 18 years of age is confirmed to be behind on immunizations. | ____________ Start date<br>Missing Immunizations:<br>____________<br>____________<br>____________<br>____________<br>____________<br>____________ |
| ↓ | |
| Educate family about the importance of immunizations. | Education provided ☐ Yes ☐ No |
| ↓ | |
| **Appointment(s) scheduled** with provider or clinic for missed immunizations. | ____________<br>____________<br>____________<br>Appointment dates |
| ↓ | ____________ Completion dates |
| **Completion** **Client's immunization record reviewed and verified to be up to date.** | ____________ Reviewer |

Record reason if Finished Incomplete: ____________

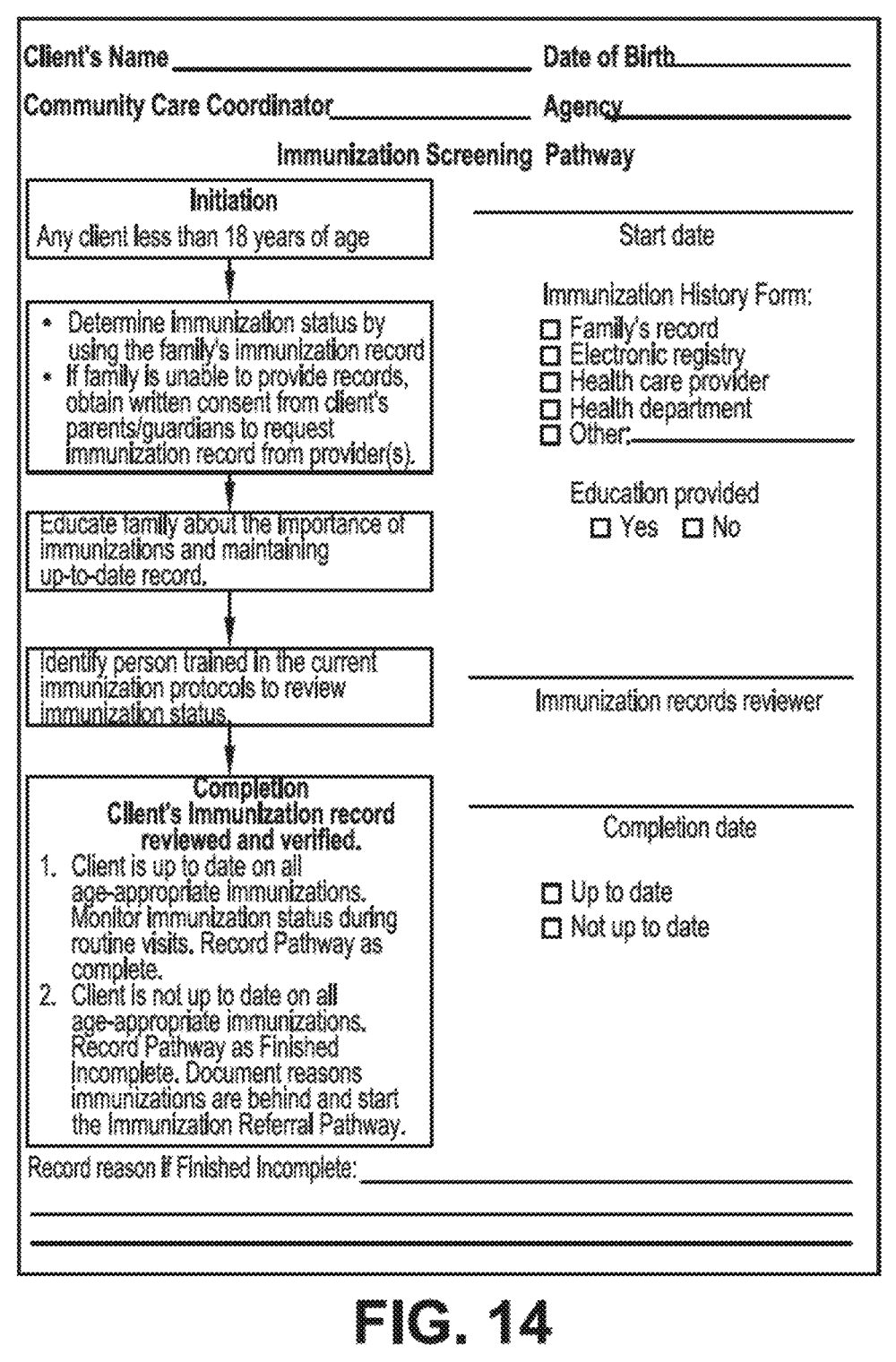

Client's Name ____________ Date of Birth ____________

Community Care Coordinator ____________ Agency ____________

Immunization Screening Pathway

Initiation
Any client less than 18 years of age

Start date ____________

- Determine immunization status by using the family's immunization record
- If family is unable to provide records, obtain written consent from client's parents/guardians to request immunization record from provider(s).

Immunization History Form:
- ☐ Family's record
- ☐ Electronic registry
- ☐ Health care provider
- ☐ Health department
- ☐ Other: ____________

Educate family about the importance of immunizations and maintaining up-to-date record.

Education provided
☐ Yes ☐ No

Identify person trained in the current immunization protocols to review immunization status.

Immunization records reviewer ____________

Completion
Client's Immunization record reviewed and verified.

1. Client is up to date on all age-appropriate immunizations. Monitor immunization status during routine visits. Record Pathway as complete.
2. Client is not up to date on all age-appropriate immunizations. Record Pathway as Finished Incomplete. Document reasons immunizations are behind and start the Immunization Referral Pathway.

Completion date ____________

- ☐ Up to date
- ☐ Not up to date

Record reason if Finished Incomplete: ____________

FIG. 14

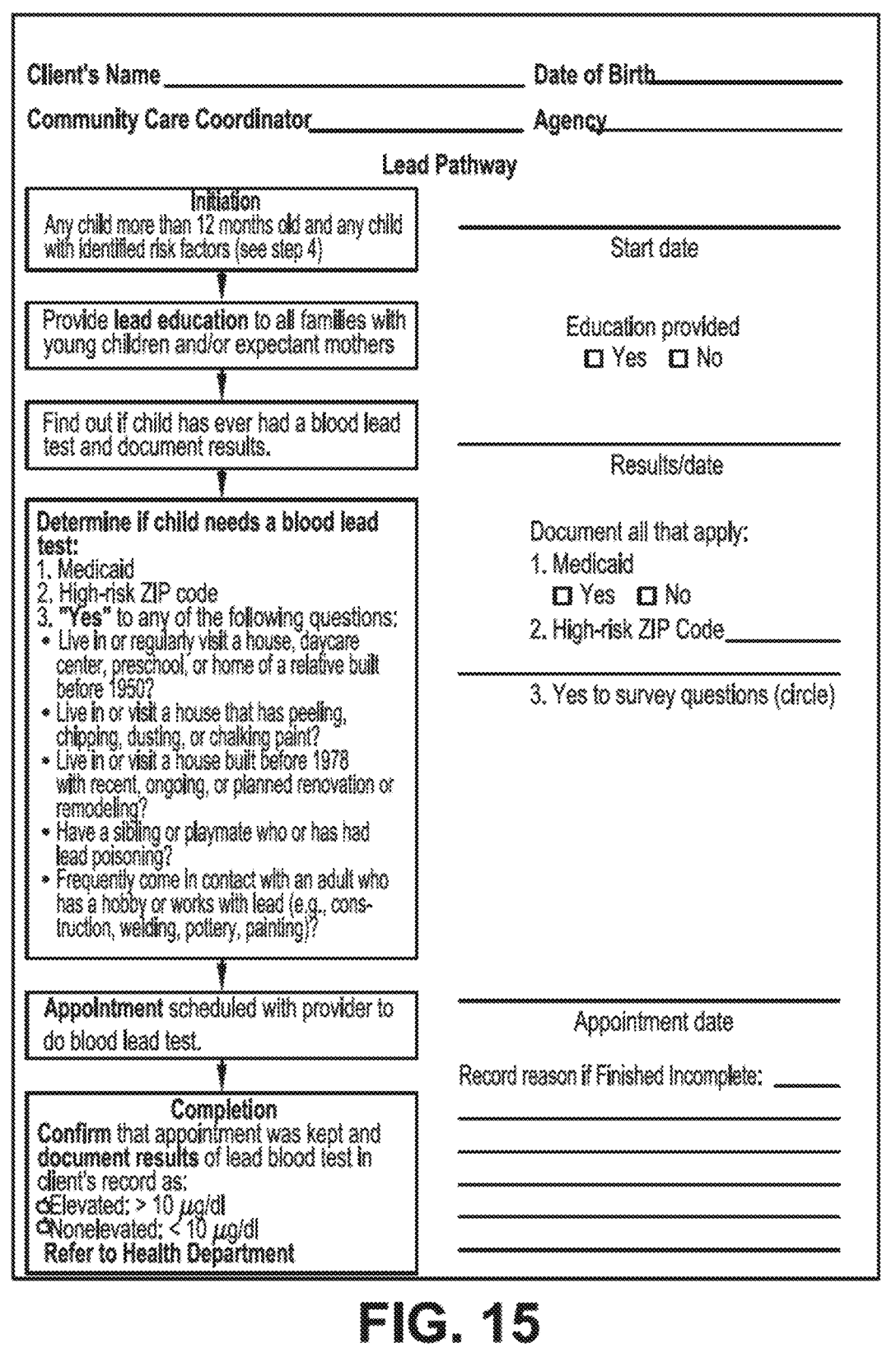

Client's Name ____________ Date of Birth ____________

Community Care Coordinator ____________ Agency ____________

Lead Pathway

| | |
|---|---|
| **Initiation**<br>Any child more than 12 months old and any child with identified risk factors (see step 4) | ____________<br>Start date |
| Provide **lead education** to all families with young children and/or expectant mothers | Education provided<br>☐ Yes ☐ No |
| Find out if child has ever had a blood lead test and document results. | ____________<br>Results/date |
| **Determine if child needs a blood lead test:**<br>1. Medicaid<br>2. High-risk ZIP code<br>3. **"Yes"** to any of the following questions:<br>• Live in or regularly visit a house, daycare center, preschool, or home of a relative built before 1950?<br>• Live in or visit a house that has peeling, chipping, dusting, or chalking paint?<br>• Live in or visit a house built before 1978 with recent, ongoing, or planned renovation or remodeling?<br>• Have a sibling or playmate who or has had lead poisoning?<br>• Frequently come in contact with an adult who has a hobby or works with lead (e.g., construction, welding, pottery, painting)? | Document all that apply:<br>1. Medicaid<br>☐ Yes ☐ No<br>2. High-risk ZIP Code ____________<br>____________<br>3. Yes to survey questions (circle) |
| **Appointment** scheduled with provider to do blood lead test. | ____________<br>Appointment date<br>Record reason if Finished Incomplete: ______ |
| **Completion**<br>**Confirm** that appointment was kept and **document results** of lead blood test in client's record as:<br>○ Elevated: > 10 μg/dl<br>○ Nonelevated: < 10 μg/dl<br>**Refer to Health Department** | ____________<br>____________<br>____________<br>____________<br>____________ |

FIG. 15

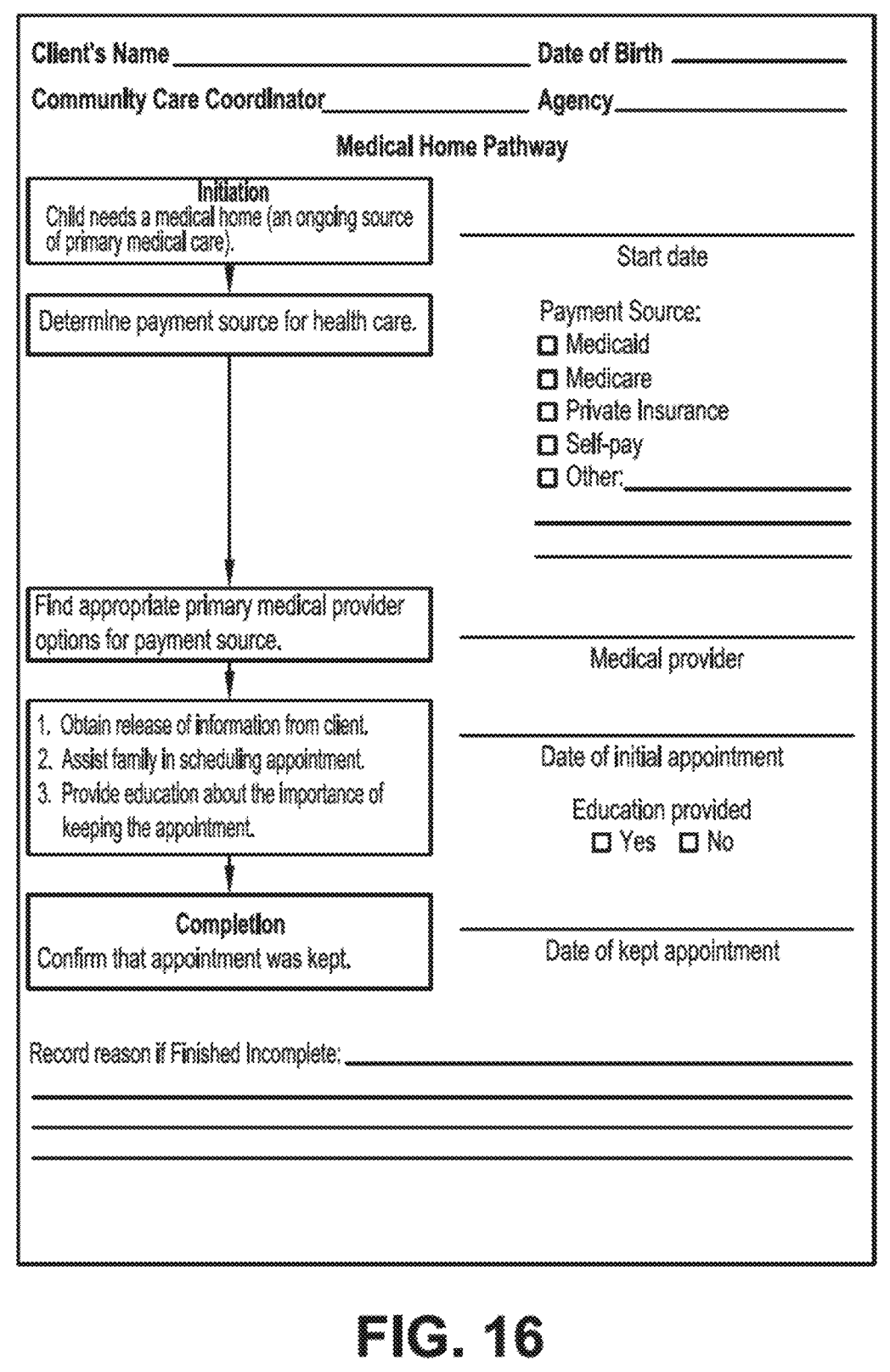

Client's Name ______ Date of Birth ______

Community Care Coordinator ______ Agency ______

Medical Home Pathway

Initiation
Child needs a medical home (an ongoing source of primary medical care).

______
Start date

Determine payment source for health care.

Payment Source:
- ☐ Medicaid
- ☐ Medicare
- ☐ Private Insurance
- ☐ Self-pay
- ☐ Other: ______

Find appropriate primary medical provider options for payment source.

______
Medical provider

1. Obtain release of information from client.
2. Assist family in scheduling appointment.
3. Provide education about the importance of keeping the appointment.

______
Date of initial appointment

Education provided
☐ Yes ☐ No

Completion
Confirm that appointment was kept.

______
Date of kept appointment

Record reason if Finished Incomplete: ______

FIG. 16

Client's Name ____________ Date of Birth ____________

Community Care Coordinator ____________ Agency ____________

Medical Referral Pathway

| | |
|---|---|
| **Initiation**<br>Client needs a **Health care** appointment.<br>Document type of appointment needed - use codes.<br>***(Only ONE code per Pathway)*** | ____________ Start date<br>____________ Referral date |
| **Educate** client/family about the importance of regular health care visits and keeping appointments. | Education provided<br>☐ Yes ☐ No |
| Appointment scheduled with health care provider / clinic. | ____________ Appointment date |
| **Completion**<br>**Verify** with health care provider that **appointment was kept.** | ____________ Date appointment kept<br>____________ Document how appointment was verified |

Code numbers for medical referralpathway

1. Primary Care
2. Specialty Medical Care ____________
3. Dental
4. Vision
5. Hearing
6. Family Planning
7. Mental Health
8. Substance Abuse
9. Speech and Language
10. Pharmacy
11. Other, please specify in record ____________

Record reason if Finished Incomplete: ____________

FIG. 17

Client's Name ______________________ Community Care Coordinator ______________________

Date of Birth ______________________ Today's Date ______________________ Agency ______________________

Medical Assessment Chart

STEP 1:

- ☐ On the chart below, list all of the medications currently used by your client. Include all medications-prescription, over the counter, herbal, alternative, topical, eye drops, etc.
- ☐ Have your client and/or client's caregiver open each of the bottles or medications containers and note any difficulties in performing the task.
- ☐ Have your client and/or client's caregiver identify each medication. Ask them to describe what the medicine is for. How many doses of the medicine are to be taken each day?
- ☐ Discuss the shape and color of the medicine with your client or client's caregiver. Explain that they should notify the health provider if the shape and color changes to make sure that they are using the correct medicine and/or dose.
- ☐ Have the patient and/or client's caregiver read the medication name on the label. Assess reading and memory problems. Review all parts of the label, including how to order refills.

Prescription Medications (need a doctor's prescription to get )

| | | | | | |
|---|---|---|---|---|---|
| | | | | | |
| | | | | | |
| | | | | | |
| | | | | | |
| | | | | | |
| | | | | | |
| | | | | | |
| | | | | | |
| | | | | | |
| | | | | | |

FIG. 18

Client's Name ______________ Community Care Coordinator ______________

Date of Birth ______________ Today's Date ______________ Agency ______________

| Name of Medicine & Dose | Can you open? yes/no | What is this medicine for? (client's description) | How many doses each day? (client's response) | Can you read the label and know how to get refills? yes/no | Comments |
|---|---|---|---|---|---|
| | | | | | |
| | | | | | |
| | | | | | |
| | | | | | |
| | | | | | |
| | | | | | |
| | | | | | |
| | | | | | |

Over the counter medicines (no prescription needed), herbal or alternative treatments

| Name of Medicine or Treatment | Can you open? yes/no | What is this medicine or treatment for? (client's description) | How many doses each day? (client's response) | Can you read the label and know how to get refills? yes/no | Comments |
|---|---|---|---|---|---|
| | | | | | |
| | | | | | |
| | | | | | |
| | | | | | |
| | | | | | |
| | | | | | |
| | | | | | |
| | | | | | |
| | | | | | |

FIG. 18 (CONT'D)

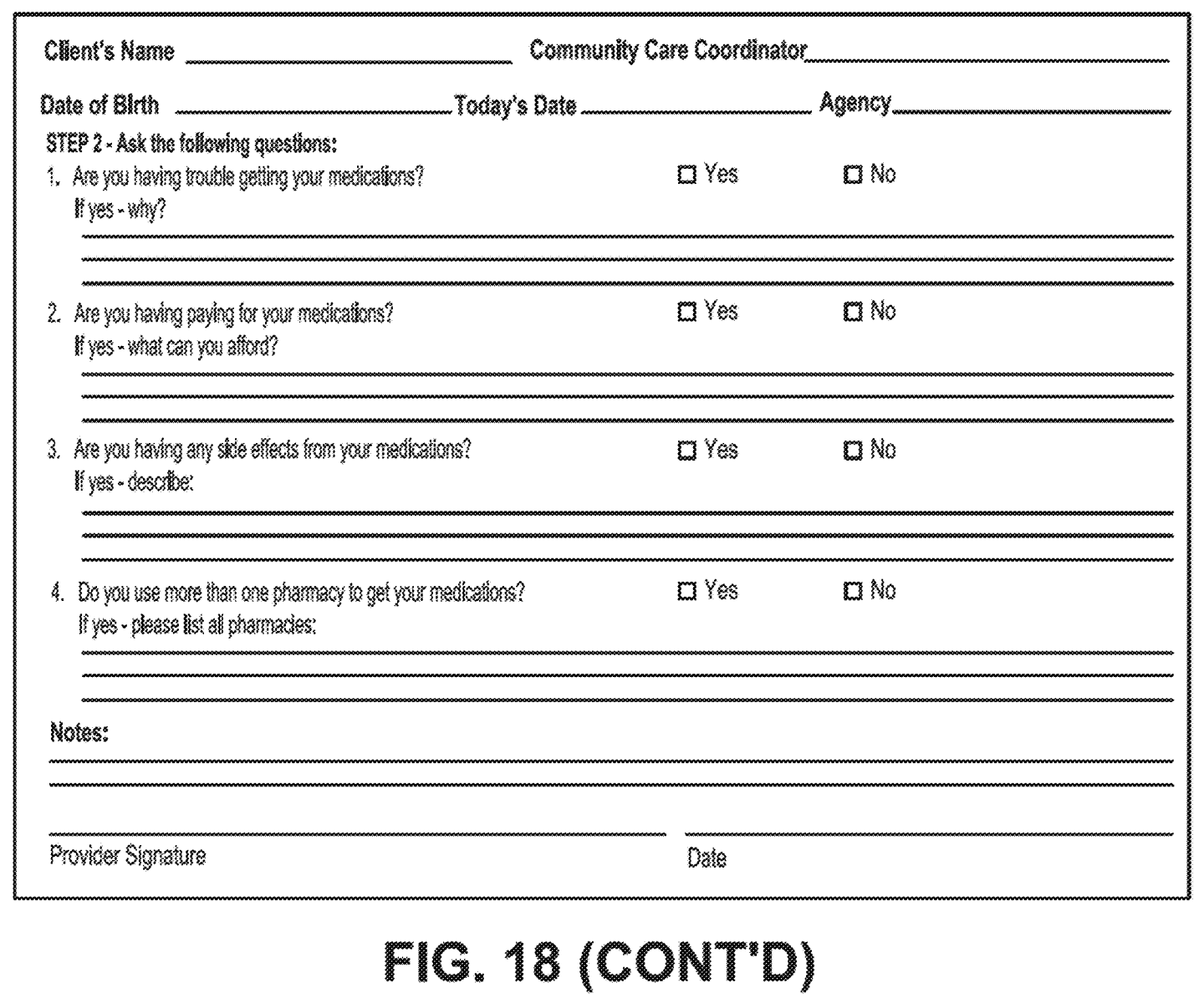

Client's Name ______________ Community Care Coordinator ______________

Date of Birth ______________ Today's Date ______________ Agency ______________

STEP 2 - Ask the following questions:

1. Are you having trouble getting your medications? ☐ Yes ☐ No
   If yes - why?
2. Are you having paying for your medications? ☐ Yes ☐ No
   If yes - what can you afford?
3. Are you having any side effects from your medications? ☐ Yes ☐ No
   If yes - describe:
4. Do you use more than one pharmacy to get your medications? ☐ Yes ☐ No
   If yes - please list all pharmacies:

Notes:

Provider Signature ______________ Date ______________

FIG. 18 (CONT'D)

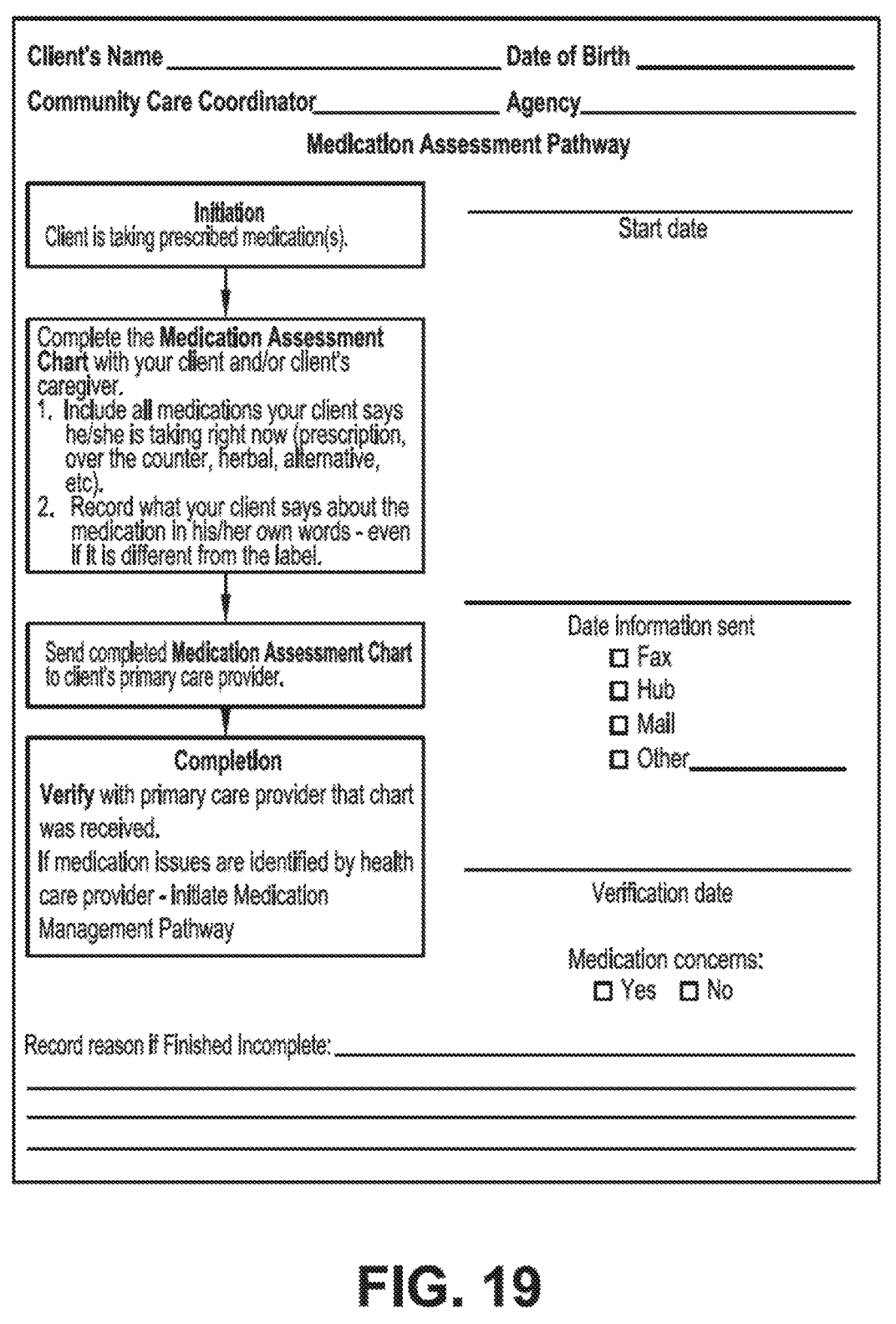

Client's Name ____________ Date of Birth ____________

Community Care Coordinator ____________ Agency ____________

Medication Assessment Pathway

Initiation
Client is taking prescribed medication(s).

____________
Start date

Complete the Medication Assessment Chart with your client and/or client's caregiver.

1. Include all medications your client says he/she is taking right now (prescription, over the counter, herbal, alternative, etc).
2. Record what your client says about the medication in his/her own words - even if it is different from the label.

Send completed Medication Assessment Chart to client's primary care provider.

____________
Date information sent

- ☐ Fax
- ☐ Hub
- ☐ Mail
- ☐ Other ____________

Completion
Verify with primary care provider that chart was received.
If medication issues are identified by health care provider - Initiate Medication Management Pathway ____________
Verification date Medication concerns:
☐ Yes ☐ No Record reason if Finished Incomplete: ____________

FIG. 19

Figure 20:
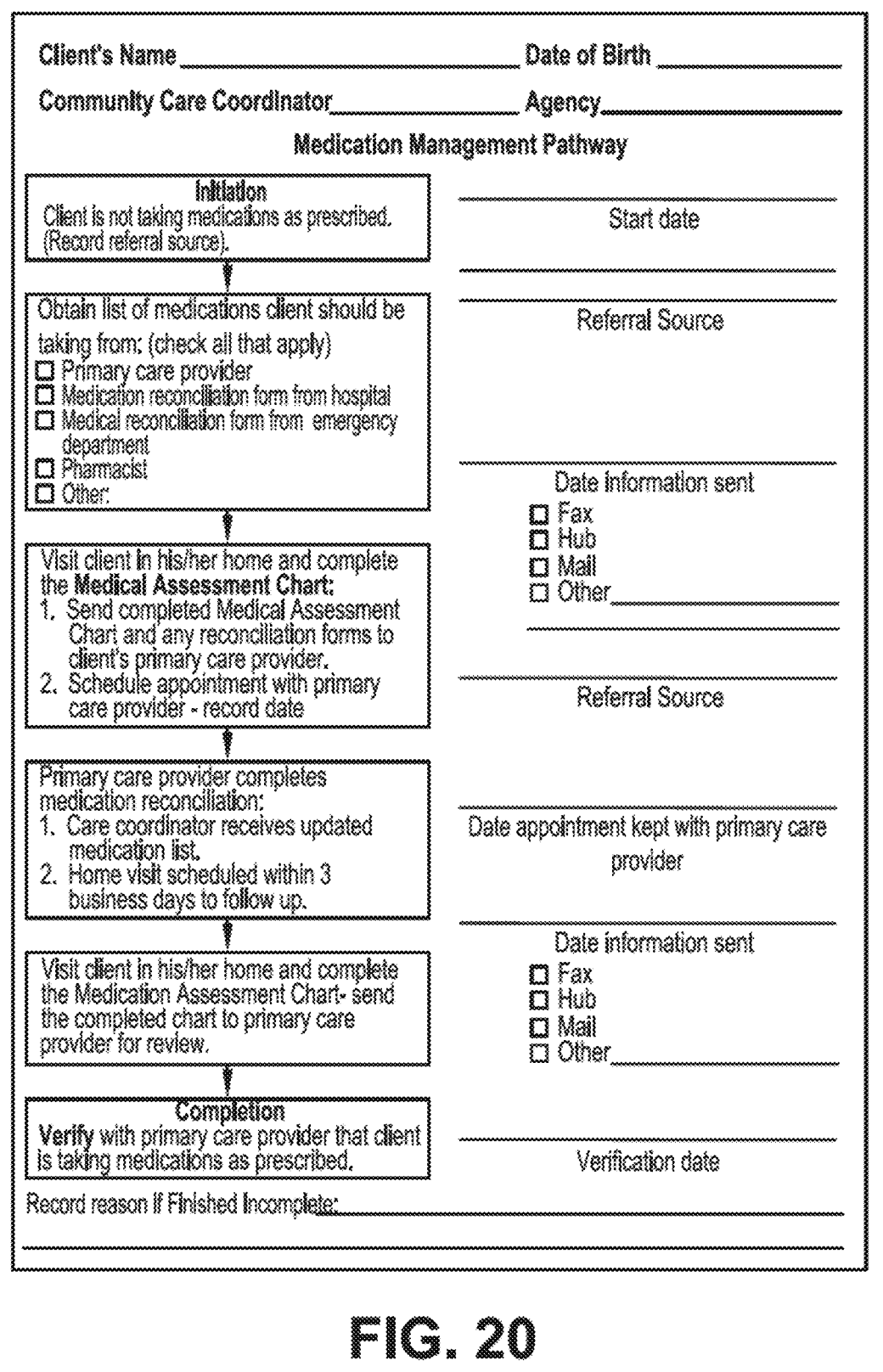

Client's Name ______________________ Date of Birth ____________

Community Care Coordinator ____________ Agency ____________

Medication Management Pathway

Initiation
Client is not taking medications as prescribed. (Record referral source).

Start date ____________

____________

Obtain list of medications client should be taking from: (check all that apply)
☐ Primary care provider
☐ Medication reconciliation form from hospital
☐ Medical reconciliation form from emergency department
☐ Pharmacist
☐ Other:

Referral Source ____________

Visit client in his/her home and complete the Medical Assessment Chart:
1. Send completed Medical Assessment Chart and any reconciliation forms to client's primary care provider.
2. Schedule appointment with primary care provider - record date Date information sent
☐ Fax
☐ Hub
☐ Mail
☐ Other____________

____________

Referral Source ____________

Primary care provider completes medication reconciliation:
1. Care coordinator receives updated medication list.
2. Home visit scheduled within 3 business days to follow up.

Date appointment kept with primary care provider ____________

Visit client in his/her home and complete the Medication Assessment Chart- send the completed chart to primary care provider for review.

Date information sent
☐ Fax
☐ Hub
☐ Mail
☐ Other____________

Completion
Verify with primary care provider that client is taking medications as prescribed.

Verification date ____________

Record reason If Finished Incomplete: ____________

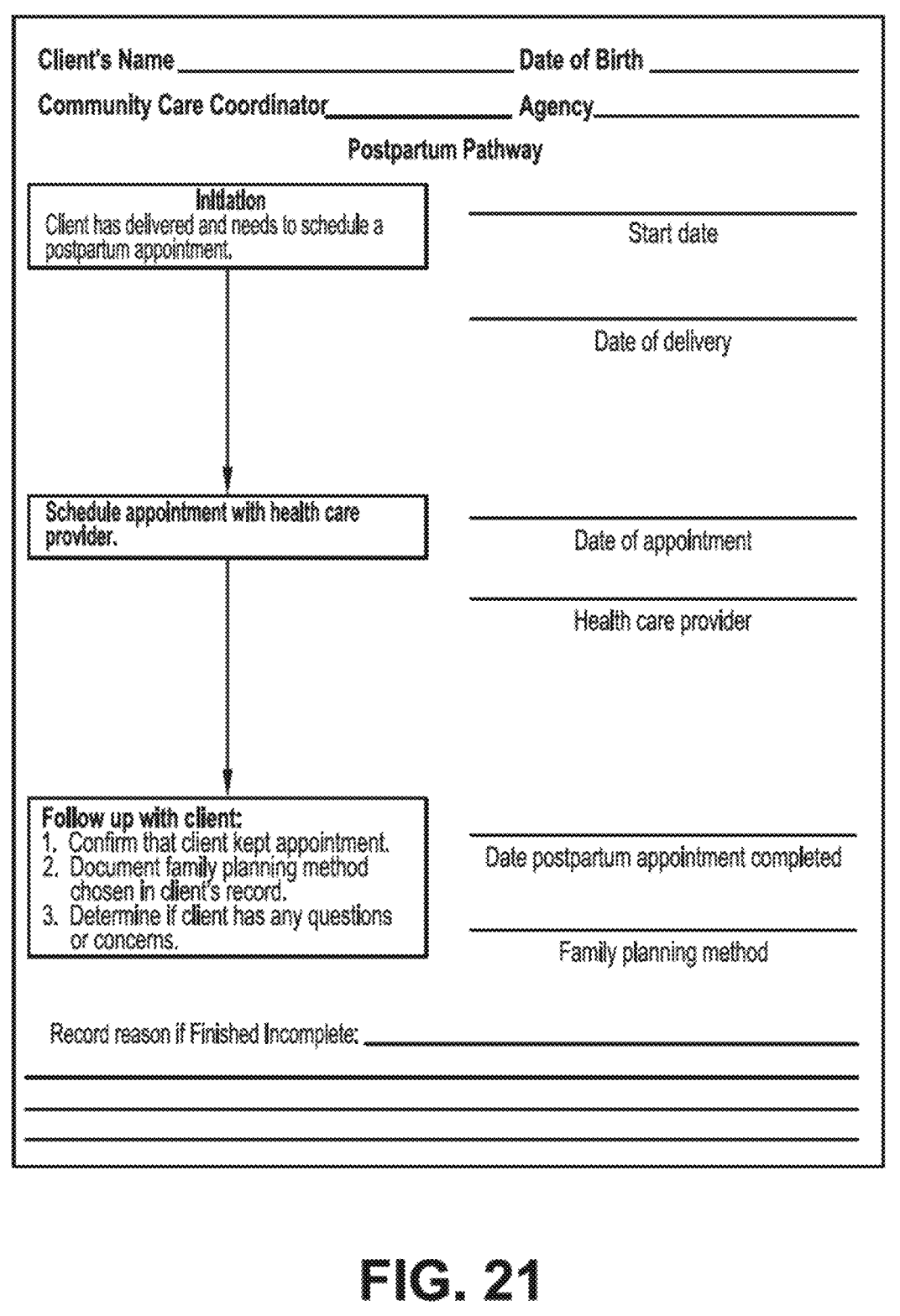

Client's Name ____________ Date of Birth ____________

Community Care Coordinator ____________ Agency ____________

Postpartum Pathway

Initiation
Client has delivered and needs to schedule a postpartum appointment.

____________
Start date

____________
Date of delivery

Schedule appointment with health care provider.

____________
Date of appointment

____________
Health care provider

Follow up with client:
1. Confirm that client kept appointment.
2. Document family planning method chosen in client's record.
3. Determine if client has any questions or concerns.

____________
Date postpartum appointment completed

____________
Family planning method

Record reason if Finished Incomplete: ____________

FIG. 21

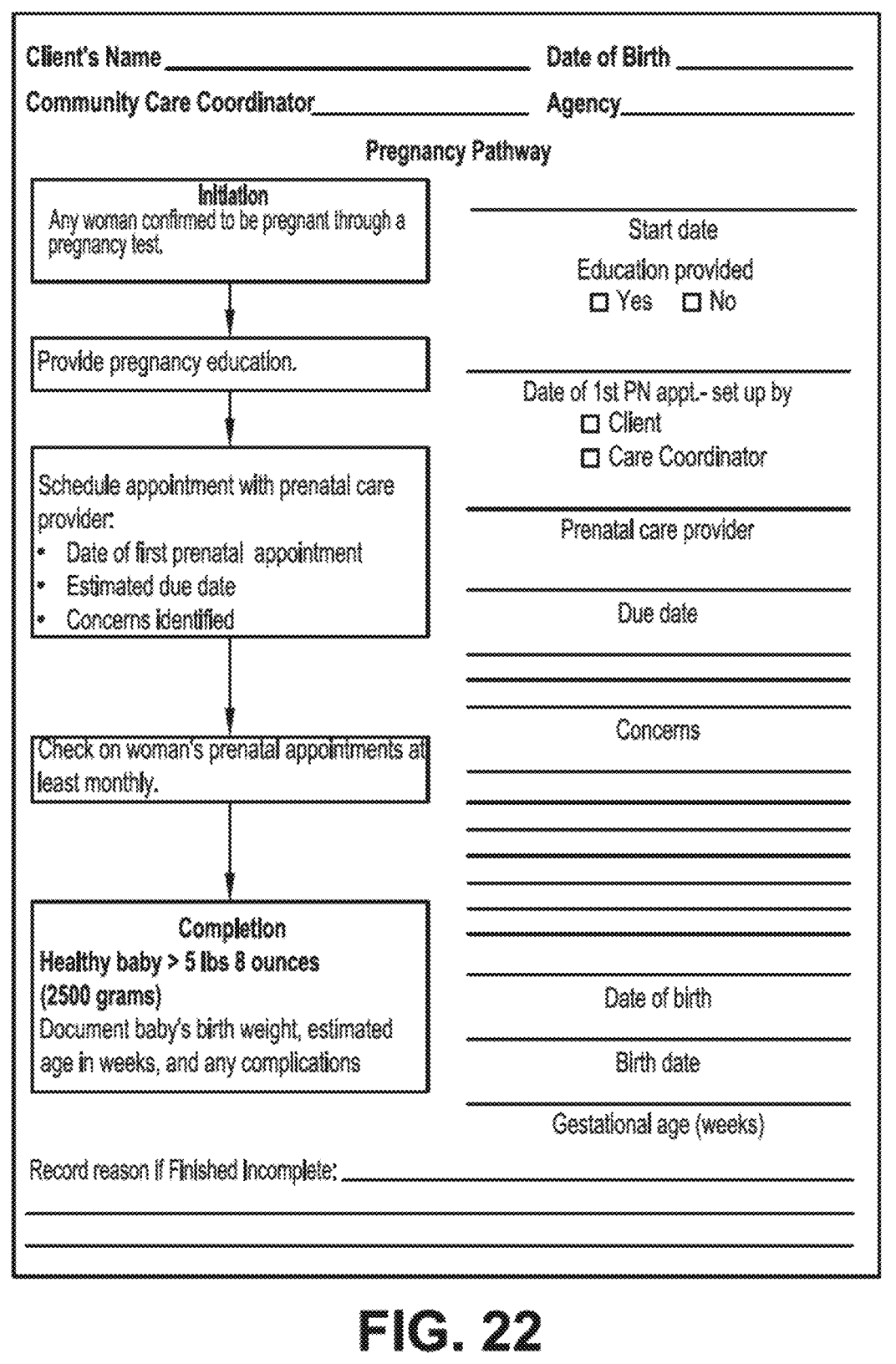

Client's Name ____________ Date of Birth ____________

Community Care Coordinator ____________ Agency ____________

Pregnancy Pathway

Initiation
Any woman confirmed to be pregnant through a pregnancy test.

____________
Start date

Education provided
☐ Yes ☐ No

Provide pregnancy education.

____________
Date of 1st PN appt.- set up by
☐ Client
☐ Care Coordinator

Schedule appointment with prenatal care provider:
- Date of first prenatal appointment
- Estimated due date
- Concerns identified ____________
Prenatal care provider ____________
Due date ____________
Concerns Check on woman's prenatal appointments at least monthly.

Completion
Healthy baby > 5 lbs 8 ounces (2500 grams)
Document baby's birth weight, estimated age in weeks, and any complications ____________
Date of birth ____________
Birth date ____________
Gestational age (weeks)

Record reason if Finished Incomplete: ____________

FIG. 22

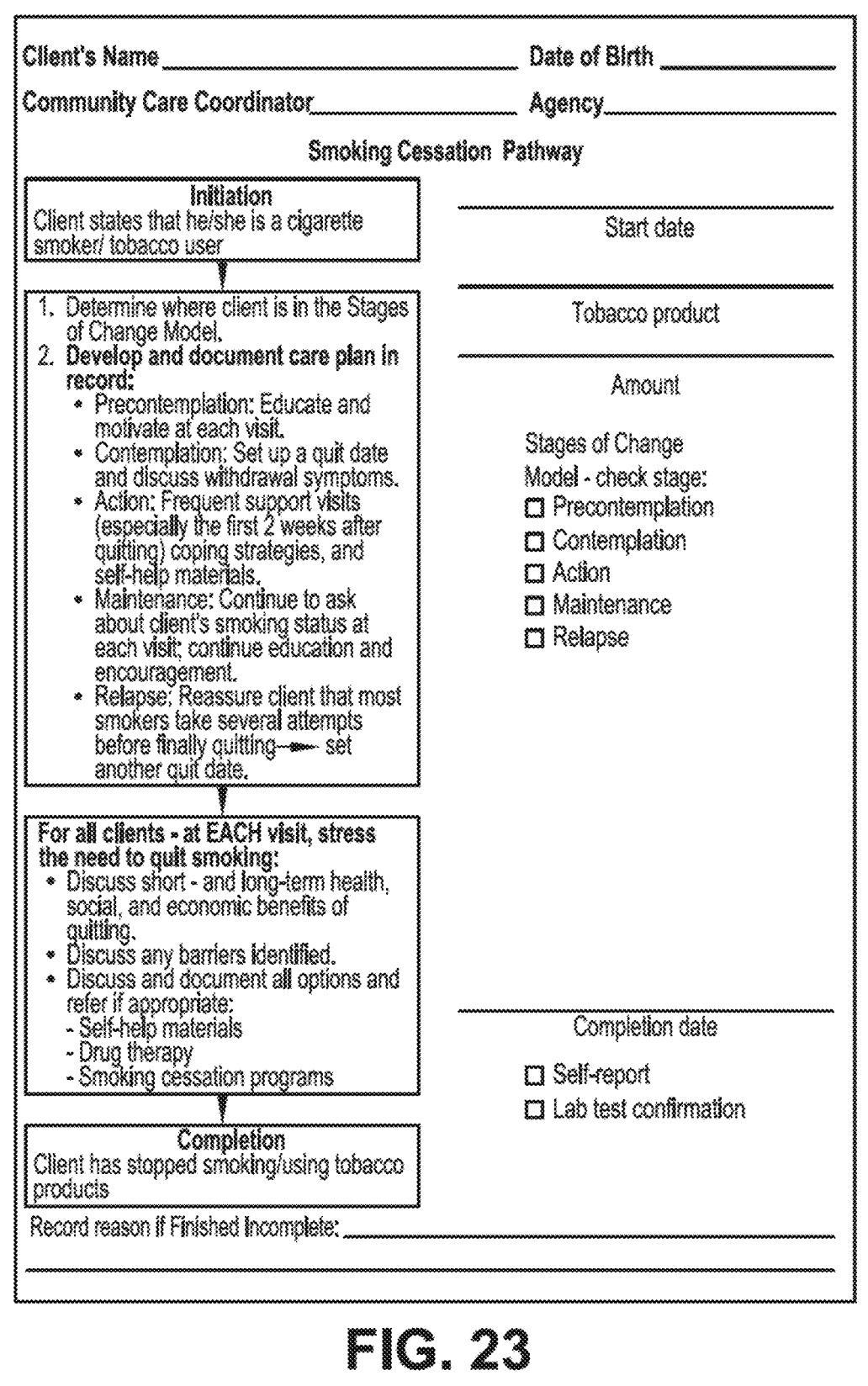

Client's Name ______________ Date of Birth ______________

Community Care Coordinator ______________ Agency ______________

Smoking Cessation Pathway

Initiation
Client states that he/she is a cigarette smoker/ tobacco user

1. Determine where client is in the Stages of Change Model.
2. Develop and document care plan in record:
   - Precontemplation: Educate and motivate at each visit.
   - Contemplation: Set up a quit date and discuss withdrawal symptoms.
   - Action: Frequent support visits (especially the first 2 weeks after quitting) coping strategies, and self-help materials.
   - Maintenance: Continue to ask about client's smoking status at each visit; continue education and encouragement.
   - Relapse: Reassure client that most smokers take several attempts before finally quitting→ set another quit date.

For all clients - at EACH visit, stress the need to quit smoking:
- Discuss short - and long-term health, social, and economic benefits of quitting.
- Discuss any barriers identified.
- Discuss and document all options and refer if appropriate:
  - Self-help materials
  - Drug therapy
  - Smoking cessation programs

Completion
Client has stopped smoking/using tobacco products

______________ Start date

______________ Tobacco product

______________ Amount

Stages of Change Model - check stage:
- ☐ Precontemplation
- ☐ Contemplation
- ☐ Action
- ☐ Maintenance
- ☐ Relapse ______________ Completion date

- ☐ Self-report
- ☐ Lab test confirmation

Record reason if Finished Incomplete: ______________

FIG. 23

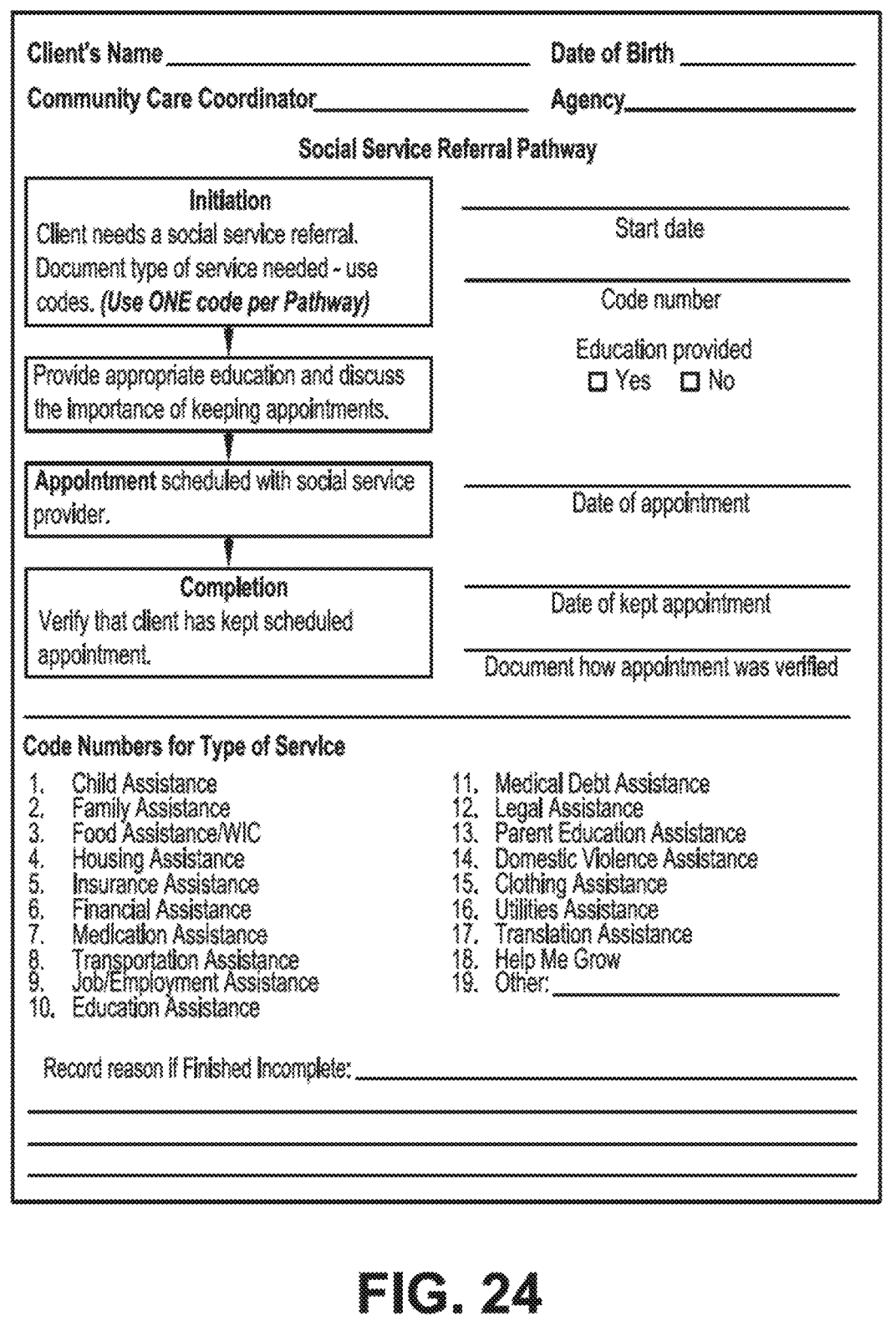

Client's Name ____________ Date of Birth ____________

Community Care Coordinator ____________ Agency ____________

Social Service Referral Pathway

Initiation
Client needs a social service referral. Document type of service needed - use codes. *(Use ONE code per Pathway)*

____________ Start date

____________ Code number

Provide appropriate education and discuss the importance of keeping appointments.

Education provided
☐ Yes ☐ No

Appointment scheduled with social service provider.

____________ Date of appointment

Completion
Verify that client has kept scheduled appointment.

____________ Date of kept appointment

____________ Document how appointment was verified

Code Numbers for Type of Service

1. Child Assistance
2. Family Assistance
3. Food Assistance/WIC
4. Housing Assistance
5. Insurance Assistance
6. Financial Assistance
7. Medication Assistance
8. Transportation Assistance
9. Job/Employment Assistance
10. Education Assistance
11. Medical Debt Assistance
12. Legal Assistance
13. Parent Education Assistance
14. Domestic Violence Assistance
15. Clothing Assistance
16. Utilities Assistance
17. Translation Assistance
18. Help Me Grow
19. Other: ____________

Record reason if Finished Incomplete: ____________

FIG. 24

Figure 25:
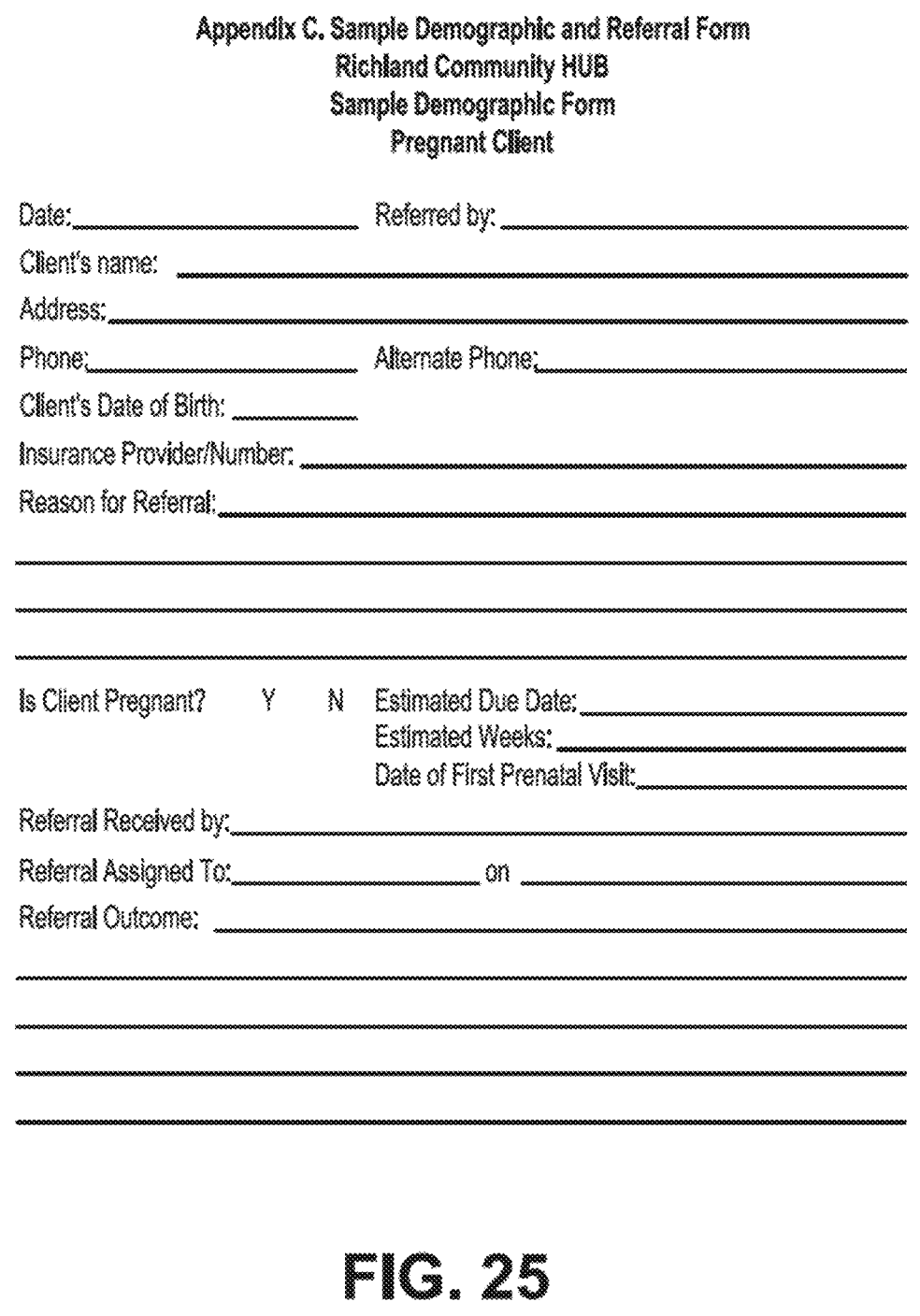

Appendix C. Sample Demographic and Referral Form
Richland Community HUB
Sample Demographic Form
Pregnant Client

Date:________________ Referred by:________________________

Client's name: ________________________________________

Address:______________________________________________

Phone:________________ Alternate Phone:____________________

Client's Date of Birth: ________

Insurance Provider/Number: ______________________________

Reason for Referral:____________________________________

______________________________________________________

______________________________________________________

______________________________________________________

Is Client Pregnant? Y N Estimated Due Date:________________
Estimated Weeks:________________
Date of First Prenatal Visit:____________

Referral Received by:___________________________________

Referral Assigned To:______________ on ____________________

Referral Outcome: ______________________________________

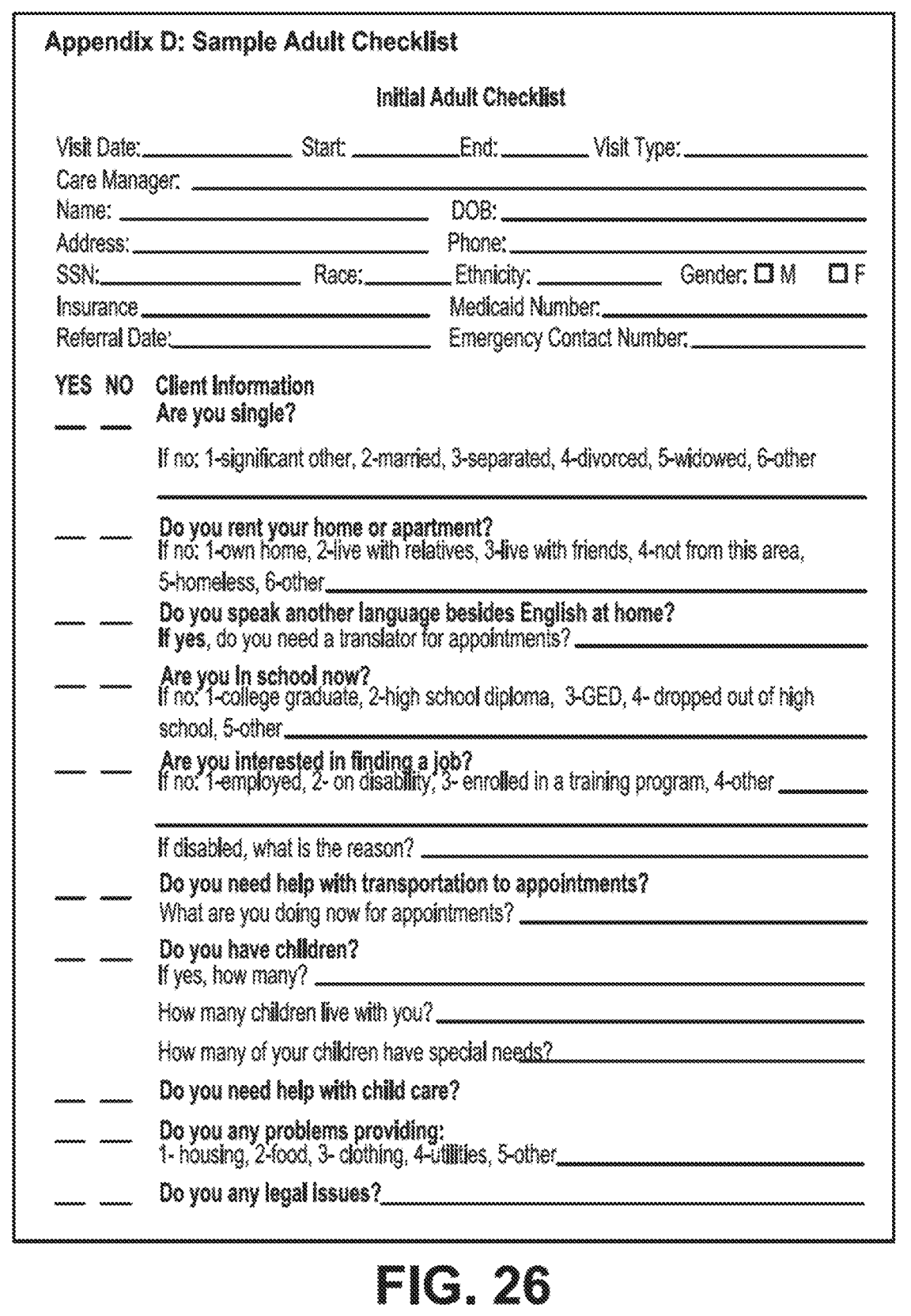

Appendix D: Sample Adult Checklist

Initial Adult Checklist

Visit Date:______ Start: ______ End: ______ Visit Type: ______

Care Manager: ______

Name: ______ DOB: ______

Address: ______ Phone: ______

SSN: ______ Race: ______ Ethnicity: ______ Gender: ☐ M ☐ F

Insurance ______ Medicaid Number: ______

Referral Date: ______ Emergency Contact Number: ______

YES NO Client Information

___ ___ Are you single?

If no: 1-significant other, 2-married, 3-separated, 4-divorced, 5-widowed, 6-other ______

___ ___ Do you rent your home or apartment?
If no: 1-own home, 2-live with relatives, 3-live with friends, 4-not from this area, 5-homeless, 6-other ______

___ ___ Do you speak another language besides English at home?
If yes, do you need a translator for appointments? ______

___ ___ Are you in school now?
If no: 1-college graduate, 2-high school diploma, 3-GED, 4- dropped out of high school, 5-other ______

___ ___ Are you interested in finding a job?
If no: 1-employed, 2- on disability, 3- enrolled in a training program, 4-other ______

If disabled, what is the reason? ______

___ ___ Do you need help with transportation to appointments?
What are you doing now for appointments? ______

___ ___ Do you have children?
If yes, how many? ______

How many children live with you? ______

How many of your children have special needs? ______

___ ___ Do you need help with child care?

___ ___ Do you any problems providing:
1- housing, 2-food, 3- clothing, 4-utilities, 5-other ______

___ ___ Do you any legal issues? ______

FIG. 26

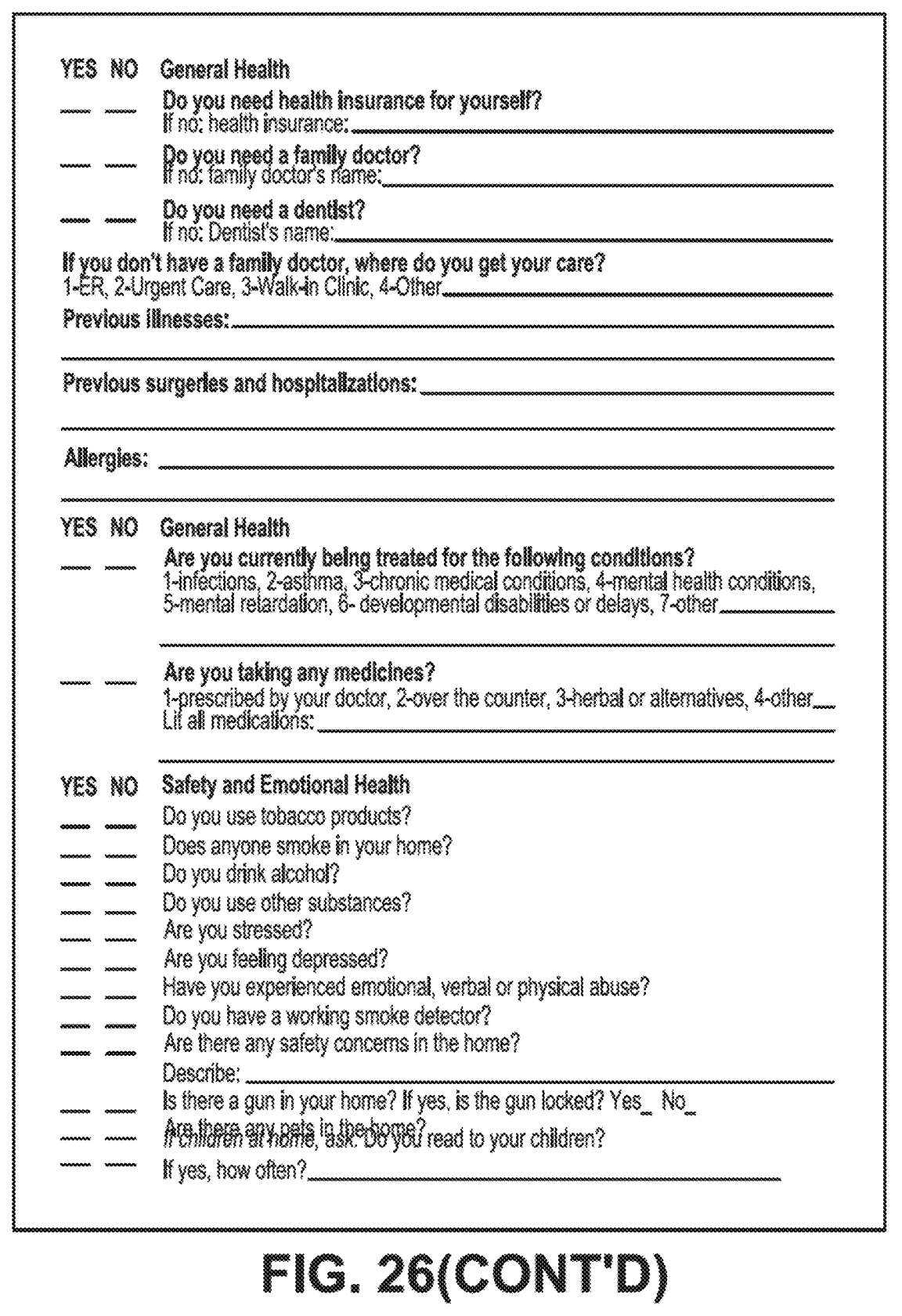

YES NO General Health

___ ___ Do you need health insurance for yourself?
If no: health insurance: __________

___ ___ Do you need a family doctor?
If no: family doctor's name: __________

___ ___ Do you need a dentist?
If no: Dentist's name: __________

If you don't have a family doctor, where do you get your care?
1-ER, 2-Urgent Care, 3-Walk-in Clinic, 4-Other __________

Previous illnesses: __________

Previous surgeries and hospitalizations: __________

Allergies: __________

YES NO General Health

___ ___ Are you currently being treated for the following conditions?
1-infections, 2-asthma, 3-chronic medical conditions, 4-mental health conditions, 5-mental retardation, 6- developmental disabilities or delays, 7-other __________

___ ___ Are you taking any medicines?
1-prescribed by your doctor, 2-over the counter, 3-herbal or alternatives, 4-other ___
Lit all medications: __________

YES NO Safety and Emotional Health

___ ___ Do you use tobacco products?
___ ___ Does anyone smoke in your home?
___ ___ Do you drink alcohol?
___ ___ Do you use other substances?
___ ___ Are you stressed?
___ ___ Are you feeling depressed?
___ ___ Have you experienced emotional, verbal or physical abuse?
___ ___ Do you have a working smoke detector?
___ ___ Are there any safety concerns in the home?
Describe: __________
___ ___ Is there a gun in your home? If yes, is the gun locked? Yes_ No_
___ ___ Are there any pets in the home?
*If children at home*, ask: Do you read to your children?
___ ___ If yes, how often? __________

FIG. 26(CONT'D)

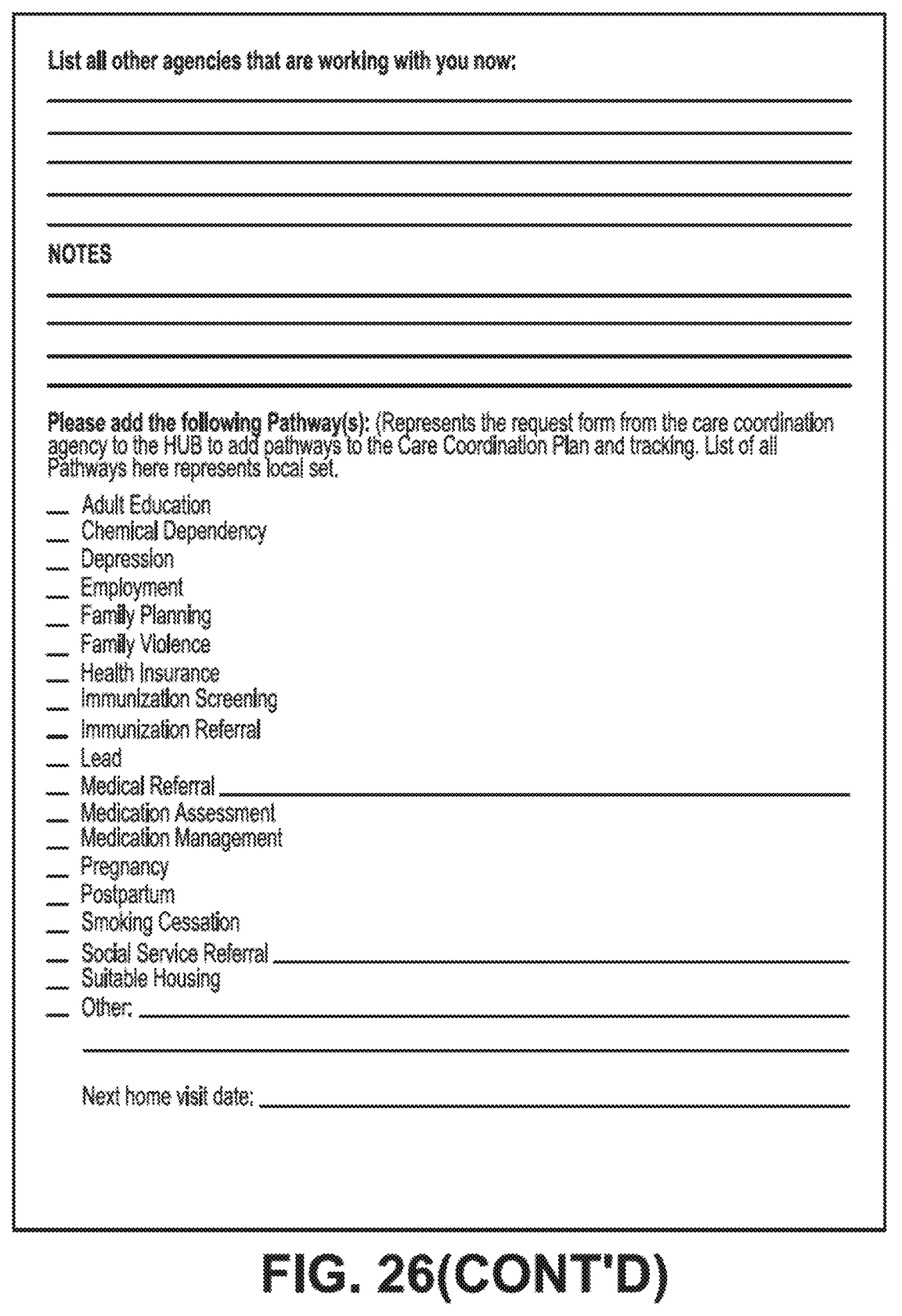

List all other agencies that are working with you now:

________________________________________
________________________________________
________________________________________
________________________________________
________________________________________

NOTES

________________________________________
________________________________________
________________________________________
________________________________________

Please add the following Pathway(s): (Represents the request form from the care coordination agency to the HUB to add pathways to the Care Coordination Plan and tracking. List of all Pathways here represents local set.

__ Adult Education
__ Chemical Dependency
__ Depression
__ Employment
__ Family Planning
__ Family Violence
__ Health Insurance
__ Immunization Screening
__ Immunization Referral
__ Lead
__ Medical Referral ____________________________
__ Medication Assessment
__ Medication Management
__ Pregnancy
__ Postpartum
__ Smoking Cessation
__ Social Service Referral __________________________
__ Suitable Housing
__ Other: __________________________________
________________________________________

Next home visit date: ____________________________

FIG. 26(CONT'D)

| COMMUNITY -HUB - HEALTH ENGAGEMENT TEAMS (recommended example) | | | |
|---|---|---|---|
| Core Team | Primary Care Provider | Nurse Practioner (ARNP) or appropriate RN (BSN) | Master Social Worker (MSW) |
| | Community Health Worker (CHW)/Navigator | Pharmacist | Behavioral Health Provider |
| Additional Team Members | Primary Care Medical Home Representative | EMS / Paramedics | Nutritionist |
| Population Dependent | MSS / Health Homes / TBD | Criminal justice stakeholder | Payer-based Clinician and/or MCO Case Manager |

HET Care Team member review meetings every two weeks includes the Primary Care, Pharmacist and Behavioral Health Provider to review care plan and progress.

Multiple HET Care Teams may be facilitated, simultaneously, in differing initiatives with different team composition and specializations.

FIG. 28

Health Engagement Team Timeline

| | Planning - 3-4 Months | Implementation - 3-4 Months | Optimization - 3-4 Months |
|---|---|---|---|
| Communication<br>• Set up steering committee<br>• Identify Project Coordinator<br>• HET team | Steering Committee-meet bi-weekly<br><br>Share plans with team | HET Team - meet weekly<br><br>Steering Committee - review bi-weekly | HET - meet weekly<br><br>Steering Committee - review bi-weekly |
| Education<br>• HET overview<br>• HET software<br>• HET processes/target population/outcomes/ measures/reporting<br>• CCM/TCM | HET Review<br>• C-suite<br>• Managers<br>• Steering Committee<br>• Team members | HET software/HET process<br>• team members<br>• managers<br>CCM/TCM<br>• team members | HET review<br>• all staff |
| Project Design<br>• Overall vision<br>• Timeline/phases<br>• Target Population<br>• Outcomes/goals<br>• Measures and strategies<br>• Reporting process | C-suite - overall vision<br>Steering Committee - work out details<br><br>Share with team prior to January | Report on measures and outcome to Steering Committee/C-suite and HET team on regular basis | Report to all staff, C-suite after implementation |
| Team Development<br>• Internal<br>•Team structure<br>•Members<br>•Hiring/developing<br>• External-partners/referrals/coordination with community<br>• Protocols/EBGuidelines<br>• Workflow among and between partners<br>• Governance structures | C-suite - overall vision<br>Steering Committee - work out details<br><br>Management - hiring<br><br>Community coordination - CHWs/care Coordinators | Initiate team structure, communication, reporting, training, protocols, etc.<br>Steering Committee/C-suite/management - update for problem solving / QI | Report to all staff |
| Solution and Technology<br>• HET setup and flow<br>• CCM/TCM<br>• Find AI RiskQ analysis<br>• Notify/EMR integration | C-suite - overall vision<br>Steering Committee - work out details<br>Analyze population data and estimate potential<br>CCS develop additional modules | Initiate workflow with team<br><br>Report to Steering Committee on progress | |

FIG. 41

Real-Time Reporting Results

| HET id | Total Inservice Days(Z↓ | PreService Hospital Costs | PreService - ER Costs | InService - Hospital Costs | InService - ER Costs | PreService Hospital Stays | PreService ER Visits | InService Hospital Stays | InService - ER Visits |
|---|---|---|---|---|---|---|---|---|---|
| 1710-02-S4 | 383 | 162,000 | 2,000 | -20,000 | | 16 | 1 | 2 | 0 |
| 1710-04-S3 | 378 | 48,000 | 2,000 | | | 4 | 1 | 0 | 0 |
| 1710-06-S5 | 378 | 11,400 | | -42,000 | -2,000 | 3 | 0 | 3 | 1 |
| 1710-09-S1 | 369 | 62,000 | 8,000 | -16000 | | 6 | 3 | 1 | 0 |
| 1710-10 | 365 | 6,000 | | | | 1 | 0 | 0 | 0 |
| 1711-01 | 364 | 102,000 | 2,000 | -54,000 | -4,000 | 10 | 1 | 5 | 2 |
| 1710-13-S7 | 359 | 102,000 | 6,000 | | | 4 | 3 | 0 | 0 |
| 1710-18-S8 | 359 | 70,000 | | | | 4 | 0 | 0 | 0 |
| 1710-05 | 346 | 14,000 | 2,000 | | -2,000 | 1 | 1 | 0 | 1 |
| 1711-06 | 331 | 36,000 | | -34,000 | -6,000 | 3 | 0 | 2 | 3 |
| 1712-14 | 322 | 54,000 | 4,000 | | | 7 | 2 | 0 | 0 |
| 1712-07 | 326 | 20,000 | | -18,000 | -2,000 | 1 | 0 | 1 | 1 |
| 1711-17 | 317 | 226,000 | | | | 5 | 0 | 0 | 0 |
| 1712-03 | 314 | 112,000 | 6,000 | -62,000 | -10,000 | 14 | 3 | 8 | 5 |

FIG. 43

ACTIVE CLIENTS INACTIVE CLIENTS OBUs
11,445 36,826 1,502,346
-0.8% +2.1% +2.7%
Month -over - Month Month -over - Month Month -over - Month
(All)
Program Name
(All)
As of Date
1/18/2021
ACTIVE, ENROLLED Clients by Type
Active Clients with OBUs by PAyers
PEDIATRIC 413
NA 1
ADULT 684
4,502
PREGNANT 1,696
MATERNAL 1,708
FOSTERING HEALTHY COMMUNITIES 1
ADULT 684
UNITED HEALTHCARE 250
3,571
CARESOURCE 341
PARAMOUNT 346
NO PAYER 2,026

Figure 68A:
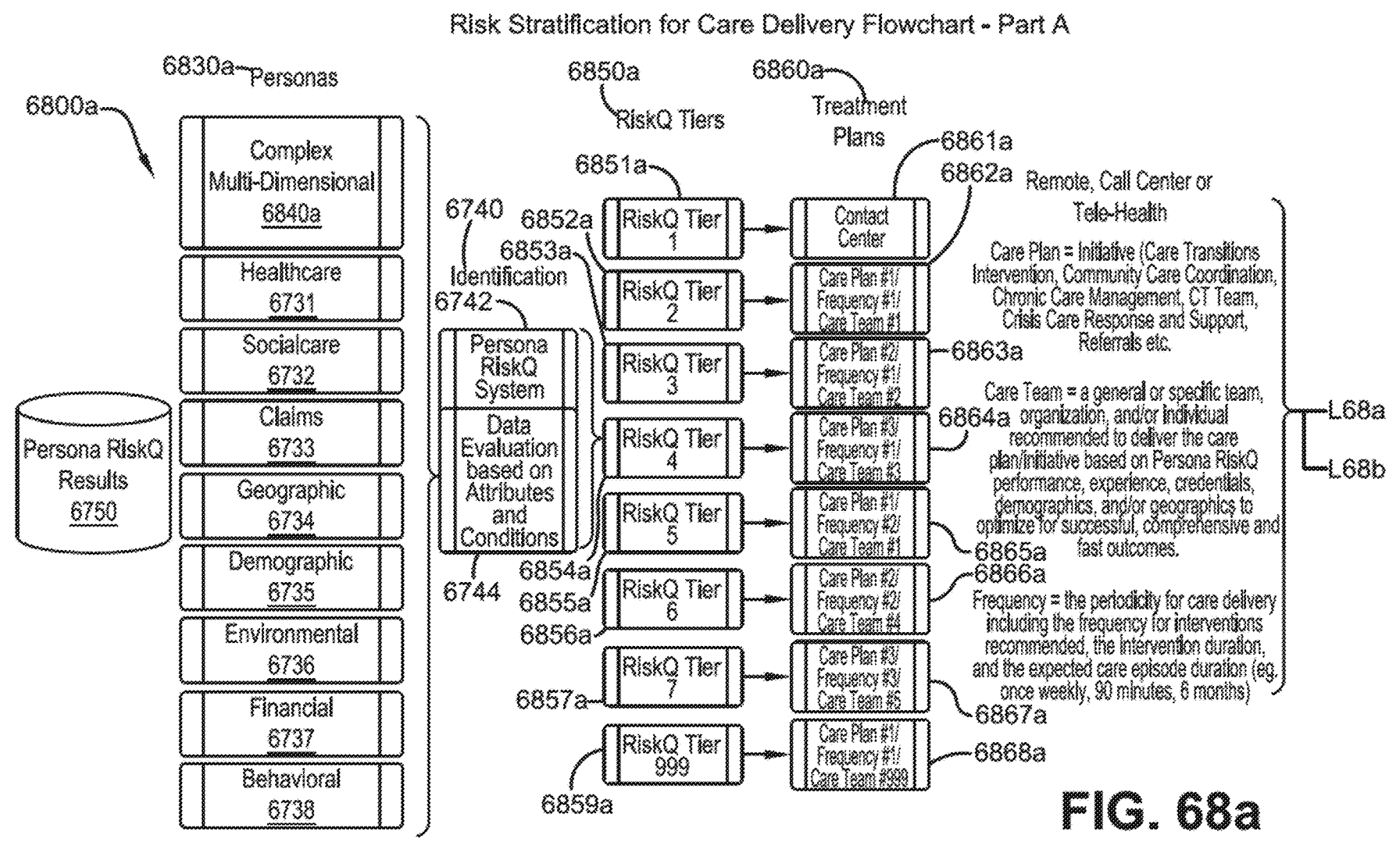

Risk Stratification for Care Delivery Flowchart - Part A

6800a

6830a Personas

Complex Multi-Dimensional 6840a

Healthcare 6731

Socialcare 6732

Claims 6733

Geographic 6734

Demographic 6735

Environmental 6736

Financial 6737

Behavioral 6738

Persona RiskQ Results 6750

6740 Identification

6742 Persona RiskQ System

Data Evaluation based on Attributes and Conditions 6744

6850a RiskQ Tiers

6851a RiskQ Tier 1

6852a RiskQ Tier 2

6853a RiskQ Tier 3

6854a RiskQ Tier 4

6855a RiskQ Tier 5

6856a RiskQ Tier 6

6857a RiskQ Tier 7

6859a RiskQ Tier 999

6860a Treatment Plans

6861a Contact Center

6862a Care Plan #1/ Frequency #1/ Care Team #1

6863a Care Plan #2/ Frequency #1/ Care Team #2

6864a Care Plan #3/ Frequency #1/ Care Team #3

6865a Care Plan #1/ Frequency #2/ Care Team #1

6866a Care Plan #2/ Frequency #2/ Care Team #4

6867a Care Plan #3/ Frequency #3/ Care Team #5

6868a Care Plan #1/ Frequency #1/ Care Team #999

Remote, Call Center or Tele-Health

Care Plan = Initiative (Care Transitions Intervention, Community Care Coordination, Chronic Care Management, CT Team, Crisis Care Response and Support, Referrals etc.

Care Team = a general or specific team, organization, and/or individual recommended to deliver the care plan/initiative based on Persona RiskQ performance, experience, credentials, demographics, and/or geographics to optimize for successful, comprehensive and fast outcomes.

Frequency = the periodicity for care delivery including the frequency for interventions recommended, the intervention duration, and the expected care episode duration (eg. once weekly, 90 minutes, 6 months)

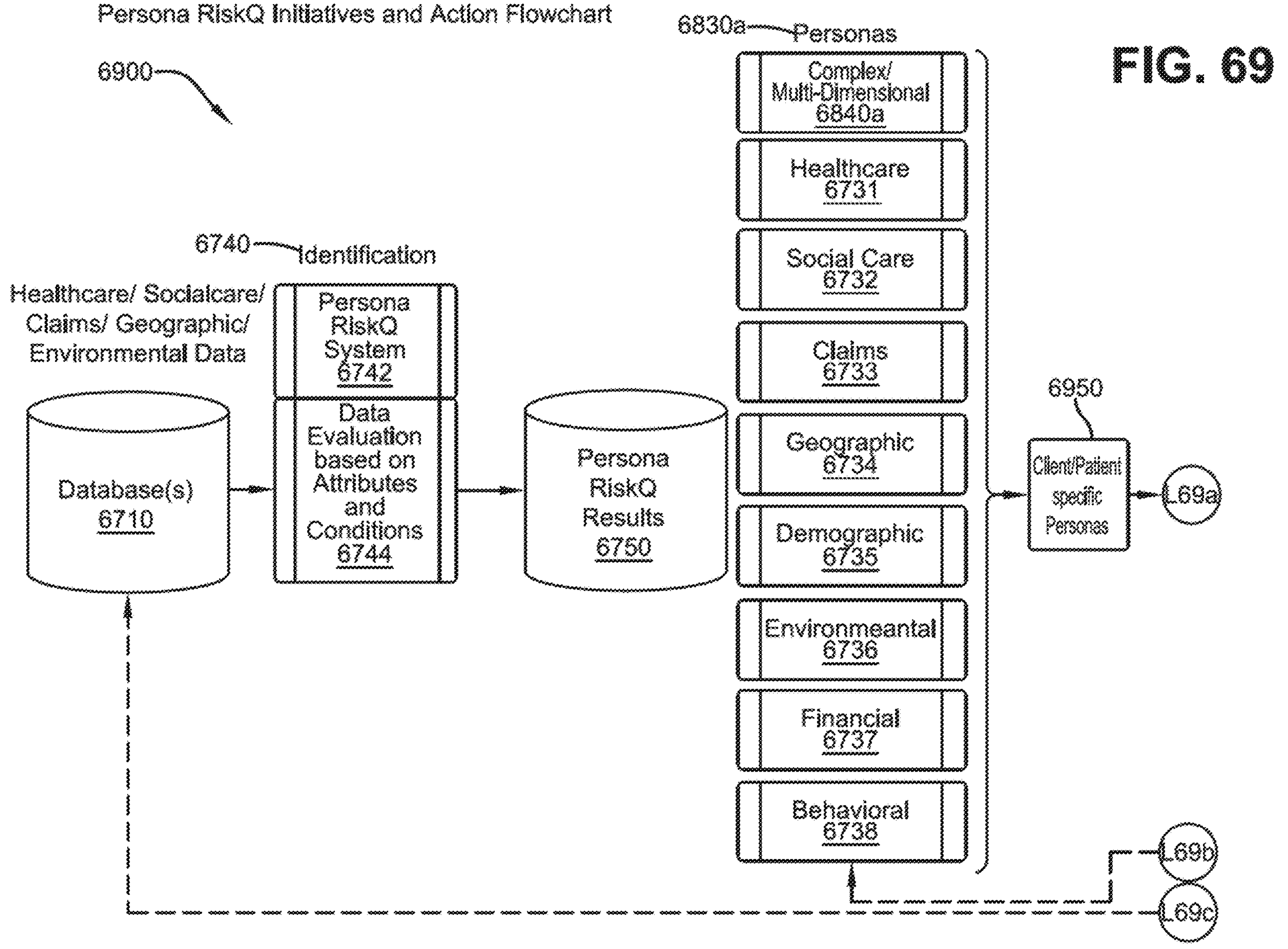

Persona RiskQ Initiatives and Action Flowchart
6900
6830a
Personas
FIG. 69
Complex/ Multi-Dimensional 6840a
Healthcare 6731
Social Care 6732
Claims 6733
Geographic 6734
Demographic 6735
Environmeantal 6736
Financial 6737
Behavioral 6738
6740
Identification
Healthcare/ Socialcare/ Claims/ Geographic/ Environmental Data
Persona RiskQ System 6742
Data Evaluation based on Attributes and Conditions 6744
Database(s) 6710
Persona RiskQ Results 6750
6950
Client/Patient specific Personas
L69a
L69b
L69c

SYSTEM AND METHOD FOR IMPLEMENTING HEALTH CARE COST SAVINGS

CROSS-REFERENCES TO RELATED APPLICATIONS

This application is a Continuation-In-Part of U.S. Ser. No. 18/400,093, filed Dec. 29, 2023, which is a Continuation of U.S. Ser. No. 17/805,452, filed Jun. 4, 2022, which is a continuation of U.S. Ser. No. 16/514,626, now U.S. Pat. No. 11,393,563, filed Jul. 17, 2019, which claims priority to U.S. Ser. No. 62/819,947, filed Mar. 18, 2019, the contents of which are herein incorporated by reference.

FIELD

The present disclosure relates generally to a system and method of reducing the administrative costs of medical care without expense to the Federal Government or State Governments to implement.

BACKGROUND

Medicare and Medicaid costs the U.S. Federal Government and State Governments over $1.6 trillion per year. An estimated 20%-25% of this is deemed wasted annually by health systems. This is not related to clinical operations but is mainly attributable to administrative and general inefficiencies. Reducing these inefficiencies results in higher profitability for hospitals.

Community health initiatives while resolving and reducing social health risks, also reduce hospital readmissions, hospital utilization, emergency room utilization, skilled nursing facility utilization, and ambulance transits. Community and home health in a coordinated care network (CCN) provide lower cost and high-quality care outside the hospital and in the patient/client's home or place of comfort. More care provided outside of the hospital benefits the hospital, reducing capacity and workforce stress, and greater profitability per patient with a more focused care approach.

This system and method include a network of healthcare, socialcare, community-based, and home health delivery organizations coordinates and pairs with other methods, processes, training, systems, interoperability, and advisory services to reduce Federal and State Medicaid and Federal Medicare annual spending by between 5% and 15%.

The objective of this CCN is to reduce Medicare and Medicaid annually by at least $100B at the state and federal levels, which can be achieved without cost to the federal or state governments. Enabling the sustainability to deliver high quality care while reducing the uncompensated and unnecessary care costs in the healthcare systems is paramount. Achieving the $100B Medicare and Medicaid savings without required cost to government is the key objective of this disclosure.

For the CCN and its interoperability with other systems, the network leverages the applicant's current existing CCS Health technologies, care models, reporting, invoicing, and processes with artificial intelligence and predictive analytics as detailed herein. The foundation of this system is documenting the infrastructure required and that which was developed for a sustainable Community HUB to be viable, collaborative, and interoperative, continuously, with healthcare stakeholders, community members, and government.

The purpose of the present disclosure is to document the requirements for sustainably financing a healthcare-community care network, increasing profitability and viability for health systems, urban and rural, and reducing Medicare/Medicaid care costs without federal and state funding. Support including endorsement and collaboration is all that is required to achieve the significant benefits listed.

The applicant has already proven that communities can be coordinated and aligned to sustainably improve peoples' lives, health, and reduce care costs. There exists a previously unrecognized significant return on investment (ROI) for the efforts and successes generated by community health. The community health organizations cannot benefit from the ROI results they generate. The ROI benefits are realized by federal, state, health insurance companies, hospitals, and accountable care organizations.

Today, the ROI results available to the above groups are not consistent or significant since the sustainable funding of community health at the local level is meager or nonexistent. Where sustainable community health is present with CCS Health, measured health outcomes and ROI results have been documented for 12+ years. Yet, this is not at the standards required for a state-wide or nation-wide coordinated care network.

A Socially Motivated Fund (SMF) is a private investment fund that is long-term focused and incentivized to fund projects that benefit the public and produce return on investment through growth and shared savings. The most efficient use of capital from SMF should be applied to health systems, urban and rural with a focus on increasing health systems net patient revenue through streamlined and efficient administrative services. SMFs take on the risk solely for the upfront healthcare and community funding with the goal of maintaining an evergreen fund through the return on investment earned from the SMF share of growth in profitability of the funded healthcare systems.

An Area Agency on Aging (AAA) is a public or private non-profit agency, designated by the Federal and State Governments through the Older Americans Act (OAA) federal legislation to address the needs and concerns of all older people at the regional and local levels. AAAs coordinate and offer services that help older adults remain in their homes aided by meal services, homemaker assistance, and whatever else it may take to make independent living a viable option.

A Community Treatment Order (CTO) is a legal mechanism that allows individuals with mental health conditions to receive supervised treatment in the community rather than being detained in a hospital, with certain conditions they must follow, and potential recall to a hospital if those conditions are breached or their condition deteriorates.

A Federally Qualified Health Center (FQHC) is a community-based, patient-directed primary care practice that serves medically underserved areas, offering comprehensive services and a sliding fee scale, regardless of a patient's ability to pay.

Critical Time Intervention (CTI) is a time-limited, intensive case management model designed to prevent homelessness and support individuals during critical transitions, such as discharge from institutions or housing instability, by providing targeted support and linking them to community resources.

Conversation Training Therapy (CTT) is a voice therapy approach that focuses on voice awareness and production in conversational speech from the outset of treatment, using patient-driven conversation as the primary therapeutic stimulus, rather than a traditional therapeutic hierarchy.

For purposes of this disclosure, the terms "client" and "patient" and "client/patient" are all interchangeable and equivalent to one another. For purposes of this disclosure, the terms "information" and "data" are interchangeable and equivalent to one another. For purposes of this disclosure, the phrases "at least one" and "one or more" are interchangeable and equivalent to one another.

SUMMARY

The present disclosure relates to a system and method for funding/financing the healthcare/socialcare networks to provide Medicaid and Medicare cost savings for Federal and State purposes through reducing medical care costs while improving community engagement, community quality of life, and overall population health, including: a hub computing device which operates as a hub portal comprising a processor, a display and a non-transitory computer-readable storage medium containing a set of instructions encoded thereon; a data collection component, wherein the data collection component allows for a listing of clients including client information, a listing of medical, health and social service providers to be uploaded onto the hub portal by an associated hub user, and for recording of a patient's community health data, social determinants of health data and financial data with various service providers through use of the system; a graphical user interface for integrating the data collection component and the hub computing device, wherein the set of instructions encoded on the non-transitory computer-readable storage medium including the steps of: analyzing data collected by the data collection component; extracting analyzed data and applying it to at least one condition in a set of pre-set conditions; and calculating an initiative cost per client, a client's required sustainability level and a break-even point between a payer and an administrator in delivering services to the client, wherein the calculation is completed in real-time upon entry of data for the client into the data collection component and delivered to a service provider at various intervals in real-time through the graphical user interface; an artificial intelligence engine, comprising non-transitory computer-readable storage medium containing a set of instructions encoded thereon, the instructions including: training at least one AI model using information from external client databases regarding client information and care network partners to create at least one trained ROI AI model, which can predict the ROI of a given care plan for the client; predicting the ROI and the timing of a given care plan for the client using the at least one trained ROI AI model; establishing care plan priorities to achieve objectives; routing to appropriate care network partners; developing key performance indicators and milestones per client and care model displaying data for users to self-evaluate performance per client; and implementing the care plan via a Healthcare and community-based socialcare team, resulting in increased efficiency and savings, wherein the artificial intelligence engine is a neural network; the information contained within the external client databases includes information regarding the specific persona(s), the healthcare, social care, claims, geographic, and environmental information of the client; the artificial intelligence engine evaluates data entered into the system during treatment with respect to changes in the client's care plan and makes changes to its ROI and timing predictions in light of the changes; the artificial intelligence engine determines whether the budget over the care episode timeline was adhered to and whether the Healthcare and community-based socialcare team achieved the system's expectations; after the client's care plan is completed, the artificial intelligence engine determines in real-time whether the client is to be referred to another agency or requires a further treatment plan, and if so, calculates a new ROI and timing of a new care plan; and the artificial intelligence engine includes structured query language (SQL) software and robotic process automation (RPA) software, wherein structured query language (SQL) software manages the relationship between data within disparate databases, performs operations on the data and wherein the robotic process automation (RPA) software builds, deploys and manages software robots to interact with the data, digital systems and software and identifies and extracts data and performs defined actions; a CCN component for using the savings from the implementation of the care plan crafted by the artificial intelligence engine, comprising non-transitory computer-readable storage medium containing a set of instructions encoded thereon, the instructions including: sending money from an SMF to a money management organization to begin the CCN process and for redistribution; sending money saved via the artificial intelligence engine implementing the care plan to the money management organization for redistribution; and redistributing the money to various beneficiaries based on need, wherein the various beneficiaries comprise at least one CBO, at least one AAA, at least one hospital, at least one FQHC, at least one aging network, at least one CTO, at least one health system, a federal Medicare/Medicaid program, at least one state Medicaid program, and the SMF; the CCS health system provides ransomware-proof/quantum-safe IT security to provide encryption to relevant data, helping to prevent costly data breaches from occurring and extortion by third-party bad actors; and any leftover money is given back to the SMF for further investment.

BRIEF DESCRIPTION OF THE DRAWINGS

FIGS. 4 through 24 are examples of various Community Hub Pathways.

FIG. 25 is a sample demographic and referral form.

FIG. 26 is a sample Adult Checklist.

FIG. 28 is a chart showing an example community hub health engagement team.

FIG. 41 is a chart illustrating the activities of the health engagement team over a period of time.

FIG. 43 is an example of the real-time reporting results provided by a Care Coordination System software application.

FIGS. 68*a* and 68*b* provide a Risk Stratification for Care Delivery Flowchart.

FIG. 69 provides a Persona RiskQ Initiatives and Actions Flowchart.

DETAILED DESCRIPTION OF THE DISCLOSURE

Figure 1:
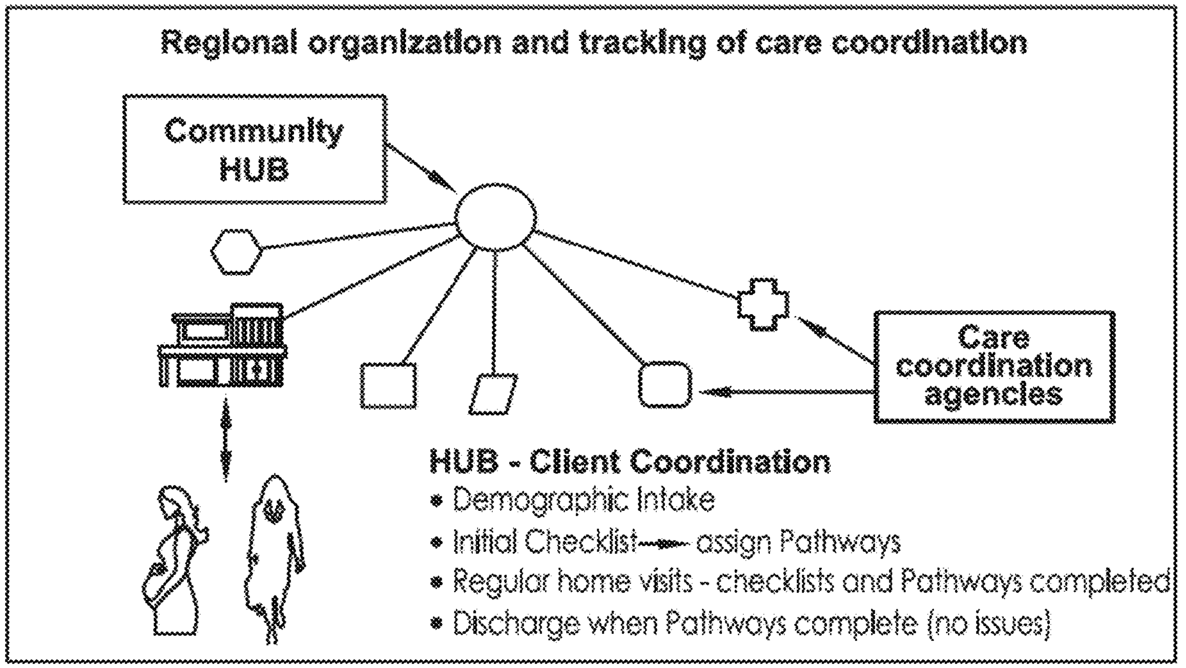
FIG. 1 is a diagram showing the regional organization and tracking of care coordination.
Figure 2:
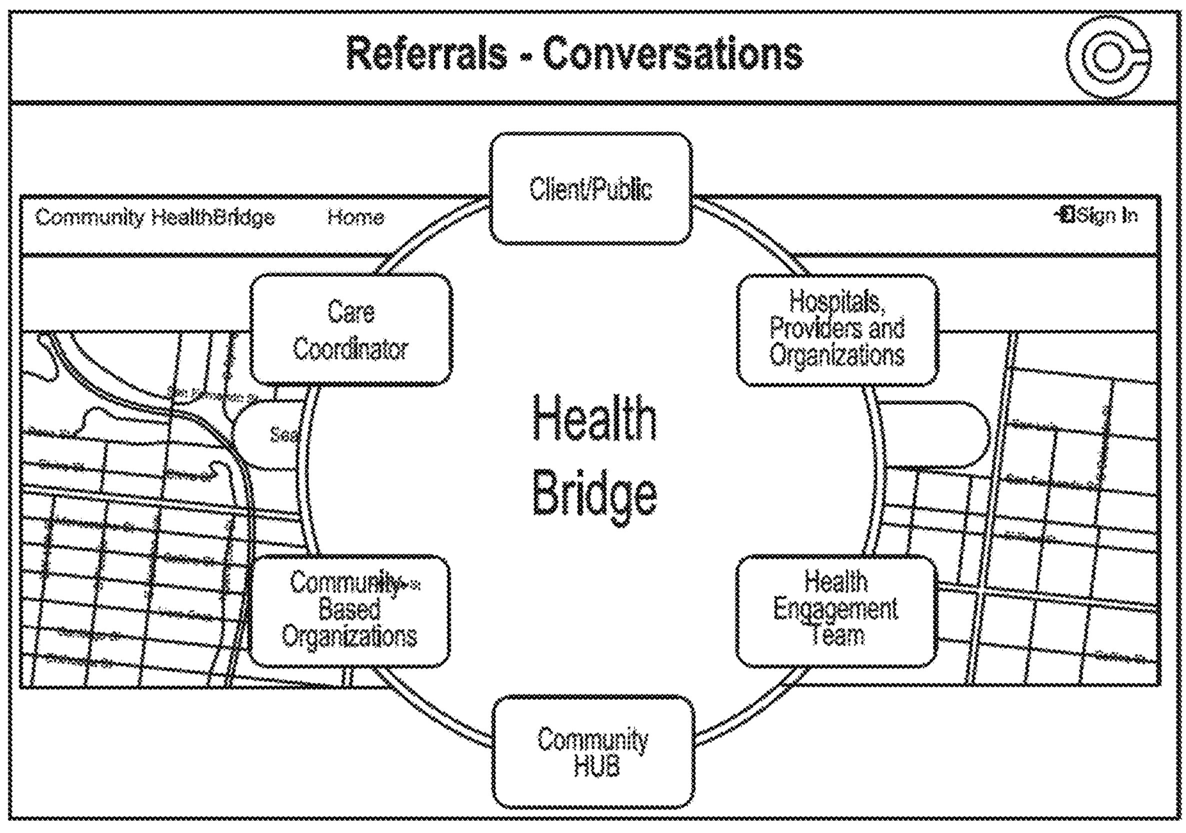
FIG. 2 is a diagram showing how the health bridge connects various parts of the coordinating care system.
Figure 3:
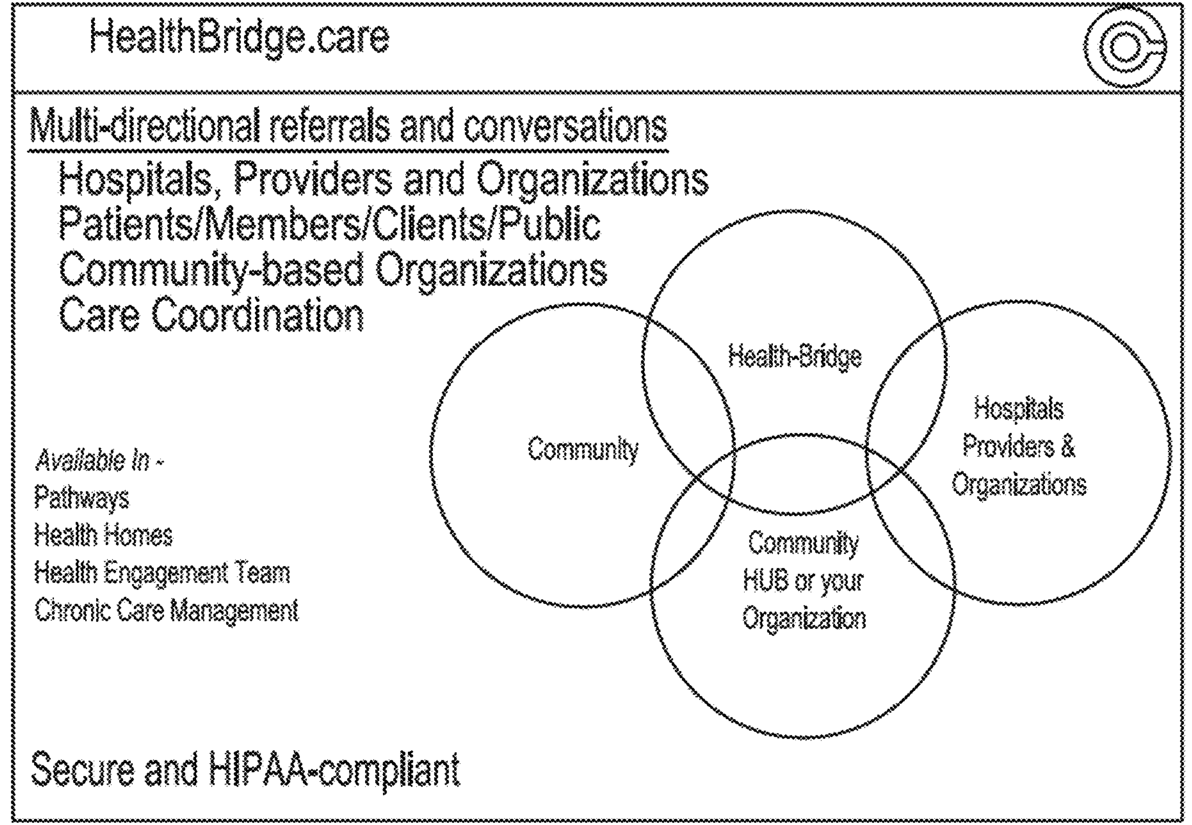
FIG. 3 is a diagram showing the interconnection of the parties of the coordinating care system.
Figure 27:
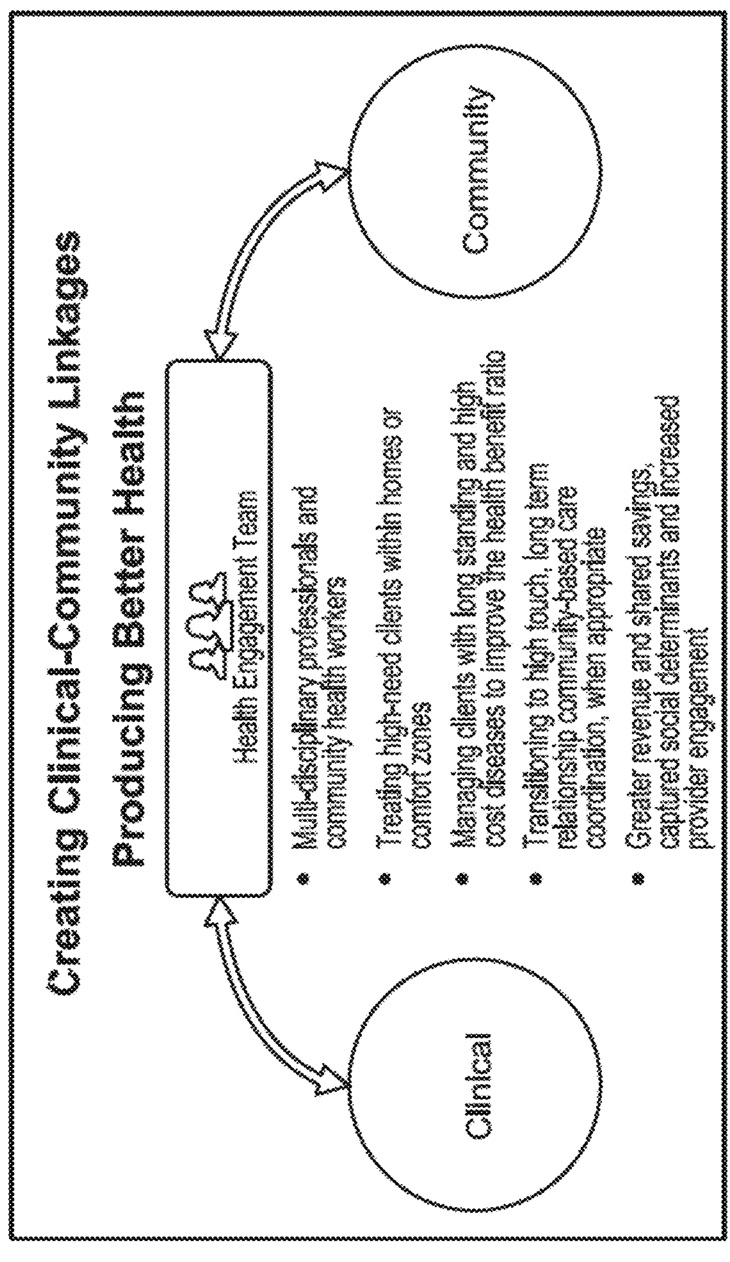
FIG. 27 is a diagram showing how a health engagement team creates a clinical-community linkage to produce better health among patients.
Figure 29:
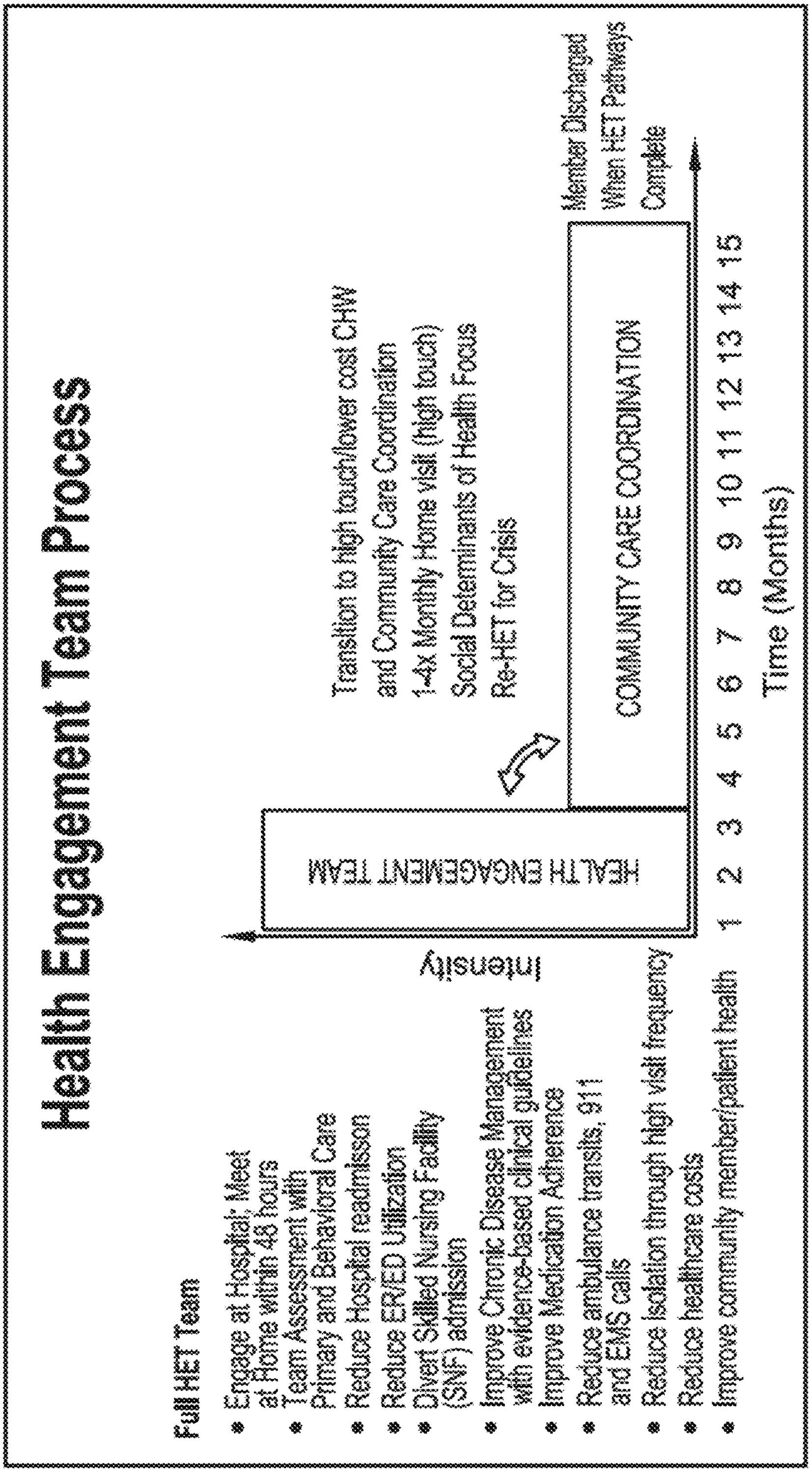
FIG. 29 is a chart illustrating the health engagement team process.
Figure 30:
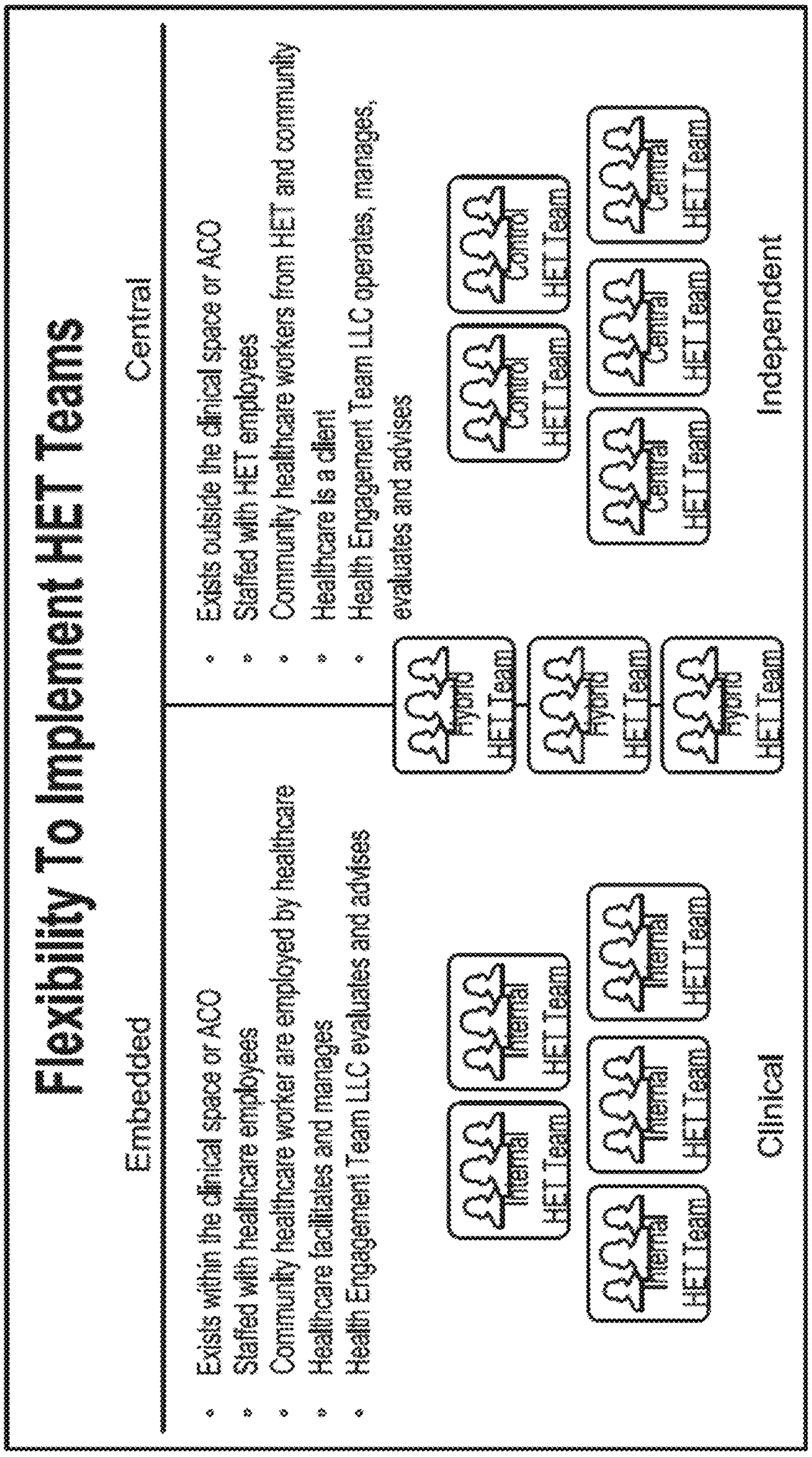
FIG. 30 is a chart illustrating the flexibility with implementing health engagement teams.
Figure 31:
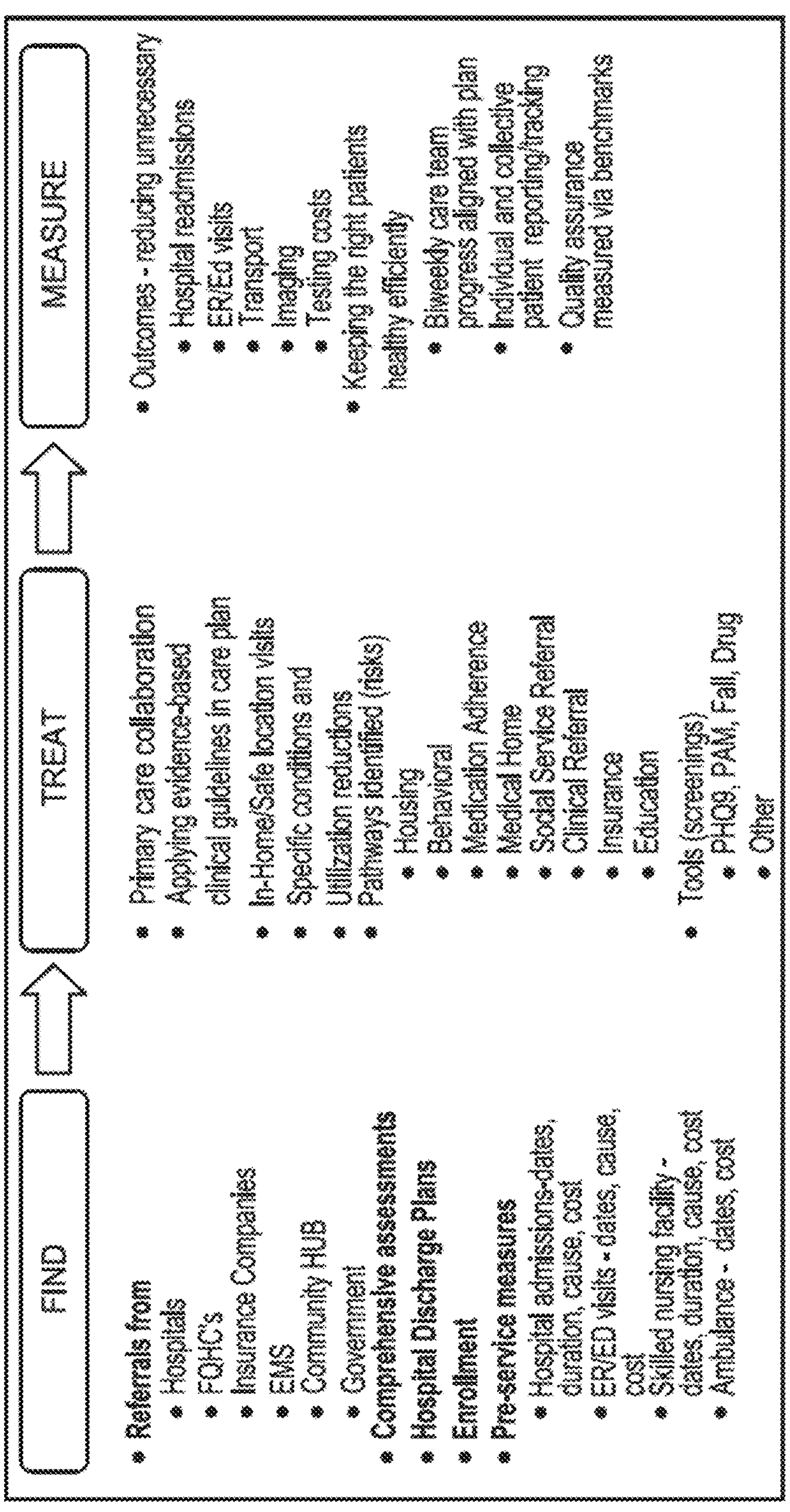
FIGS. 31 and 32 are charts illustrating the find, treat, measure activities of the Pathways Community HUB model.
Figure 32:
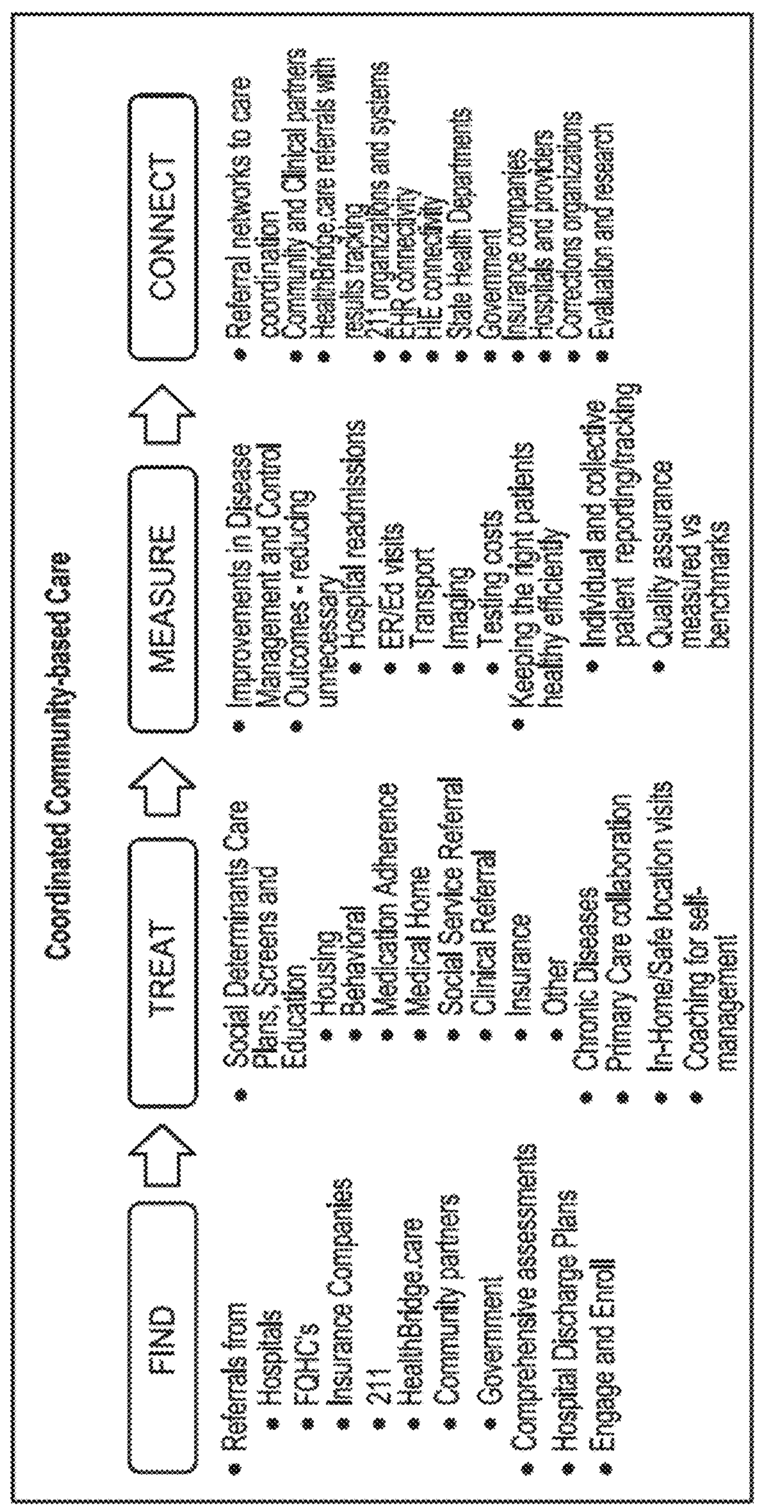
Figure 33:
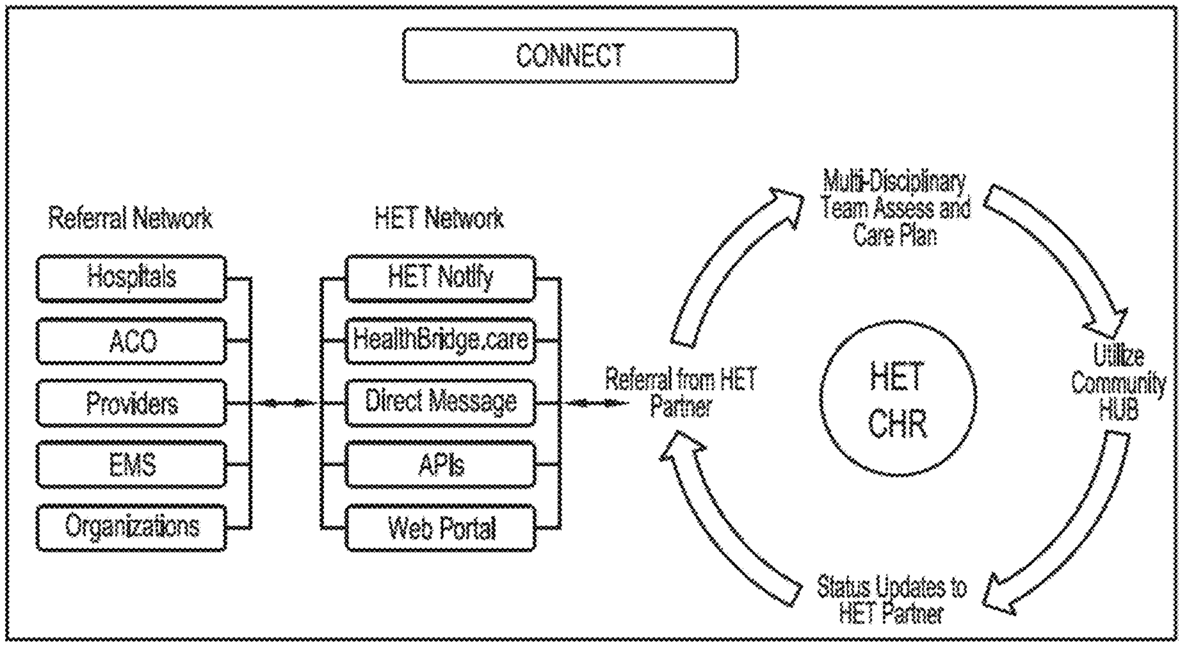
FIGS. 33 and 34 are diagrams showing how the health engagement team connects the referral network with the Pathways Community HUB.
Figure 34:
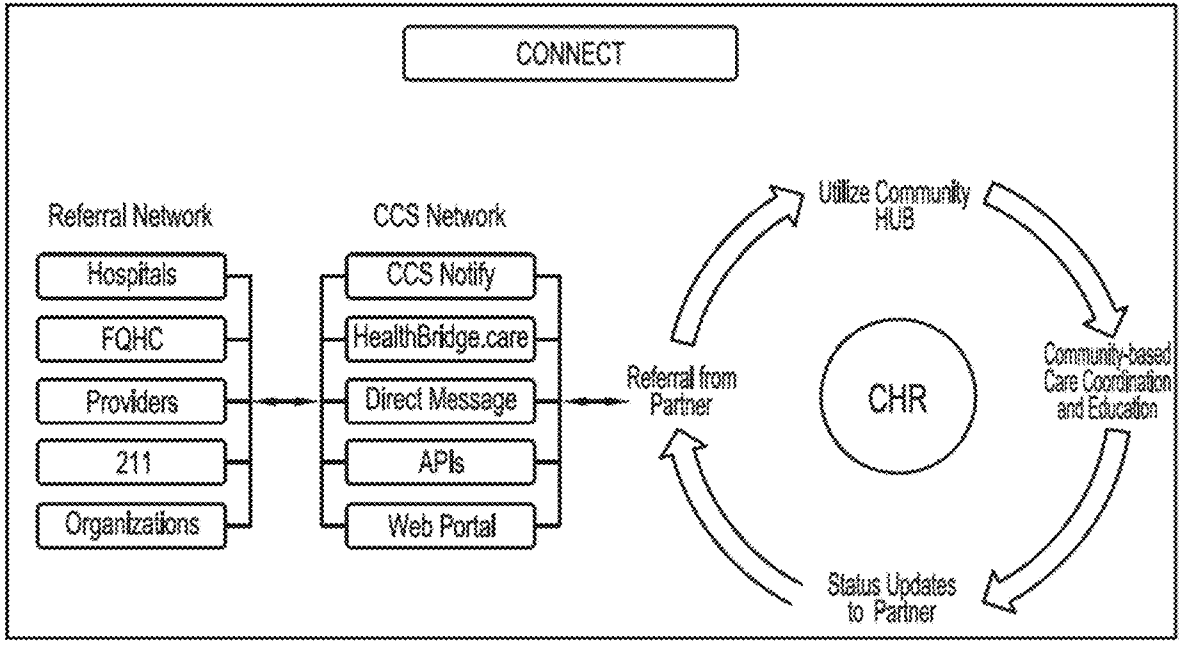
Figure 35:
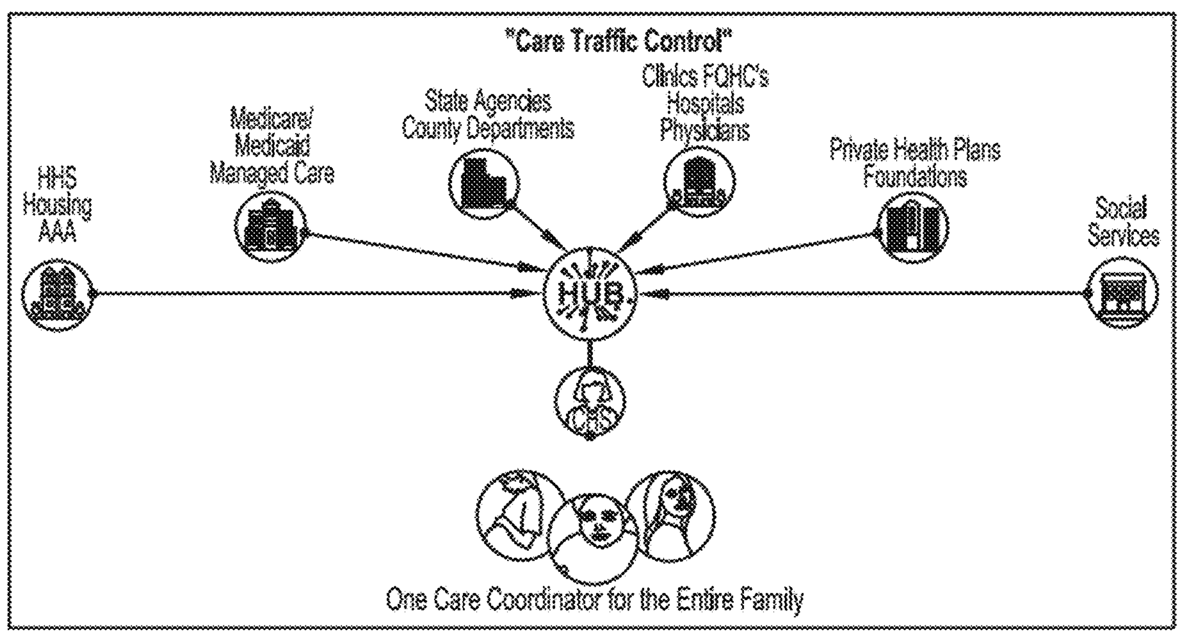
FIG. 35 is a diagram showing how the HUB connects the Community Health Worker with various organizations.
Figure 36:
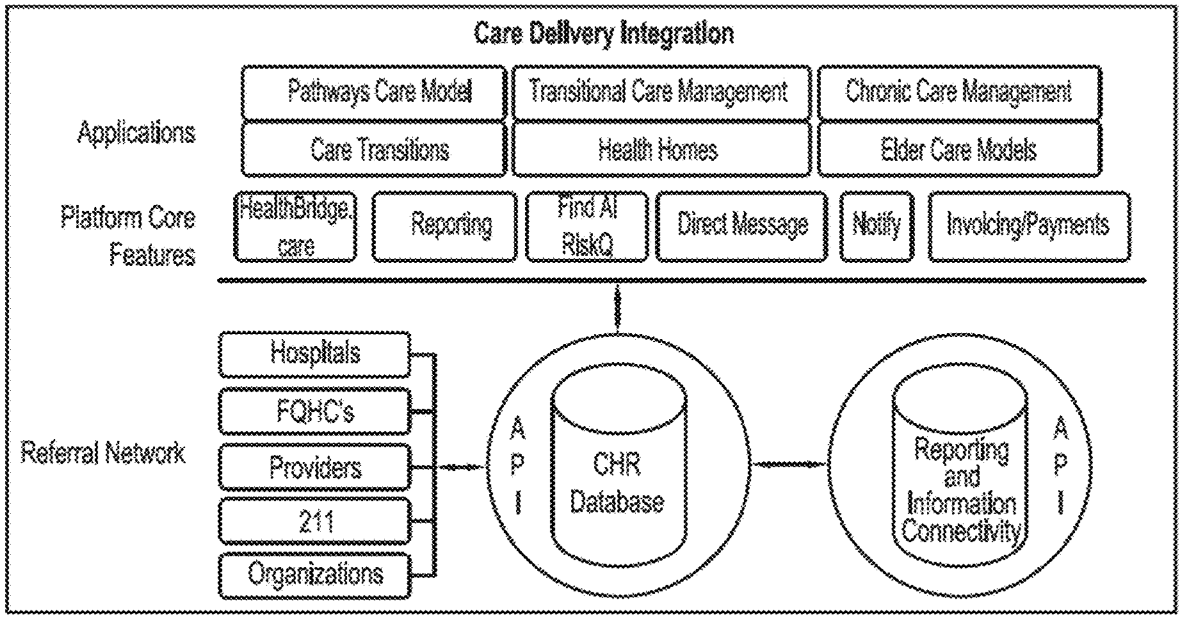
FIG. 36 is a diagram showing the integration of care delivery through the health engagement team.
Figure 37:
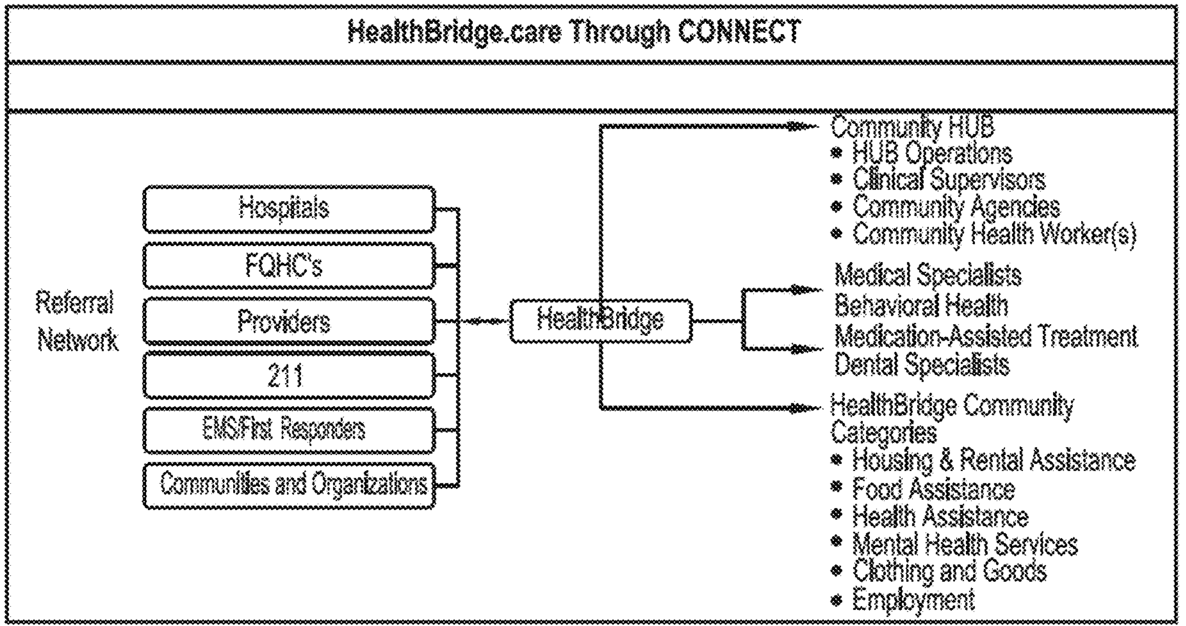
FIG. 37 is a diagram showing how the healthbridge connects the referral network with the health engagement team, medical and dental providers, and providers within community based-organizations.
Figure 38:
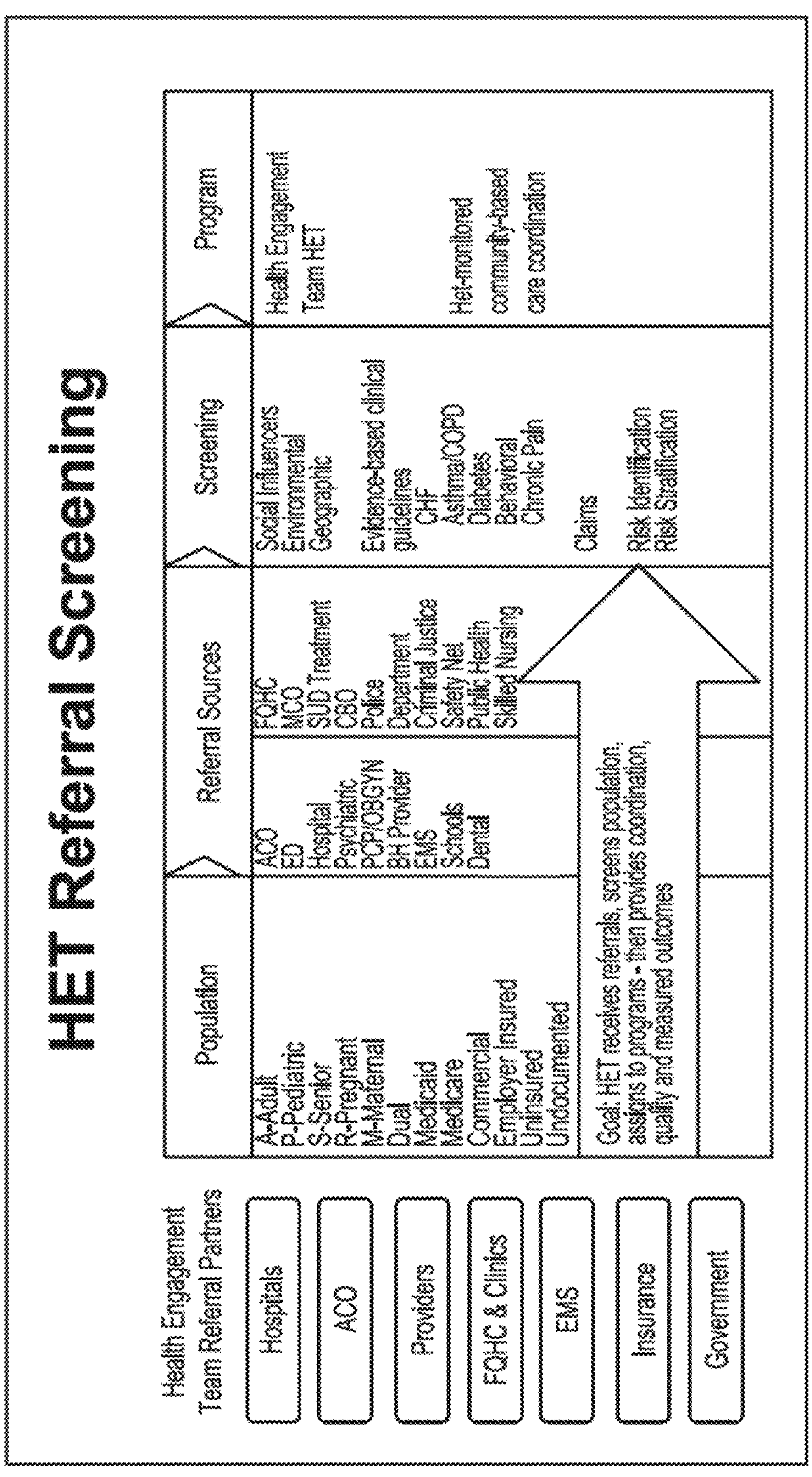
FIG. 38 is a chart illustrating the health engagement team screening process.
Figure 39:
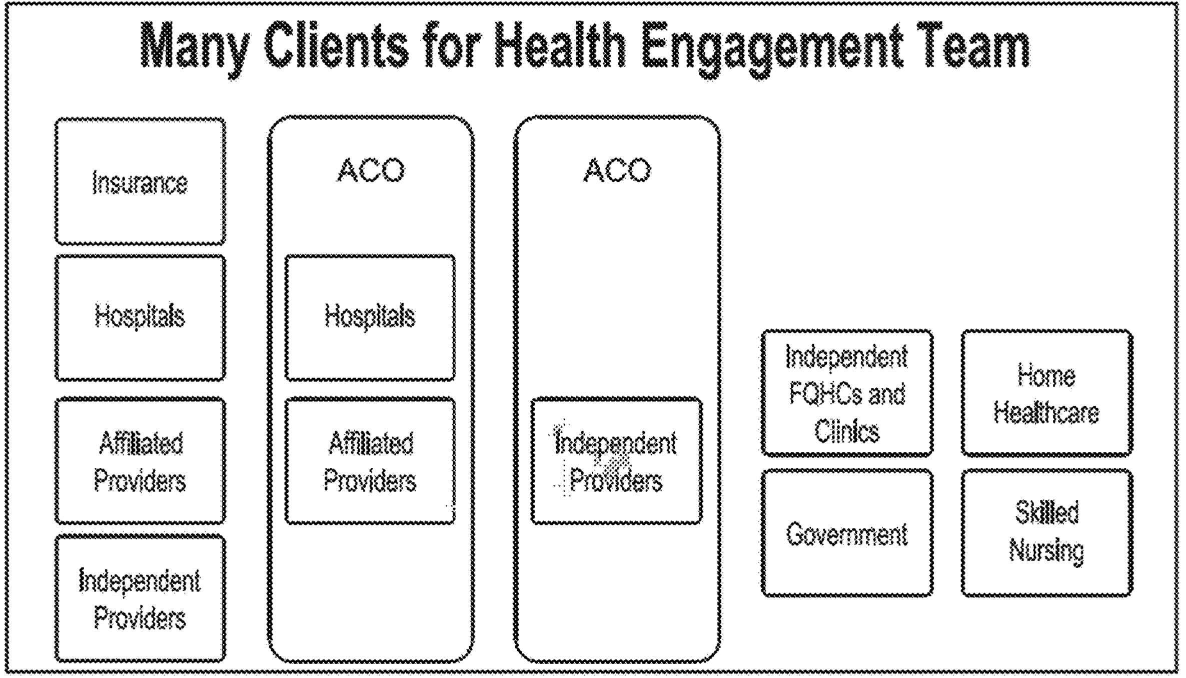
FIG. 39 is a chart listing the clients of the health engagement team.
Figure 40:
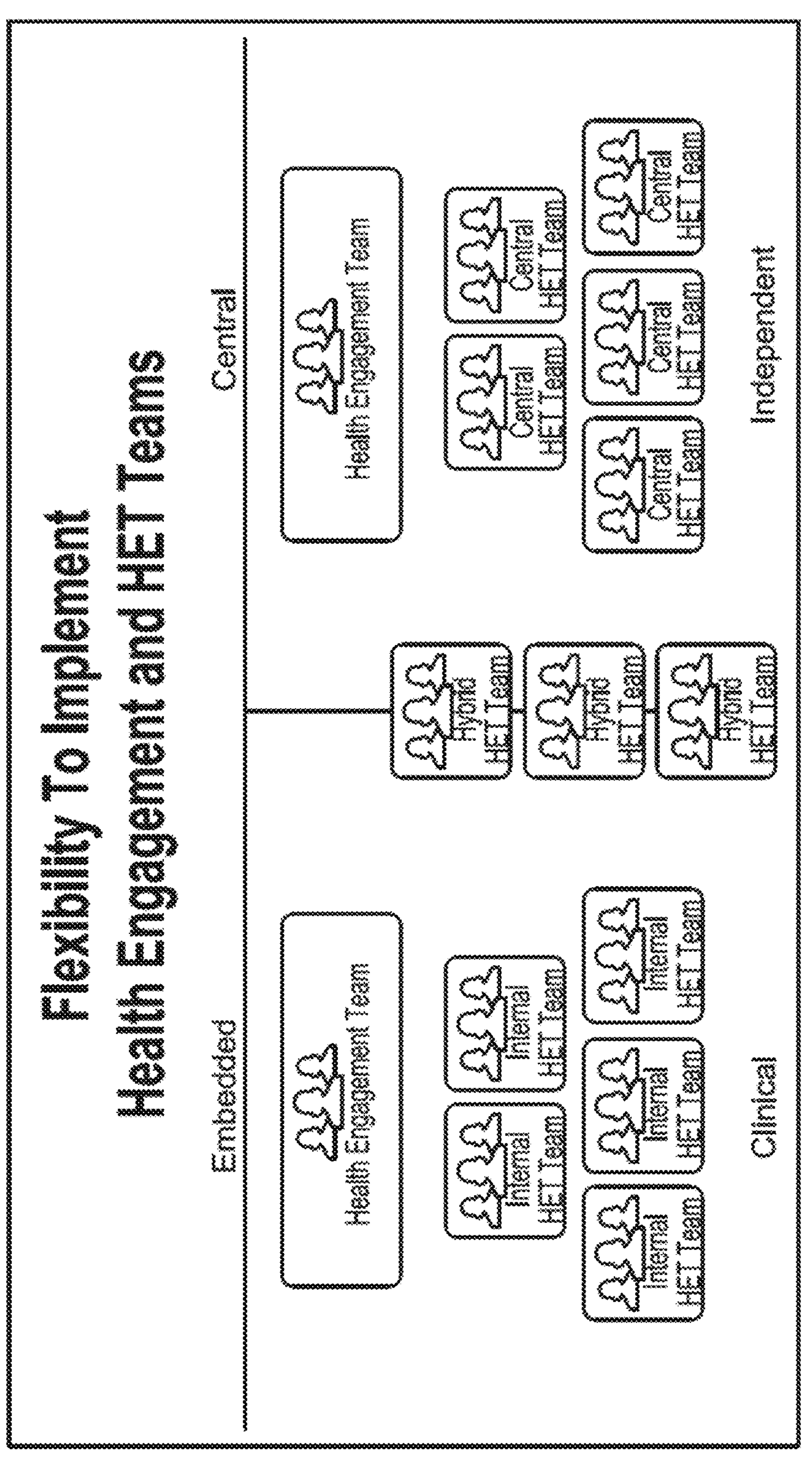
FIG. 40 is a chart illustrating options for implementing a health engagement team.
Figure 42:
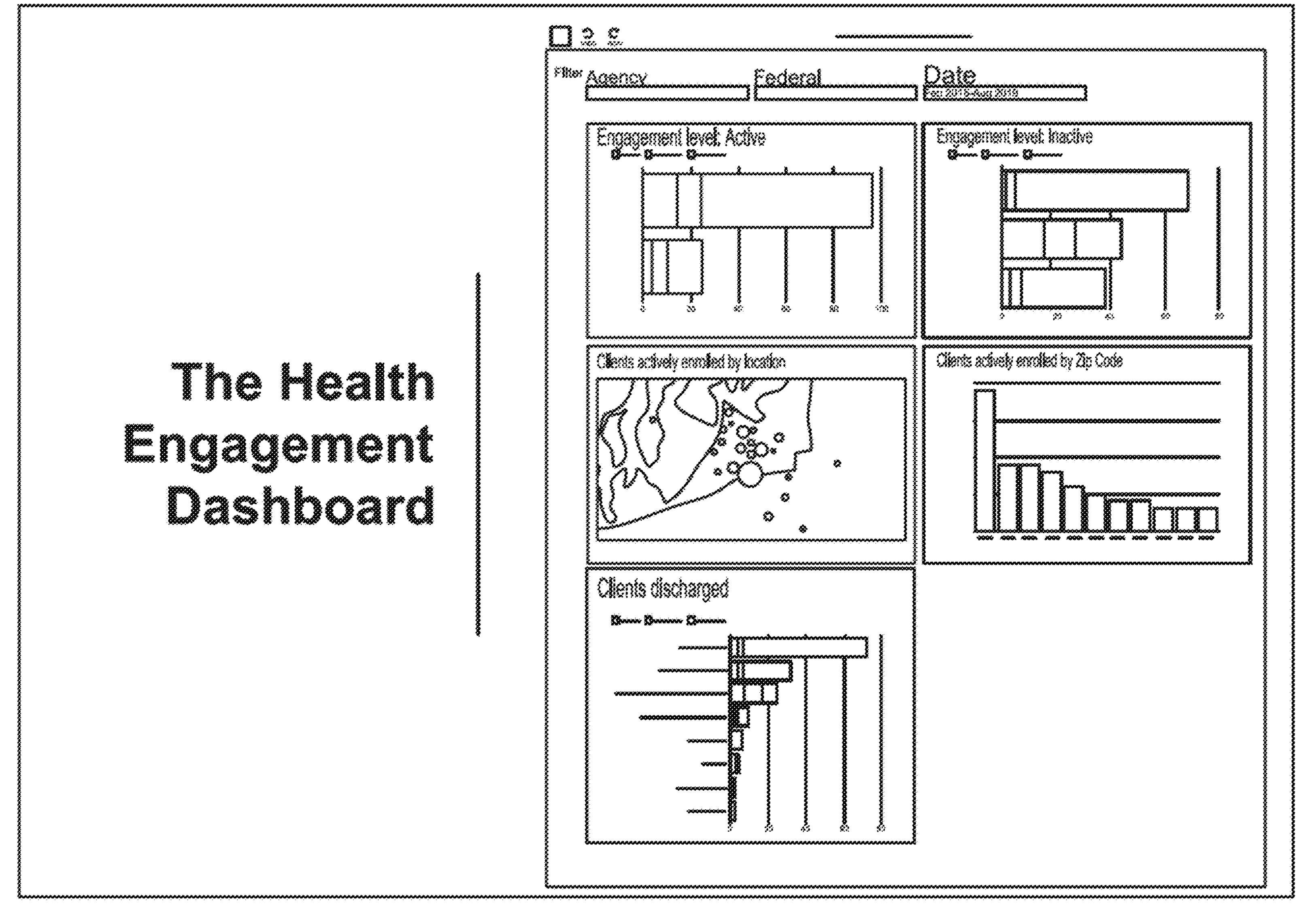
FIG. 42 is an example of a health engagement dashboard.
Figure 44:
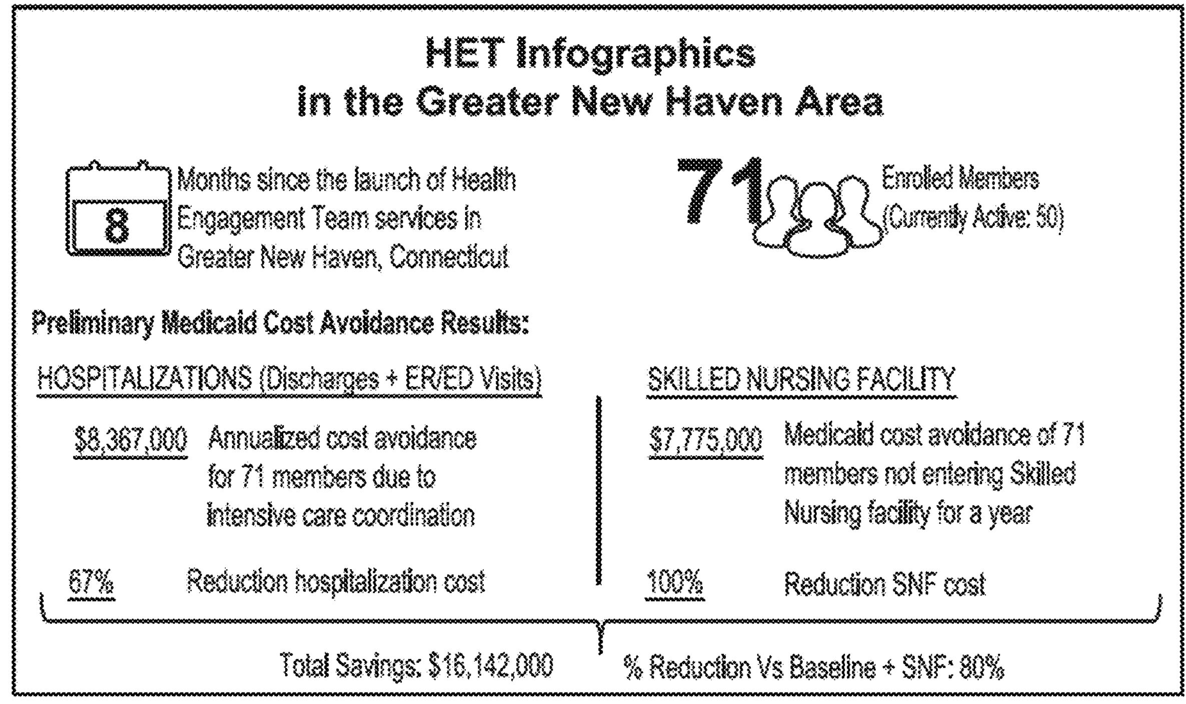
FIG. 44 is chart showing the financial benefits of implementing the Pathways Community HUB model within the Greater New Haven area.
Figure 45:
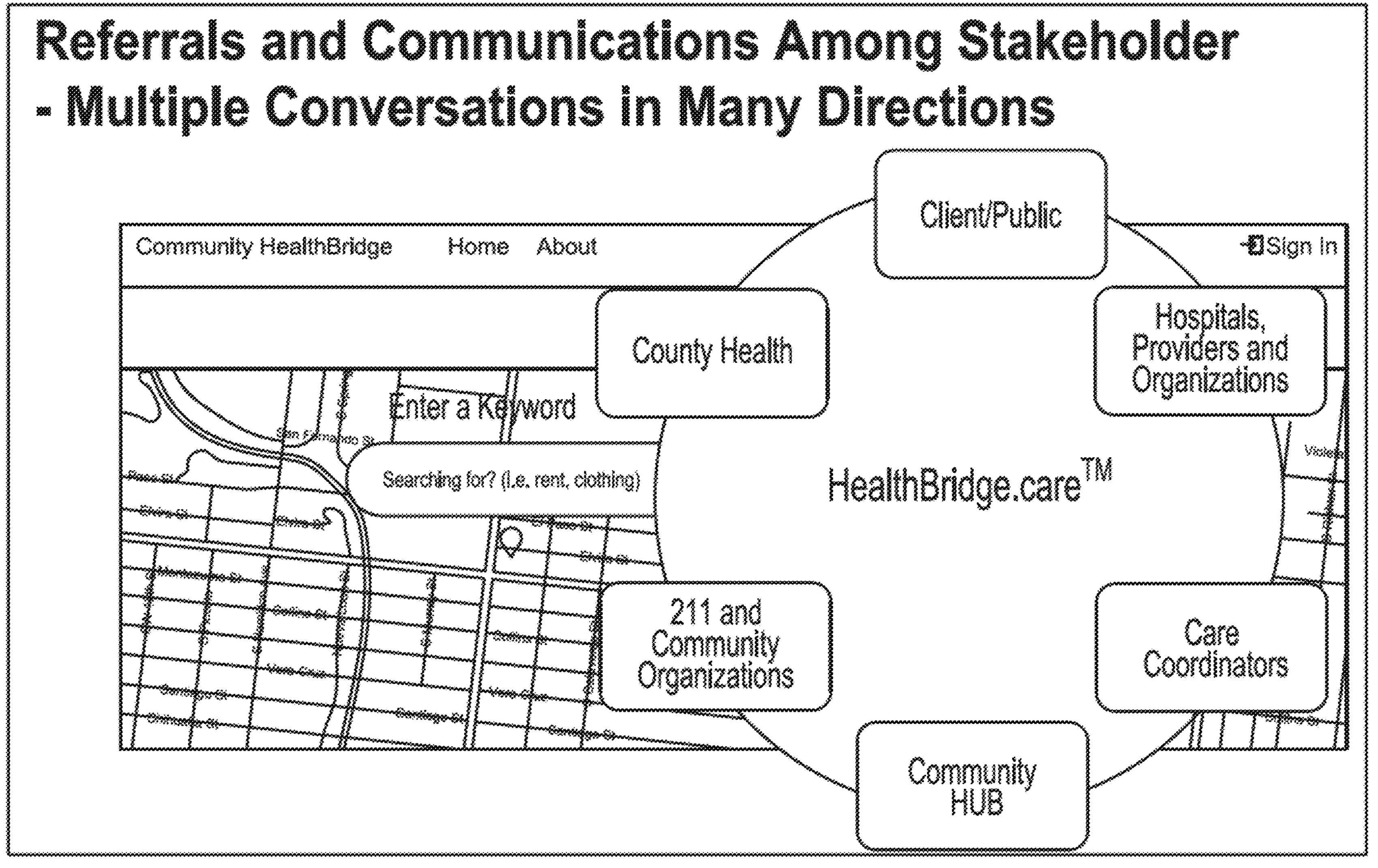
FIG. 45 is a diagram showing how the Care Coordination System software application acts as a central hub connecting Care Coordinators with patients and Care Coordinators and patients with various organizations.
Figure 46:
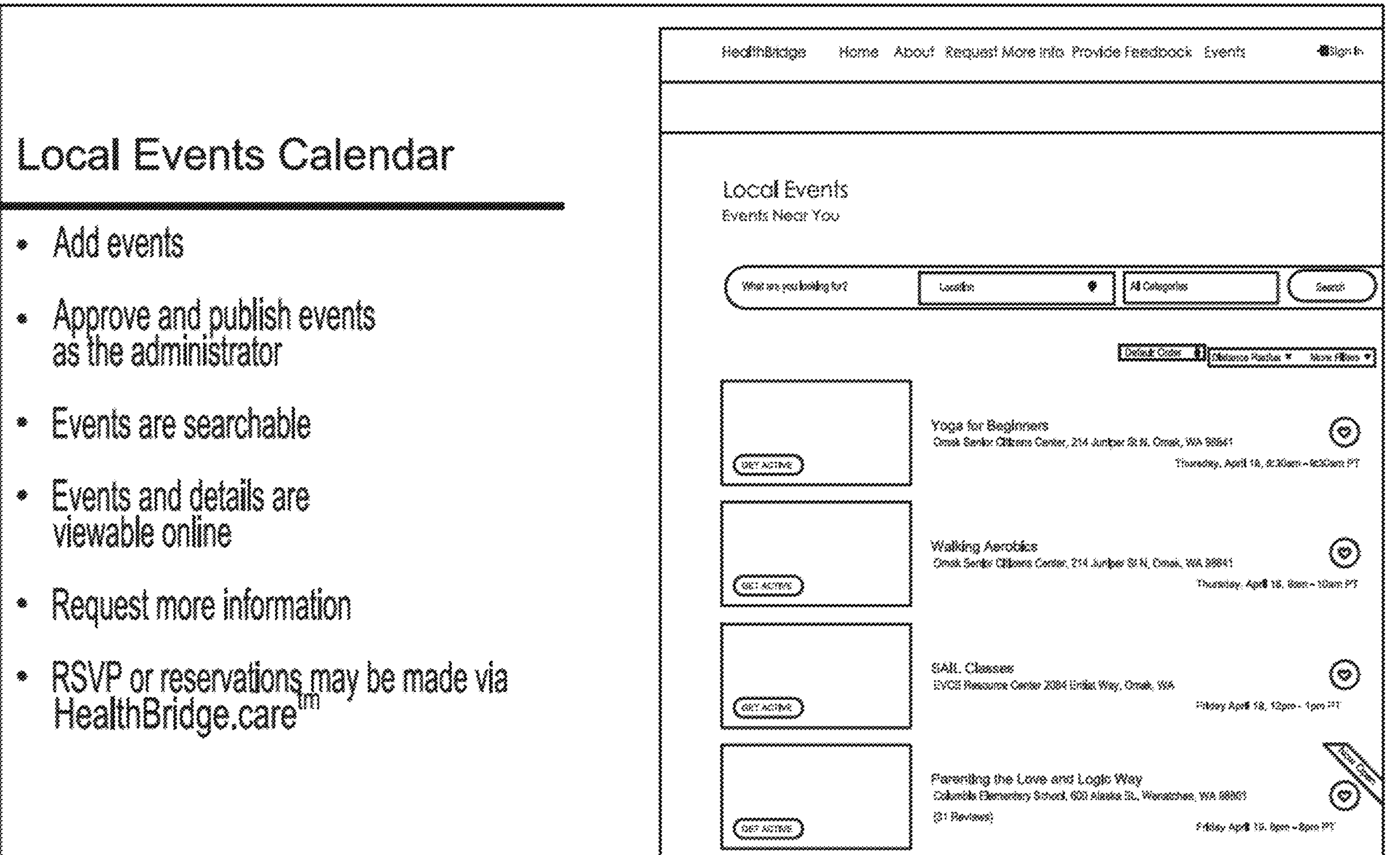
FIGS. 46-54 are screenshots of the Care Coordination System software application.
Figure 47:
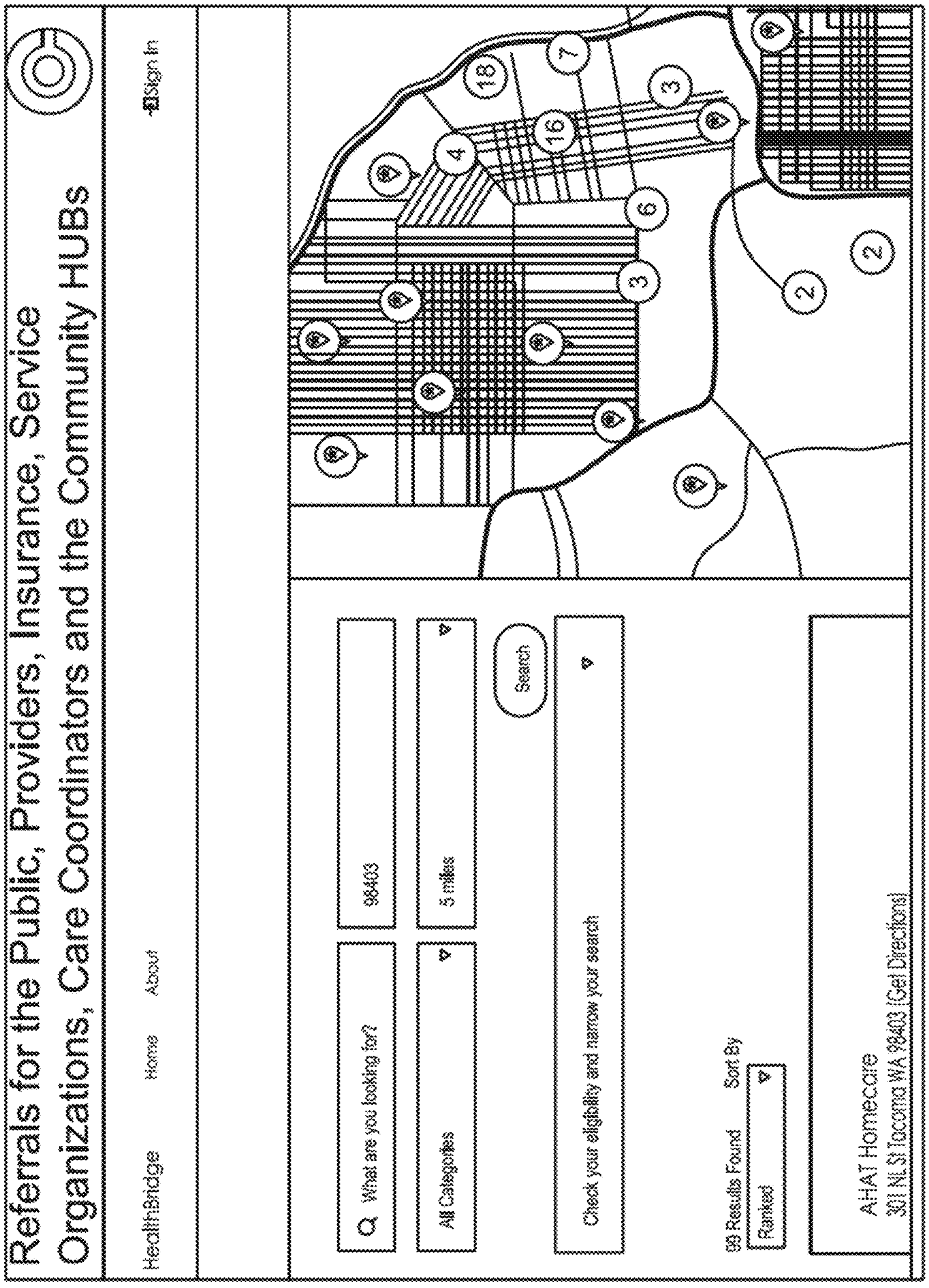
Figure 48:
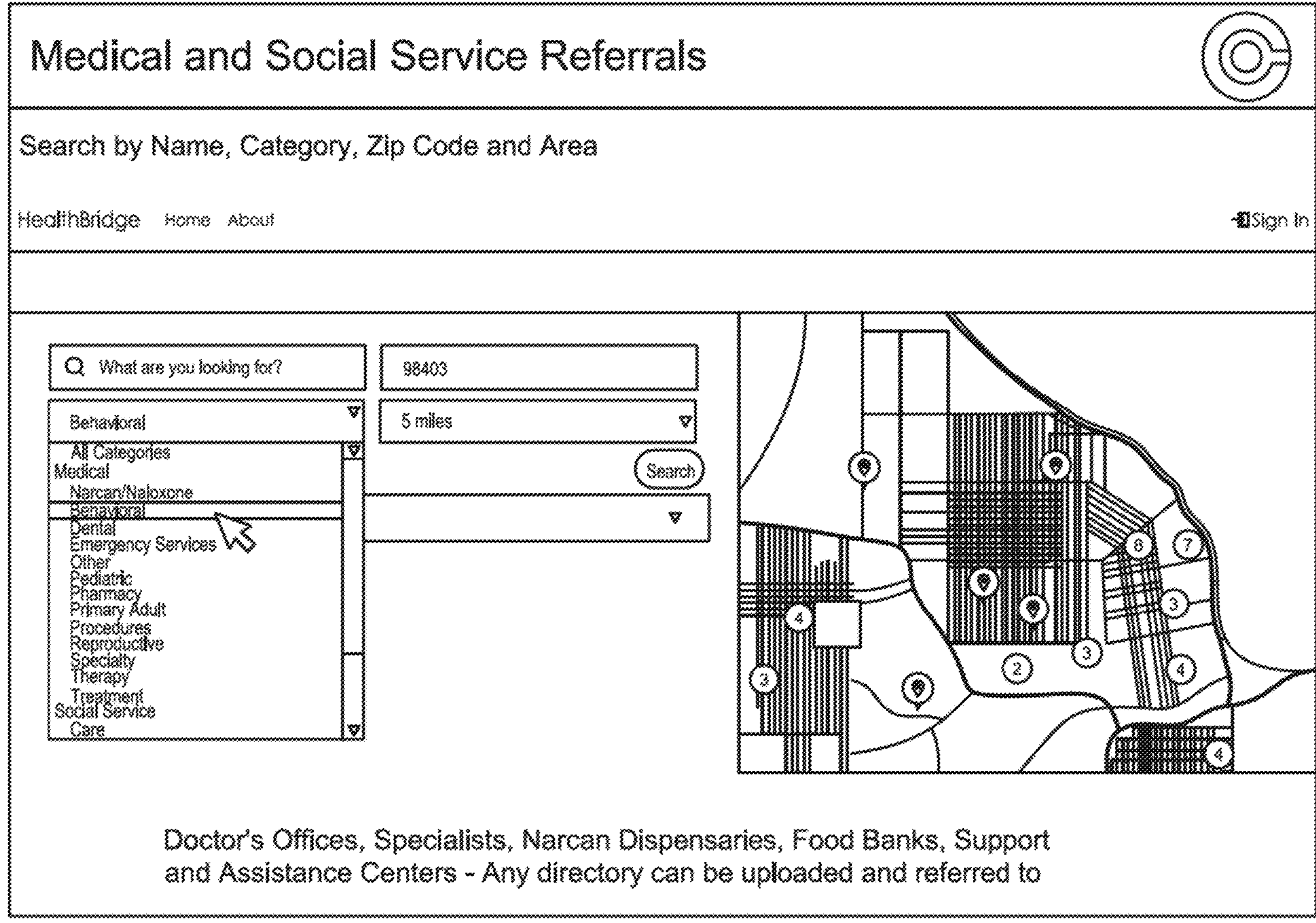
Figure 49:
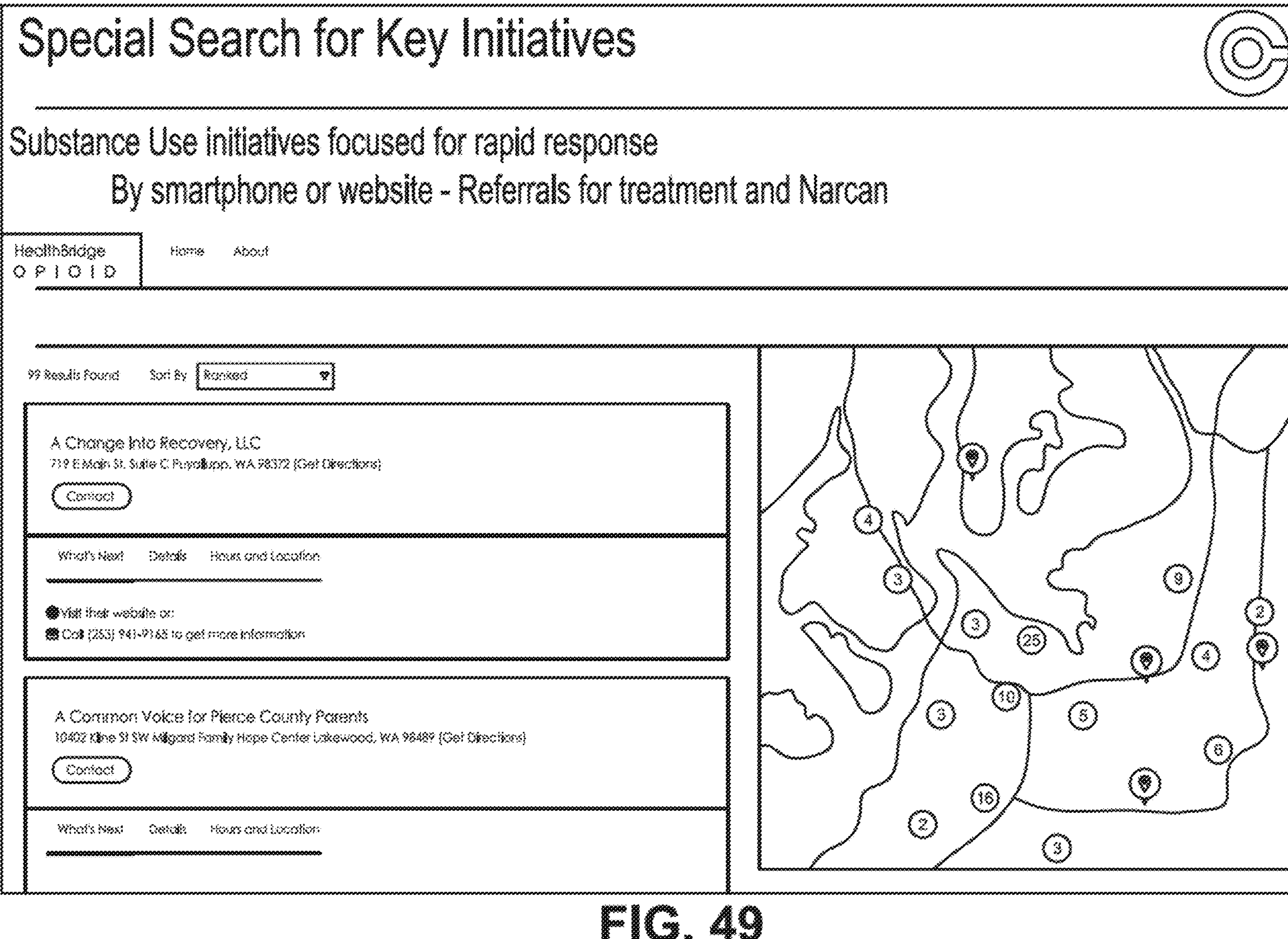
Figure 50:
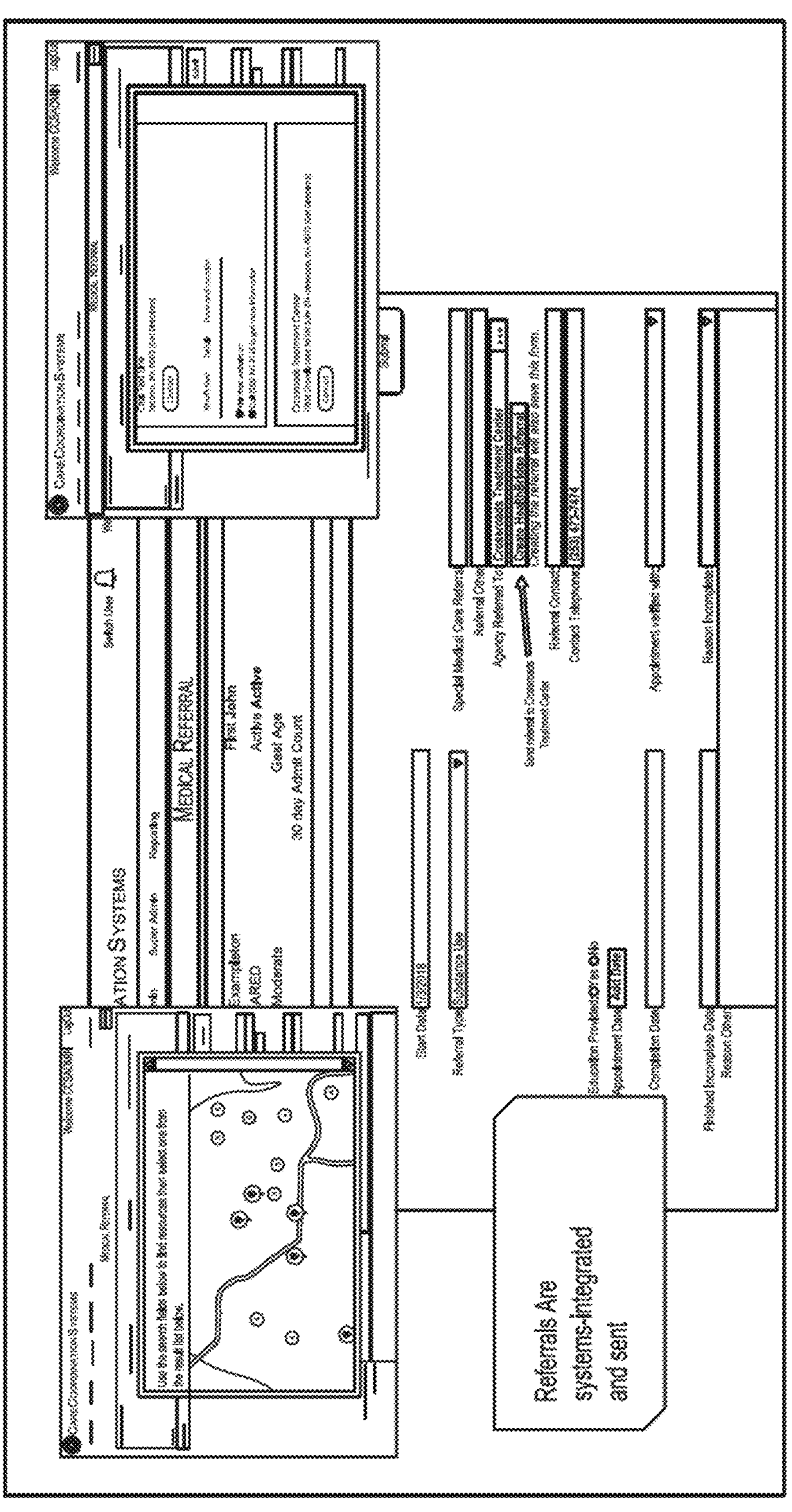
Figure 51:
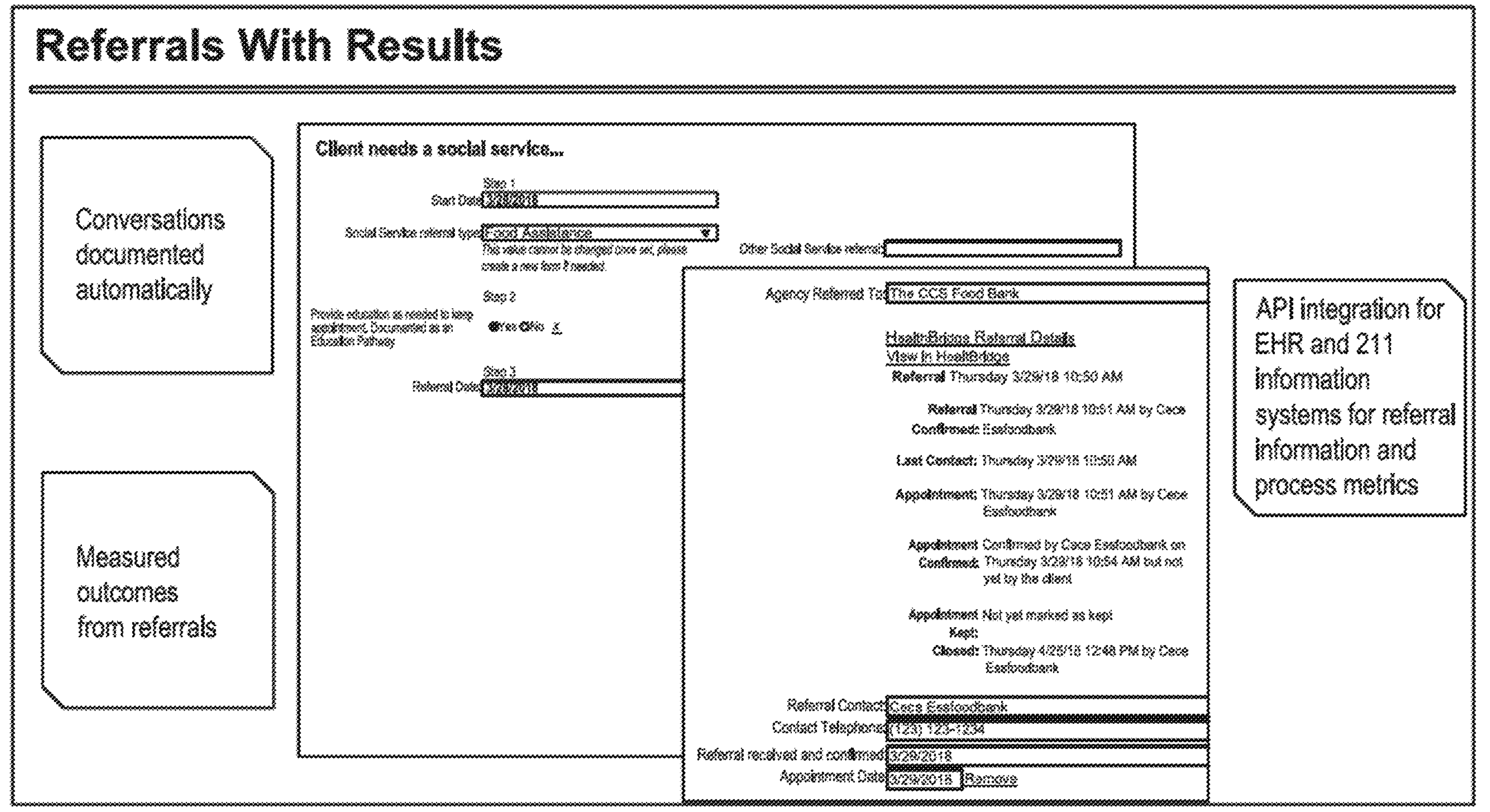
Figure 52:
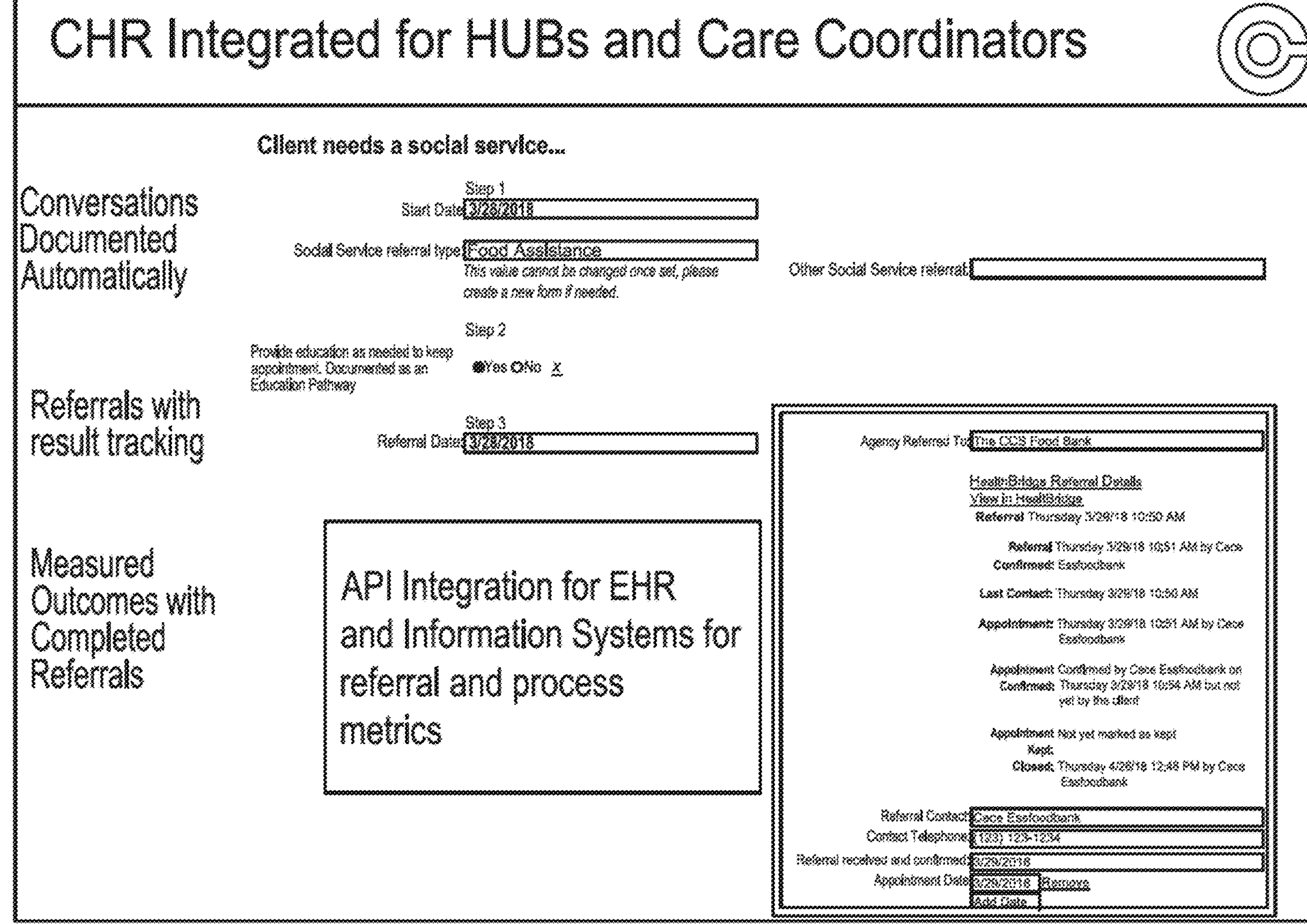
Figure 53:
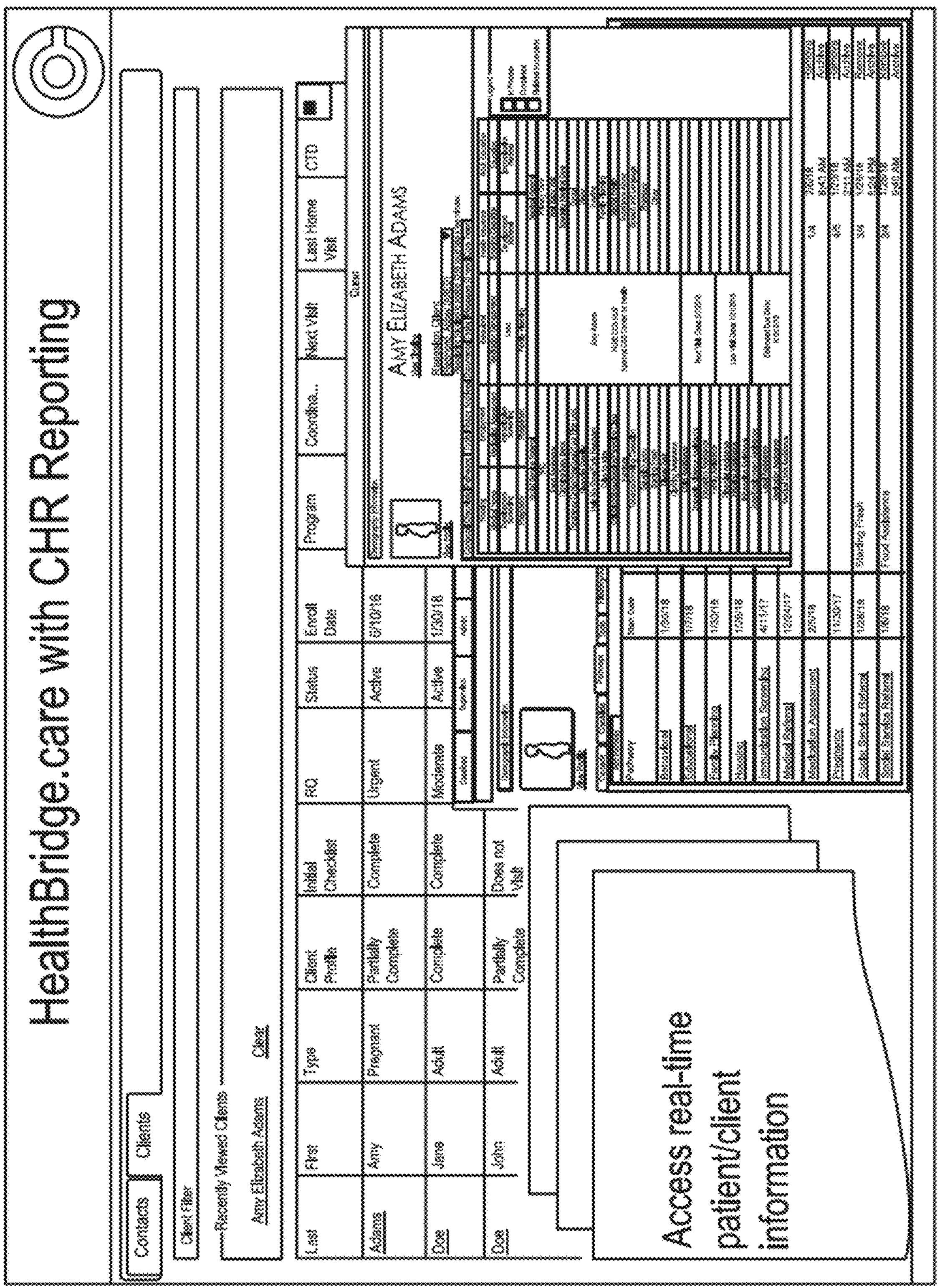
Figure 54:
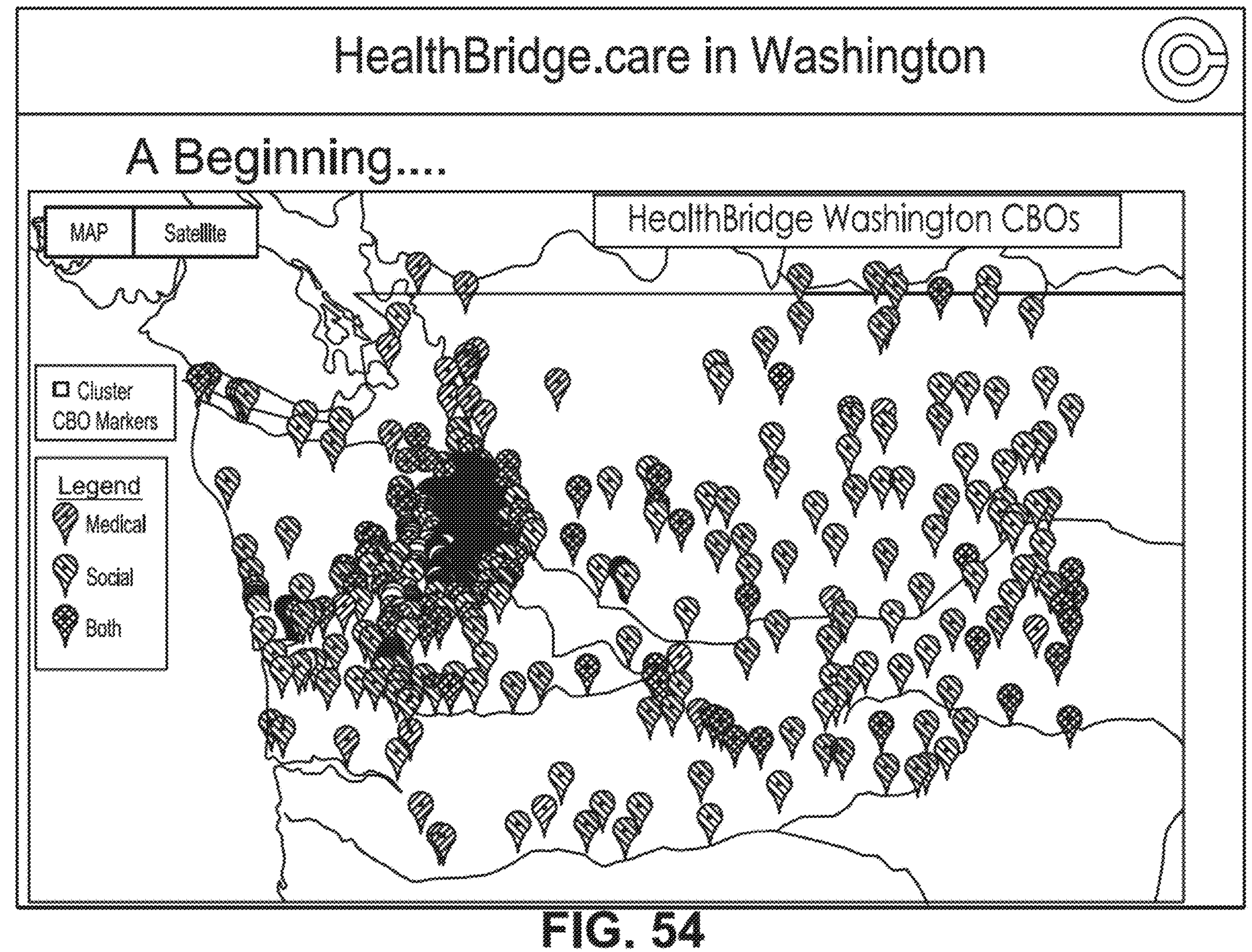
Figure 55:
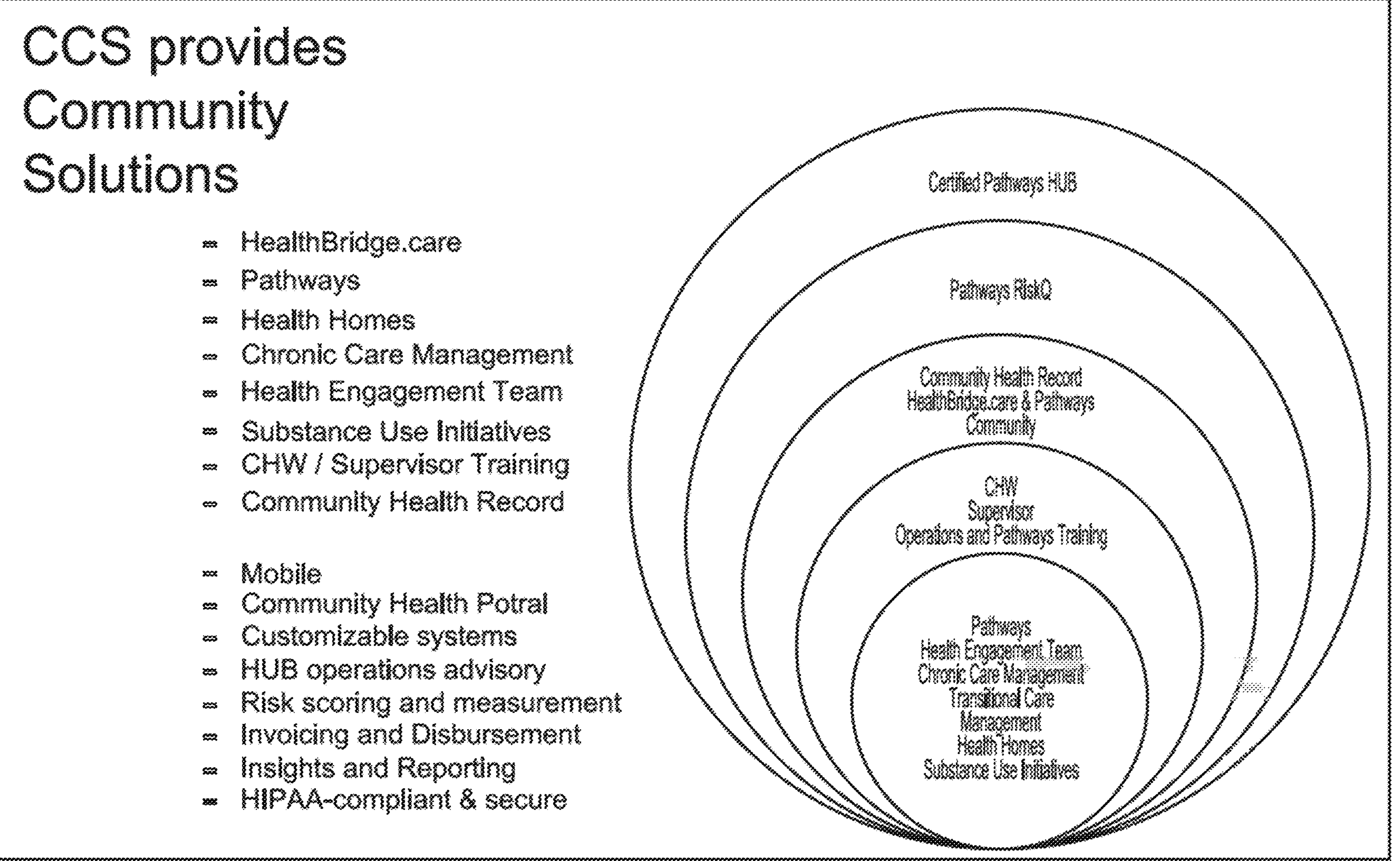
FIG. 55 is a chart showing the integration of component parts of the care coordination system.
Figure 56:
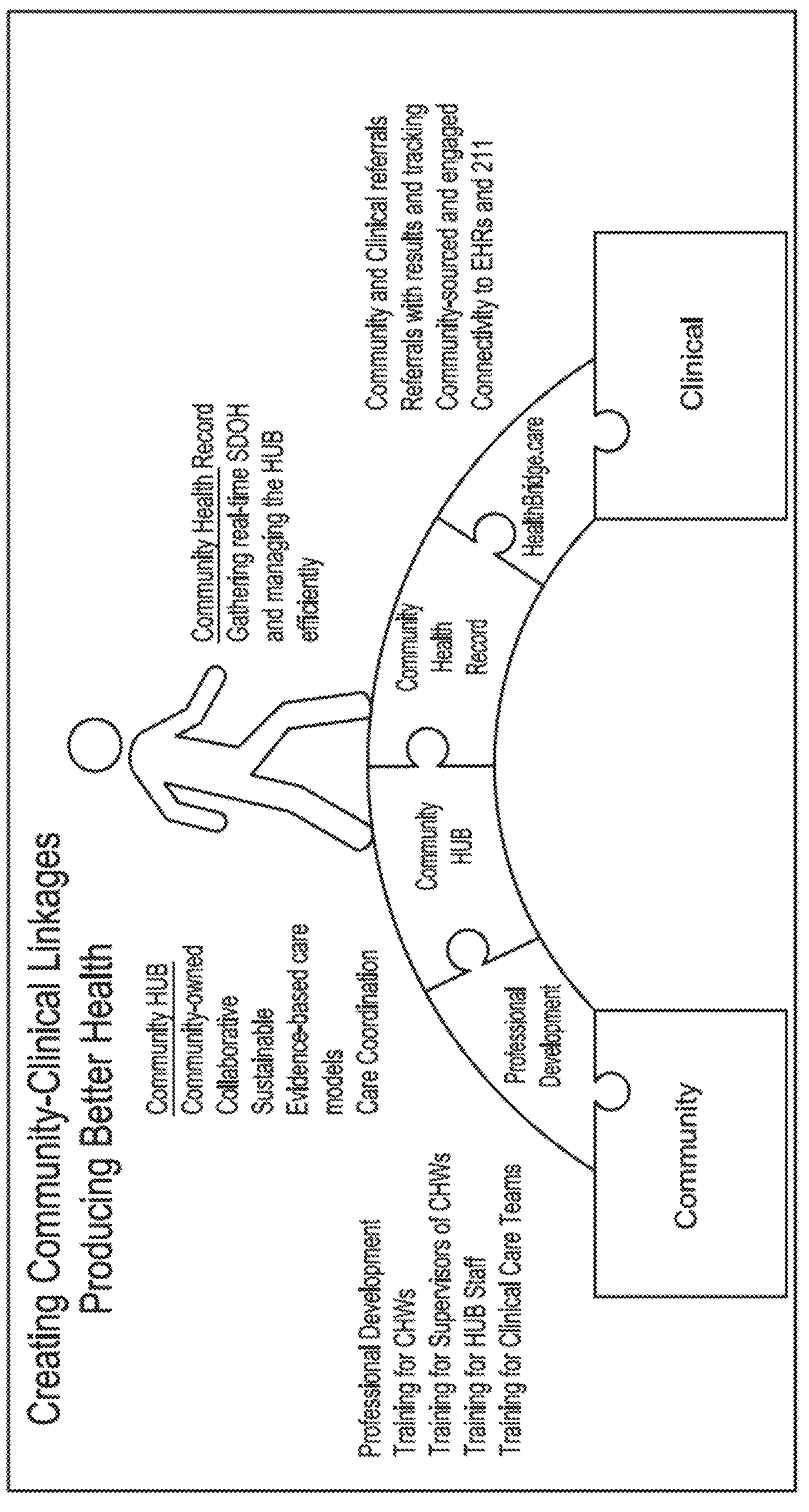
FIG. 56 is a bridge diagram showing how the community to clinical linkage is established.
Figure 57:
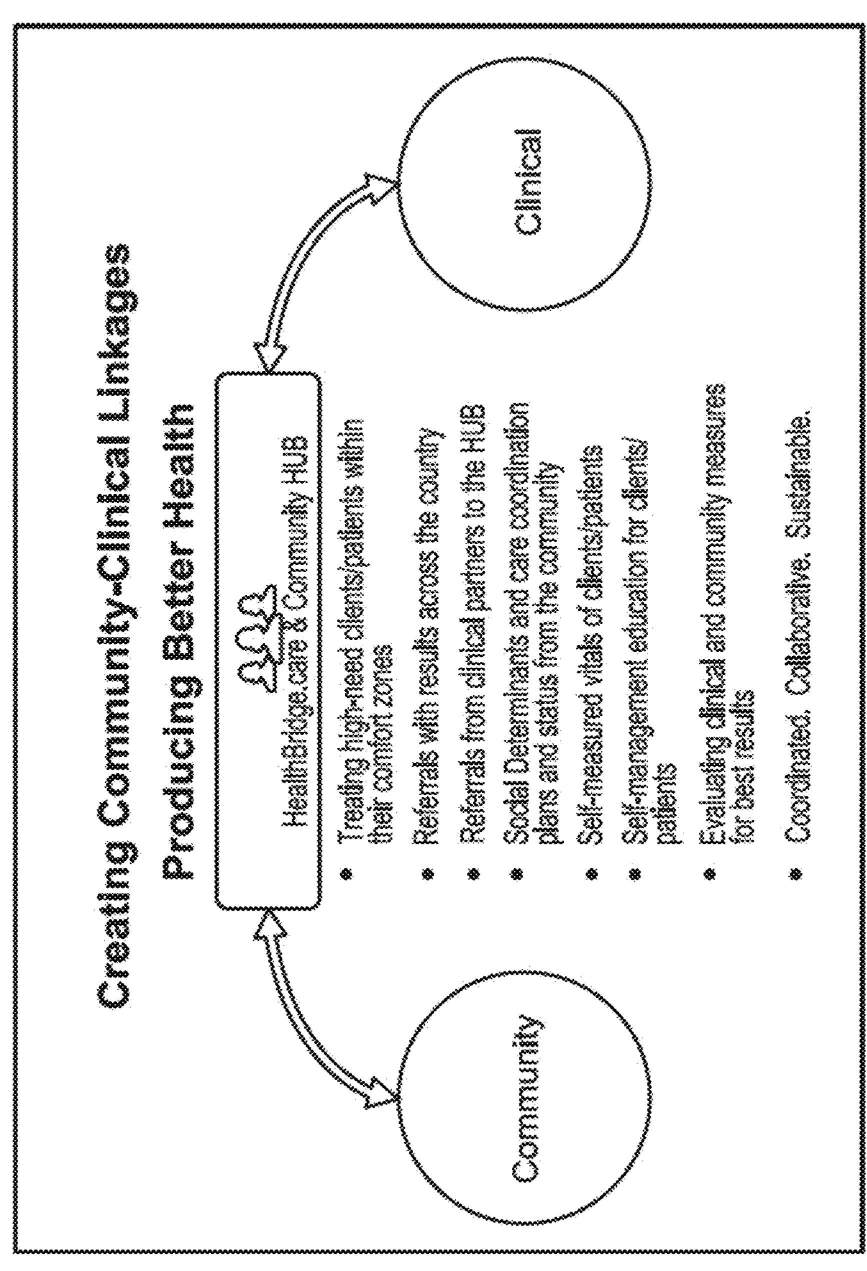
FIGS. 57 and 58 are diagrams which show features of the Care Coordination System software used to establish community to clinical and clinical to community linkages.
Figure 58:
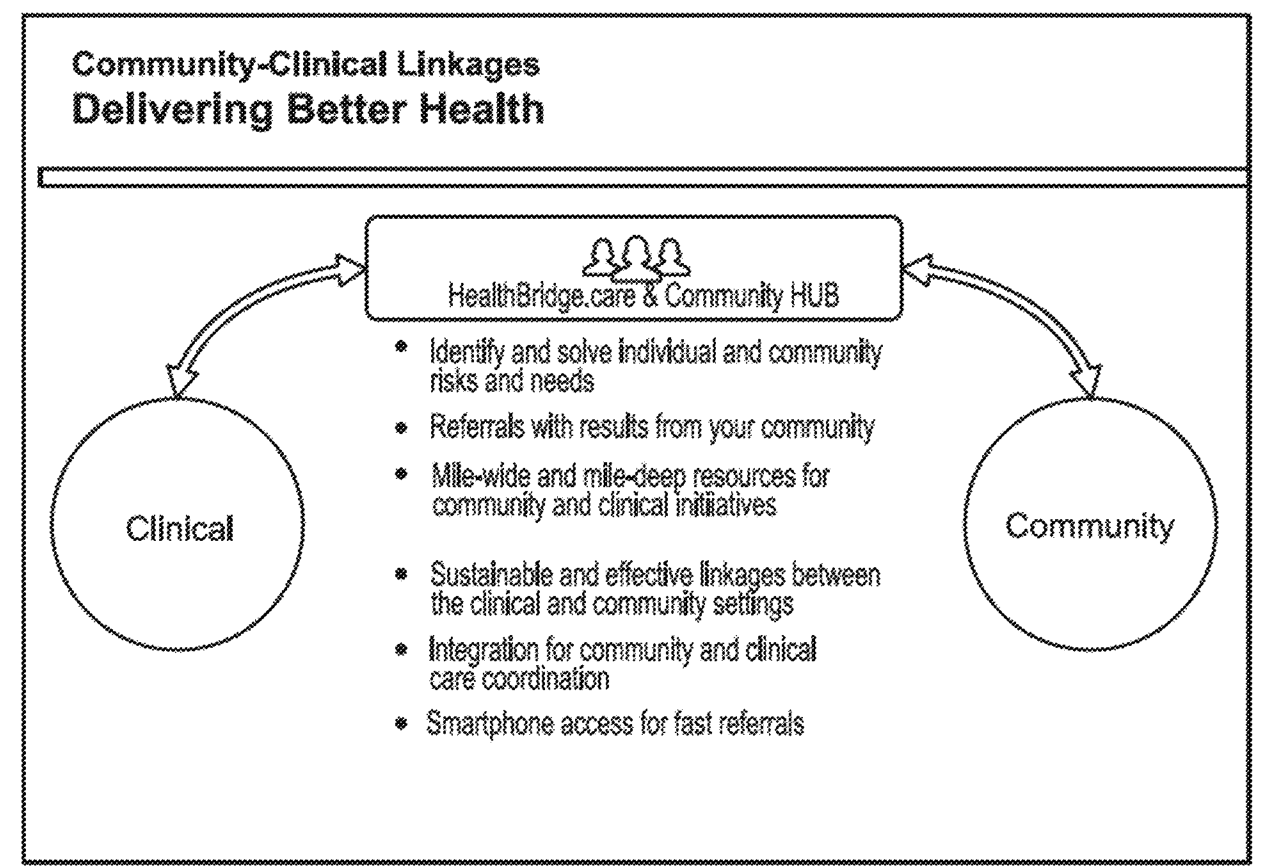
Figure 59:
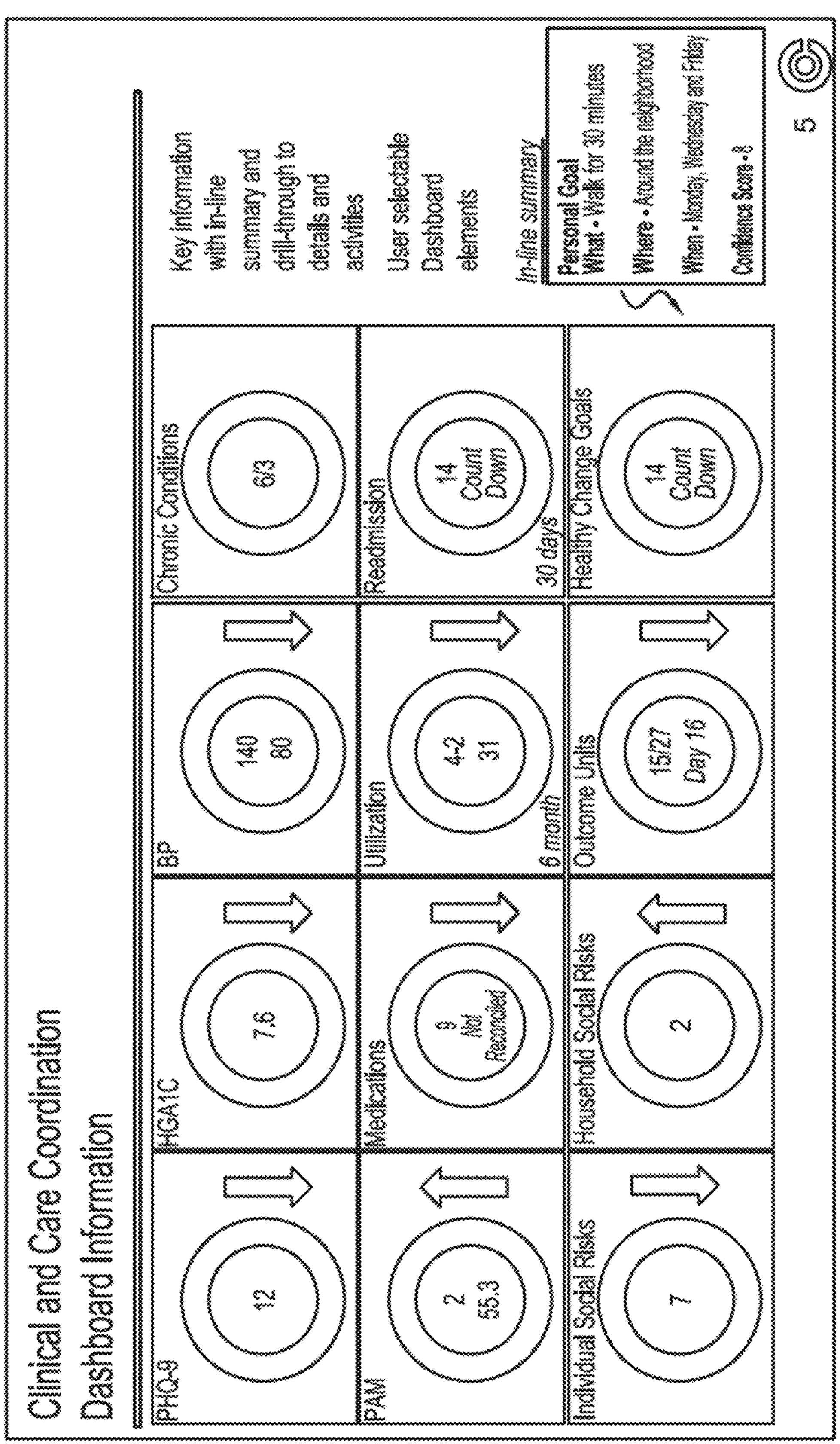
FIG. 59 shows a clinical and care coordination dashboard.
Figure 60:
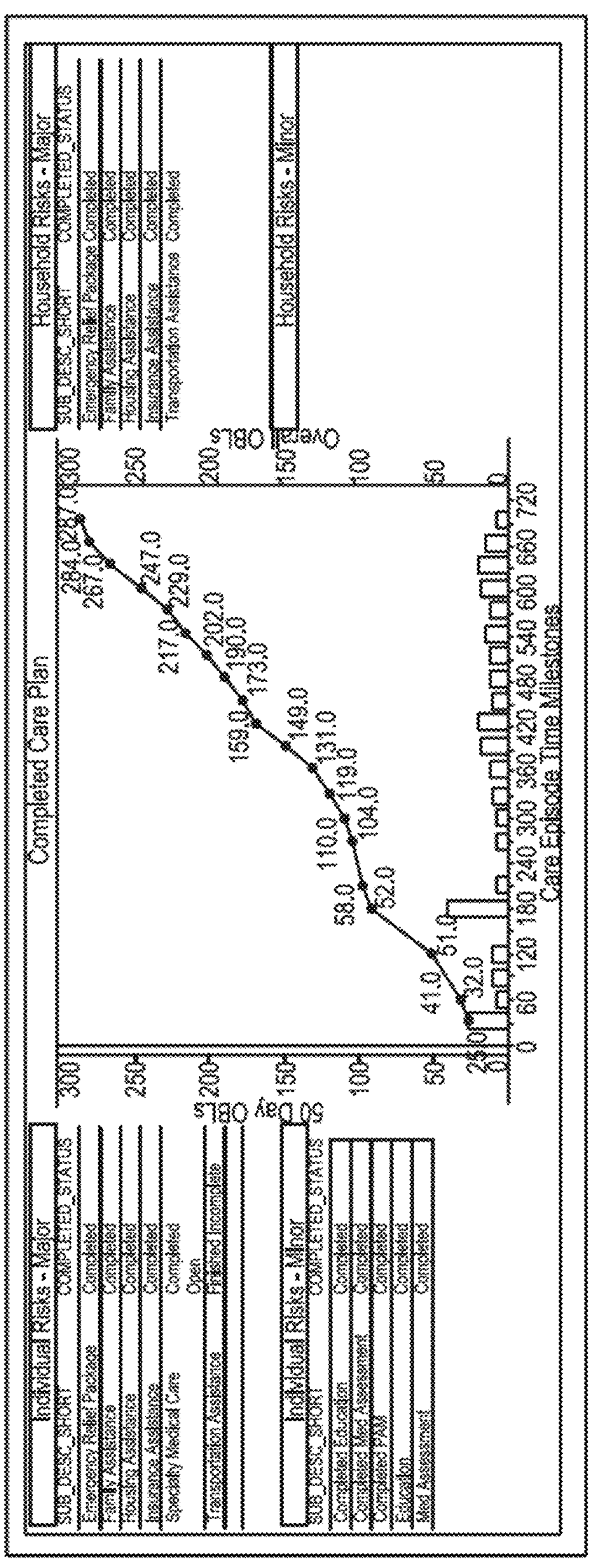
FIG. 60 shows a summary of a completed care plan.
Figure 61:
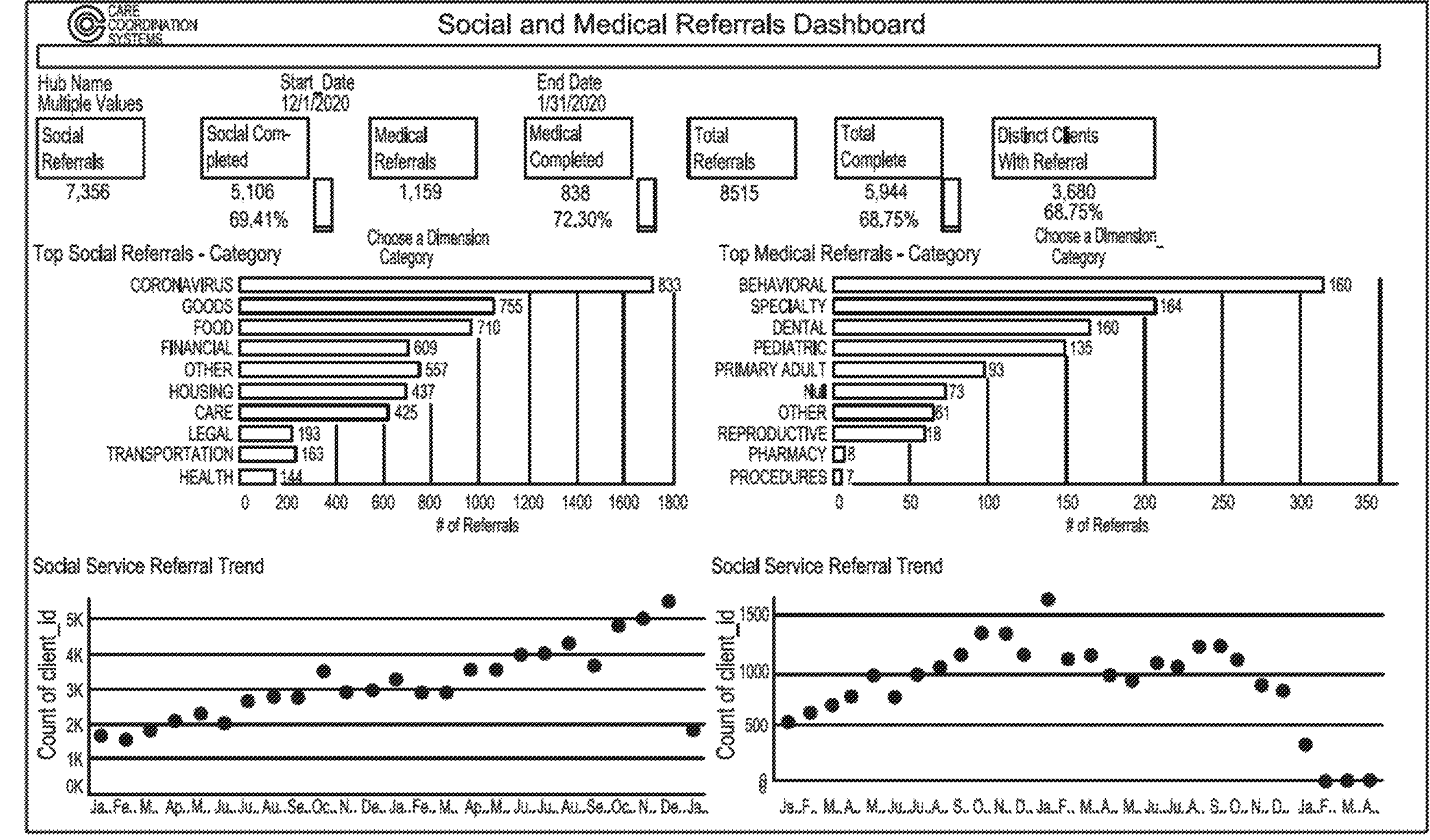
FIG. 61 shows a social and medical referral dashboard.
Figure 62:
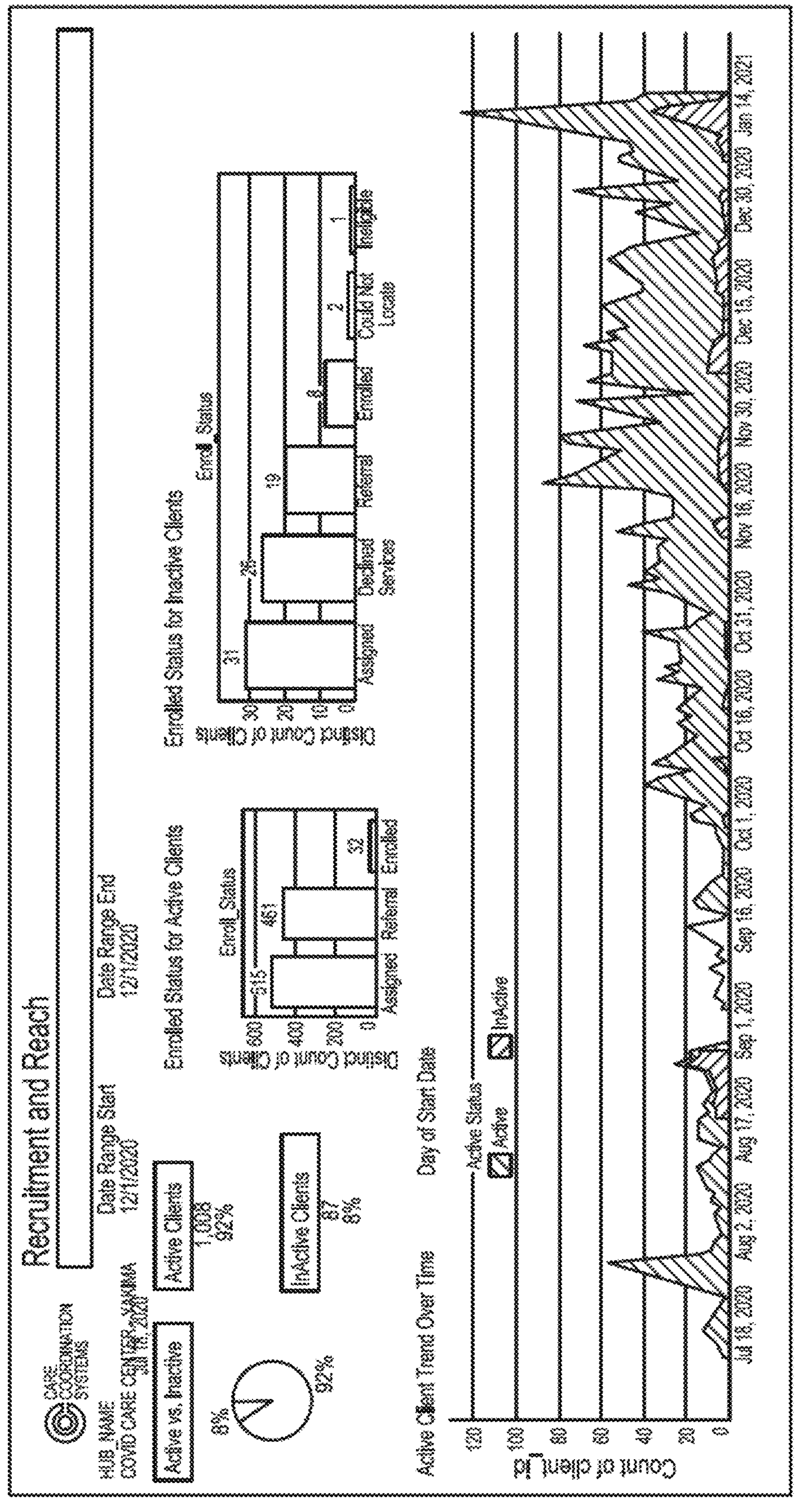
FIGS. 62-65 show various client data.
Figure 63:
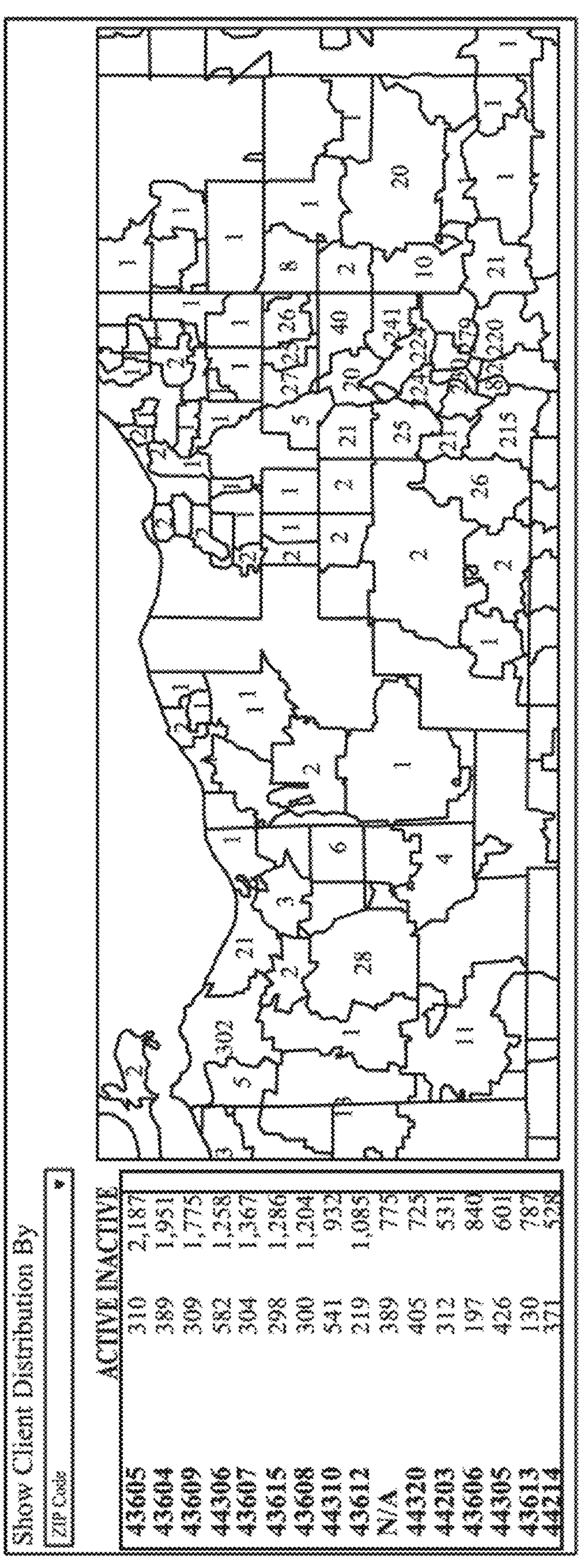
Figures 64, 65:
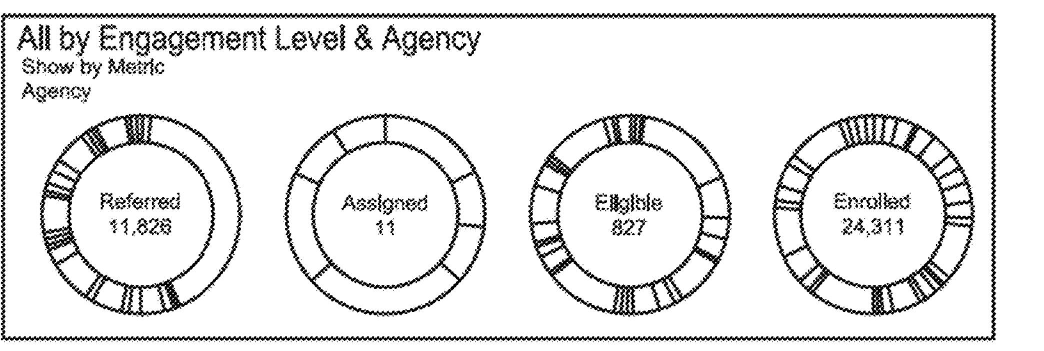
Figure 66:
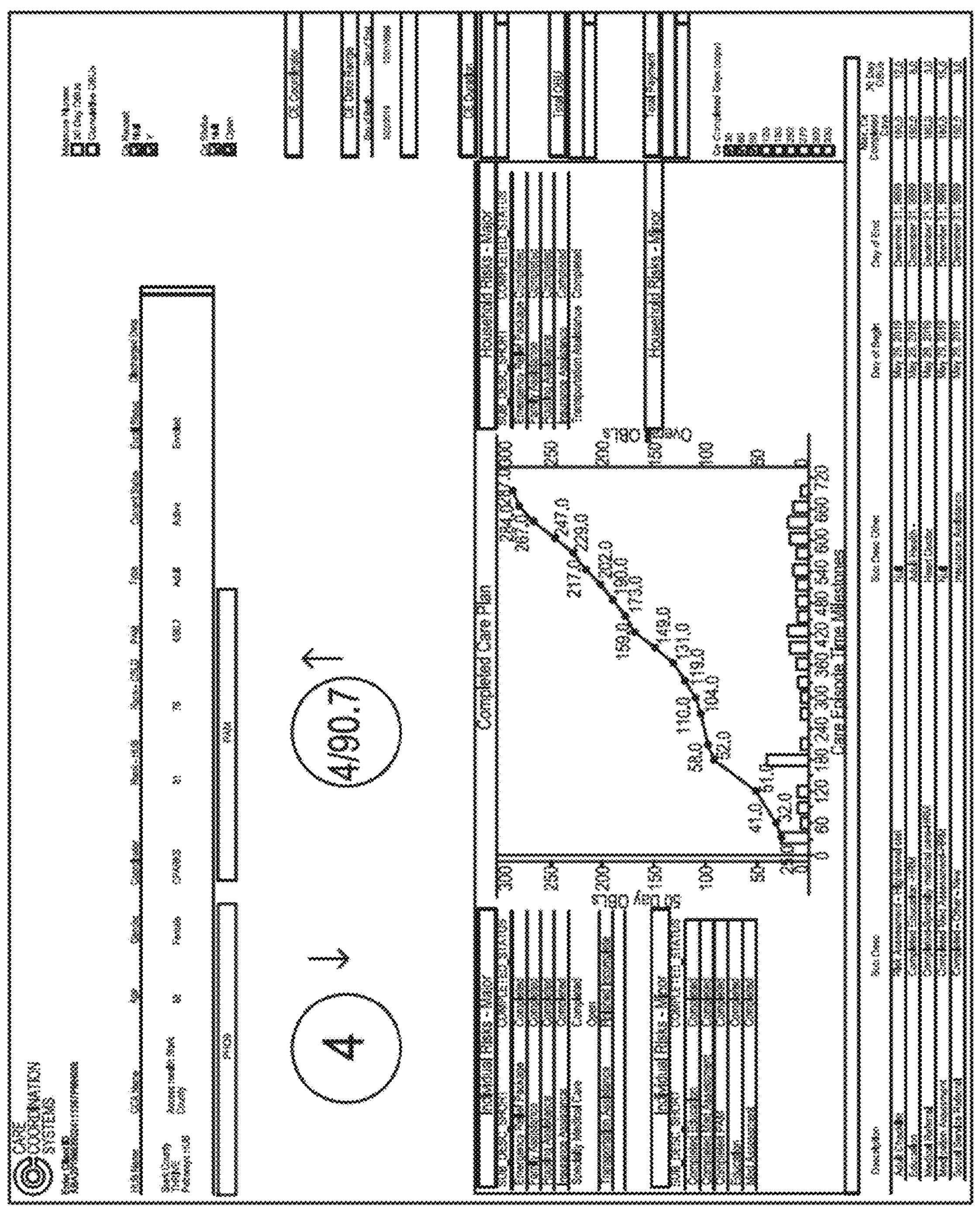
FIG. 66 shows behavioral and clinical information.

Provided is a system and method for creating, using, and managing a Pathways Community Hub. A Pathways Community Hub is a network of care coordination agencies which focus their mission towards reaching individuals having the greatest health-related and socio-economic risks, identifying associated risk factors, and addressing identified risk factors of such individuals. Care coordination agencies typically represent any agency which deploys community care coordinators (CCCs). Community care coordinators include but are not limited to community health workers, nurses, social workers, and others which reach out to individuals within the community and assist them connect with needed care. Care coordination agencies include local community organizations, outreach centers, health departments and care coordinators who are part of a community health center.

The Pathways Community Hub (HUB) is operated by a Hub Agency which leads the network of care coordination agencies and develops contracts and requirements for care coordination agencies to participate within the HUB. Pathways Community Hubs must adhere to certain national standards. Central Hub Agencies obtain national HUB certification through the Pathways Community HUB Institute (HUB Institute). The central Hub Agency ensures that these national standards are adhered to and are built into the accountability, function, and billing process for the hub network.

Communities considering this model need to complete, or have access to, a thorough, up-to-date community needs assessment to determine the population of interest. Examples of recommended strategies for the assessment process include geocoding of health and social data, risk-scoring methodology, screening tools, and key stakeholder surveys that encompass at-risk community members. When the HUB is operational, strategies must be developed not only to "find" the at-risk individuals, but also to engage them in care coordination services.

The HUB is a neutral entity that does not directly provide care coordination services. Rather, the HUB gathers multiple care coordination agencies together into an organized team, trains and supports them to identify those in the community who are at the greatest risk and assesses and tracks each modifiable risk with standardized pathways for treatment. As noted, the HUB does not hire or deploy care coordinators but rather supports, coordinates and tracks outcomes for all agencies that provide direct on-the-ground, community-based care coordination.

When in use, a Pathways Community HUB provides the following three basic services: 1.) Finds at-risk individuals in need of medical, health-related, and/or social services. 2.) Treats the risk-factor identified within the individual patient; and 3) Measures an individual's or patient's risk status over time.

As mentioned above, the HUB model includes a network of agencies that deploy community care coordinators to engage at-risk individuals in a pathways-focused care coordination. By pathways focused, it is meant that a set of treatments are identified for the patient to follow towards wellness.

New clients may be obtained or discovered through referrals or community outreach programs. When referrals for new clients are obtained, the community care coordinator completes all of the required paperwork to protect personal health information and submits it to the HUB. This step is completed before the client is registered as a new client within the HUB. One role for the HUB is to monitor and notify community care coordinators of any duplication of service. Once engaged, the community care coordinator and the patient are linked in the HUB. This allows the HUB to flag further attempts to register the patient for care coordination services. In certain cases, it is permissible for an at-risk patient to have more than one care coordinator, however, the reasons behind this type of decision need to be made clear.

For each risk factor identified by the community care coordinator, a specific standardized Pathway is assigned, and then each Pathway is tracked step by step through completion by the HUB. An at-risk individual may have many Pathways being addressed simultaneously, reflecting multiple health and social issues identified by the community care coordinator. The completion of each Pathway ensures the delivery of one or more evidence-based or best practice interventions to address the risk factor.

Pathways are the standardized outcome measurement tools the HUB tracks. As risk factors are identified and addressed, the Pathways are completed and a reduction in risk is recorded. HUBs need to have the capacity to measure and track an individual's risk status over time. HUBs may identify and treat risk reduction in specific areas, such as health, behavioral health, social factors, and financial security. Data obtained from such Pathways may be used to study the impact of care coordination over time. One element employed by the HUB to effectuate health system transformation is an intense focus on what factors are actually causing the poor health outcomes in a community and how these factors can be addressed most quickly and cost effectively.

The effectiveness of Pathways used both as a single measure and as a comprehensive group of measures has been tested and researched. The model and its impact affirm that like many other effective interventions that require more than one component, more than one risk factor must be addressed to demonstrate changes in health outcomes. A comprehensive assessment and multiple Pathways are employed to achieve a positive outcome. The measurement of specific items within the Pathways and multiple specific Pathways was conducted by Westat as part of a National Institutes of Health initiative.

HUBs must first be certified by the national HUB institute before they may participate within the community. To receive HUB certification by the national HUB Institute, a HUB must use the standardized Pathways. A list of 20 approved Pathways, as well as a chart used with two of the Pathways, is found within FIGS. 4 to 24. Pathways are specifically designed to be clear and concise. New HUBs are not required to use all 20 Pathways when they start up, however, they are expected to gain experience with the Pathways and to develop new Pathways when needed, with the support of the HUB Institute. By standardizing the Pathways, HUBs can compare outcomes across care coordinators, agencies, communities, regions, and States. Standardization also allows the development of universal billing codes to tie payment to outcomes. In Ohio, Medicaid managed care plans have developed contracts based on Pathway completion.

Many communities want to track more comprehensive measures, such as overall reductions in emergency department visits, improvements in hemoglobin A1c, and reductions in hospital readmissions. The HUB continues to track individual Pathways but can also "bundle" Pathways together to achieve a larger objective. For example, to reduce emergency department visits, most individuals may need to receive:

- Ongoing primary care (Medical Home or Medical Referral Pathway);
- Help with medication (Medication Assessment or Medication Management Pathway);
- Education about their conditions, medication, or needed services (Education Pathway);
- Help with housing (Housing Pathway); and
- Help with barriers to connecting to other social services (Social Service Referral Pathway).

The Pathway bundle has a specific billing code, and funders can offer an incentive payment if all of the identified Pathways are successfully completed.

In some situations, some Pathways may not be completed, and the desired outcomes may not be reached for a given individual. In such cases, the Pathway still needs to be closed. The HUB record such cases as "finished incomplete." Pathway incompletion data is monitored by the HUB. The community care coordinator is required to document why the Pathway was not successfully completed. The HUB tracks which Pathways are not completed and compiles the reasons. For example, Pathways may not be completed because the resources are not available in a community. The community uses this data provided by the HUB to evaluate gaps in services and other issues that can be addressed on a policy level.

Pathways are the metric that focuses on successful resolution of an identified issue. Pathways are also the mechanism the HUB uses to tie financial accountability to completion. Completion of Pathways have demonstrated a significant improvement in patient outcomes and cost savings. The HUB provides the infrastructure communities need to support multiple and diverse agencies and related resources so they can work collaboratively to address health inequities and achieve real improvements for at-risk individuals.

Pathways Community HUBs may start in a variety of ways. Most HUBs have developed through the efforts of a small group of community-focused individuals determined to make a difference for their most at-risk citizens. For example, a HUB may start with the dedication of a few individuals such as community organizers, physicians, and community leaders. HUBs are transformative by design, and it takes a determined core group of individuals with vision and dedication to make a HUB a reality. The HUB's primary focus starts with finding those most at risk in the community and ensuring that risk is reduced. This leads to better health outcomes and lower costs. The right community partners are engaged in the process to allow the appropriate connections to be established in building the network. A sense of community support and ownership lends ongoing support to the HUB. Most communities begin with a segment of the at-risk population, such as high-risk pregnant women, adults with multiple chronic conditions, or frequent users of hospital emergency departments. Once the infrastructure is in place, HUBs are designed to grow as the community gains experience with the model. Pathway funders are engaged at the very beginning of the community discussion about implementing a HUB. Health plans, hospitals, social service agencies, accountable care organizations (ACOs), foundations, and other identified "Pathway purchasers" are involved in defining the at-risk population and standard Pathways to be used. Care coordination agencies move from working in competitive silos to working as an unduplicated team with contracts and payments focused on outcomes in an accountable, business-focused model. Strong care coordination agencies that are effectively serving high-risk community members typically find that their reimbursement is increased with the HUB approach. Agencies that are not successfully engaging at-risk individuals or that do not follow up to connect them to services typically do not do well with this model. Payment is based on outcomes, and agencies must be able to confirm that risk factors have been effectively addressed. To achieve sustainability, the HUB develops and works toward expanding the number of funders supporting the HUB network. Agreements with the funders are designed to reflect the risk identification and risk reduction components of the HUB model. The HUB Institute has developed coding strategies for Pathways that can be used with multiple funders to achieve "braided funding." Individuals at high risk for poor health outcomes have many different risk factors, and one funder usually cannot cover all the Pathways that need to be addressed. Identifying which funders will pay for specific Pathways is employed to develop braided funding and to adequately funding the community care coordinator. As community care coordinators in the field start to reach out and engage those at greatest risk, they begin the data collection process by completing the comprehensive assessment. As they use Pathways to address the risk factors identified by the assessment, the HUB provides an effective data flow and evaluation methodology to the community care coordinators that is easily accessible as well as simple operational reports for community care coordinators, supervisors, and administrators. These reports allow a quick view of how this "outcome production" process is proceeding at all levels: individual, community care coordinators caseload, agency, and across the entire HUB network. The reports are employed for the model to reach its maximum potential. The questions that reports answer include: "Are we reaching those at greatest risk?"; "What risk factors are being identified within the population we are serving?"; "How much time does it take to address these risk factors?"; "Which care coordinators and which agencies are able to address the risk factors the fastest?"; "What strategies are the most efficient care coordinators and agencies using to quickly address the risk factors?"; and "What risk factors are taking the longest to address or cannot be addressed, and what are the reasons?" Obtaining effective technical support and carefully understanding the evidence-based standards and principles of the HUB model are components of effective HUBs. The HUB Institute provides technical assistance in key areas of model implementation, especially in support of the national standards. The original Community Care Coordination Learning Network (CCCLN), supported by the Agency for Healthcare Research and Quality (AHRQ), provides the foundation for the development of the national certification process. There are also vendors available to provide operational support to HUBs with regard to implementation, training, technology, and contracting for care coordination services. Newly developed and existing HUBs are designed to focus on and work toward national HUB certification. When the CCCLN evaluated HUBs that developed over the past 10 years, it found that as many as one-third were not successful or sustainable. HUBs that did not seek specific technical support for the model and did not focus on the evidence-based standards were unable to demonstrate outcomes. It is very difficult to make a case to funders to support the HUB infrastructure without demonstrating improved outcomes and reduced costs. HUBs that focus on the national standards and enroll in certification demonstrate significantly better outcomes and sustainability.

HUB directors, public health leaders, third party payers, policymakers, and other community stakeholders have requested certification of the HUB model. This certification provides standards and expectations for HUB implementers and payers. The HUB Institute—with funding from the Kresge Foundation and in partnership with the Community Health Access Project, Communities Joined in Action, Georgia Health Policy Center, and Rockville Institute—is leading the HUB certification process. Certification supports current and future HUBs by requiring (1) the evidence-based and best practice components known to be essential for high-quality community care coordination services and (2) an efficient regional infrastructure that can lead to improved health outcomes and reduced costs. The standards support a basic framework of quality that encourages local variation and innovation within various cultural and geographic settings. Certification enables funders and policymakers to make wise investments in care coordination services that ensure quality, health improvement, and the value of contracted services. The complete prerequisites and standards for HUB certification can be found on the HUB Institute Web page. This section highlights some of the key elements that are required.

By definition, the HUB is a neutral and independent legal entity that has legal capacity to enter into agreements or contracts. Many of the certification prerequisites and standards tie directly into the governance of the HUB, including the following items.

Governance Documents

1. The HUB coordinates a network of care coordination agencies serving at-risk clients. The HUB has legal documents describing the relationship between the HUB and care coordination agency members. The HUB model is designed to use what is already working in communities, including existing care coordinators and agencies. Most communities have funding in place for a variety of care coordination work, but the infrastructure for creating a network of agencies together is lacking.
2. The HUB has contracts with a minimum of two payers to ensure comprehensive and sustainable care coordination services. Contracts confirm that a minimum of 50 percent of all payments are related to an individual's intermediate and final outcomes/Pathway steps.
3. The HUB documents that it complies with the Health Information Privacy and Accountability Act through training, policies, and signed agreements.
4. The HUB operates in a transparent and accountable manner and has policies around conflict of interest and distribution of referrals to care coordination agency members. It is a requirement that the HUB not directly provide care coordination services.

Needs Assessment

The HUB reviews and/or conducts community needs assessments. This assessment should include local data specific to medical, behavioral health, social, environmental, and educational factors and guide the HUB in its efforts to improve health and reduce inequities. The HUB needs to show how it uses the community needs assessment to identify the populations to be targeted for community care coordination services.

Care Coordination Program Requirements

The HUB creates agreements with each care coordination agency to delineate expectations around hiring, training, and supervision of CCCs. In addition, the administrative staff of the community agencies need training and support to become part of a network of agencies focused on finding those most at risk and connecting them to care. Experienced, capable, and creative HUB leadership is needed to help agencies move away from being competitive silos and make the transition toward functioning as a team.

The HUB is responsible for monitoring the performance of its care coordination agency members and for improving the quality of care coordination services. Written agreements are required to ensure clarity and transparency of the roles of the HUB and care coordination agency members and the financial arrangements between them.

Many of the HUB standards define policies and expectations for participating programs, agencies, and providers or for community care coordination services. It is required that the HUB have operational policies and procedures in place that cover client enrollment, allocation and monitoring of referrals, documentation requirements, ratios of CCCs to clients, and other key operational items.

Data Collection and Payment System Linked to Outcomes Pathways

The HUB is required to use standardized Pathways approved by the HUB Institute. Pathways are to be used as defined, and new Pathways cannot be developed without submission to the HUB Institute for review. Pathways outline key stages required for the delivery of high-quality and efficient care coordination services. Each Pathway focuses on one significant client need or problem and identifies and documents the key steps that lead to a desired, measurable outcome. In addition, standardized Pathways allow research, evaluation, and best practices using standard metrics.

The 20 standardized Pathways link billing codes to Pathway steps. Payment for outcomes is a key component of the HUB model and promotes accountability, quality, equity, health improvement, and value. Contracts with payers must specify that at least 50 percent of all payments are related to an individual's intermediate and final Pathway steps. Prior to the launch of HUB operations, a tracking and payment system must be developed that rewards participating organizations and individuals based on the completion of Pathways. Participating agencies within a HUB must be rewarded and incentivized to work in collaboration with other agencies to reach those at greatest risk and connect them to care, recognizing that those individuals require more time and expertise to serve.

Client Information

The HUB collects client demographics and other relevant information to effectively address the medical, behavioral health, social, environmental, and educational needs of the at-risk client. FIG. 25 is an example of a demographic intake form, which is used to obtain key information about the client upon enrollment in the HUB. Checklists capture specific information about the client's health and social issues at each face-to-face encounter. The checklists should document any identified risk factors and provide information for the initiation of Pathways. A more comprehensive checklist is used at the initial visit, and shorter checklists are used on an ongoing basis to monitor changes between visits. FIG. 26 is an example of a checklist used for adult clients. Other client information can be gathered through standard tools or screens, such as the Patient Health Questionnaire (PHQ), a depression screener; Ages & Stages Questionnaire (ASQ); and Patient Activation Measure (PAM).

Risk Assessment

To ensure an at-risk individual's needs are being addressed and met—and an efficient use of limited resources—the HUB assesses and monitors each client's risk factors. The HUB describes how risk measurement translates into intensity of care coordination services.

Data System

The HUB tracks, monitors, and reports on client services and promotes collaboration, intersectoral teamwork, and community-clinical linkages. Although a complex data system is not mandatory, the HUB develops accurate and efficient methods for tracking and monitoring data collection for at-risk clients. Most HUBs will rely on information technology to perform this task. Whatever approach is used, this system ensures the protection of client information at all times. The HUB ensures that clients (1) are identified and engaged; (2) are evaluated to determine their needs, risk factors, and risk level; (3) have an individualized care plan; (4) are assigned to appropriate standardized Pathways; (5) are monitored through the completion of the appropriate Pathways; (6) receive home visits; (7) are reevaluated to determine needs, risk level, and service adjustments; and (8) are discharged when their needs are met. Communication and data sharing among practitioners, agencies, community care coordinators, and the client help ensure quality and continuity of services.

Quality Assurance

The HUB is responsible for monitoring and improving the quality of care coordination services provided to those who are at risk. Therefore, the HUB has a quality improvement plan and regularly evaluates its services as well as those services provided by care coordination agency members. The HUB quality improvement plan should describe how quality improvement projects are selected, managed, and monitored. The HUB implements a communication strategy that covers planned quality improvement activities and processes and how updates will be communicated regularly to all involved.

The HUB is to also monitor the performance of its care coordination agency members and offer technical assistance to ensure quality and client safety.

Community Care Coordinator Requirements and Training

Many different types of professionals can serve as community care coordinators, including but not limited to social workers, community health workers, nurses, and case managers. By definition, these individuals spend the majority of their time meeting face-to-face with clients in a community setting, including the home. To ensure the provision of high-quality services and effective collaboration across all providers, each HUB develops basic human resource requirements for care coordinators, along with a comprehensive training program. Individuals receiving care coordination services are often dealing with complex health and social issues, and community care coordinators need adequate preparation. The HUB employs clear policies and procedures on all aspects of training, documentation, and accountability for results.

The HUB model of care coordination focuses on improving health, advancing equity, improving quality, and eliminating disparities, and all HUB and care coordination agency personnel complete cultural competency training.

Community care coordinators are supported and supervised by a competent professional, working within the scope of his or her license. The level of supervision varies based on the training of the community care coordinator. It is required that community health workers have supervisors who review and sign off on documentation.

Education, training, and support for community health workers and for community care coordinators other than community health workers are employed to achieve improved outcomes for those clients at risk. The HUB provides documentation that community care coordinators meet the minimum training requirements required as part of certification.

For example, Community Care Coordination training may consist of ten days of classroom instruction and group activities to build competency in health knowledge, care coordination, relational skills, coaching skills, community outreach, and basic organizational skills, with integrated software training. Training may also consist of online E-Lessons which covers the human life span with a focus on physical, cognitive, mental & social development from a Community Health Worker perspective. Additional training may be provided in the form of a community-based practicum consisting of a minimum of 130 hours over 6 weeks in the field at the trainee's agency to enhance care coordination experience. Training of supervisors of Community Health Workers and Community Care Coordinators may consist of dynamic interactive and experiential training wherein a coat-team approach is utilized for achieving successful coordination and productive care coordinators.

Health Engagement Team

The Pathways Community Hub model also provides the opportunity to implement a health engagement team. A health engagement team is a combination of multi-disciplinary professionals and community health workers which typically includes a primary care physician, nurse practitioner, mater social worker, behavioral health specialist, pharmacist, and community social workers. The health engagement team may be specifically tailored or customized to the patient. Oftentimes, a health engagement team is employed to help manage a client's long standing and high cost health conditions. Health engagement teams also assist in transitioning the patient to a high touch, long-term relationship community-based care coordination when appropriate.

The community care coordination process typically begins with the health engagement team engaging with the patient in the hospital setting. After the patient is released from the hospital, members of the health engagement team may meet with the patient at his or her home or other comfort setting. The health engagement team establishes a team assessment of the patient's condition and develops a protocol for primary and behavioral care.

There are numerous advantages to implementing a health engagement team. These advantages include the following: reduced emergency room visits and emergency department utilization, reduced admissions to skilled nursing facilities by diverting care, improving chronic disease management with evidence-based clinical guidelines, improved medication adherence, reduced ambulance transits, reduced 911 and EMS calls, reduced isolation through high visit frequency by health engagement team members, reduced healthcare costs, improved patient health. The benefits of employing a health engagement team are indispensable. For the accountable care organization, the health engagement team provides increased provider engagement, substantial new revenues, reduction in non-primary controllable costs, improved health benefit ratio, significant shared savings and gains, efficient outsourcing to health engagement team services from providers and the establishment of clinical-community linkages. A health engagement team may be instituted as a component part of the Pathways Community HUB model and as discussed in greater detail below, may provide numerous interested parties or service providers involved with utilizing the community care system software application disclosed herein.

Summary of HUB Model

The identification and strategic reduction of an individual's risk factors represent an opportunity to address disparities and reduce costs. The Pathways Community HUB model builds the community infrastructure and provides the tools, standards, and strategies to implement this approach for individuals and populations. Across the Nation, there are effective and capable community organizers; with support, they can use existing resources to implement this HUB model and bring about transformative change.

Software Application

As used in this application, the terms "component," "module," "system," "interface," or the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. The term "client" referred to below, refers to any individual accessing and using the computerized method and system or software application.

Provided is a computerized method and system for coordinating medical care, health treatments, social services, and other types of services between patients, care coordination agencies, community care coordinators through a Pathways Community Hub. The system comprises one or more client devices and a server computer. The client device may be any type of computerized device capable of executing instructions stored on the client device. The client device may be a laptop computer, desktop computer, tablet computer, or wireless cellular device. The server computer is communicatively coupled to a plurality of client devices. The server computer may be directly linked to the client devices or communicatively coupled through a network connection, like the internet. The system may have one or more software modules stored on the server computer and client device. The software may be fully executed on the server computer while the client interacts with the software module from the client device through a network connection. Alternatively, certain software modules may be stored and executed on the server computer while other software modules are stored and executed on the client device. In one aspect, each client utilizing the system, including patients, care coordination agencies, community care coordinators, creates a unique user ID and password for accessing information.

The computerized method and system may be in the form of a web-based software application referred to as a Care Coordination System (CCS). The web-based software application allows clients or patients to log-in to the system and to seek various types of medical services, health services, social services, or other types of services. The application operates by allowing a patient to enter a query within a search engine integrated within the CCS or software application to search for the types of medical, health or social services desired. After entering the query and submitting the search, the CCS or software application returns a number of hits which include facilities or service providers who are capable of fulfilling the patient's request for services. The information provided to the patient in response to the patient's query includes information about each service provider including but not limited to information concerning the service provider's location and hours of operation. After finding the desired service provider, the patient can send the service provider a message through the CCS software application requesting an appointment to obtain the medical, health or social service desired. The patient's request or referral is received by a community-based organization (CBO) member who manages the community-based organization's patient referrals. In certain instances, the CBO member receives an email alert (or any other type of electronic alert within the purview of a person of ordinary skill in the art) containing the patient's referral. The CBO member may then confirm receipt of the referral through the CCS software application, for example, by clicking a confirmation button. The patient and CBO member can view the following information on the display page of the CCS software application: the service provider, contact date, referral request, referral confirmation, appointment date, appointment confirmation and messaging screen.

Communication between the CBO member and the patient may occur directly within the messaging screen within the software application. This allows for the creation of and confirmation of an appointment directly within the software application.

The computerized method, system and web-based software application also includes a Care Coordination System (CCS) hub portal. The CCS hub portal is managed by a hub portal user. The CCS hub portal includes a listing of clients or patients, including client information and referral information. Community resource listings are uploaded by the HUB user and maintained by agencies through agency logins where they also track and respond to referrals. The CCS hub portal user can enter a patient's account for the referral and view the entered information. The CCS hub portal user can also monitor the communication between the patient and the CBO member, Community Health Worker (CHW), community care coordinator or service provider to make sure that everything is running smoothly and that the patient is obtaining the help he or she needs. Once the appointment is kept, the service provider may send a message through the messaging screen on the CCS software application to the patient to conclude the service. This will cause the CCS hub user to close the referral. The referral is then closed for the sake of tracking. The CCS hub user may then move or archive the referral to the historic tab and be complete the task without any further interaction from the service provider, community care coordinator or community health worker.

The computerized method, system and web-based software application may include a health bridge referral component. To create a health bridge referral from within the CCS hub portal, the CCS hub portal user first enters the patient's account to access the patient's client view. The CCS hub portal user may be any interested party including but not limited to a member of a health engagement team, a hospital, physician, health care provider, a community care coordinator, a community health worker, a community-based organization or agency, etc. The CCS hub portal user then adds the type of referral requested (e.g., medical referral, social service referral, health referral, etc.) conducts a search through the search engine of the CCS software application and selects a service provider, community care coordinator, community health worker and/or community-based organization to treat the patient. Fields related to the referral are then populated with information concerning the service request (e.g., the service provider, appointment date, location, time of appointment, etc.). This information is then populated within the referral form. The referral may then be made through an input button on the CSS software application. The service provider, community care coordinator or community health worker representative receives a communication (e.g., an email, text, etc.) to notify the selected service provider, community care coordinator or community health worker of the referral. The service provider, community care coordinator or community health worker representative then enters the CCS software application and confirms receipt of the referral. The service provider, community care coordinator or community health worker representative then sets an appointment date and sends a message through the message screen on the CCS application directly to the patient. The service provider, community care coordinator or community health worker representative can then confirm the appointment within the CCS hub portal by clicking an input button to transmit a notification to the patient on the CCS software application that the appointment has been confirmed. The CCS hub portal user can confirm that the appointment is kept within the CCS hub portal and send a message to the patient community care coordinator, community health worker or community-based organization. The CCS hub portal user may enter the hub portal, view the entire conversation between the patient and the service provider, community care coordinator or community health worker representative, view that the appointment was kept and view all of the information that was automatically entered within the CCS hub portal. The patient may also enter the CCS hub portal and view the conversation, the appointment details and enter comments about the services provided. Through this process, the patient, the service provider, community care coordinator or community health worker representative, the community-based organization, the client, etc. is kept up to date with clear concise tracking of the services provided. HealthBridge is an information referral platform integrated with the Pathways HUB Connect platform (CHR) as a standard feature providing security of information, reporting, auto-generation of pathways for HUB clients, and integrated resources for care coordinators to select and send referrals to agencies. The public-facing website and public integration with the HUB is the stand-alone and an optional integrated feature. Healthbridge may be used to partner with 211 systems, add other directories, and engage with community organizations for better health. Healthbridge is smart-phone and text enabled and connects with HER systems and provides patient referral results. It is integrated with the Community Health Record for community-based care coordination and sustainability and provides real-time information for all stakeholders.

In certain aspects, the computerized method, system and web-based software application functions as a community resource and referral source offering a secure portal for public and HUB client use. The computerized method, system and web-based software application facilitates and tracks multi-directional conversations/referrals between a client, the care coordinator and community-based organizations (and care coordinators). A public-facing website is provided which is a stand-alone application that exceeds the capabilities of other information and referral (I&R) services not only in that it provides a much more interactive platform between patients and service providers but it also takes an active approach in processing patient data for invoicing, future referrals and tracking successful completion of pathways for patient satisfaction, future pathway referral recommendations as well as for billing purposes. Additionally, when a Pathways HUB is also involved, the public-facing website integrates with the HUB to benefit community members, HUB clients, care coordinators, community service organizations, hospitals, providers, and managed care organizations.

Public and HUB clients may seek local referral sources through a search engine within the web-based software application and send requests to third party agencies or community-based organizations or to community care coordinators or community health workers. Public and HUB clients may maintain secure user logins for their referrals and communications with such third-party agencies. These agencies are notified via email when a referral is made to them.

The computerized method, system and web-based software application may include a scheduling component. As described above, the scheduling component allows for appointments to be created between the patient and the service provider, community care coordinator or community health worker.

The computerized method, system and web-based software application may include an appointment feedback component. The appointment feedback component provides notice to the party referring the patient for an appointment with a service provider that an appointment has been kept. The appointment feedback component may transmit such notice to the referring party electronically, for example, via email, text message or any other means within the purview of a person of ordinary skill in the art.

HUB clients have added benefits as their community care coordinator is also receiving the referral information.

The computerized method, system and web-based software application may include a health record integration component which allows physicians, health care providers, hospitals, clinics, etc. to merge an individual's "electronic health record" with a health care organization (e.g., a hospital, clinic, physician's office, etc.) with a "community health record" established through use of the CCS software application. The health record integration component may be established through an input button on the CCS software application which may be clicked by the physician, physician assistant, health care provider, etc. to upload a patient's electronic medical records onto a patient's account on the CCS software application. This allows both patients and users of the CCS software application to view both a patient's electronic medical records and community health records entered into the system through appointments made through the CCS software application.

The computerized method, system and web-based software application may include a messaging component. The messaging component may allow for multi-user, real-time communication between the patient and the service provider such as a community care coordinator, community health worker, community-based organization, physician, hospital, etc. In certain aspects, the computerized method, system, and web-based software application may include a direct messaging component.

The computerized method, system and web-based software application may include a monitoring component. As described above, the monitoring component may allow health care providers such as physicians, health workers, clinics, hospitals, etc. to monitor communications between the patient and the service provider, community care coordinator or community health worker within the CCS software application including communications made via email, communications made within the messaging component of the CCS software application and any other communications made through the CCS software application. The monitoring component will also allow health care providers to monitor a patient's community health records entered into a patient's account within the CCS software application.

The direct messaging component allows the patient to communicate with the service provider, community care coordinator, community health worker, community-based organization, physician, hospital, etc. confidentially in a secure environment. Communications sent through the direct messaging component are not recorded within the patient's file or community health record and are not viewable by third parties.

The computerized method, system and web-based software application may include a tracking component. Information is entered into the system or software application from completed Pathway forms. Thus, pathways track the outcomes as agencies community-based organizations perform.

The computerized method, system and web-based software application may include an archiving component. The archiving component allows for recording and storing of patient community health records related to service visits, general patient records, general data entry related to the specific services provided, etc.

The computerized method, system and web-based software application may include an auto-invoicing component. The auto-invoicing component may work in conjunction with the archiving component to automatically generate bills for the services provided to the patient.

The computerized method, system, and web-based software application, may also measure, display and process data related to the care delivery process. For example, upon entry of data related to a patient's community health record, the CCS software application may run processes analyzing such data and output recommendations further pathway referrals. The CCS software application may also run processes analyzing multiple patient data within a particular region and output data directed health related trends within a particular region and provide pathway recommendations for individuals having similarly situated health issues within a particular region.

The computerized method, system and web-based software application provided above allows HUB clients to use their own community care coordinators to receive referrals.

The computerized method, system and web-based software application also includes a referral resource ranking component. Community care coordinators, community health workers and other service providers are provided with a curated list of referral resources that are ranked according to performance, as well as, curated and maintained by HUB operations. This provides for rapid response and modifications to the community resources listings and better referral resources for the community care coordinator, community health worker, service providers and community members.

The computerized method, system and web-based software application provides a secure web portal for clients and family members providing access to community resources, health decision support, appointments, and communication with their care team. In one aspect of the present disclosure, the care team may be a Healthcare and community-based socialcare team. Health risk assessments (HRAs) are completed annually by the clients or patients and linked with the care team and Pathways Community HUB. Deeper medical knowledge is available to the client or patient through the health decision support and e-learning. Social information, clinical information, care plans and care team converge to assist the client with Pathways Community educational and engagement resources and action tracking tools.

The computerized method, system and web-based software application also includes options for an online and paper-based or larger health risk assessments designed specifically for Medicaid plan members (newborns through adult allowing for individuals with guardians and IDDs) for priority-driven targeted outreach and care management.

Health risk assessments can be completed via an online portal, through paper questionnaires (mailed or emailed), and/or by health plan staff during phone calls to/from plan members and/or visits to home. Health risk assessments and online portal may be branded with additional customization options—e.g., questions, reports, risk-logic, content, rewards-action tracking functions, SSO and other links. The online portal may also include e-lessons, videos, and decision tools for elective procedures and other topics.

Content, tools, and functions vary by member, administrative and clinical login. Health risk assessments and the online portal are HIPAA, ADA, GINA, and FCC compliant.

The computerized method, system and web-based software application also integrates community resources with Pathways referrals and measurements. This allow the HUB and its community-based care coordination to be linked with other non-HUB community service organizations. The community care coordinator, community health worker or service provider determines which organization should be contacted to help the client or patient with their needs. The community service organization receives a secure referral and emails from the platform that they acknowledge. Communication and appointment tracking occur with the entry of Pathways within the web-based software application.

In certain aspects, the computerized method, system, and web-based software application provides the following additional features:

- The ability to have two, three, four, or more documented bi-directional conversations regarding a referral in the field of care coordination;
- The ability to have conversations via smartphone, text, tablet, desktop, or any web browser enabled device;
- The ability to record/document conversations in a database, displayed in structured documents which may be transmitted via API or direct messaging to be consumed by other systems and/or posted to client/patient records;
- Metrics related to the conversations are recorded/documented in a database, displayed in structured documents, and maybe transmitted via API or direct messaging to be consumed by other systems and/or posted to client/patient records. These values include but are not limited to, IP address of referral, referral date/time, referral type, referral category, referral eligibility requirements selected, confirmation date/time by recipient, acknowledgement by sender, appointment created (logical), time to create an appointment, appointment date set, appointment date/time/place, appoint kept (logical), appoint kept date/time, appoint kept with notes, follow up required;
- The ability for all stakeholders to review conversations and date/times;
- The ability for administrators to designated resources as favorites;
- Favorites are positioned in lists at the top
- Metrics are scored and ranking of scores of resources are placed in the lists based on the best rankings at the top for the specified search category or search criteria;
- Reporting on referrals which are made available for all stakeholders based on their role in the referral process;
- Multiple administrators are available to add, delete, deactivate, modify, curate resources;
- Any geo-location resource or information may be displayed and available via multiple metadata search tags;
- Special splash pages based on search criteria or category may be generated by the system for further engagement with the client;
- Marketing sponsorship pages and positions in lists may be made available;
- Payments due to resources are determined by rankings, results, surveys, favorites, and performance;
- Administrators may designate which resources are involved in payments;
- Sponsorships may enter into contracts for referrals or views;
- Integrated with the Community Heath Record (CHR) platform to enable usage of the resources administered with the CHR;
- Given a client/patient is a member in the CHR, the referral will auto-generate a structured care coordination document for stakeholders in the CHR domain;
- A client/patient's health and social needs/risks can be used by the CHR using artificial intelligence (AI)/machine learning to suggest possible recommended referrals;
- A client/patient's health and social needs/risks can be used by the CHR using artificial intelligence (AI)/machine learning to suggest possible recommended health education modules that the client is asked to implement through the learning management system;
- A care coordinator/supervisor/HUB staff or the CHR system may designate specific learning modules for the client/patient—The engagement is tracked and notifications made to all stakeholders;
- The system may include engagement incentives for the client/patient and methodology from the CHR, sponsors or other contracts;
- Specific forms, screenings, measurements can be designated for a client/patient to complete (with or without incentives); and
- Vital signs can be recorded or smart phone trackings enabled by the client/patient that are integrated with the CHR and their client record.

What has been described above includes examples of the claimed subject matter. It is, of course, not possible to describe every conceivable combination of components or methodologies for purposes of describing the claimed subject matter, but one of ordinary skill in the art can recognize that many further combinations and permutations of such matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

The foregoing method descriptions and the process flow diagrams are provided merely as illustrative examples and are not intended to require or imply that the steps of the various aspects must be performed in the order presented. As will be appreciated by one of skill in the art the order of steps in the foregoing aspects may be performed in any order. Words such as "thereafter," "then," "next," etc. are not intended to limit the order of the steps; these words are simply used to guide the reader through the description of the methods. Further, any reference to claim elements in the singular, for example, using the articles "a," "an," or "the" is not to be construed as limiting the element to the singular.

The various illustrative logical blocks, modules, circuits, and algorithm steps described in connection with the aspects disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present teaching.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor unit, but, in the alternative, the processor may be any conventional processor, controller, microcontroller, or state machine. A processor may also be implemented as a combination of computing devices, e.g., a combination of a DSP and a microprocessor unit, a plurality of microprocessor units, one or more microprocessor units in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored on or transmitted over as one or more instructions or code on a computer-readable medium. The steps of a method or algorithm disclosed herein may be embodied in a processor-executable software module, which may reside on a tangible, non-transitory computer-readable storage medium. Tangible, non-transitory computer-readable storage media may be any available media that may be accessed by a computer. By way of example, and not limitation, such non-transitory computer-readable media may comprise RAM, ROM, EEPROM, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of non-transitory computer-readable media. Additionally, the operations of a method or algorithm may reside as one or any combination or set of codes and/or instructions on a tangible, non-transitory machine readable medium and/or computer-readable medium, which may be incorporated into a computer program product.

With reference now to FIGS. 67 to 70*b*, the present teaching provides the value of effort, perceived or actual, required to properly provide care services for a client. The client's personas are determined based on the data gathered in care coordination regarding the social determinants of health (SDoH). SDoH includes non-medical factors and variables that play a role in and influence health outcomes. Such factors include the conditions under which people are born, grow, learn, live, work, play, worship, and age. Additional factors that play a role in influencing health outcomes include economic policies and systems, development agendas, social norms, social policies, and political systems. SDoH are the environmental conditions that influence a person's state of health. Certain academics have grouped these environmental conditions into five categories—1) economic stability; 2) education access and quality; 3) health care access and quality; 4) neighborhood and built environment; and 5) social and community context. Within these categories, there are numerous factors that may be identified and characterized as SDoH. Such factors include but are not limited to: income level; education level; language and literacy skills; unemployment and job security; the degree of social protection provided by income; the degree of social protection provided by family, friends, peers, etc.; work life conditions; food security; housing options and availability; amenities provided by housing; access to safe housing; access to transportation; access to safe transportation; access to safe neighborhoods; amenities provided by the community; the condition of the environment (e.g., whether the environment is clean or if the air and water is polluted); issues related to and affecting early childhood development; language and literacy skills; issues related to and affecting social inclusion and non-discrimination; presence or non-presence of racism, discrimination and violence within social structures; access to nutritious foods; physical activity opportunities; structural conflict within economic and social systems; structural conflict within employment systems and among family and peers; and access to affordable quality health services. SDoH play a significant role in determining health outcomes and has been shown by some research to be more important than health care services and lifestyle choices.

Data related to the SDoH is collected by community health workers (including community care coordinators, the care team, and service providers in general) in real-time at the point of service and entered into the care coordination system. The care coordination system is an interactive system between community care workers, clients and health and social service providers. The care coordination system processes the SDoH data through an artificial intelligence engine and generates an output in real-time of additional follow up questions based on the client's answers for the community health worker to inquire with the client about to obtain additional data and information from the client related to SDoH. A feedback loop is thus created regarding the collection of data related to the SDoH. Moreover, the artificial intelligence engine allows the community health worker to be more comprehensive and accurate in their questioning of the client. After the client's answers and data are entered into the care coordination system, the care coordination system based on the information provided concerning SDoH, generates an output of the proper treatment options for the community health worker (including community care coordinators, the care team, and service providers in general) to follow and the proper pathways for the client to follow in real-time. Thus, the artificial intelligence engine provides directions for the community care coordinator to follow with the client. This allows community health workers to treat the client in the most effective manner and to communicate the proper pathways for the client to follow to receive the most beneficial and effective health outcome. The generation of instructions and treatment direction to the community health worker and recommended pathways for the most effective and beneficial treatment course of action is based on the development of client personas by the artificial intelligence engine based data collected on the SDoH.

As mentioned above, data based on the SDoH is used by the artificial intelligence engine to develop a client persona, i.e., a detailed semi-fictional representation of the client based on qualitative and quantitative data. A client will have multiple personas that are used to determine which key performance indicators are used to determine the care plan and evaluate quality of care delivered.

Expected costs of care coordination are also determined and the effect a client's personas have on the care coordinator's caseload capacity. Factors such as service duration, expected service activities, environmental, and client intensity level are included in the present teaching. The artificial intelligence engine allows community health workers (including community care coordinators, the care team, and service providers in general) to serve clients more comprehensibly with greater data, including data related to estimated risk. The personas inform the community health worker whether or not they are behind the efficiency curve. In evaluating estimated risk, the outcome-based units of actual services performed for the care are based on an annualized rate for comparability. In the persona cases of COVID/Crisis, since the time period is short, the risk is not annualized. The artificial intelligence engine assesses three disparate sets of data, i.e., SDoH, clinical data and financial data to provide assistance to community health workers (including community care coordinators, the care team, and service providers in general).

In evaluating and processing the disparate sets of data, the artificial intelligence engine generates an action, i.e., a workflow process for the community health worker to follow with respect to the respective client. The artificial intelligence system works in real-time, meaning that as data related to SDoH, clinical data, financial data is entered into the system, etc. it is being processed in real-time to generate the next or subsequent workflow process directly to the community health worker (including community care coordinators, the care team, and service providers in general).

The artificial intelligence engine is embodied within Persona. Persona serves as the foundation for client risk identification, client risk management, predictive analytics for care management, predictive patient outcome based tools, review and analysis of client and service provider data, assistance for health workers (e.g., coordinators, coaches, transition coaches, care teams, and service providers in general), optimized sustainability value-based care payments to organizations and service providers. Persona identifies client risks, conditions, best practices, tips/techniques for faster, more efficient care delivery, language translation/documentation, and language interpretation documenting the meaning and tone of the conversation. All of the attributes and results of data analysis are documented in the client longitudinal record in the care coordinating system through Persona's artificial intelligence and predictive analytics machine engine.

The artificial intelligence engine and predictive analytics engine constitute much more than displayable narratives in various care initiatives. The artificial intelligence engine and predictive analytics engine are actionable in the entire care delivery process through Persona. The Persona algorithms are produced through the analysis of the proprietary data gathered in the care coordination process. The algorithms are learned based on comparison of client personas (including multiple measures within and across client personas), algorithms, target budgets, personalized care plans, personnel assignments, and process performance benchmarks that are identified at the beginning of a care episode and after assessment when action can be taken for the clients' benefit, not after the care delivery has occurred. In summary:

1) Personas influence the care delivery timeline for supervision and payment. Exceptions to the "persona timeline" are flagged and corrective actions are implemented to re-align care plans, care delivery, and care budgets/invoicing.
2) Persona exceptions for care delivery automatically initialize care plan changes to accurately meet the care plan objective for the primary/major Personas for a client. New documents, risk topics, assessment questions, and changes to each are impacted by the comparison with the Persona criteria and actions are taken to realign/modify the plan.
3) Care management personnel have unique attributes and talents as individuals. They also have unique successes and weaknesses with various Personas. The artificial intelligence engine evaluates the assets, liabilities, and requirements to offer suggestions as the best fit for care delivery to meet a client's goals/needs. The suggestion for assignment may be changed based on new information uncovered and new Personas that appear through the new information.
4) Target budgets and timelines are critical to the sustainability and performance of a care coordinator, supervisor, and organization. The identified Persona(s) for a client create custom time, expense, revenue, and successful risk reduction budgets. The number of units of effort, the time to deliver the effort, the revenue potential of the care plan, and possible alternatives to the personalized care plan are administered by the initiatives and the Personas identified for clients.

Persona RiskQ™ is an artificial intelligence engine capable of determining in real-time the persona(s), risk levels, and estimated costs of care of patients based on their preexisting conditions, health data, SDoH, and financial data. The Persona RiskQ™ is constantly updating these data sets and training its models as new information becomes available. The Persona RiskQ™ is also capable of assigning an appropriate treatment plan to a patient (also referred to as a client) based on the patient's assigned persona(s), risk levels, and estimated costs of care. The Persona RiskQ™ assigns an appropriate care team to the patient based on the prior experiences, prior results and availability of care teams, along with the patient's assigned persona(s), risk levels, estimated costs of care, and treatment plan. The Persona RiskQ™ is also capable of facilitating the implementation of the patient's treatment plan with the appropriate care team, as well as identifying documents or tasks that are missing or were omitted from the patient's treatment plan and will notify the appropriate community health worker (including community care coordinator, the care team, and service provider in general) of the issue so it may be resolved in a quick and efficient manner to improve the quality of care and reduce the cost of care.

Figure 67:
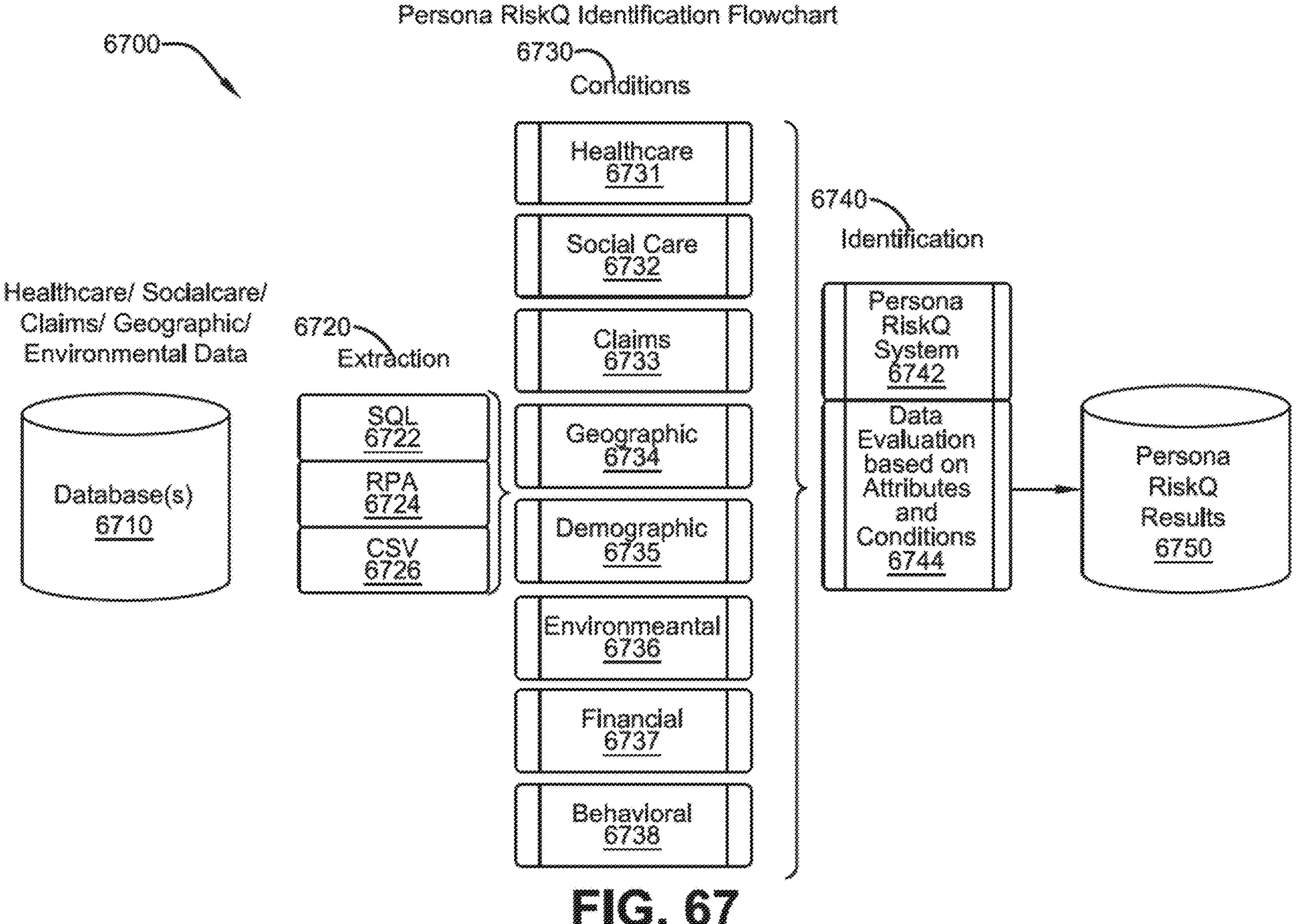
FIG. 67 provides a Persona RiskQ Identification Flowchart.

FIG. 67 schematically presents a Persona RiskQ™ Identification Flowchart 6700 showcasing how the Persona RiskQ™ system identifies different risks associated with different patients. The Persona RiskQ™ Identification Flowchart 6700 includes a Databases group 6710, an Extraction process 6720, a Conditions group 6730, an Identification group 6740, and a Persona RiskQ™ Results database 6750. The Extraction process 6720 includes an SQL Data Extraction Method 6722, an RPA Data Extraction Method 6724, and a CSV Data format 6726. The Conditions group 6730 includes a Healthcare conditions bucket 6731, a Social Care conditions bucket 6732, a Claims conditions bucket 6733, a Geographic conditions bucket 6734, a Demographic conditions bucket 6735, an Environmental conditions bucket 6736, a Financial conditions bucket 6737, and a Behavioral conditions bucket 6738. The Identification group 6740 includes a Persona RiskQ™ System 6742 and a Data Evaluation based on Attributes and Conditions process 6744.

The Databases group 6710 is a group of databases, including but not limited to databases containing the healthcare, social care, claims, geographic, and environmental information of patients. Thus, the Databases group includes health related data, client data on social determinants of health and financial data.

The Extraction process 6720 is a process of data extraction for extracting data from the databases comprising the Databases group 6710 for placement into at least one of the buckets comprising the Conditions group 6730.

The SQL Data Extraction Method 6722 is a data extraction method that utilizes SQL (structured query language) to extract data from at least one database from the Databases group 6710 for placement into at least one of the buckets comprising the Conditions group 6730. SQL is a domain-specific language used in programming and designed for managing data held in a relational database management system (RDBMS), or for stream processing in a relational data stream management system (RDSMS).

The RPA Data Extraction Method 6724 is a data extraction method that utilizes RPA (robotic process automation) to extract data from at least one database from the Databases group 6710 for placement into at least one of the buckets including the Conditions group 6730. RPA is a form of business process automation that is based on software robots or artificial intelligence agents. RPA automates the process of data extracting.

The CSV Data format 6726 is a text file format that utilizes CSV (comma separated values). A CSV file stores tabular data (numbers and text) in plain text, where each line of the file typically represents one data record. Each record consists of the same number of fields, and these are separated by commas in the CSV file. If the field delimiter appears within a field, fields can be surrounded with quotation marks. Raw data is often stored in the CSV format.

The Conditions group 6730 is a group of data buckets that correspond to several different conditions, including but not limited to the healthcare, social care, claims, geographic, demographic, environmental, financial, and behavioral conditions of patients. The Conditions group 6730 may contain other data buckets, the data buckets included in this disclosure are exemplary and not limiting.

The Healthcare conditions bucket 6731 is a digital bucket where information regarding the current healthcare conditions and statuses of patients is collected and digitally stored.

The Social Care conditions bucket 6732 is a digital bucket where information regarding the current social care conditions and statuses of patients is collected and digitally stored.

The Claims conditions bucket 6733 is a digital bucket where information regarding historical and current claims of patients is collected and digitally stored.

The Geographic conditions bucket 6734 is a digital bucket where information regarding the current and historical geographic locations and situations of patients is collected and digitally stored.

The Demographic conditions bucket 6735 is a digital bucket where information regarding the demographic data of patients is collected and digitally stored.

The Environmental conditions bucket 6736 is a digital bucket where information regarding the current and historical environmental conditions and situations of patients is collected and digitally stored.

The Financial conditions bucket 6737 is a digital bucket where information regarding the current and historical financial situations of patients is collected and digitally stored.

The Behavioral conditions bucket 6738 is a digital bucket where the information regarding current and historical behavioral conditions of patients is collected and digitally stored.

The Identification process 6740 is a process wherein the information from the 6730 is processed to identify a particular patient's Persona RiskQ™ results.

The Persona RiskQ™ System 6742 is a system that analyzes the information from the buckets comprising the Conditions group 6730 via performing the Data Evaluation based on Attributes and Conditions process 6744.

The Data Evaluation based on Attributes and Conditions process 6744 is a process wherein the information from the buckets comprising the Conditions group 6730 is analyzed and processed.

The Persona RiskQ™ Results database 6750 is a database of all of the risk factors and conditions associated with patients.

The flow of the Persona RiskQ™ Identification Flowchart 6700 is described herein. Information from the Databases group 6710 is extracted using the Extraction process 6720. The information extracted by the Extraction process 6720 is placed into at least one bucket comprising the Conditions group 6730. Information from the buckets including the Conditions group 6730 is used by the Persona RiskQ™ System 6742 to perform the Data Evaluation based on Attributes and Conditions process 6744. The results from the Data Evaluation based on Attributes and Conditions process 6744 are placed into the Persona RiskQ™ Results database 6750.

Thus, FIG. 67 provides a flowchart for what is referred to as the Persona RiskQ™ Identification step of the process. As shown in FIG. 67, data is collected and is entered, depending on type, into several disparate databases related to healthcare data, social care data, claims data, geographic data and environmental data. The data is then reviewed, analyzed, processed, and displayed using various software including structured query language (SQL) and robotic process automation (RPA), and is converted into and stored in the comma separated values file format (CSV). SQL, RPA, and CSV in conjunction form a critical part of the artificial intelligence engine and are related to what is referred to as the Persona RiskQ™ function of the system. SQL manages the relationship between data within the disparate databases and performs operations on the data. RPA builds, deploys, and manages software robots which interact with the data, digital systems, and software, identifies and extracts data, and performs defined actions. SQL and RPA in conjunction evaluate the data in accordance with a level or degree within various conditions, various criteria, and personal attributes which make up and define a persona. These conditions include but are not limited to healthcare related conditions, social care related conditions, conditions related to claims, geographic related conditions, demographic related conditions, environmental related conditions, financial related conditions, and behavioral related conditions. After the data is evaluated with respect to the various conditions, criteria, and attributes, the SQL and RPA assigns the client to a particular persona within the Persona RiskQ™ system. The results are extracted into a database table which is created in the CSV text file format to allow the data to be saved in a tabular format. The CSV text file format forms the basis for the workflow instructions communicated by the artificial intelligence engine to the care coordinator or health worker discussed in greater detail below. In this overall process, the artificial intelligence engine has the ability not only to update data but to modify and change any pre-set conditions and to create new conditions based on the data collected.

FIG. 68*a* schematically presents a Risk Stratification for Care Delivery Flowchart-Part A 6800*a* showcases how the Persona RiskQ™ system stratifies the various risk factors of patients into different tiers and how the Persona RiskQ™ system creates treatment plans based on the risk factors and tiers of patients. The Risk Stratification for Care Delivery Flowchart-Part A 6800*a* includes the Persona RiskQ™ Results database 6750 found in FIG. 67, a Personas group 6830*a*, the Identification process 6740 found in FIG. 67, a RiskQ™ Tiers group 6850*a*, and a Treatment Plans group 6860*a*. The Personas group 6830*a* includes a Complex/Multi-Dimensional conditions bucket 6840*a*, the Healthcare conditions bucket 6731 found in FIG. 67, the Social Care conditions bucket 6732 found in FIG. 67, the Claims conditions bucket 6733 found in FIG. 67, the Geographic conditions bucket 6734 found in FIG. 67, the Demographic conditions bucket 6735 found in FIG. 67, the Environmental conditions bucket 6736 found in FIG. 67, the Financial conditions bucket 6737 found in FIG. 67, and the Behavioral conditions bucket 6738 found in FIG. 67. The Identification process 6740 includes the Persona RiskQ™ System 6742 found in FIG. 67 and the Data Evaluation based on Attributes and Conditions process 6744 found in FIG. 67. The RiskQ™ Tiers group 6850*a* includes a RiskQ™ Tier 1 6851*a*, a RiskQ™ Tier 2 6852*a*, a RiskQ™ Tier 3 6853*a*, a RiskQ™ Tier 4 6854*a*, a RiskQ™ Tier 5 6855*a*, a RiskQ™ Tier 6 6856*a*, a RiskQ™ Tier 7 6857*a*, and a RiskQ™ Tier 999 6859*a*. The Treatment Plans group 6860*a* includes a Contact Center plan 6861*a*, a Care Plan #1/Frequency #1/Care Team #1 plan 6862*a*, a Care Plan #2/Frequency #1/Care Team #2 plan 6863*a*, a Care Plan #3/Frequency #1/Care Team #3 plan 6864*a*, a Care Plan #1/Frequency #2/Care Team #1 plan 6865*a*, a Care Plan #2/Frequency #2/Care Team #4 plan 6866*a*, a Care Plan #3/Frequency #3/Care Team #5 plan 6867*a*, and a Care Plan #4/Frequency #4/Care Team #999 plan 6869*a*.

The Personas group 6830*a* is a group of Personas, wherein each Persona represents a given patient condition, status, or circumstance. The Personas group 6830*a* may include other data buckets as the data buckets included in this disclosure are exemplary and not limiting.

The Complex/Multi-Dimensional conditions bucket 6840*a* is a digital bucket, where the information regarding an issue that the patient is dealing with is complex (i.e., it takes multiple factors into account) or multi-dimensional to be labeled with any of the other personas including the Personas group 6830*a*.

The RiskQ™ Tiers group 6850*a* is a group of tiers that may be assigned to a patient based on the Persona(s) they are assigned. According to certain aspects of the present teaching, the lower the tier number, the more severe the patient's condition generally is. However, in other aspects of the present teaching, higher levels of severity of the patient's condition may be associated with higher tier numbers or the tier numbers may have no relation whatsoever with the level of severity of the patient's condition.

The RiskQ™ Tier 1 6851*a* is the first tier in the RiskQ™ tier group. According to certain aspects of the present teaching, RiskQ™ Tier 1 corresponds to the most serious/dangerous conditions and personas.

The RiskQ™ Tier 2 6852*a* is the second tier in the RiskQ™ tier group 6850*a*. According to certain aspects of the present teaching, RiskQ™ Tier 2 corresponds to conditions and personas that are generally less serious/dangerous than RiskQ™ Tier 1.

The RiskQ™ Tier 3 6853*a* is the third tier in the RiskQ™ tier group 6850*a*. According to certain aspects of the present teaching, RiskQ™ Tier 3 corresponds to conditions and personas that are generally less serious/dangerous than RiskQ™ Tiers 1 and 2.

The RiskQ™ Tier 4 6854*a* is the fourth tier in the RiskQ™ tier group 6850*a*. According to certain aspects of the present teaching, RiskQ™ Tier 4 corresponds to conditions and personas that are generally less serious/dangerous than RiskQ™ Tiers 1 through 3.

The RiskQ™ Tier 5 6855*a* is the fifth tier in the RiskQ™ tier group 6850*a*. According to certain aspects of the present teaching, RiskQ™ Tier 5 corresponds to conditions and personas that are generally less serious/dangerous than RiskQ™ Tiers 1 through 4.

The RiskQ™ Tier 6 6856*a* is the sixth tier in the RiskQ™ tier group 6850*a*. According to certain aspects of the present teaching, RiskQ™ Tier 6 corresponds to conditions and personas that are generally less serious/dangerous than RiskQ™ Tiers 1 through 5.

The RiskQ™ Tier 7 6857*a* is the seventh tier in the RiskQ™ tier group 6850*a*. According to certain aspects of the present teaching, RiskQ™ Tier 7 corresponds to conditions and personas that are generally less serious/dangerous than RiskQ™ Tiers 1 through 6.

The RiskQ™ Tier 999 6859*a* is the 999th tier in the RiskQ™ tier group 6850*a*. According to certain aspects of the present teaching, RiskQ™ Tier 999 corresponds to conditions and personas that are generally less serious/dangerous than RiskQ™ Tiers 1 through 998. The RiskQ™ Tier 999 6859*a* is included to show that there can be any number of tiers comprising the RiskQ™ Tier group 6850*a*, and that the number of tiers comprising the RiskQ™ Tier group 6850*a* is not intended to be limited to a specific number by the present disclosure.

The Treatment Plans group 6860*a* is a group of plans that include either a contact center recommendation or a combination of a care plan number, a frequency number, and a care team number. These plans are processed and carried out by a remote center, call center, or tele-health provider. A Care Plan is an Initiative, which includes but is not limited to: Care Transitions Intervention, Community Care Coordination, Chronic Care Management, CT Team, Crisis Care Response and Support, and Referrals. Frequency is the periodicity for care delivery including the frequency for interventions recommended, intervention duration, and the expected care episode duration (e.g., once weekly, 90 minutes, 6 months). A Care Team is a general or specific team, organization, and/or individual recommended to deliver the care plan/initiative based on Persona RiskQ™ performance, experience, credentials, demographics, and/or geographics to optimize for successful, comprehensive, and fast outcomes. Each initiative and frequency is recommended based on the dominant Persona RiskQ™ (lowest RiskQ™ number) from the RiskQ™ Tier group 6850*a* identified for the patient.

The Contact Center plan 6861*a* is the plan corresponding to a patient assigned to RiskQ™ Tier 1. For this plan, the remote center, call center, or tele-health provider is contacted for immediate assistance for the patient.

The Care Plan #1/Frequency #1/Care Team #1 plan 6862*a* is the plan corresponding to a patient assigned to RiskQ™ Tier 2. For this plan, the Care Plan #1 and the Care Team #1 are assigned to the patient, with the frequency value set to 1.

The Care Plan #2/Frequency #1/Care Team #2 plan 6863*a* is the plan corresponding to a patient assigned to RiskQ™ Tier 3. For this plan, the Care Plan #2 and the Care Team #2 are assigned to the patient, with the frequency value set to 1.

The Care Plan #3/Frequency #1/Care Team #3 plan 6864*a* is the plan corresponding to a patient assigned to RiskQ™ Tier 4. For this plan, the Care Plan #3 and the Care Team #3 are assigned to the patient, with the frequency value set to 1.

The Care Plan #1/Frequency #2/Care Team #1 plan 6865*a* is the plan corresponding to a patient assigned to RiskQ™ Tier 5. For this plan, the Care Plan #1 and the Care Team #1 are assigned to the patient, with the frequency value set to 2.

The Care Plan #2/Frequency #2/Care Team #4 plan 6866*a* is the plan corresponding to a patient assigned to RiskQ™

Tier 6. For this plan, the Care Plan #2 and the Care Team #4 are assigned to the patient, with the frequency value set to 2.

The Care Plan #3/Frequency #3/Care Team #5 plan 6867*a* is the plan corresponding to a patient assigned to RiskQ™ Tier 7. For this plan, the Care Plan #3 and the Care Team #5 are assigned to the patient, with the frequency value set to 3.

The Care Plan #4/Frequency #4/Care Team #999 plan 6869*a* is the plan corresponding to a patient assigned to RiskQ™ Tier 999. For this plan, the Care Plan #4 and the Care Team #999 are assigned to the patient, with the frequency value set to 4. The Care Plan #4/Frequency #4/Care Team #999 plan 6869*a* is included to show that there can be any number of plans comprising the Treatment Plans group 6860*a*, and that the number of plans comprising the Treatment Plans group 6860*a* is not intended to be limited to a specific number by the present disclosure.

The flow of the Risk Stratification for Care Delivery Flowchart-Part A 6800*a* is described herein. Information regarding the at least one condition of a patient that has been placed into the Persona RiskQ™ Results database 6750 found in FIG. 67 is used to assign at least one persona from the Personas group 6830*a* to the patient. The information regarding the at least one persona assigned to the patient is used by the Persona RiskQ™ System 6742 found in FIG. 67 to perform the Data Evaluation based on Attributes and Conditions process 6744 found in FIG. 67. The results from the Data Evaluation based on Attributes and Conditions process 6744 are used to assign a RiskQ™ Tier from the RiskQ™ Tiers group 6850*a* to the patient. Once a RiskQ™ tier has been assigned to the patient, a plan from the Treatment Plans group 6860*a* is selected based on the RiskQ™ tier assigned to the patient. Once a plan is assigned to the patient, that information is sent to a system described in FIG. 68*b* via line L68*a* and to a system described in FIG. 70*b* via line L68*b*.

Figure 68B:
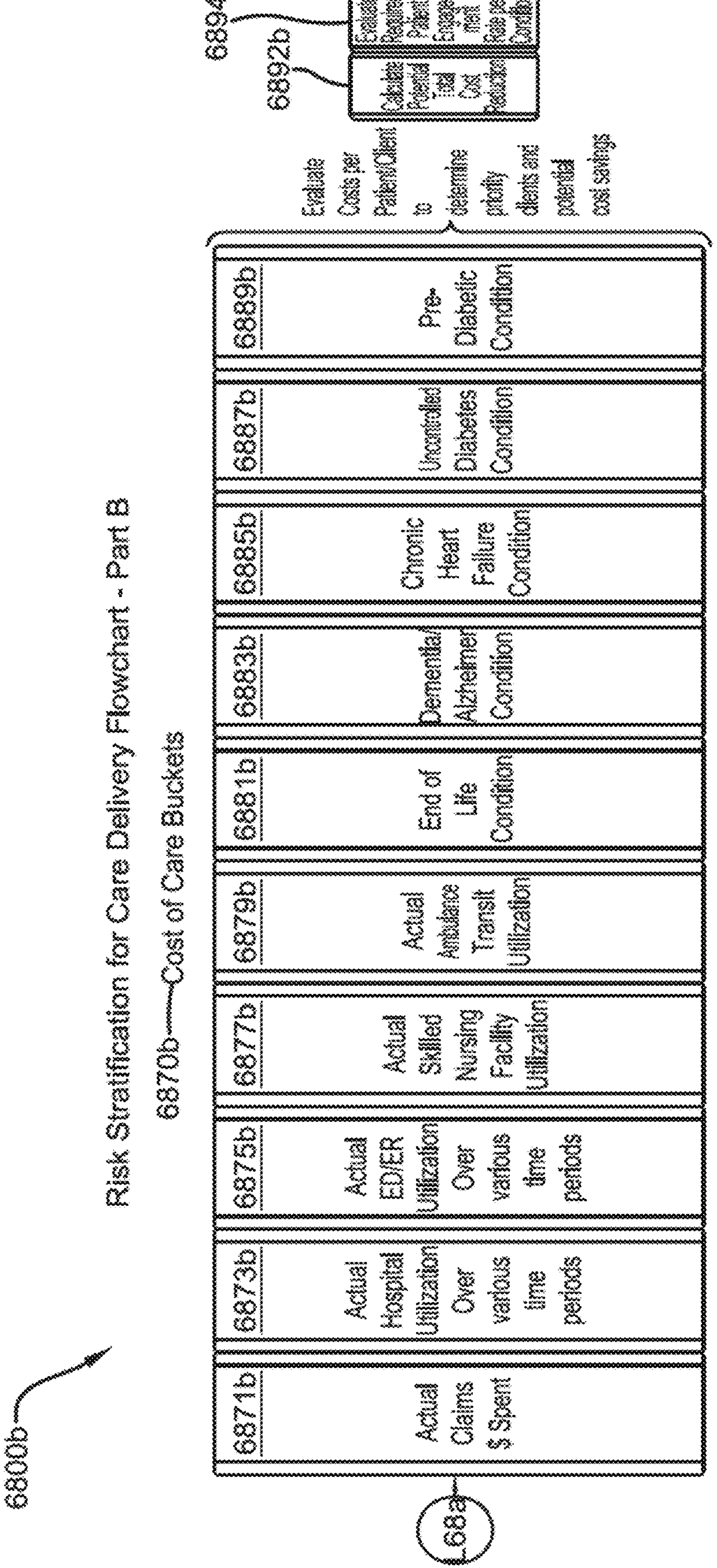

FIG. 68*b* schematically presents a Risk Stratification for Care Delivery Flowchart-Part B 6800*b* showcasing how the Persona RiskQ™ system calculates the cost of care based on the risk factors, RiskQ™ tiers, and treatment plans determined in FIG. 68*a*. The Risk Stratification for Care Delivery Flowchart-Part B 6800*b* includes a Cost of Care Buckets group 6870*b*, a Calculate Potential Total Cost Reduction process 6892*b*, and an Evaluate Required Patient Engagement Rate per Condition process 6894*b*. The Cost of Care Buckets group 6870*b* includes an Actual Claims Money Spent bucket 6871*b*, an Actual Hospital Utilization Over Various Time Periods bucket 6873*b*, an Actual Emergency Department/Emergency Room (ED/ER) Utilization Over Various Time Periods bucket 6875*b*, an Actual Skilled Nursing Facility Utilization bucket 6877*b*, an Actual Ambulance Transit Utilization bucket 6879*b*, an End of Life Condition bucket 6881*b*, a Dementia/Alzheimer Condition bucket 6883*b*, a Chronic Heart Failure Condition bucket 6885*b*, an Uncontrolled Diabetes Condition bucket 6887*b*, and a Pre-Diabetic Condition bucket 6889*b*.

The Cost of Care Buckets group 6870*b* is a group of data buckets that correspond to the various actual costs and applications of the treatment plans from the Treatment Plans group 6860*a* found in FIG. 68*a*. The Cost of Care Buckets group 6870*b* may contain other data buckets, the data buckets included in this disclosure are exemplary and not limiting.

The Actual Claims Money Spent bucket 6871*b* is a digital bucket including information regarding the money spent on patients' actual claims.

The Actual Hospital Utilization Over Various Time Periods bucket 6873*b* is a digital bucket including information regarding the actual utilization of hospitals and hospital resources by patients.

The Actual ED/ER Utilization Over Various Time Periods bucket 6875*b* is a digital bucket including information regarding the actual utilization of the ED and/or ER by patients over various time periods.

The Actual Skilled Nursing Facility Utilization bucket 6877*b* is a digital bucket including information regarding the actual utilization of skilled nursing facilities by patients.

The Actual Ambulance Transit Utilization bucket 6879*b* is a digital bucket including information regarding the actual utilization of ambulance transit services by patients.

The End of Life Condition bucket 6881*b* is a digital bucket including information regarding the costs and statistics associated with patients who are in the end of life stage.

The Dementia/Alzheimer Condition bucket 6883*b* is a digital bucket including information regarding the costs and statistics associated with patients who suffer from Dementia and/or Alzheimer's Disease.

The Chronic Heart Failure Condition bucket 6885*b* is a digital bucket including information regarding the costs and statistics associated with patients who suffer from chronic heart failure.

The Uncontrolled Diabetes Condition bucket 6887*b* is a digital bucket including information regarding the costs and statistics associated with patients who suffer from uncontrolled diabetes.

The Pre-Diabetic Condition bucket 6889*b* is a digital bucket including information regarding the costs and statistics associated with patients who are pre-diabetic.

The Calculate Potential Total Cost Reduction process 6892*b* is a process wherein the Persona RiskQ™ uses data from the various buckets including the Cost of Care buckets 6870*b* to calculate the potential total cost reduction resulting from the execution of a treatment plan assigned to a patient from the Treatment Plan group 6860*a* found in FIG. 68*a*.

The Evaluate Required Patient Engagement Rate per Condition process 6894*b* is a process wherein the Persona RiskQ™ uses data from the various buckets including the Cost of Care buckets 6870*b* to determine what level of care and what steps are necessary to competently execute a treatment plan assigned to a patient from the Treatment Plan group 6860*a* found in FIG. 68*a* in the most efficient manner that is most likely to achieve a positive health outcome. The Persona RiskQ™ compares its determinations regarding the level of care and the steps necessary to competently execute the treatment plan to the actual level of care and the steps taken by a care team assigned to the patient and determines if there are any deficiencies in the level of care or the steps taken by the care team. If there are deficiencies, the Persona RiskQ™ will notify the care team of the deficiencies so that they can resolve the issue quickly and efficiently to ensure the patient is receiving adequate care.

The flow of the Risk Stratification for Care Delivery Flowchart-Part B 6800*b* is described herein. Information regarding the plan assigned to the patient in FIG. 68*a* is sent to the Cost of Care Buckets 6870*b* via line L68*a*. The information is then sorted into at least one of the buckets comprising the Cost of Care Buckets 6870*b*. Once sorted, the information is used in the Calculate Potential Total Cost Reduction process 6892*b* and the Evaluate Required Patient Engagement Rate per Condition process 6894*b* to evaluate costs per patient to determine priority clients and identify potential cost savings.

Thus, FIGS. 68*a* and 68*b* provide a flowchart showcasing the risk stratification for care delivery. Risk stratification refers to a client population being divided into homogeneous subpopulations referred to as strata based on characteristics of a defined persona. As mentioned above with respect to FIG. 67, after the data is evaluated with respect to the various conditions, criteria and attributes, the SQL and RPA assigns the client to a particular persona within the Persona RiskQ™ system. FIGS. 68*a* and 68*b* pick up here with respect to a client being assigned to a particular persona based on the Persona RiskQ™ Results of the data analysis in view of a defined set of characteristics of a particular persona. Such characteristics include but are not limited to complex/multi-dimensional related data, healthcare related data, social care related data, data related to claims, geographic related data, demographic related data, environmental related data, financial related data, and behavioral related data. The Persona RiskQ™ System then evaluates the client data based on persona related conditions, various criteria and personal attributes and assigns the client to a particular tier for care or treatment, referred to as a RiskQ™ Tier. Each RiskQ™ Tier includes a defined treatment plan for the client to follow based on the client's persona as defined by the client's circumstances related to social determinants of health which include factors related not only to the client's health condition, medical history, financial history, etc. but also socio-economic and environmental factors which have an impact on the overall health of the client. For example, in the chart shown in FIGS. 68*a* and 68*b*, a client classified under RiskQ™ Tier 1 may be referred to remote treatment, a call center or tele-health for obtaining healthcare treatment. Other tiers including RiskQ™ Tiers 2 through 7 each include a specific Care Plan, Care Team, and treatment frequency. Care Plans refer to the treatment plan for delivering care to the client. They include implementing various types of initiatives such as care transitions intervention, community care coordination, chronic care management, working with a care transitions team, crisis care response and support, referrals etc. Care Team refers to a general or specific team, organization and/or individual recommended to deliver the care plan and/or initiative based on the Persona RiskQ™ performance, experience, credentials, demographics, and/or geographics to optimize successful, comprehensive, and fast outcomes. Frequency refers to how often delivery of care is provided including the frequency of recommended interventions, intervention duration and the expected care episode duration (e.g., frequency may be weekly, monthly, every six months, etc. and duration may be 15 minutes, 30 minutes, 60 minutes, 90 minutes, etc.). Thus, risk stratification refers to how personas are implemented for care delivery. In this system, the artificial intelligence engine assigns clients to various RiskQ™ tiers/care plans based various client data related to the client persona. Changes in the client's conditions or data may result in a change in the RiskQ™ Tier. The artificial intelligence engine monitors these changes by prompting the community health workers to continuously monitor the client for a change in circumstances at various intervals and to enter such changes in data within the system. The artificial intelligence engine reviews, analyzes, and evaluates such changes in the client's data instantaneously and may recommend changes in the client's RiskQ™ Tier referral, care, or treatment plan in real-time if needed. In addition, the artificial intelligence engine may create new personas and new RiskQ™ Tiers based on changes in the client's data. This allows future clients having similar circumstances to obtain better services and to be more promptly treated.

FIGS. 68*a* and 68*b* also provide a flowchart with respect to the risk stratification for care delivery and analysis and workflow generated by the artificial intelligence engine. According to the embodiment illustrated within FIGS. 68*a* and 68*b*, the artificial intelligence engine assigns a dominant persona to the client based on the acquired data. In this case, after the data is evaluated with respect to the various conditions, criteria and attributes, the SQL and RPA assigns the client to a specific dominant persona within the Persona RiskQ™ system. Dominant personas according to FIGS. 68*a* and 68*b* include but are not limited to a complex/multi-dimensional persona, a healthcare persona, a social care persona, a claims persona, a geographic persona, a demographic persona, an environmental persona, a financial persona, and a behavioral persona. The Persona RiskQ™ System then evaluates the client data based on persona related conditions, various criteria and personal attributes and assigns the client to a particular tier for care or treatment, referred to as a RiskQ™ Tier. Each RiskQ™ Tier includes a defined treatment plan for the client to follow based on the client's dominant persona as defined by the client's circumstances related to social determinants of health which include factors related not only to the client's health condition, medical history, financial history, etc. but also socio-economic and environmental factors which have an impact on the overall health of the client. The artificial intelligence engine of Persona RiskQ™ identifies and recommends initiatives/care or treatment plans and service frequency based on the dominant persona identified by Persona RiskQ™ for the client. The artificial intelligence engine then budgets an allocation of relative value units (RVU) per outcome based units (OBU) over a care episode timeline. The goal is to deliver a successful, comprehensive, and fast and efficient care episode which enhances return on investment and sustainability of the initiative, care team and organization. Over time with the client's participation in the care/treatment plan, the artificial intelligence engine reviews collected data and analyzes, evaluates, and processes the data to determine the achieved to-date relative value units (RVU) per outcome based units (OBU) over a care episode timeline (i.e., RVU/OBU). This value is then compared to the budgeted RVU/OBU value to determine the effectiveness of the program for both the client and the service provider. This comparison of data is available to all care team members and is used to manage performance and sustainability of performance of the team members. The artificial intelligence engine further updates care team members with benchmark status and client risk status based on real-time data captured. The updates provided by the artificial intelligence engine are provided in real-time and are further provided with recommended changes in client care and treatment protocol to allow the client to achieve better achieve benchmark status and to reduce client risk status through improved processes for care and treatment. As care and treatment improves through the instruction and guidance of the artificial intelligence engine, the artificial intelligence engine calculates a return on investment for care and treatment activities. The return on investment is calculated in real-time and relayed in real-time to the initiative, organization, care team, and Persona RiskQ™ data report. The artificial intelligence engine further relays and feedbacks the new information related to the care and treatment activities and associated return on investment of the client in real-time to the overall Persona RiskQ™ system. This allows the Persona RiskQ™ system to further refine and to provide improved assistance in real-time to other participating individuals in the care coordination system including other care coordinators, health workers, care teams, etc. as they provide assistance and service to other clients. Thus, the Persona RiskQ™ process is iterative and self-learning through the feedback of real-time care data.

The Persona RiskQ™ artificial intelligence engine acts as an active assistant. For example, a persona ranking may place a client/patient in a particular tier or category based on certain answers the client provided in their assessment and evaluation. The artificial intelligence engine reviews, analyzes, evaluates, and processes the client's answers and determines if the answers provided fit a typical client having the identified persona. If the answers do not fit, the artificial intelligence engine identifies additional questions to ask the client. The artificial intelligence engine further considers the persona and questions not answered and identifies additional attributes the persona typically has that the care coordinator should inquire about. The care coordinator probes the client further and obtains additional data from the client. Upon review of this additional data, the artificial intelligence engine identifies a new care plan to launch based on the existing persona or creates an entirely new persona with an associated alternative care plan to follow. The artificial intelligence engine acts as a personal assistant for the community health worker, advising and assisting the community health worker with the next task or project. For example, when the community health worker is serving the next patient, the artificial intelligence engine advises the community health worker to present the client with specific questions to ask the client or add to an existing questionnaire to present to the client. The artificial intelligence engine also ensures that the care plan or pathways recommended by the community health worker to the client are the most appropriate for the client's condition or situation and provides alternative routes (e.g., care plans and pathways) for the client to follow based on the client's answers, condition, or situation. The artificial intelligence engine automatically launches the documents associated with the care plan or pathways to address the client's needs and/or risk. Thus, the artificial intelligence engine, depending on the end user provides, not only provides a predictive analysis with respect to recommended pathways for the best outcome, but it provides a form of coach assist, community health worker (CHW) assist, community care coordinator assist and supervisor assist, all of which are powered by the persona identified by the artificial intelligence engine. With respect to these different end users, the artificial intelligence engine does not perform the task for the end user, but rather instructs and trains the end user how to perform and complete its task. It performs a skill transfer in that it identifies tasks that may still need to be performed by the coach, health worker, etc. based on the persona and predictive analytics. This contrasts with the typical job of a community health worker or community care coordinator which is to complete a task for the client.

Another aspect of the artificial intelligence engine is that it is functional with all members of a particular household. If a household has a household care coordinator assigned to it, the household leader and all members of the household family is in the care of the artificial intelligence engine. This means that the artificial intelligence engine will carry out its analysis to other family members in the household. For example, if the risk or SDoH identified is that of a housing risk or unsafe housing, this factor is applied not just to the household leader but to his or her spouse and children. The other members of the family may or may not have the same care coordinator as the household leader, nonetheless, the artificial intelligence engine conducts its analysis for the relationship within the household and assigns factors or risks based on its assessment. The artificial intelligence engine draws links between family members, for example, who is part of the household, who are the caregivers for individuals within the household, who are associated friends and individuals within the individual's personal support team. When a particular client record is brought up, the artificial intelligence engine prompts the care coordinator to ask the same questions to other members in the family. It also notifies the care coordinator that an analysis for another family member has already been done, that similar factors may apply to other family members and that similar changes in treatment, care treatment and recommended pathways may also apply to other family members.

FIG. 69 schematically presents a Persona RiskQ™ Initiatives and Actions Flowchart 6900 showcasing how the Persona RiskQ™ system uses the various risk factors and conditions of patients to create patient specific personas. The Persona RiskQ™ Initiatives and Actions Flowchart 6900 includes the Databases group 6710 found in FIG. 67, the Identification group 6740 found in FIG. 67, the Persona RiskQ™ Results database 6750 found in FIG. 67, the Personas group 6830*a* found in FIG. 68*a*, and a Client/Patient specific Persona(s) process 6950. The Identification group 6740 includes the Persona RiskQ™ System 6742 found in FIG. 67 and the Data Evaluation based on Attributes and Conditions process 6744 found in FIG. 67. The Personas group 6830*a* includes the Complex/Multi-Dimensional conditions bucket 6840*a* found in FIG. 68*a*, the Healthcare conditions bucket 6731 found in FIG. 67, the Social Care conditions bucket 6732 found in FIG. 67, the Claims conditions bucket 6733 found in FIG. 67, the Geographic conditions bucket 6734 found in FIG. 67, the Demographic conditions bucket 6735 found in FIG. 67, the Environmental conditions bucket 6736 found in FIG. 67, the Financial conditions bucket 6737 found in FIG. 67, and the Behavioral conditions bucket 6738 found in FIG. 67.

The Client/Patient specific Persona(s) process 6950 is a process wherein at least one patient specific persona is created based on the persona(s) from the Personas group 6830*a* found in FIG. 68*a*. This at least one patient specific persona is specifically tailored to a patient, based on data gathered as mentioned above with respect to their background, situation, and needs.

The flow of the Persona RiskQ™ Initiatives and Actions Flowchart 6900 is described herein. Information from the Databases group 6710 found in FIG. 67 is used by the Persona RiskQ™ System 6742 found in FIG. 67 to perform the Data Evaluation based on Attributes and Conditions process 6744 found in FIG. 67. The results from the Data Evaluation based on Attributes and Conditions process 6744 are placed into the Persona RiskQ™ Results database 6750 found in FIG. 67. Information from the Persona RiskQ™ Results database 6750 is used to assign at least one persona from the Personas group 6830*a* found in FIG. 68*a* to the patient. The information regarding the at least one persona assigned to the patient is used by the Client/Patient Specific Persona(s) process 6950 to create at least one persona that is specifically tailored to a patient, based on their background, situation, and needs. Information regarding this at least one persona is sent to a system described in FIG. 70*b* via line L69*a*. Information from the system described in FIG. 70*b* is sent to the Personas group 6830*a* via line L69*b* and to the Databases group 6710 via line L69*c*.

FIG. 69 showcases how the client/patient specific personas are created. The system draws information from databases containing information regarding the healthcare, social care, claims, geographic, health data, and environmental data of the patient (as a non-exhaustive list) to craft a persona or personas for that client/patient. These personas include but are not limited to complex/multi-dimensional persona, the healthcare persona, the social care persona, the claims persona, the geographic persona, the demographic persona, the environmental persona, the financial persona, and the behavioral persona. The system uses information from these personas to create a client/patient specific persona that is unique to that client/patient.

Figure 70A:
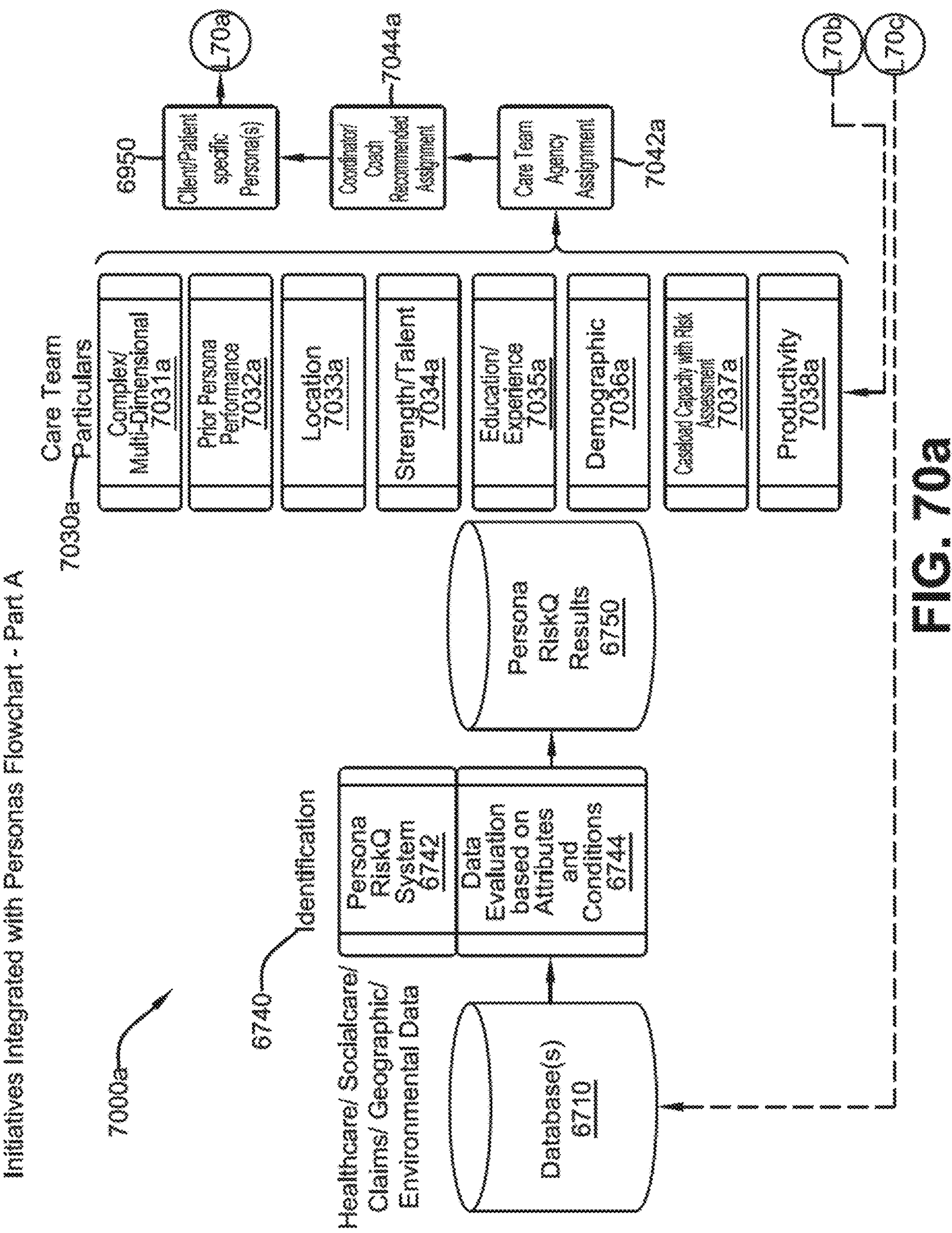
FIGS. 70*a* and 70*b* provide an Initiatives Integrated with Personas Flowchart.
Figure 70B:
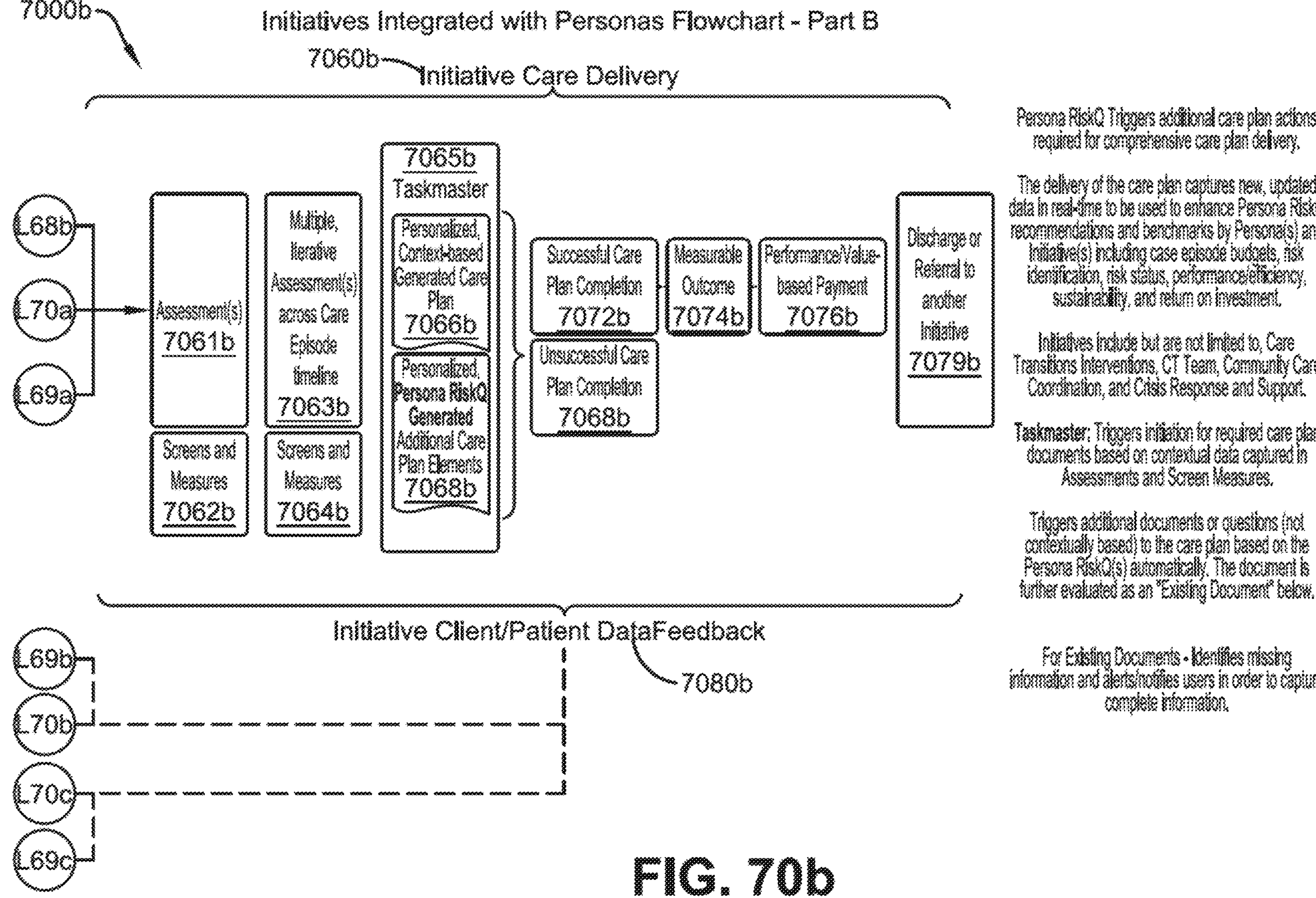

FIG. 70*a* schematically presents an Initiatives Integrated with Personas Flowchart-Part A 7000*a* showcasing how the system chooses which care team(s) and health workers/coordinator(s)/coach(es) are assigned to a patient. The Initiatives Integrated with Personas Flowchart-Part A 7000*a* includes the Databases group 6710 found in FIG. 67, the Identification group 6740 found in FIG. 67, the Persona RiskQ™ Results database 6750 found in FIG. 67, a Care Team Particulars group 7030*a*, a Care Team Agency Assignment process 7042*a*, a Coordinator/Coach Recommended Assignment process 7044*a*, and the Client/Patient Specific Persona 6950 found in FIG. 69. The Identification group 6740 includes the Persona RiskQ™ System 6742 found in FIG. 67 and the Data Evaluation based on Attributes and Conditions process 6744 found in FIG. 67. The Care Team Particulars group 7030*a* includes a Complex/Multi-Dimensional bucket 7031*a*, a Prior Persona Performance bucket 7032*a*, a Location bucket 7033*a*, a Strength/Talent bucket 7034*a*, an Education/Experience bucket 7035*a*, a Demographic conditions bucket 7036*a*, a Caseload Capacity with Risk Adjustment bucket 7037*a*, and a Productivity bucket 7038*a*.

The Care Team Particulars group 7030*a* is a group of particulars wherein each particular represents a data bucket containing information regarding a given care team condition, status, or circumstance. The Care Team Particulars group 7030*a* may include other data buckets, the data buckets included in this disclosure are exemplary and not limiting.

The Complex/Multi-Dimensional bucket 7031*a* is a is a digital bucket, where the issue the patient is dealing with is complex (i.e., it takes multiple factors into account) or multi-dimensional to be labeled with any of the other care teams particular comprising the Care Team Particulars group 7030*a*.

The Prior Persona Performance bucket 7032*a* is digital bucket where information regarding the performance of the care team regarding patients with the same persona(s) as the current patient is collected and digitally stored.

The Location bucket 7033*a* is a digital bucket where information regarding the location of the care team is collected and digitally stored.

The Strength/Talent bucket 7034*a* is a digital bucket where information regarding the strengths and talents of the care team is collected and digitally stored.

The Education/Experience bucket 7035*a* is a digital bucket where information regarding the education and experience levels of the members of the care team is collected and digitally stored.

The Demographic conditions bucket 7036*a* is a digital bucket where information regarding the demographics of the members of the care team is collected and digitally stored.

The Caseload Capacity with Risk Adjustment bucket 7037*a* is a digital bucket where information regarding the caseload capacity of a given care team, adjusted for risk, is collected and digitally stored.

The Productivity bucket 7038*a* is a digital bucket where information regarding the productivity levels of the care team is collected and digitally stored.

The Care Team Agency Assignment process 7042*a* is a process wherein a specific Care Team Agency is recommended for a patient, based on their background, situation, and needs.

The Coordinator/Coach Recommended Assignment process 7044*a* is a process wherein a specific coordinator or coach is recommended for a patient, based on their background, situation, and needs.

The flow of the Initiatives Integrated with Personas Flowchart-Part A 7000*a* is described herein. Information from the Databases group 6710 found in FIG. 67 is used by the Persona RiskQ™ System 6742 found in FIG. 67 to perform the Data Evaluation based on Attributes and Conditions process 6744 found in FIG. 67. The results from the Data Evaluation based on Attributes and Conditions process 6744 are placed into the Persona RiskQ™ Results database 6750 found in FIG. 67. Information from the Persona RiskQ™ Results database 6750 is used to analyze the particulars of a care team, separating the information into the corresponding buckets including the Care Team Particulars group 7030*a*. Information from the various buckets including the Care Team Particulars group 7030*a* is used in the Care Team Agency Assignment process 7042*a* and the Coordinator/Coach Recommended Assignment process 7044*a*. The information regarding the assigned care team agency from the Care Team Agency Assignment process 7042*a* and the Coordinator/Coach Recommended Assignment process 7044*a* is used by the Client/Patient Specific Persona(s) process 6950 found in FIG. 69 to create at least one create a care team assignment that is specifically tailored to a patient, based on their background, situation, and needs. Information from the Client/Patient Specific Persona(s) process 6950 is sent to the system described in FIG. 70*b* via the L70*a* line. Information from systems described in FIG. 70*b* is sent to the Care Team Particulars group 7030*a* via line L70*b* and to the Databases group 6710 via line L70*c*.

FIG. 70*a* showcases how care teams and coordinators/coaches are assigned by the Persona RiskQ™ system to specific clients/patients. The system draws information from databases containing information regarding health data, financial data and social determinants of health (e.g., healthcare, social care, claims, geographic, healthcare, and environmental data) of the patient to match that client/patient to a specific care team and coordinator/coach. Characteristics of the care teams are analyzed by the system to determine which care team is the best fit for the client/patient. Some of the characteristics analyzed include but are not limited to: complex/multi-dimensional particulars, prior persona performances, physical location of the care team, the strengths and talents of the care team, the education levels and prior experiences of the individual members of the care team, the demographics of the individual members of the care team, the caseload capacity of the care team (adjusted for risk), and the productivity levels of the care team. The system uses information from these particulars to create a client/patient specific persona that is unique to that client/patient via the assignment of a particular care team agency and a coordinator/coach.

FIG. 70*b* schematically presents an Initiatives Integrated with Personas Flowchart-Part B 7000*b* showcasing how the Persona RiskQ™ system uses the patient specific Personas and the Care Team Particulars to create personalized care plans using a Taskmaster and coordinate the implementation of those personalized care plans. The Initiatives Integrated with Personas Flowchart-Part B 7000*b* includes an Initiative Care Delivery process 7060*b* and an Initiative Client/Patient Data Feedback process 7080*b*. The Initiative Care Delivery process 7060*b* includes an Assessment(s) process 7061*b*, a Screens and Measures process 7062*b*, a Multiple, Iterative Assessment(s) across Care Episode Timeline process 7063*b*, a Screens and Measures process 7064*b*, a Taskmaster 7065*b*, a Personalized Context-based Generated Care Plan 7066*b*, a Personalized Persona RiskQ™ Generated Additional Care Plan Elements process 7068*b*, a Successful Care Plan Completion process 7072*b*, a Measurable Outcome process 7074*b*, a Performance/Value-based Payment process 7076*b*, an Unsuccessful Care Plan Completion process 7078*b*, and a Discharge or Referral to Another Initiative process 7079*b*.

The Initiative Care Delivery process 7060*b* is a process wherein care is delivered to the patient by the assigned health worker/care team, per the treatment plan assigned to the patient by the system from the Treatment Plans group 6860*a* found in FIG. 68*a*.

The Assessment(s) process 7061*b* is a process wherein the system conducts initial assessment(s) of the treatment plan assigned to the patient by the system from the Treatment Plans group 6860*a* found in FIG. 68*a*, the health worker/care team assigned to the patient, and the care to be delivered to the patient and compares it to how the care should be delivered to the patient. Additionally, this is the process where the system focuses on the one significant client need or problem that the treatment plan was designed and assigned to solve and identifies steps that will lead to a desired, measurable outcome. The system then budgets an allocation of relative value units (RVU) per outcome based units (OBU) over a care episode timeline.

The Screens and Measures process 7062*b* is a process wherein data retrieved from the initial assessment is screened and measured with respect to baseline data for changes in patient data, changes in patient persona identification and changes in persona conditions. The aforementioned changes are analyzed and evaluated for changes in the patient's assigned persona, changes in the patient's treatment plan, changes in the patient's care team and/or for changes requiring an addition of a new persona and/or reidentification of the client with the new persona. The system displays its findings from the Assessment(s) process 7061*b* and sends the assigned care team and the health worker/coordinator/coach a notification regarding its findings in real-time.

The Multiple, Iterative Assessment(s) across Care Episode Timeline process 7063*b* is a process wherein the system is continuously monitoring the progress of the care delivered to the patient and compares it to how the care should be delivered to its patient.

The Screens and Measures process 7064*b* is a process wherein data retrieved from the Multiple, Iterative Assessment(s) (continuous assessment) is screened and measured with respect to baseline data for in patient data, changes in patient persona identification and changes in persona conditions. The aforementioned changes are analyzed and evaluated for changes in the patient's assigned persona, changes in the patient's treatment plan, changes in the patient's care team and/or for changes requiring an addition of a new persona and/or reidentification of the client with the new persona. The system displays its findings from the Multiple, Iterative Assessment(s) across Care Episode Timeline process 7063*b* and sends the assigned care team and the health worker/coordinator/coach a notification regarding the findings in real-time.

The Taskmaster 7065*b* is a computer program that monitors the progress of tasks assigned to care teams and notifies said care teams/health workers/coordinators/coaches if they fall behind schedule for the completion of their tasks.

The Personalized Context-based Generated Care Plan 7066*b* is a plan generated by the system that takes into account not only the treatment plan assigned to the patient by the system from the Treatment Plans group 6860*a* found in FIG. 68*a* but also the specific context of the situation the patient finds themselves in at the time. This plan is constantly being evaluated by the system and is changed when the patient's situation changes, such as to necessitate the change or make the change advantageous to the patient.

The Personalized Persona RiskQ™ Generated Additional Care Plan Elements process 7068*b* is a plan that is generated by the system if the system determines at any given time that the current plan assigned to the patient is insufficient to treat the patient adequately or if the patient's situation changes such that they need either an additional or an entirely new treatment plan.

The Successful Care Plan Completion process 7072*b* is a process wherein the system analyzes the status of the care given to the patient, compares it with the assigned treatment plan and the expected progress/outcome of that treatment plan determined in the Assessment(s) process 7061*b*, and determines that the care given to the patient was satisfactory and that the patient's treatment is successfully completed.

The Measurable Outcome process 7074*b* is a process wherein the system looks at the desired, measurable outcome determined in the Assessment(s) process 7061*b* and determines whether the desired, measurable outcome was achieved and to what extent it was achieved.

The Performance/Value-based Payment process 7076*b* is a process wherein the system determines whether the budget of relative value units (RVU) per outcome based units (OBU) over the care episode timeline determined in the Assessment(s) process 7061*b* was adhered to, and whether care team performance achieved the system's expectations.

The Unsuccessful Care Plan Completion process 7078*b* is a process wherein the system analyzes the status of the care given to the patient, compares it with the assigned treatment plan and the expected progress/outcome of that treatment plan determined in the Assessment(s) process 7061*b*, and determines that the care given to the patient was not satisfactory and that the patient's treatment is not successfully completed.

The Discharge or Referral to Another Initiative process 7079*b* is a process wherein after the patient's assigned treatment plan has been completed, the system determines whether the patient needs to be referred to another agency, requires another treatment plan, or if the patient needs no other treatment and may be discharged. If needed, the system will make the referral or select/create another treatment plan from the Treatment Plans group 6860*a* found in FIG. 68*a*.

The Initiative Client/Patient Data Feedback process 7080*b* is a process wherein information regarding the results from the Initiative Care Delivery process 7060*b* is sent to the system in FIG. 69 via the L69*b* and L69*c* lines and the system in FIG. 70*a* via the L70*b* and L70*c* lines.

The flow of the Initiatives Integrated with Personas Flowchart-Part B 7000*b* is described herein. The Assessment(s) process 7061*b* receives information regarding the assigned treatment plan from the Treatment Plans group 6860*a* found in FIG. 68*a* via the L68*b* line, information regarding the client/patient specific persona(s) from the Client/Patient specific Persona(s) process 6950 found in FIG. 69 via the L69*a* line, and information regarding specific care teams and coordinators/coaches from the Care Team Agency Assignment process 7042*a* and the Coordinator/Coach Recommended Assignment process 7044*a* respectively from the L70*a* line. That information is used in the Assessment(s) process 7061*b* and the Multiple, Iterative Assessment(s) across Care Episode Timeline process 7063*b*, the results of which are displayed and/or communicated via the Screens and Measures process 7062*b* and the Screens and Measures process 7064*b* respectively. The Taskmaster 7065*b* monitors the progress of tasks assigned to care teams and notifies said care teams if they fall behind schedule for the completion of their tasks. Information from the Assessment(s) process 7061*b*, the Multiple, Iterative Assessment(s) across Care Episode Timeline process 7063*b*, and the Taskmaster 7065*b* are used to determine the successfulness of the delivery of care via the Successful Care Plan Completion process 7072*b* and Unsuccessful Care Plan Completion process 7078*b*. If the delivery of care is deemed successful by the system, the system will perform the Measurable Outcome process 7074*b* and the Performance/Value-based Payment process 7076*b* to determine the efficacy of the delivery of care. All of the information from the Initiative Care Delivery process 7060*b* is sent to the systems in FIG. 69 via the L69*b* and L69*c* lines and the system in FIG. 70*a* via the L70*b* and the L70*c* lines.

FIG. 70*b* showcases how the Persona RiskQ™ system uses the treatment plan assigned to the patient in FIG. 68*a*, the client/patient specific persona(s) assigned to the patient in FIG. 69, and the care team and coordinator/coach assigned to the patient in FIG. 70*a* to deliver care to the patient in an efficient and effective manner. The Persona RiskQ™ system first assesses the treatment plan assigned to the patient by the system, the care team assigned to the patient, and the care to be delivered to the patient and compares it to how the care should be delivered to the patient. Additionally, this system focuses on the one significant client need or problem that the treatment plan was designed and assigned to solve and identifies the key steps that will lead to a desired, measurable outcome. The system then budgets an allocation of relative value units (RVU) per outcome based units (OBU) over a care episode timeline. The system displays its findings from this initial assessment for the care team and the coordinator/coach to view, either on a screen or as a message or notification. The system carries out this assessment repeatedly throughout the timeline of care to monitor the progress of the care delivered to the patient and compares it to how the care should be delivered to the patient. The system displays its findings from these assessments for the care team and the coordinator/coach to view, either on a screen or as a message or notification. If the care team and/or health worker/the coordinator/coach is/are behind schedule or providing deficient care, the system may use a Taskmaster, which will notify the appropriate person/people of the deficiency. The system also creates a personalized context-based generated care plan, which is a plan that takes into account not only the treatment plan assigned to the patient by the system but also the specific context of the situation the patient finds themselves in at the time. This plan is constantly being evaluated by the system and is changed when the patient's situation changes, such as to necessitate the change or make the change advantageous to the patient. The system may also create a personalized Persona RiskQ™ generated additional care plan, which is a plan that is generated by the system if the system determines at any given time that the current plan assigned to the patient is insufficient to treat the patient adequately or if the patient's situation changes such that they need either an additional or an entirely new treatment plan. Once the care team claims that their delivery of care to the patient is complete, the system then determines the successfulness of the delivery of care. If the delivery of care was successfully completed, the system then determines the efficacy of the delivery of care by looking at the completion of the measurable outcome and the RVU/OBU metric and comparing them to what the initial assessment determined. If the delivery of care is determined to have not been successful, the system will notify the care team and the health worker/coordinator/coach and instruct them to continue care or correct the deficiencies in their delivery of care to the patient. Once the delivery of care is completed, the system will, if necessary, determine whether the patient needs to be referred to another agency or requires another treatment plan. If so, the system will make the referral or select/create another treatment plan for the patient. Otherwise, the patient may be discharged. All of the information gathered and determinations made during this whole process is sent back to the systems depicted in FIGS. 69 and 70*a* to help retrain the models and update the databases utilized by the artificial intelligence engine in those systems.

Artificial Neural Networks (ANNs, also shortened to Neural Networks (NNs) or neural nets) are a branch of machine learning models that are built using principles of neuronal organization discovered by connectionism in the biological neural networks constituting human brains. Neural Networks teach computers how to process data in a way that is inspired by the human brain.

A Neural Network is based on a collection of connected units or nodes called artificial neurons, which loosely model the neurons in a biological brain. Each connection, like the synapses in a biological brain, can transmit a signal to other neurons. An artificial neuron receives signals then processes them and can signal neurons connected to it. The "signal" at a connection is a real number, and the output of each neuron is computed by some non-linear function of the sum of its inputs. The connections are called edges. Neurons and edges typically have a weight that adjusts as learning proceeds. The weight increases or decreases the strength of the signal at a connection. Neurons may have a threshold such that a signal is sent only if the aggregate signal crosses that threshold.

Typically, neurons are aggregated into layers. Different layers may perform different transformations on their inputs. Signals travel from the first layer (the input layer) to the last layer (the output layer), possibly after traversing the layers multiple times.

Figure 71:
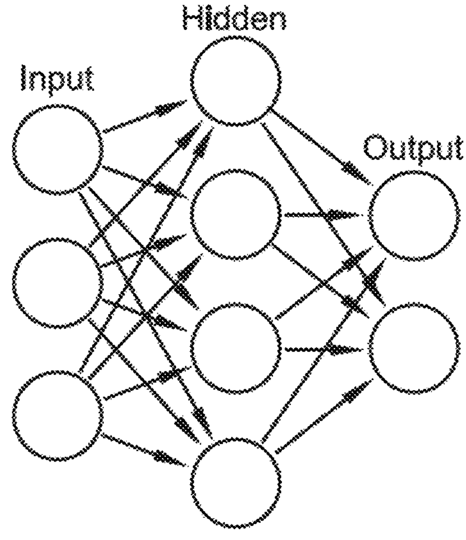
FIG. 71 is an illustration of an exemplary neural network schematic having a plurality of layers.

The "neuron" inside of the neural network is a function whose value is a number between 0 and 1. A neural network is made up of a plurality of layers of these "neurons," the first layer being the "input layer," the last being the "output layer," and the rest of the layers in the middle being "hidden layers" (if applicable). This architecture is shown in FIG. 71. Neurons contained within a "hidden layer" have a weight and bias attached to them, which are used in data processing to accentuate some data points and suppress others, depending on what the Neural Network is attempting to achieve.

An exemplary neural network schematic is shown in FIG. 71, wherein the neural network is an interconnected group of nodes, inspired by a simplification of neurons in a brain. Here, each circular node represents an artificial neuron, and an arrow represents a connection from the output of one artificial neuron to the input of another. An algorithm or group of algorithms is used to process the data as it is sent from one layer to the next.

The neural network "learns" through data processing and comparing with a set of test data. Test data is a dataset created by humans that represents what the output should be for a given input and is used by the neural network to train itself. During the learning process, when data reaches the output layer of the neural network, it is compared with the test data to see how accurate the output data is. If the data has errors, the neural network will adjust the weights and biases of the appropriate neurons to account for the error. The neural network will repeat this process until the error reaches 0.

Once the error has approximately reached 0, the neural network is trained and is ready for use, neural networks continue to train themselves as new and different data is added to the test dataset, and does this in real-time.

Ultimately, neural networks are an amalgamation of algorithms and functions, wherein the neural network is able to change the values of the various parameters contained within the algorithms and functions to achieve the desired results.

More specifically, the neural network creates outputs by taking inputs and processing them through an algorithm or a series of algorithms. Each layer after the input layer represents an algorithm that the neural network is using to process the input data. An exemplary fundamental algorithm is shown in the formulas below. An individual neuron always has a number value of 0 to 1, 0 being "off" and 1 being "on". Any number between 0 and 1 may be "on" or "off", depending on the weight and bias of the neuron.

$$y_n = \sigma(x)\sum_{j=0}^{n}(w_{kj} * x_j + b_j)$$

Fundamental Neural Network Algorithm

Figure 72:
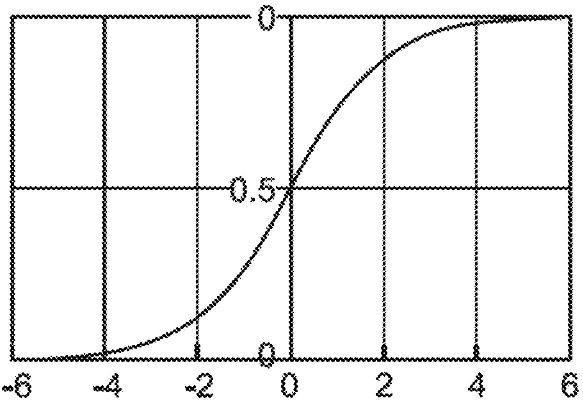
FIG. 72 is a graph of a Sigmoid function.

The mathematical algorithm shown above is an exemplary fundamental algorithm used by neural networks in each of their given layers. The variables used in this algorithm are as follows: "y" is the output; "x" is the input, "n" is the input/output number; "w" is the weight given to a neuron; "k" is the number of the associated neuron from the previous layer for weighting purposes; "j" is the neuron number (from neuron #0 to neuron #n); and "b" is the bias. cr(x) is the Sigmoid function, which is shown below. A graph of the Sigmoid function is provided in FIG. 72. The weight given to a neuron helps to accentuate certain datapoints and suppress others. The bias changes the threshold that a neuron needs to hit in order to be "on" versus "off."

$$\sigma(x) = \frac{1}{1 + e^{-x}}$$

Sigmoid Function

The purpose of adding the sigmoid function to the front of an algorithm is to ensure that the output is always between 0 and 1, fitting within the neuron. The algorithms shown above are exemplary and not limiting. A neural network may have any number of neurons and layers, depending on the application of the neural network.

According to further aspects of the present disclosure the neural network may include any of the functions described below. The neural network may machine learn from data received to change, modify and update a set of pre-set conditions. The neural network may machine learn from data received to create new conditions. The changed, modified and updated pre-set conditions and new conditions may then be entered into the care coordination system program. The neural network may machine learn from data received to change, modify and update personas. The neural network may machine learn from data received to create new personas. The change, modified and updated personas and new personas may then be entered into the care coordination system program. The neural network may further review, analyze and evaluate data during treatment with respect to changes in client conditions, machine learn from the data and create a new modified persona and I or a new modified risk tier treatment plan. The new or modified risk tier treatment plan may include a new or modified care plan, a new or modified care team and I or new treatment frequencies. The neural network may identify a risk tier. The neural network may identify a risk tier and an artificial intelligence engine may determine the best intervention and I or treatment plan to resolve the risks of a specific risk tier. The neural network may further identify discrepancies in the cost of treatment plans between average cost according to a condition bucket, projected cost of a client's current treatment plan and the current cost of a client's current treatment plan. If the projected and current cost of the client's current treatment plan exceeds the average cost of the treatment plan, the neural network may learn from data received what steps need to be taken to reduce current and projected costs of the client's treatment plan. The neural network may further review additional data collected from the client to change and I or modify a treatment plan or to implement a new treatment plan in real-time. The neural network may further conduct an initial assessment of the treatment plan assigned to the client, of the care team assigned to the client and of the care to be and being delivered to the client. The neural network may learn from data gathered how or what care should be delivered. This may be determined by the neural network budgeting an allocation of relative value units (RVU) per outcome based units (OBU) over a care episode timeline and the neural network triggering additional care plan actions for improving comprehensive treatment plan delivery based on an allowed budget. The neural network may further continuously monitor and assesses progress of care delivered to the client and review, analyze and evaluate data received concerning administration of care in view of baseline data with respect to delivery of care for treating a client having a particular condition. The neural network may further review, analyze and evaluate status of care given to the client in view of the assigned treatment plan and expected progress and expected outcome of the treatment plan and determine whether service provided to the client was satisfactory or not and whether or not the client's treatment is successfully being completed or is successfully completed. If the client's treatment is successfully being completed or was successfully completed, the artificial intelligence engine may consider a desired, measurable outcome and determine whether the desired, measurable outcome was achieved and to what extent it was achieved. The neural network of the artificial may further learn factors that lead towards the treatment successfully being completed or of the treatment's successful completion and update persona conditions, personas, and risk tier treatment plans to increase the likelihood of future success. If the artificial intelligence engine determines that the client's treatment is not progressing towards successful completion, that the client's treatment was not successfully completed or that improvements in the client's treatment should be made, the neural network may review, analyze, and evaluate the treatment plan's effectiveness for both the client and the service provider. The neural network may then modify a persona, assign a different persona, create a new persona, modify a treatment plan, change a treatment plan and I or create and assign a new treatment plan in real-time based on data received. If an assigned budget over a care episode timeline was adhered to the neural network may review, analyze, and evaluate the treatment plan's effectiveness and modify a treatment plan, assign a different treatment plan and I or create and assign a new treatment plan in real-time based on data received. The neural network may further determine in real-time whether the client is to be referred to another service provider and whether the client requires a further treatment plan after a client's treatment plan is completed. The neural network may further generate outputs that are entered into the system by the artificial intelligence engine and provided to the client, care team and I or service provider in real-time by the artificial intelligence system through a graphical user interface. It is to be understood that all of the functions of the artificial intelligence engine and of the neural network may be continuous and are capable of being performed in real-time.

The care coordination system further includes a separate artificial intelligence engine which extends into translation and interpretation of language. The artificial intelligence engine is capable of translating communications from one language to another language instantaneously (e.g., in a matter of seconds). Recipients or multiple recipients of the translations can respond to communications in their own language and the artificial intelligence engine will translate responses to another language (e.g., English) instantaneously. This tool may be used in many applications including communications with clients for the purpose of retrieving data related to SDoH, clinical data, financial data, etc. as well as internally between service providers within the care coordination system. The artificial intelligence engine, however, extends beyond simple translation and also provides interpretation of language communicated into the system. For example, the artificial intelligence engine is capable of evaluating inflections of oral or spoken language to determine, including but not limited to, sincerity, defensiveness, emotion, and mental health around an answer. Translations are recorded into the client database and client record and logged so that staff can comment on the communications received. The artificial intelligence engine, through an algorithm, reviews and analyzes this data and determines and assigns a grade as to how truthful the client was with respect to a particular question and categorizes the response within a particular truth scale. This information may then be used by the artificial intelligence engine at the persona level to prompt the care coordinator, health worker, etc. with further courses of action, pathways, questions to ask the client, etc. to improve overall treatment.

Figure 73:
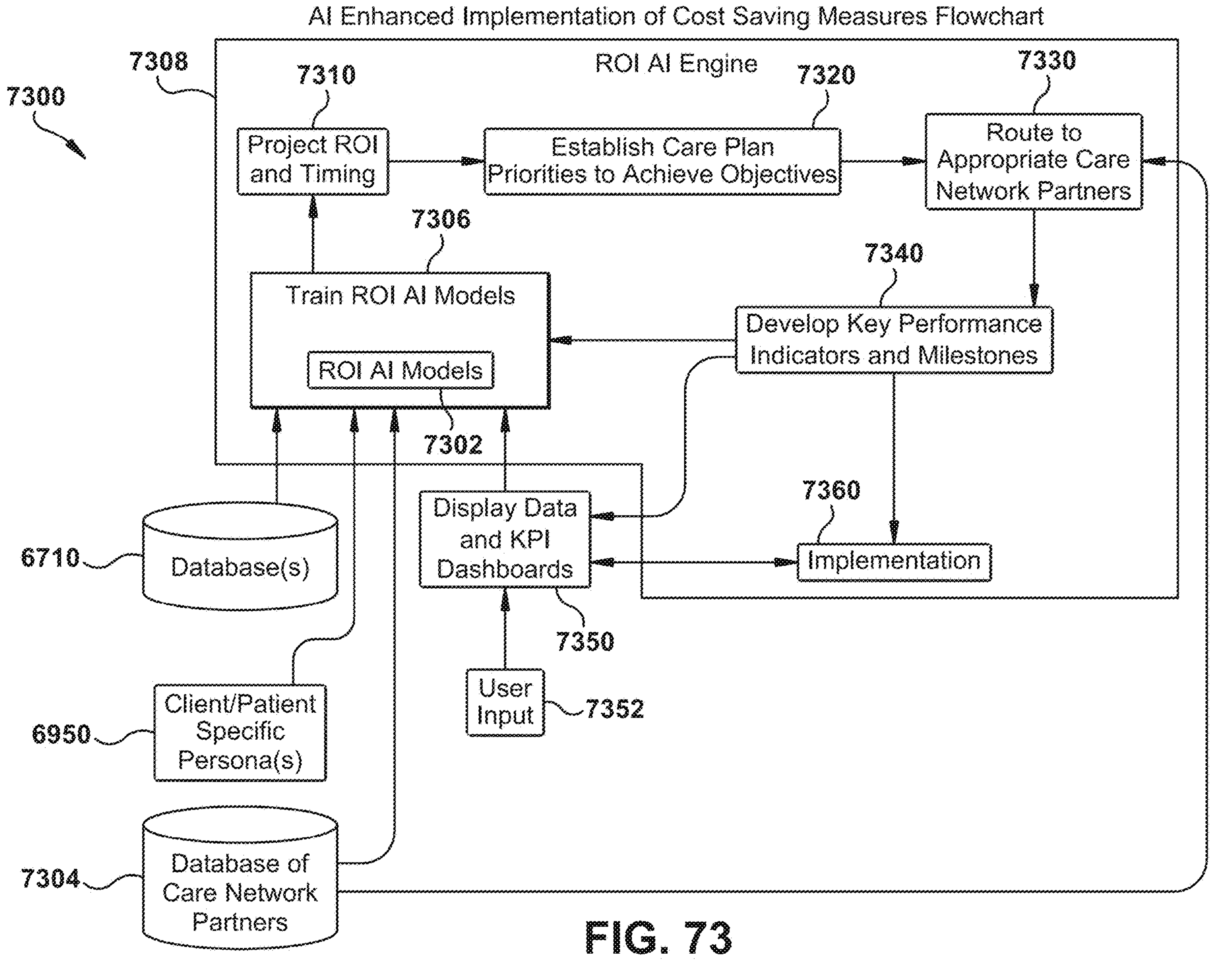
FIG. 73 provides an AI Enhanced Implementation of Cost Savings Measures Flowchart.

FIG. 73 schematically presents an AI Enhanced Implementation of Cost Savings Measures Flowchart 7300, showcasing how the system calculates ROIs, generates care plan priority lists, and implements care plans. The AI Enhanced Implementation of Cost Savings Measures Flowchart 7300 includes at least one ROI AI Model 7302, a Care Network Partners Database 7304, a Train ROI AI Model step 7306, an ROI AI Engine 7308, the Databases group 6710 from FIG. 67, the Client/Patient specific Persona(s) process 6950 from FIG. 69, a Project ROI and Timing step 7310, an Establish Care Plan Priorities to Achieve Objectives step 7320, a Route to Appropriate Care Network Partners step 7330, a Develop Key Performance Indicators and Milestones step 7340, a Display Data and KPI Dashboards step 7350, a User Input 7352, and an Implementation step 7360.

The at least one ROI AI Model 7302 is an AI model which is trained to calculate ROIs for various different treatment methods and pathways for a given client/patient.

The Care Network Partners Database 7304 is a database in which the system stores information regarding the different care network partners that the system partners with to provide care to clients/patients.

The Train ROI AI Model step 7306 is a step in which the ROI AI Engine 7308 trains the at least one ROI AI Model 7302 using information from the Care Network Partners Database 7304, the Databases group 6710, and the Client/Patient specific Persona(s) process 6950, as well as feedback from the Develop Key Performance Indicators and Milestones step 7340, the Display Data and KPI Dashboards step 7350, and the Implementation step 7360.

The ROI AI Engine 7308 is an artificial intelligence engine that uses the at least one ROI AI Model 7302 to perform the Project ROI and Timing step 7310, the Establish Care Plan Priorities to Achieve Objectives step 7320, the Route to Appropriate Care Network Partners step 7330, the Develop Key Performance Indicators and Milestones step 7340, and the Implementation step 7360 automatically without human intervention. The ROI AI Engine 7308 also continuously and automatically trains the at least one ROI AI Model 7302 by continuously performing the Train ROI AI Model step 7306. In one aspect of the present disclosure, the ROI AI Engine 7308 is a neural network.

The Project ROI and Timing step 7310 is a step in which the system utilizes AI models to calculate the ROIs and the timings for the treatment/care of a client/patient, based on information from the Databases group 6710 and the Client/Patient specific Persona(s) process 6950 regarding the client/patient.

The Establish Care Plan Priorities to Achieve Objectives step 7320 is a step in which the system utilizes at least one ROI AI Model 7302 to generate a list of care plan priorities to maximize ROI while still giving the client/patient the best care possible.

The Route to Appropriate Care Network Partners step 7330 is a step in which the system determines which care network partner is best suited to serve the needs of the client/patient while being as efficient as possible. The system pulls information from the Establish Care Plan Priorities to Achieve Objectives step 7320 and the Care Network Partners Database 7304 when performing the Route to Appropriate Care Network Partners step 7330.

The Develop Key Performance Indicators and Milestones step 7340 is a step in which the system creates performance indicators and milestones to better track the progress and efficiency of the care given to a client/patient.

The Display Data and KPI Dashboards step 7350 is a step in which the system displays the results of the Develop Key Performance Indicators and Milestones step 7340 and allows the user to view these results and evaluate the performance of the system to ensure that it is working efficiently to provide the best care to the client/patient at the best possible price.

The User Input 7352 is a GUI which allows the user to make any changes to the care plan for the client/patient that the user sees fit, allowing the user to correct any errors made by the system.

The Implementation step 7360 is a step in which the system implements the care plan and the performance indicators and milestones developed by the system during the Establish Care Plan Priorities to Achieve Objectives step 7320, the Route to Appropriate Care Network Partners step 7330, and the Develop Key Performance Indicators and Milestones step 7340, along with the any changes made by the user in the User Input 7352 via the Display Data and KPI Dashboards step 7350. In one aspect of the present disclosure, the ROI AI Engine 7308 sets a budget during this step for the care team to adhere to for a given care plan.

The flow of the AI Enhanced Implementation of Cost Savings Measures Flowchart 7300 is described herein. The system begins the process showcased in the AI Enhanced Implementation of Cost Savings Measures Flowchart 7300 via the ROI AI Engine 7308 performing the Train ROI AI Model step 7306, wherein the ROI AI Engine 7308 trains the at least one ROI AI Model 7302 to calculate the ROI and best method of care for a given client/patient. The ROI AI Engine 7308 trains the at least one ROI AI Model 7302 using information from the Databases group 6710 regarding health related data, client data on social determinants of health and financial data, information from the Client/Patient specific Persona(s) process 6950 regarding the client/patient specific Persona created by the system during the performance of the Client/Patient specific Persona(s) process 6950, information from the Care Network Partners Database 7304 regarding the different care network partners that the system partners with to provide care to clients/patients, information from the Develop Key Performance Indicators and Milestones step 7340 regarding the performance indicators and milestones created by the system during the performance of the Develop Key Performance Indicators and Milestones step 7340, information from the Display Data and KPI Dashboards step 7350 regarding any user-made changes entered by the user into the User Input 7352, and information from the Implementation step 7360 regarding how the care plan developed by the system is implemented. The ROI AI Engine 7308 then uses the at least one ROI AI Model 7302 to perform the Project ROI and Timing step 7310, wherein the system calculates the projected ROI and timing of the treatment of a given client/patient using the at least one ROI AI Model 7302. The ROI AI Engine 7308 then uses the at least one ROI AI Model 7302 to perform the Establish Care Plan Priorities to Achieve Objectives step 7320, wherein the system generates a list of care plan priorities to maximize ROI while still giving the client/patient the best care possible using the projected ROI and timing of the treatment of a given client/patient determined during the performance of the Project ROI and Timing step 7310. The ROI AI Engine 7308 then uses the at least one ROI AI Model 7302 to perform the Route to Appropriate Care Network Partners step 7330, wherein the system determines which care network partner is best suited to serve the needs of the client/patient while being as efficient as possible by using information from the Care Network Partners Database 7304 regarding care network providers, along with the list of care plan priorities to maximize ROI while still giving the client/patient the best care possible generated during the performance of the Establish Care Plan Priorities to Achieve Objectives step 7320. The ROI AI Engine 7308 then uses the at least one ROI AI Model 7302 to perform the Develop Key Performance Indicators and Milestones step 7340, wherein the system creates performance indicators and milestones to better track the progress and efficiency of the care given to a client/patient using information regarding which care network partner is best suited to serve the needs of the client/patient while being as efficient as possible determined by the system during the performance of the Route to Appropriate Care Network Partners step 7330. The system then performs the Display Data and KPI Dashboards step 7350, wherein the system displays the results of the Develop Key Performance Indicators and Milestones step 7340, wherein the user may view these results and evaluate the performance of the system to ensure that it is working efficiently to provide the best care to the client/patient at the best possible price. If the user believes that changes need to be made to the care plan or any other aspect of the client/patient's care, the user may do so via the User Input 7352. Any changes made through the User Input 7352 are then passed along to the Train ROI AI Model step 7306 to adjust the at least one ROI AI Model 7302 to reflect the changes. The ROI AI Engine 7308 then performs the Implementation step 7360, wherein the system implements the care plan and the performance indicators and milestones developed by the system during the Develop Key Performance Indicators and Milestones step 7340, along with implementing any changes made through the User Input 7352 via the Display Data and KPI Dashboards step 7350. The results of the Implementation step 7360 are also displayed during the performance of the Display Data and KPI Dashboards step 7350.

Figure 74:
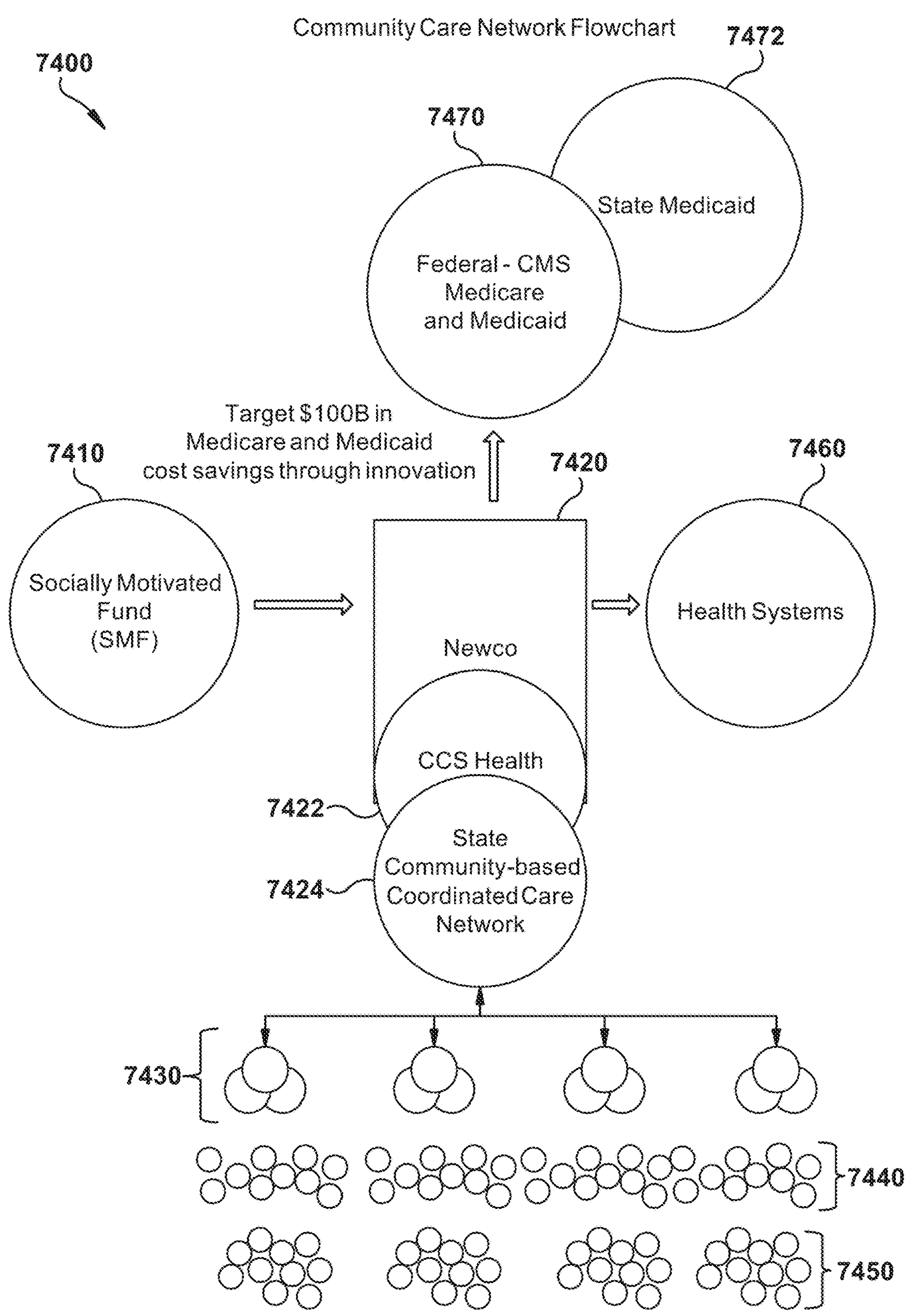
FIG. 74 provides a Community Care Network Flowchart.

FIG. 74 schematically presents a Community Care Network Flowchart 7400, showcasing an example of how CCNs reallocate money that was saved by the system. The Community Care Network Flowchart 7400 includes a Socially Motivated Fund (SMF) 7410, a Newco Organization 7420, a CCS Health system 7422, a State Community-Based Coordinated Care Network 7424, at least one Care Provider group 7430, at least one Community Care Contracted Service Delivery Partners group 7440, at least one Community Information Exchange Organizations group 7450, at least one Health System 7460, a Federal Medicare/Medicaid Beneficiary 7470, and a State Medicaid Beneficiary 7472.

The Socially Motivated Fund (SMF) 7410 is a savings fund where the money saved by this method can be stored and used for various health care related activities and purposes.

The Newco Organization 7420 is a money management organization for collaboration of the SMF, Healthcare, Other Partners/Stakeholders, and CCS Health with a given CCN. Healthcare and community health initiatives are identified, funded, implemented, managed, and evaluated at the Newco Organization 7420.

The CCS Health system 7422 is a system that manages the CCN and receives the payments for the realized ROI results generated by the CCN and distributes to the CCN stakeholder partners accordingly.

The State Community-Based Coordinated Care Network 7424 is a network of care providers that are approved by the state to provide care to patients within the state.

The at least one Care Provider group 7430 is a group of care providers that partner with the State Community-Based Coordinated Care Network 7424. The at least one Care Provider group 7430 includes one or more of the following: at least one CBO, at least one AAA, at least one hospital, at least one aging network, and/or at least one FQHC.

The at least one Community Care Contracted Service Delivery Partners group 7440 is a group of care providers under contract to provide care in the community and of court orders requiring specific care for a client/patient that partner with the State Community-Based Coordinated Care Network 7424. The at least one Community Care Contracted Service Delivery Partners group 7440 includes one or more of the following: at least one CBO and/or at least one CTO.

The at least one Community Information Exchange Organizations group 7450 is a group of organizations that handle patient referrals within a given community that partner with the State Community-Based Coordinated Care Network 7424. The at least one Community Information Exchange Organizations group 7450 includes at least one CBO.

The at least one Health System 7460 is a not-for-profit hospital involved and funded by the SMF.

The Federal Medicare/Medicaid Beneficiary 7470 is the Federal Medicare/Medicaid program, which is a beneficiary of this CCN.

The at least one State Medicaid Beneficiary 7472 is at least one State Medicaid program that is a beneficiary of this CCN.

The flow of the Community Care Network Flowchart 7400 is described herein. An initial investment from the Socially Motivated Fund (SMF) 7410 is made in the Newco Organization 7420 to begin the CCN. The CCN helps the care providers included within the State Community-Based Coordinated Care Network 7424, including those within the Care Provider group 7430, the Community Care Contracted Service Delivery Partners group 7440, and the Community Information Exchange Organizations group 7450. This money saved by the care providers included within the State Community-Based Coordinated Care Network 7424 is managed by the CCS Health System 7422 and is then sent to the Newco Organization 7420 for disbursement. The Newco Organization 7420 then disburses this money between the State Community-Based Coordinated Care Network 7424, the at least one Health System 7460, the Federal Medicare/Medicaid Beneficiary 7470, and the at least one State Medicaid Beneficiary 7472 based on the individual needs of each organization/program, with a target of at least $100 Billion in savings across the CCN. Any leftover money is given back to the Socially Motivated Fund (SMF) 7410 for further investment.

Figure 75:
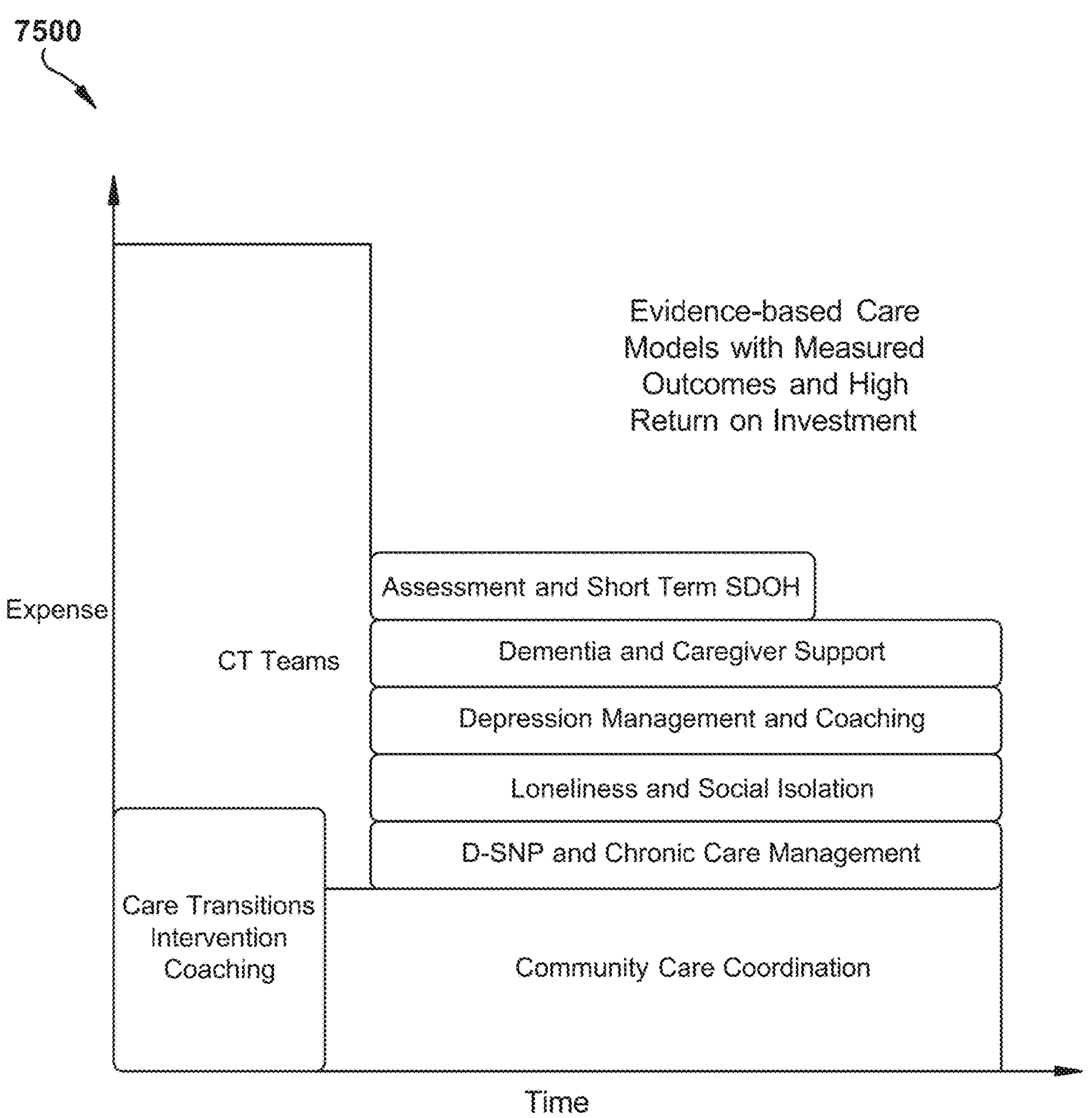
FIG. 75 is a graph showing the return on investment of various programs and teams.

FIG. 75 graphically presents an Evidence-Based Care Models with Measured Outcomes and High Return on Investments graph 7500, wherein the relationship between expense and time with respect to several aspects of the present disclosure are plotted.

In one aspect of the present disclosure, the savings generated by the process detailed in the AI Enhanced Implementation of Cost Savings Measures Flowchart 7300 are applied to the State Community-Based Coordinated Care Network 7424 and are distributed by the Newco Organization 7420 to the State Community-Based Coordinated Care Network 7424, the at least one Health System 7460, the Federal Medicare/Medicaid Beneficiary 7470, and the at least one State Medicaid Beneficiary 7472 based on the individual needs of each organization/program.

In another aspect of the present disclosure, the ROI AI Engine 7308 determines whether the budget of the care plan was adhered to and whether the care team achieved the system's expectations.

In yet another aspect of the present disclosure, when a client/patient's care plan is completed, the ROI AI Engine 7308 determines whether the client is to be referred to another agency or requires a further treatment plan, and if so, calculates a new ROI and timing of a new care plan.

In another aspect of the present disclosure, the artificial intelligence engine utilizes structured query language (SQL) software and robotic process automation (RPA) software, wherein the structured query language (SQL) software manages the relationship between data within disparate databases, performs operations on the data and wherein the robotic process automation (RPA) software builds, deploys and manages software robots to interact with the data, digital systems and software and identifies and extracts data and performs defined actions.

In one aspect of the present disclosure, the most efficient use of capital from SMF should be applied to health systems, urban and rural with a focus on increasing health systems net patient revenue (NPR) through streamlined and efficient administrative services.

In another aspect of the present disclosure, to induce SMF to fund the health care system and coordinated care network, the federal government through CMS provides the innovation with shared savings agreements based on actual savings realized. The baseline is the prior complete financial year for Medicare and Medicaid expenditures for the state or region. The following allocations for the shared saving payments are recommended:

Socially Motivated Fund (SMF)—20%; The SMF is taking on the risk solely for the upfront healthcare and community funding with the goal of maintaining an evergreen fund through the return on investment earned from the SMF share of growth in profitability of the funded healthcare systems.

The Coordinated Care Network 15%; Performance payment to be distributed to CCN stakeholders and delivery partners instrumental in achieving the shared savings and funding further solution incentives producing further shared savings. A sustainability investment in the state's community care network for further cost savings, better health outcomes, and higher quality of life.

State and/or State Medicaid 15%; To reduce state Medicaid costs and further funding of Medicaid related programs Returned to Solution Funders and Stakeholders: 50%; Similar to a Medicare Shared Saving Program or ACO Reach model where 50% of the savings provided to CMS from the Healthcare/Community solution are returned to further fund and incentivize the solution funders and stakeholders for continued and greater gains.

In one aspect of the present disclosure, the artificial intelligence engine reviews invoicing for further recommendations for treatment options for the health worker (including community care coordinator, supervisor, care team, general service provider, etc.) to follow and the proper pathway recommendations for the client to follow in real-time. For example, an invoice may identify a service for cardiac heart failure. The client would be identified with cardiac heart failure as part of their persona. Other factors within the client's persona may include depression and anxiety. The artificial intelligence engine evaluates these items listed in the invoicing system and in the client's persona and identifies further questions to ask and data to retrieve, further courses of action, further treatment options, etc. For example, the artificial intelligence engine may indicate that in other cases, a certain percentage of clients were also missing certain forms of treatment. For example, 75% of clients with these conditions may have also been provided with these three medications which are not present in the current client's medication list. Therefore, a further inquiry would be entered and presented to the care coordinator, health worker, etc. as to why these medications are not prescribed to the current client. The artificial intelligence engine also conducts a timeframe treatment analysis based on invoicing to determine if care to the client is on schedule, behind schedule or ahead of schedule. For example, based on the persona, the artificial intelligence engine determines whether certain treatments should have occurred within a particular time period (e.g., 60 days). If treatments are not occurring within a determined time period, the artificial intelligence engine notifies the care coordinator, health worker, etc. that treatment is behind the curve on delivering quality of care to the individual based on the persona built in the artificial intelligence program. Therefore, billable events are lower than what they should be within the system. This allows the artificial intelligence system to influence invoicing as it prompts the care coordinator, health worker, etc. to provide additional service to the client and generate additional billable events, thereby increasing overall revenue. In this sense, the artificial intelligence engine does more than simply provide a reminder to the care coordinator, health worker, etc., rather, it provides notice as to the specific questions that must be asked and answered in providing care and launches forms that must be filled out and completed in the process. It further evaluates the number of activities performed for a client of a particular persona within a certain time period and determines if the number of activities is characteristic of that persona in real-time.

The system of the present teaching is used in calculating the required sustainability level, break-even point, for care coordination efforts (CHW cost+Supervisor Cost)/(1−Admin Retention %) and Administrative unit (hub or Agency). Determining the Persona RiskQ™ for a potential initiative is helpful in determining the capacity available and opportunity cost for the Care Coordination efforts and the Administrative units. The higher the estimated Persona RiskQ™, the higher the initiative cost per client required from the Payer to compensate for the care coordination and the Administrative unit's efforts to achieve break-even for the care coordination and the Administrative units. An administrative percentage would be applied to the Persona RiskQ™ estimated cost per client to provide for required service growth or additional incentive to service.

In estimating the Persona RiskQ™, a normal client care plan, applied for twelve months (duration), has an estimated annualized outcome based units (OBU) amount of service activities, in normal/moderate conditions [1×] (environmental), and the client intensity level is expressed in the estimated annualized OBUs of service activities. The expression would be 1 client of 100 OBUs=1 Persona RiskQ™ client. The client cost of a Persona RiskQ™ client would be the estimated OBU times the outcome-based rate (OBR). For example, 100 OBUs times a $30 OBR equals $3,000 per client per year. For simplification, the administrative fee percentage can be included in, or applied in addition to, the total cost of the client. For example, with an OBR of $25 and an administrative rate of 20%, the adjusted OBR equals $30 ($25+$5 (20%*$25)). When the administrative rate is applied in addition to the OBR, the same value is provided-$3,000 per client (100 OBU*$25 OBR=$2,500+20% Admin or $500).

The Persona RiskQ™ caseload value is used in evaluating the caseload capacity and availability for a care coordinator factoring in the multiple client personas that exist in each care coordinator's, agency, and administrative unit/hub's caseload. The sum of the Persona RiskQ™ Caseload values in a caseload can be used comparatively with other caseloads as well as with the Pathways RiskQ®, the SDoH and Individual/Household Risks risk value, to evaluate each caseload and risk-adjusted capacity based on Persona RiskQ™ and Pathways RiskQ®. Additionally, Clinical RiskQ™ can be determined and used separately or in conjunction with Persona RiskQ™.

The duration of services is a factor in the Persona RiskQ™ and quantifies the effect produced by actual client intensity and any environmental effects. Hence, delivering 100 OBUs of service in 6 months=200 OBUs of service in 12 months (annualized) and delivering 150 OBUs in 18 months=100 OBUs annualized.

Another factor is the environment where conditions may affect the number of services that can be delivered. Examples are the standard substantive visits possible with a client in normal service times versus in a pandemic, homelessness, blizzard, hurricane, fire, other crises, social conditions, or highly challenging geographic/travel. In these cases, the OBUs able to be delivered are lower, or restricted by the environmental conditions. To adjust Persona RiskQ™ the estimated required OBUs are applied with a multiplying factor. For example, with a care plan requiring substantive visits in person during the COVID pandemic, the OBUs for substantive visits might be multiplied three to four times. Yet, if the care plan may be accomplished by video or voice visits during COVID pandemic, the expected multiplier effect may be only one time.

Client intensity level is affected by the conditions, social and clinical, that define the care plan to be provided in servicing the client. The estimated OBUs for the care plan delivery should adequately account for the activity in most cases. Yet, each client will have multiple personas attributed. A client is not only Adult. Non-limiting examples of client types are as follows: Adult, Adult 24-40, Adult-Pregnant, Adult-Homeless, Adult-Substance Use, Adult-Mental Health, and Adult-Behavioral Health. A very complex and not abnormal condition. Estimating OBU activity would be complex so that a Client Intensity multiplier ranging from 1.0 to a maximum 2.5 could be used. Tables 1-6 below show various examples of the OBRs and OBUs.

TABLE 1

Adult Persona RiskQ ™

| Persona | Estimated Outcome-Based Units | Duration (months) | Annualized OBU | Environmental Multiplier | Client Intensity Multiplier | Persona RiskQ |
|---|---|---|---|---|---|---|
| Adult | 75 | 9 | 100 | 1.0 | 1.0 | 100 |
| 18/24 | 75 | 9 | 100 | 1.0 | 1.0 | 100 |
| 25/40 | 75 | 9 | 100 | 1.0 | 1.0 | 100 |
| 41/54 | 75 | 9 | 100 | 1.0 | 1.0 | 100 |
| 55/64 | 75 | 9 | 100 | 1.0 | 1.0 | 100 |
| 65/79 | 75 | 9 | 100 | 1.0 | 1.0 | 100 |
| >=80 | 100 | 12 | 100 | 1.0 | 1.0 | 100 |
| Asthma | 60 | 6 | 120 | 1.0 | 1.0 | 120 |
| Pregnant | 90 | 9 | 120 | 1.0 | 1.0 | 120 |
| Maternal | 100 | 12 | 100 | 1.0 | 1.0 | 100 |
| Senior | 100 | 12 | 100 | 1.0 | 1.0 | 100 |
| Homeless | 75 | 9 | 100 | 1.5 | 2.0 | 300 |

TABLE 1-continued

| Adult Persona RiskQ ™ | | | | | | |
|---|---|---|---|---|---|---|
| Persona | Estimated Outcome-Based Units | Duration (months) | Annualized OBU | Environmental Multiplier | Client Intensity Multiplier | Persona RiskQ |
| Behavioral | 100 | 9 | 133.3 | 1.0 | 2.0 | 266.6 |
| Substance Use | 100 | 9 | 133.3 | 1.2 | 2.5 | 399.9 |
| Undocumented | 75 | 9 | 100 | 1.0 | 1.2 | 120 |
| High Utilizer | 75 | 9 | 100 | 1.0 | 1.2 | 120 |
| Readmission | 75 | 9 | 100 | 1.0 | 1.0 | 100 |
| Mental Health | 75 | 9 | 100 | 1.0 | 2.0 | 200 |
| Chronic Conditions-Major > 3 | 75 | 9 | 100 | 1.0 | 2.0 | 200 |
| Diabetes | 75 | 9 | 100 | 1.0 | 1.5 | 150 |
| Hypertension | 75 | 9 | 100 | 1.0 | 1.5 | 150 |
| Disabled | 75 | 9 | 100 | 1.0 | 2.2 | 220 |
| Food Security and Nutrition | 75 | 9 | 100 | 1.0 | 1.3 | 130 |
| Poverty | 75 | 9 | 100 | 1.2 | 1.3 | 156 |
| Housing Insecurity | 90 | 9 | 120 | 1.2 | 1.3 | 187.2 |
| Palliative | 20 | 3 | 80 | 1.0 | 2.5 | 200 |
| Care Transitions | 25 | 1 | 300 | 1.0 | 1.0 | 300 |
| COVID Care | 20 | 0.5 | 20 | 4.0 | 1.0 | 80 |
| Crisis Care | 20 | 0.5 | 20 | 4.0 | 1.0 | 80 |

TABLE 2

| Adult Persona RiskQ ™ Charge | | | | |
|---|---|---|---|---|
| Persona | Persona RiskQ | Outcome-Based Rate | Administrative Rate | Persona RiskQ Charge |
| Adult | 100 | $25.00 | 20.00% | $3,000.00 |
| 18-24 | 100 | $25.00 | 20.00% | $3,000.00 |
| 25-40 | 100 | $25.00 | 20.00% | $3,000.00 |
| 41-54 | 100 | $25.00 | 20.00% | $3,000.00 |
| 55-64 | 100 | $25.00 | 20.00% | $3,000.00 |
| 65-79 | 100 | $25.00 | 20.00% | $3,000.00 |
| >=80 | 100 | $25.00 | 20.00% | $3,000.00 |
| Asthma | 100 | $25.00 | 20.00% | $3,600.00 |
| Pregnant | 100 | $25.00 | 20.00% | $3,600.00 |
| Maternal | 100 | $25.00 | 20.00% | $3,000.00 |
| Senior | 100 | $25.00 | 20.00% | $3,000.00 |
| Homeless | 300 | $25.00 | 20.00% | $9,000.00 |
| Behavioral | 266.6 | $25.00 | 20.00% | $7,998.00 |
| Substance Use | 399.9 | $25.00 | 20.00% | $11,997.00 |
| Undocumented | 120 | $25.00 | 20.00% | $3,600.00 |
| High Utilizer | 120 | $25.00 | 20.00% | $3,600.00 |
| Readmission | 100 | $25.00 | 20.00% | $3,000.00 |
| Mental Health | 200 | $25.00 | 20.00% | $6,000.00 |
| Chronic Conditions-Major > 3 | 200 | $25.00 | 20.00% | $6,000.00 |
| Diabetes | 150 | $25.00 | 20.00% | $4,500.00 |
| Hypertension | 150 | $25.00 | 20.00% | $4,500.00 |
| Disabled | 220 | $25.00 | 20.00% | $6,600.00 |
| Food Security and Nutrition | 130 | $25.00 | 20.00% | $3,900.00 |
| Poverty | 156 | $25.00 | 20.00% | $4,680.00 |
| Housing Insecurity | 187.2 | $25.00 | 20.00% | $5,616.00 |
| Palliative | 200 | $25.00 | 20.00% | $6,000.00 |
| Care Transitions | 300 | $25.00 | 20.00% | $9,000.00 |
| COVID Care | 80 | $25.00 | 20.00% | $2,400.00 |
| Crisis Care | 80 | $25.00 | 20.00% | $2,400.00 |

TABLE 3

| Adult Persona RiskQ ™ Caseload | | | |
|---|---|---|---|
| Persona | Persona RiskQ | Persona RiskQ Charge | Persona RiskQ Caseload |
| Adult | 100 | $3,000.00 | 1 |
| 18-24 | 100 | $3,000.00 | 1 |
| 25-40 | 100 | $3,000.00 | 1 |

TABLE 3-continued

| Adult Persona RiskQ ™ Caseload | | | |
|---|---|---|---|
| Persona | Persona RiskQ | Persona RiskQ Charge | Persona RiskQ Caseload |
| 41-54 | 100 | $3,000.00 | 1 |
| 55-64 | 100 | $3,000.00 | 1 |
| 65-79 | 100 | $3,000.00 | 1 |
| >=80 | 100 | $3,000.00 | 1 |
| Asthma | 100 | $3,600.00 | 1.2 |
| Pregnant | 100 | $3,600.00 | 1.2 |
| Maternal | 100 | $3,000.00 | 1 |
| Senior | 100 | $3,000.00 | 1 |
| Homeless | 300 | $9,000.00 | 3 |
| Behavioral | 266.6 | $7,998.00 | 2.7 |
| Substance Use | 399.9 | $11,997.00 | 4 |
| Undocumented | 120 | $3,600.00 | 1.2 |
| High Utilizer | 120 | $3,600.00 | 1.2 |
| Readmission | 100 | $3,000.00 | 1 |
| Mental Health | 200 | $6,000.00 | 2 |
| Chronic Conditions-Major > 3 | 200 | $6,000.00 | 2 |
| Diabetes | 150 | $4,500.00 | 1.5 |
| Hypertension | 150 | $4,500.00 | 1.5 |
| Disabled | 220 | $6,600.00 | 2.2 |
| Food Security and Nutrition | 130 | $3,900.00 | 1.3 |
| Poverty | 156 | $4,680.00 | 1.6 |
| Housing Insecurity | 187.2 | $5,616.00 | 1.9 |
| Palliative | 200 | $6,000.00 | 2 |
| Care Transitions | 300 | $9,000.00 | 3 |
| COVID Care | 80 | $2,400.00 | 0.8 |
| Crisis Care | 80 | $2,400.00 | 0.8 |

TABLE 4

| Pediatric Persona RiskQ ™ | | | | | | |
|---|---|---|---|---|---|---|
| Persona | Estimated Outcome-Based Units | Duration (months) | Annualized OBU | Environmental Multiplier | Client Intensity Multiplier | Persona RiskQ |
| Pediatric | 60 | 12 | 60 | 1.0 | 1.0 | 60 |
| 0-5 | 60 | 12 | 60 | 1.0 | 1.0 | 60 |
| 6-12 | 60 | 12 | 60 | 1.0 | 1.0 | 60 |
| 13-17 | 60 | 12 | 60 | 1.0 | 1.0 | 60 |
| Developmental | 75 | 9 | 100 | 1.0 | 1.0 | 100 |
| Asthma | 60 | 6 | 120 | 1.0 | 1.0 | 120 |
| Homeless | 75 | 9 | 100 | 1.5 | 2.0 | 300 |
| Behavioral | 100 | 9 | 133.3 | 1.0 | 2.0 | 266.6 |
| Substance Use | 100 | 9 | 133.3 | 1.2 | 2.5 | 399.9 |
| Undocumented | 75 | 9 | 100 | 1.0 | 1.2 | 120 |
| High Utilizer | 75 | 9 | 100 | 1.0 | 1.2 | 120 |
| Readmission | 75 | 9 | 100 | 1.0 | 1.0 | 100 |
| Mental Health-Youth | 75 | 9 | 100 | 1.0 | 2.0 | 200 |
| Mental Health-0-12 | 75 | 9 | 100 | 1.0 | 2.0 | 200 |
| Diabetes | 75 | 9 | 100 | 1.0 | 2.0 | 200 |
| Chronic Conditions-Major > 3 | 75 | 9 | 100 | 1.0 | 1.5 | 150 |
| Low/Very Low Birth Weight | 75 | 9 | 100 | 1.0 | 1.0 | 100 |
| Pre-Term Birth | 75 | 9 | 100 | 1.0 | 1.0 | 100 |
| Multiple Birth | 75 | 9 | 100 | 1.0 | 1.0 | 100 |
| Disabled | 75 | 9 | 100 | 1.0 | 2.2 | 220 |
| Food Security and Nutrition | 75 | 9 | 100 | 1.0 | 1.3 | 130 |
| Poverty | 75 | 9 | 100 | 1.2 | 1.3 | 156 |
| Housing Insecurity | 90 | 9 | 100 | 1.2 | 1.3 | 187.2 |
| Pregnant | 90 | 9 | 120 | 1.0 | 1.0 | 120 |
| Care Transitions | 25 | 1 | 300 | 1.0 | 1.0 | 300 |
| COVID Care | 20 | 0.5 | 20 | 4.0 | 1.0 | 80 |
| Crisis Care | 20 | 0.5 | 20 | 4.0 | 1.0 | 80 |

TABLE 5

| Pediatric Persona RiskQ ™ Charge | | | | |
|---|---|---|---|---|
| Persona | Persona RiskQ | Outcome-Based Rate | Administrative Rate | Persona RiskQ Charge |
| Pediatric | 60 | $25.00 | 20.00% | $1,800.00 |
| 0-5 | 60 | $25.00 | 20.00% | $1,800.00 |
| 6-12 | 60 | $25.00 | 20.00% | $1,800.00 |
| 13-17 | 60 | $25.00 | 20.00% | $1,800.00 |
| Developmental | 100 | $25.00 | 20.00% | $3,000.00 |
| Asthma | 120 | $25.00 | 20.00% | $3,600.00 |
| Homeless | 300 | $25.00 | 20.00% | $9,000.00 |
| Behavioral | 266.6 | $25.00 | 20.00% | $7,998.00 |
| Substance Use | 399.9 | $25.00 | 20.00% | $11,997.00 |
| Undocumented | 120 | $25.00 | 20.00% | $3,600.00 |
| High Utilizer | 120 | $25.00 | 20.00% | $3,600.00 |
| Readmission | 100 | $25.00 | 20.00% | $3,000.00 |
| Mental Health-Youth | 200 | $25.00 | 20.00% | $6,000.00 |
| Mental Health-0-12 | 200 | $25.00 | 20.00% | $6,000.00 |
| Diabetes | 200 | $25.00 | 20.00% | $6,000.00 |
| Chronic Conditions-Major > 3 | 150 | $25.00 | 20.00% | $4,500.00 |
| Low/Very Low Birth Weight | 100 | $25.00 | 20.00% | $3,000.00 |
| Pre-Term Birth | 100 | $25.00 | 20.00% | $3,000.00 |
| Multiple Birth | 100 | $25.00 | 20.00% | $3,000.00 |
| Disabled | 220 | $25.00 | 20.00% | $6,600.00 |
| Food Security and Nutrition | 130 | $25.00 | 20.00% | $3,900.00 |
| Poverty | 156 | $25.00 | 20.00% | $4,680.00 |
| Housing Insecurity | 187.2 | $25.00 | 20.00% | $5,616.00 |
| Pregnant | 120 | $25.00 | 20.00% | $3,600.00 |
| Care Transitions | 300 | $25.00 | 20.00% | $9,000.00 |
| COVID Care | 80 | $25.00 | 20.00% | $2,400.00 |
| Crisis Care | 80 | $25.00 | 20.00% | $2,400.00 |

TABLE 6

| Pediatric Persona RiskQ ™ Caseload | | | |
|---|---|---|---|
| Persona | Persona RiskQ | Persona RiskQ Charge | Persona RiSkQ Caseload |
| Pediatric | 60 | $1,800.00 | 0.6 |
| 0-5 | 60 | $1,800.00 | 0.6 |
| 6-12 | 60 | $1,800.00 | 0.6 |
| 13-17 | 60 | $1,800.00 | 0.6 |
| Developmental | 100 | $3,000.00 | 1 |
| Asthma | 120 | $3,600.00 | 1.2 |
| Homeless | 300 | $9,000.00 | 3 |
| Behavioral | 266.6 | $7,998.00 | 2.7 |
| Substance Use | 399.9 | $11,997.00 | 4 |
| Undocumented | 120 | $3,600.00 | 1.2 |
| High Utilizer | 120 | $3,600.00 | 1.2 |
| Readmission | 100 | $3,000.00 | 1 |
| Mental Health-Youth | 200 | $6,000.00 | 2 |
| Mental Health-0-12 | 200 | $6,000.00 | 2 |
| Diabetes | 200 | $6,000.00 | 2 |
| Chronic Conditions-Major > 3 | 150 | $4,500.00 | 1.5 |
| Low/Very Low Birth Weight | 100 | $3,000.00 | 1 |
| Pre-Term Birth | 100 | $3,000.00 | 1 |
| Multiple Birth | 100 | $3,000.00 | 1 |
| Disabled | 220 | $6,600.00 | 2.2 |
| Food Security and Nutrition | 130 | $3,900.00 | 1.3 |
| Poverty | 156 | $4,680.00 | 1.6 |
| Housing Insecurity | 187.2 | $5,616.00 | 1.9 |
| Pregnant | 120 | $3,600.00 | 1.2 |
| Care Transitions | 300 | $9,000.00 | 3 |
| COVID Care | 80 | $2,400.00 | 0.8 |
| Crisis Care | 80 | $2,400.00 | 0.8 |

With continuing reference to FIGS. 59-66, clinical care coordination dashboards contain various types of health information with in-line summaries and drill-through details and activities. The dashboard, using a graphical user interface, contains user selectable elements, which can be manipulated and selected as needed. The various health information scores are visible and have in-line summaries with screening dates. The history and details are available via the drill-through. The screens and measured information is gathered in the CHR platform and available as a visual dashboard element. Interactive charts and graphs are available for viewing as well. Demographics, behavioral and clinical information, individual and social health risks are identified, and target care episode plans can be created. The individual client personas can be separately identified and tracked. Identifying a client's personas quickly provides a projection for risk, coordination capacity, and cost. The persona attributes are used to forecast and direct the care coordination efforts or the payer cost for care coordination services for that persona population.

The combination of SDoH and behavioral/clinical information and the measurement of summaries, details, and completed activities incorporate an innovative display of the data for each element. In one aspect of the present teaching, an algorithm is used to define a Care Episode, which segments the client data into logical time periods that are comparable and can be analyzed and evaluated. The system automatically determines the care episode according to system standards, which provides consistent data across all HUBS, regardless of their individual policies. This process and algorithm create more efficient processing by the computer. The present teaching also allows for the tracking of activities and progress through the Care Episode. The data is accumulated and analyzed/evaluated to determine gaps in care and sustainability.

In another aspect of the present teaching, the system adds enhanced definition to artificial intelligence, and provides thorough analysis of all data types in the Care Episode. The system defines potential care plans, targeted activities, which enable real-time care gap analysis, predictive activity suggestions, and productivity curves in relation to targeted activities. The prediction can be made early in the care coordination process instead of later in the process. Undisclosed risks such as food insecurity would be high probability flagged for the coordinator. This also enables the computer to operate faster and more efficiently as it relates to the Care Episode.

The care coordination system further includes a separate artificial intelligence engine which extends to the assignment of members to social care teams. Here, the artificial intelligence engine determines which individuals, i.e., health workers, care coordinators, etc., have shared experience with clients of a particular persona and which individuals have been most successful with clients of such personas within a recent time period (i.e., which individuals have been most successful in providing the correct level of care and obtaining the positive results within a recent time period). The artificial intelligence engine evaluates which individual is best suited for a particular client based on work with past personas, best suited to working with a particular client based on work with past personas, and which types of projects are best suited for a particular individual. The artificial intelligence engine makes judgments on assigning individuals to a particular client based on both facts and personality based on data collected. The judgments are justified by results, given what was achieved in the past and the likelihood of what will be achieved in the future based on data retrieved.

The care coordination system further includes a separate artificial intelligence engine which extends into translation and interpretation of language. The artificial intelligence engine is capable of translating communications from one language to another language instantaneously (e.g., in a matter of seconds). Recipients or multiple recipients of the translations can respond to communications in their own language and the artificial intelligence engine will translate responses to another language (e.g., English) instantaneously. This tool may be used in many applications including communications with clients for the purpose of retrieving data related to SDoH, clinical data, financial data, etc. as well as internally between service providers within the care coordination system. The artificial intelligence engine, however, extends beyond simple translation and also provides interpretation of language communicated into the system. For example, the artificial intelligence engine is capable of evaluating inflections of oral or spoken language to determine, including but not limited to, sincerity, defensiveness, emotion, and mental health around an answer. Translations are recorded into the client database and client record and logged so that staff can comment on the communications received. The artificial intelligence engine, through an algorithm, reviews and analyzes this data and determines and assigns a grade as to how truthful the client was with respect to a particular question and categorizes the response within a particular truth scale. This information may then be used by the artificial intelligence engine at the persona level to prompt the care coordinator, health worker, etc. with further courses of action, pathways, questions to ask the client, etc. to improve overall treatment.

In one aspect of the present disclosure, the CCN may be a federation of regional Community HUBs align clinically focused healthcare with local care delivery partners to provide rapid, collaborative continuous, high-quality care in the community and at home.

In another aspect of the present disclosure, the CCN may be one of the one or more CCS Health systems, interoperability with the health care systems, ransomware-proof/quantum-safe IT security systems, care methodologies, processes, reporting, invoicing, and artificial intelligence and predictive analytics provide for faster, more comprehensive communication, secure information sharing enabling significant return on investment realized at the health systems while simultaneously reducing Medicare/Medicaid costs. The CCS Health systems may also provide ransomware-proof/quantum-safe IT security to the transactions they manage.

In yet another aspect of the present disclosure, the CCN provides health systems with expanded market reach and greater patient engagement in the community even to the "kitchen table." The information interoperability with the CCN links clinical and community care teams with real-time patient data access providing comprehensive whole-person care and access to important current social determinants of health.

In another aspect of the present disclosure, stronger health systems with the SMF strategic partnership enable sustainable and stronger community care delivery partners to provide health systems with access to information, the ability to provide continuous care improvement, and catalyzing return on investment from the community to the health system and SMF.

In yet another aspect of the present disclosure, the reduction in Medicare/Medicaid care costs are delivered by the community's continuous care delivery and makes for greater engagement and greater clinical effectiveness with access to community member information.

CTI treatment provide up to 10×-20× times ROI, provided by reduction in hospital readmissions, hospital and ED utilization, uncompensated care, unnecessary care and services, skilled nursing utilization, and medication-related issues. Results provided are long-lasting patient/client behavior change with new skills activated through CTI coaching and data collection.

CTT provides up to 20×-40× times ROI, provided through collaborative clinical and community care teams providing whole-person, high-quality care at home or in the community while affecting behavior change, skills transfer, and reducing social determinants of health risk. Significant care costs are reduced through providing continuous access to care in the low-cost, community environments, yet the even more significant care costs are still reduced; hospital readmissions, hospital and ED utilization, uncompensated care, unnecessary care and services, skilled nursing utilization, and medication-related issues.

CCCs provide up to 4.5×-8× times ROI, which is achieved through identifying a vulnerable person's social health risks through time in trusted relationships and providing risk-reducing care plans to achieve better health outcomes, greater health equity, and higher quality of life. CCCs provide health systems with greater engagement and patients positively activated in their healthcare furthering the reduction in hospital readmissions, hospital and ED utilization, uncompensated care, unnecessary care and services, skilled nursing utilization, and medication-related issues and the correlated reduction of 5%-15% in Medicare/Medicaid care costs.

Some of the benefits derived simultaneously from the care cost reduction solution and the CCN, many of which are depicted in the Evidence-Based Care Models with Measured Outcomes and High Return on Investments graph 7100, are as follows:

Increase hospital net patient revenue by 4-15% annually, strengthening healthcare systems and facilitating growth.

Resolve state-wide rural hospital sustainability, maintain rural hospital independence and community brand/presence while improving profitability and enabling growth.

Strengthen the community care infrastructure with sustainable, performance-based payments, leading to better outcomes and new returns on investment for healthcare systems.

Establish nationally recognized community health forces teaching and learning center, developing a sustainable healthcare workforce supporting healthcare systems and focused on whole-person care in each state.

Accelerate economic growth and development through increased employment, technological advancements, and higher profitability.

Implement system-wide or state-wide ransomware-proof IT security for comprehensive data protection for health systems.

Establish a ransomware-proof and quantum-safe IT security with comprehensive data protection for health systems, community health, state, and health information exchanges.

Resolve food insecurity and reduce poverty through targeted initiatives.

Enhance maternal health and reduce infant mortality rates.

Improve depression-related disorders to improve quality of life and reduce mental health costs with depression management coaching Improve dementia patients' life quality and support dementia caregivers to reduce health costs.

Improve state key health metrics and rankings, within 4 years, without requiring additional state funding.

Advance the state education initiatives to support lifelong learning and workforce development.

Strengthen state economic development and growth with stronger healthcare, community health systems, and larger educated workforces.

The preceding description of the disclosed aspects is provided to enable any person skilled in the art to make or use the present teaching. Various modifications to these aspects will be readily apparent to those skilled in the art, and the generic principles defined herein may be applied to other aspects without departing from the spirit or scope of the present teaching. Thus, the present teaching is not intended to be limited to the aspects shown herein but is to be accorded the widest scope consistent with the following claims and the principles and novel features disclosed herein.

What is claimed is:

1. A system for reducing medical care costs comprising:

a hub computing device which operates as a hub portal comprising a processor, a display and a non-transitory computer-readable storage medium containing a set of instructions encoded thereon;

a data collection component, wherein the data collection component allows for a listing of clients including client information, a listing of medical, health and social service providers to be uploaded onto the hub portal by an associated hub user, and for recording of a patient's community health data, social determinants of health data and financial data with one or more service providers through use of the system;

a graphical user interface for integrating the data collection component and the hub computing device, wherein the set of instructions encoded on the non-transitory computer-readable storage medium comprise the steps of:

analyzing data collected by the data collection component;

extracting analyzed data and applying it to at least one condition in a set of pre-set conditions; and calculating an initiative cost per client, a client's required sustainability level and a break-even point between a payer and an administrator in delivering services to the client, wherein the calculation is completed in real-time upon entry of data for the client into the data collection component and delivered to at least one of the one or more service providers at intervals in real-time through the graphical user interface;

an artificial intelligence engine, comprising non-transitory computer-readable storage medium containing a set of instructions encoded thereon, the instructions comprising:

training at least one AI model using information from external client databases regarding client information and care network partners to create at least one trained ROI AI model, which can predict the ROI of a given care plan for the client;

predicting the ROI and the timing of a given care plan for the client using the at least one trained ROI AI model;

establishing care plan priorities to achieve objectives;

routing to appropriate care network partners;

developing key performance indicators and milestones per client and care model displaying data for users to self-evaluate performance per client; and implementing the care plan via a Healthcare and community-based socialcare team, resulting in increased efficiency and savings;

a CCN component for using the savings from the implementation of the care plan crafted by the artificial intelligence engine, comprising non-transitory computer-readable storage medium containing a set of instructions encoded thereon, the instructions comprising:

sending money from an SMF to a money management organization to begin the CCN process and for redistribution;

sending money saved via the artificial intelligence engine implementing the care plan to the money management organization for redistribution; and redistributing the money to one or more beneficiaries based on need via a CCS health system.

2. The system of claim 1, wherein the artificial intelligence engine comprises a neural network.

3. The system of claim 1, wherein the one or more beneficiaries comprise at least one CBO, at least one AAA, at least one hospital, at least one FQHC, at least one aging network, at least one CTO, at least one health system, a federal Medicare/Medicaid program, at least one state Medicaid program, and the SMF.

4. The system of claim 1, wherein the information contained within the external client databases comprises information regarding the specific persona(s), the healthcare, social care, claims, geographic, and environmental information of the client.

5. The system of claim 1, wherein the artificial intelligence engine evaluates data entered into the system during treatment with respect to changes in the client's care plan and makes changes to its ROI and timing predictions in light of the changes.

6. The system of claim 1, wherein the artificial intelligence engine determines whether the budget of the care plan was adhered to and whether the Healthcare and community-based socialcare team achieved the system's expectations.

7. The system of claim 1, wherein after the client's care plan is completed, the artificial intelligence engine determines in real-time whether the client is to be referred to another agency or requires a further treatment plan, and if so, calculates a new ROI and timing of a new care plan.

8. The system of claim 1, wherein the artificial intelligence engine comprises structured query language (SQL) software and robotic process automation (RPA) software, wherein structured query language (SQL) software manages the relationship between data within disparate databases, performs operations on the data and wherein the robotic process automation (RPA) software builds, deploys and manages software robots to interact with the data, digital systems and software and identifies and extracts data and performs defined actions.

9. The system of claim 1, wherein the CCS health system provides ransomware-proof/quantum-safe IT security to provide encryption to relevant data, helping to prevent costly data breaches from occurring and extortion by third-party bad actors.

10. The system of claim 1, wherein any leftover money is given back to the SMF for further investment.

11. A method for reducing medical care costs comprising the steps of:

using a hub computing device which operates as a hub portal comprising a processor, a display and a non-transitory computer-readable storage medium containing a set of instructions encoded thereon;

using a data collection component, wherein the data collection component allows for a listing of clients including client information, a listing of medical, health and social service providers to be uploaded onto the hub portal by an associated hub user, and for recording of a patient's community health data, social determinants of health data and financial data with one or more service providers through use of the system;

using a graphical user interface for integrating the data collection component and the hub computing device, wherein the set of instructions encoded on the non-transitory computer-readable storage medium comprise the steps of:

analyzing data collected by the data collection component;

extracting analyzed data and applying it to at least one condition in a set of pre-set conditions; and calculating an initiative cost per client, a client's required sustainability level and a break-even point between a payer and an administrator in delivering services to the client, wherein the calculation is completed in real-time upon entry of data for the client into the data collection component and delivered to at least one of the one or more service providers at intervals in real-time through the graphical user interface;

using an artificial intelligence engine, comprising non-transitory computer-readable storage medium containing a set of instructions encoded thereon, the instructions comprising:

training at least one AI model using information from external client databases regarding client information and care network partners to create at least one trained ROI AI model, which can predict the ROI of a given care plan for the client;

predicting the ROI and the timing of a given care plan for the client using the at least one trained ROI AI model;

establishing care plan priorities to achieve objectives;

routing to appropriate care network partners;

developing key performance indicators and milestones per client and care model displaying data for users to self-evaluate performance per client; and implementing the care plan via a Healthcare and community-based socialcare team, resulting in increased efficiency and savings;

using a CCN component for using the savings from the implementation of the care plan crafted by the artificial intelligence engine, comprising non-transitory computer-readable storage medium containing a set of instructions encoded thereon, the instructions comprising:

sending money from an SMF to a money management organization to begin the CCN process and for redistribution;

sending money saved via the artificial intelligence engine implementing the care plan to the money management organization for redistribution; and redistributing the money to one or more beneficiaries based on need.

12. The method of claim 11, wherein the artificial intelligence engine comprises a neural network.

13. The method of claim 11, wherein the one or more beneficiaries comprise at least one CBO, at least one AAA, at least one hospital, at least one FQHC, at least one aging network, at least one CTO, at least one health system, a federal Medicare/Medicaid program, at least one state Medicaid program, and the SMF.

14. The method of claim 11, wherein the information contained within the external client databases comprises information regarding the specific persona(s), the healthcare, social care, claims, geographic, and environmental information of the client.

15. The method of claim 11, wherein the artificial intelligence engine evaluates data entered into the system during treatment with respect to changes in the client's care plan and makes changes to its ROI and timing predictions in light of the changes.

16. The method of claim 11, wherein the artificial intelligence engine determines whether the budget over the care episode timeline was adhered to and whether the Healthcare and community-based socialcare team achieved the system's expectations.

17. The method of claim 11, wherein after the client's care plan is completed, the artificial intelligence engine determines in real-time whether the client is to be referred to another agency or requires a further treatment plan, and if so, calculates a new ROI and timing of a new care plan.

18. The method of claim 11, wherein the artificial intelligence engine comprises structured query language (SQL) software and robotic process automation (RPA) software, wherein structured query language (SQL) software manages the relationship between data within disparate databases, performs operations on the data and wherein the robotic process automation (RPA) software builds, deploys and manages software robots to interact with the data, digital systems and software and identifies and extracts data and performs defined actions.

19. The method of claim 11, wherein the CCS health system provides ransomware-proof/quantum-safe IT security to provide encryption to relevant data, helping to prevent costly data breaches from occurring and extortion by third-party bad actors.

20. A system for reducing medical care costs comprising:

a hub computing device which operates as a hub portal comprising a processor, a display and a non-transitory computer-readable storage medium containing a set of instructions encoded thereon;

a data collection component, wherein the data collection component allows for a listing of clients including client information, a listing of medical, health and social service providers to be uploaded onto the hub portal by an associated hub user, and for recording of a patient's community health data, social determinants of health data and financial data with one or more service providers through use of the system;

a graphical user interface for integrating the data collection component and the hub computing device, wherein the set of instructions encoded on the non-transitory computer-readable storage medium comprise the steps of:

analyzing data collected by the data collection component;

extracting analyzed data and applying it to at least one condition in a set of pre-set conditions; and calculating an initiative cost per client, a client's required sustainability level and a break-even point between a payer and an administrator in delivering services to the client, wherein the calculation is completed in real-time upon entry of data for the client into the data collection component and delivered to at least one of the one or more service providers at intervals in real-time through the graphical user interface;

an artificial intelligence engine, comprising non-transitory computer-readable storage medium containing a set of instructions encoded thereon, the instructions comprising:

training at least one AI model using information from external client databases regarding client information and care network partners to create at least one trained ROI AI model, which can predict the ROI of a given care plan for the client;

predicting the ROI and the timing of a given care plan for the client using the at least one trained ROI AI model;

establishing care plan priorities to achieve objectives;

routing to appropriate care network partners;

developing key performance indicators and milestones per client and care model displaying data for users to self-evaluate performance per client; and implementing the care plan via a Healthcare and community-based socialcare team, resulting in increased efficiency and savings, wherein the artificial intelligence engine comprises a neural network;

the information contained within the external client databases comprises information regarding the specific persona(s), the healthcare, social care, claims, geographic, and environmental information of the client;

the artificial intelligence engine evaluates data entered into the system during treatment with respect to changes in the client's care plan and makes changes to its ROI and timing predictions in light of the changes;

the artificial intelligence engine determines whether the budget over the care episode timeline was adhered to and whether the Healthcare and community-based socialcare team achieved the system's expectations;

after the client's care plan is completed, the artificial intelligence engine determines in real-time whether the client is to be referred to another agency or requires a further treatment plan, and if so, calculates a new ROI and timing of a new care plan; and the artificial intelligence engine comprises structured query language (SQL) software and robotic process automation (RPA) software, wherein structured query language (SQL) software manages the relationship between data within disparate databases, performs operations on the data and wherein the robotic process automation (RPA) software builds, deploys and manages software robots to interact with the data, digital systems and software and identifies and extracts data and performs defined actions;

a CCN component for using the savings from the implementation of the care plan crafted by the artificial intelligence engine, comprising non-transitory computer-readable storage medium containing a set of instructions encoded thereon, the instructions comprising:

sending money from an SMF to a money management organization to kickstart the CCN process and for redistribution;

sending money saved via the artificial intelligence engine implementing the care plan to the money management organization for redistribution; and redistributing the money to one or more beneficiaries based on need, wherein the one or more beneficiaries comprise at least one CBO, at least one AAA, at least one hospital, at least one FQHC, at least one aging network, at least one CTO, at least one health system, a federal Medicare/Medicaid program, at least one state Medicaid program, and the SMF;

the CCS health system provides ransomware-proof/quantum-safe IT security to provide encryption to relevant data, helping to prevent costly data breaches from occurring and extortion by third-party bad actors; and any leftover money is given back to the SMF for further investment.

* * * * *